United States Patent
Lee et al.

(10) Patent No.: US 10,584,117 B2
(45) Date of Patent: Mar. 10, 2020

(54) 1,3,4-OXADIAZOLE AMIDE DERIVATIVE COMPOUND AS HISTONE DEACETYLASE 6 INHIBITOR, AND PHARMACEUTICAL COMPOSITION CONTAINING SAME

(71) Applicant: Chong Kun Dang Pharmaceutical Corp., Seoul (KR)

(72) Inventors: Jaekwang Lee, Gyeonggi-do (KR); Moo Sung Ko, Gyeonggi-do (KR); Younghue Han, Gyeonggi-do (KR); Yuntae Kim, Gyeonggi-do (KR)

(73) Assignee: Chong Kun Dang Pharmaceutical Corp. (KR)

( * ) Notice: Subject to any disclaimer, the term of this patent is extended or adjusted under 35 U.S.C. 154(b) by 0 days.

(21) Appl. No.: 15/748,081

(22) PCT Filed: Jul. 27, 2016

(86) PCT No.: PCT/KR2016/008216
§ 371 (c)(1),
(2) Date: Jan. 26, 2018

(87) PCT Pub. No.: WO2017/018804
PCT Pub. Date: Feb. 2, 2017

(65) Prior Publication Data
US 2018/0215743 A1  Aug. 2, 2018

(30) Foreign Application Priority Data

Jul. 27, 2015 (KR) .......................... 10-2015-0106007

(51) Int. Cl.
| | | |
|---|---|---|
| *C07D 413/10* | (2006.01) | |
| *A61K 31/4245* | (2006.01) | |
| *C07D 413/12* | (2006.01) | |
| *C07D 271/10* | (2006.01) | |
| *C07D 205/04* | (2006.01) | |
| *C07D 213/02* | (2006.01) | |

(52) U.S. Cl.
CPC ........ *C07D 413/10* (2013.01); *A61K 31/4245* (2013.01); *C07D 271/10* (2013.01); *C07D 413/12* (2013.01); *C07D 205/04* (2013.01); *C07D 213/02* (2013.01)

(58) Field of Classification Search
CPC .................................................. C07D 413/10
See application file for complete search history.

(56) References Cited

U.S. PATENT DOCUMENTS

| | | | |
|---|---|---|---|
| 4,871,753 A | 10/1989 | Rorh | |
| 8,981,084 B2 | 3/2015 | Baloglu et al. | |
| 9,670,193 B2 * | 6/2017 | Hebach | C07D 413/14 |
| 2005/0288282 A1 | 12/2005 | Delorme et al. | |
| 2006/0058298 A1 | 3/2006 | Delorme et al. | |
| 2007/0293530 A1 | 12/2007 | Smil et al. | |
| 2012/0027874 A1 | 2/2012 | Charrier et al. | |
| 2012/0289495 A1 | 11/2012 | Baloglu et al. | |
| 2013/0059883 A1 | 3/2013 | Baloglu et al. | |
| 2014/0005133 A1 | 1/2014 | Trivedi et al. | |
| 2014/0142105 A1 | 5/2014 | Hebach et al. | |
| 2014/0329825 A1 | 11/2014 | Hebach et al. | |
| 2017/0015809 A1 | 1/2017 | Hawkins et al. | |
| 2018/0230114 A1 | 8/2018 | Lee et al. | |
| 2018/0251437 A1 | 9/2018 | Lee et al. | |

FOREIGN PATENT DOCUMENTS

| | | |
|---|---|---|
| CN | 104744446 | 7/2015 |
| JP | 2005513123 | 5/2005 |
| JP | 2009542752 | 12/2009 |
| JP | 2011008205 | 1/2011 |
| JP | 2011502133 | 1/2011 |
| JP | 2012211149 | 11/2012 |
| JP | 2013517278 | 5/2013 |
| JP | 2013517281 | 5/2013 |
| JP | 2014520794 | 8/2014 |

(Continued)

OTHER PUBLICATIONS

Bolden et al., *Anticancer activities of histone deacetylase inhibitors*, Nat. Rev. Drug Discov., 5(9):769-784 (2006).
Chemical Abstract compound, STN express, RN 904653-20-9, dated Aug. 25, 2006 (2 pages).
Hassig et al., *Nuclear histone acetylases and deacetylases and transcriptional regulation: HATS off to HDACs*, Curr. Opin. Chem. Biol. 1:300-308 (1997).
Hu et al., *HDAC6 α-tubulin deacetylase: A potential therapeutic target in neurodegenerative diseases*, J. Neurol. Sci. 304:1-8 (2011).
Matthias et al., *Mice Lacking Histone Deacetylase 6 Have Hyperacetylated Tubulin but Are Viable and Develop Normally*, Mol. Cell. Biol. 28:1688-1701 (2008).

(Continued)

*Primary Examiner* — Golam M Shameem
(74) *Attorney, Agent, or Firm* — Fish & Richardson P.C.

(57) ABSTRACT

The present invention relates to novel compounds having histone deacetylase 6 (HDAC6) inhibitory activity, stereoisomers thereof or pharmaceutically acceptable salts thereof, the use thereof for the preparation of therapeutic medicaments, pharmaceutical compositions containing the same, a method for treating diseases using the composition, and methods for preparing the novel compounds. The novel compounds, stereoisomers thereof or pharmaceutically acceptable salts thereof according to the present invention have histone deacetylase 6 (HDAC6) inhibitory activity and are effective for the prevention or treatment of HDAC6-mediated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities.

8 Claims, No Drawings

(56) References Cited

FOREIGN PATENT DOCUMENTS

| | | |
|---|---|---|
| JP | 2014524922 | 9/2014 |
| JP | 2014533721 | 12/2014 |
| JP | 2014533734 | 12/2014 |
| KR | 100265385 | 11/2000 |
| KR | 100903743 | 6/2009 |
| KR | 10-2014-7017436 A | 11/2012 |
| KR | 101262870 | 5/2013 |
| KR | 10-2013-0112911 A | 10/2013 |
| KR | 101320198 | 10/2013 |
| KR | 1020130112911 | 10/2013 |
| KR | 1020140097459 | 8/2014 |
| KR | 101561860 | 10/2015 |
| RU | 2515611 | 8/2012 |
| WO | WO 2003/028729 | 4/2003 |
| WO | WO 2007/011626 | 1/2007 |
| WO | WO 2007/032445 | 3/2007 |
| WO | WO 2007/107758 | 9/2007 |
| WO | WO 2009/010479 | 1/2009 |
| WO | WO 2010/123933 | 10/2010 |
| WO | WO 2010/126002 | 11/2010 |
| WO | WO 2011/088181 | 7/2011 |
| WO | WO 2011/088192 | 7/2011 |
| WO | WO 2011/104680 | 9/2011 |
| WO | WO 2011/133888 | 10/2011 |
| WO | WO 2012/013716 | 2/2012 |
| WO | 2013/066835 | 5/2013 |
| WO | WO 2013/066833 | 5/2013 |
| WO | WO 2013/066839 | 5/2013 |
| WO | WO 2013066835 A2 | 5/2013 |
| WO | WO 2013/080120 | 6/2013 |
| WO | WO 2015/033301 | 3/2015 |
| WO | WO 2015/087151 | 6/2015 |
| WO | WO 2016/082930 | 6/2016 |
| WO | WO 2017/018803 | 2/2017 |
| WO | WO 2017/018804 | 2/2017 |
| WO | WO 2017/018805 | 2/2017 |
| WO | WO 2017/023133 | 2/2017 |
| WO | WO 2017/065473 | 4/2017 |

OTHER PUBLICATIONS

Methot et al., *Exploration of the internal cavity of histone deacetylase (HDAC) with selective HDAC1/HDAC2 inhibitors (SHI-1:2)*, Bioorg. Med. Chem. Lett. 18:973-978 (2008).
Piekarz et al., *Clinical Toxicities of Histone Deacetylase Inhibitors*, Pharmaceuticals, 3:2751-2767 (2010).
Rajack et al., *2,5-Disubstituted-1,3,4-oxadiazoles/thiadiazole as surface recognition moiety: Design and synthesis of novel hydroxamic acid based histone deacetylase inhibitors*, Bioorganic & Medical Chemistry Letters, 21:5735-5738 (2011).
Santo et al., *Preclinical activity, pharmacodynamic, and pharmacokinetic properties of a selective HDAC6 inhibitor, ACY-1215, in combination with bortezomib in multiple myeloma*, Blood 119:2579-2589 (2012).
Vishwakarma et al., *Tubastatin, a selective histone deacetylase 6 inhibitor shows anti-inflammatory and anti-rheumatic effects*, International Immunopharmacology, 16:72-78 (2013).
Warrell et al, *Therapeutic Targeting of Transcription in Acute Promyelocytic Leukemia by Use of an Inhibitor of Histone Deacetylase*, J. Natl. Cancer Inst. 90:1621-1625 (1998).
Wiest et al., *Computational Exploration of Zinc Binding Groups for HDAC Inhibition*, J. Org. Chem. 78:5051-5055 (2013).
Witt et al., *HDAC family: What are the cancer relevant targets?* Cancer Letters, 277:8-21 (2009).
Woster et al., *Discovery of a new class of histone deacetylase inhibitors with a novel zinc binding group*, Med. Chem. Commun., online publication (2015).
Yao et al., *Regulation of the Dynamics of hsp90 Action on the Glucocorticoid Receptor by Acetylation/Deacetylation of the Chaperone*, Mol. Cell, 18:601-607 (2005).
International Search Report of ISA/KR for PCT/KR2016/008216 (dated Nov. 21, 2016).
Chemical Abstract compounds, STN Express (Aug. 25, 2006).
Rajak et al., Bioorganic & Medicinal Chemistry letters 21, 5735-5738 (2011).
Cancer [online], [retrieved on Jul. 6, 2007]. Retrieved from the internet, URL http://www.nlm.nih.gov/mededlineplus/cancer.html (10 pages).
Golub et al., Molecular Classification of Cancer: Class Discovery and Class Prediction by Gene Expression Monitoring, Science 286:531-537 (1999).
Lala et al., Role of nitric oxide in tumor progression: Lessons from experimental tumors, Cancer and Metastasis Reviews 17(1):91-106 (1998).
U.S. Appl. No. 15/747,952, filed Jan. 26, 2018, Lee et al.
U.S. Appl. No. 15/747,850, filed Jan. 26, 2018, Lee et al.
U.S. Appl. No. 15/748,081, filed Jan. 26, 2018, Lee et al.
U.S. Appl. No. 15/750,067, filed Feb. 2, 2018, Lee et al.
U.S. Appl. No. 15/763,972, filed Mar. 28, 2018, Kim et al.
AU Office Action for AU App No. 2016299484, dated Aug. 28, 2018 (6 pages).
AU Office Action for AU App No. 2016299486, dated Jul. 31, 2018 (5 pages).
Chen, J.J. et al., *Discovery of 2-methylpyridine-based biaryl amides as y-secretase modulators for the treatment of Alzheimer's disease*, Bioorganic & Medicinal Chemistry letters, 2013, 23(23):6447-6454.
International Preliminary Report on Patentability and Written Opinion for Intl. App. No. PCT/KR2016/008214 dated Jan. 30, 2018 (8 pages).
International Preliminary Report on Patentability and Written Opinion for Intl. App. No. PCT/KR2016/008216 dated Jan. 30, 2018 (9 pages).
International Preliminary Report on Patentability and Written Opinion for Intl. App. No. PCT/KR2016/008218 dated Jan. 30, 2018 (8 pages).
International Preliminary Report on Patentability and Written Opinion for Intl. App. No. PCT/KR2016/008622 dated Feb. 6, 2018 (8 pages).
International Preliminary Report on Patentability and Written Opinion for Intl. App. No. PCT/KR2016/011355 dated Apr. 17, 2018 (6 pages).
International Search Report for Int. App. No. PCT/KR2016/011355, dated Jan. 26, 2017 (5 pages).
International Search Report of ISA/KR for PCT/KR2016/0008218 (dated Nov. 21, 2016).
International Search Report of ISA/KR for PCT/KR2016/008214, dated Nov. 24, 2016 (5 pages).
International Search Report of ISA/KR for PCT/KR2016/008218, dated Nov. 21, 2016 (5 pages).
International Search Report of ISA/KR for PCT/KR2016/008622, dated Feb. 17, 2017 (5 pages).
Japan Office Action for JP App No. 2018-505725 dated Sep. 12, 2018 (3 pages).
Korea Office Action for KR Application No. 10-2016-0095332, dated Sep. 5, 2017 (15 pages).
Korea Office Action for KR Application No. 10-2016-0095334, dated Sep. 5, 2017 (17 pages).
Korea Office Action for KR Application No. 10-2016-0099508, dated Sep. 5, 2017 (20 pages).
Korea Office Action for KR Application No. 10-2016-0131245, dated Sep. 5, 2017 (7 pages).
Manku, et al., Synthesis and evaluation of lysine derived sulfamides as histone deacetylase inhibitors, Bioorganic & Medicinal Chemistry Letters 19, 1866-1870 (2009).
Pal et al., Hydroxamic acid—A novel molecule for anticancer therapy, Journal of Advanced Pharmaceutical Technology & Research, 3(2), 92-99 (Apr.-Jun. 2012).
STN Express; Chemical Abstract compound RN: 1355844-43-7 (Feb. 8, 2012).
STN Express; Chemical Abstract compound RN: 1708354-35-1 (May 20, 2015).

(56) References Cited

OTHER PUBLICATIONS

STN Express; Chemical Abstract compound RN: 1790675-44-3 (Jun. 29, 2015).
STN Express; Chemical Abstract compound RN: 1798074-73-3 (Jul. 9, 2015).
Taiwan Office Action for TW App No. 105132939 dated Nov. 2, 2017 (with English translation) (8 pages).
AU Office Action for AU App No. 2016299484, dated Dec. 18, 2018 (3 pages).
AU Office Action for AU App No. 2016299485, dated Sep. 13, 2018 (7 pages).
CA Office Action for CA App No. 2987570, dated Oct. 18, 2018 (5 pages).
CA Office Action for CA App No. 2993918, dated Dec. 4, 2018 (5 pages).
CAS Registry No. 904529-79-9 (Aug. 25, 2006).
CAS Registry No. 904541-56-6 (Aug. 25, 2006).
CAS Registry No. 904541-91-9 (Aug. 25, 2006).
CAS Registry No. 904548-90-9 (Aug. 25, 2006).
CAS Registry No. 904549-01-5 (Aug. 25, 2006).
CAS Registry No. 904549-10-3 (Aug. 25, 2006).
CAS Registry No. 904556-59-8 (Aug. 25, 2006).
CAS Registry No. 904568-68-9 (Aug. 25, 2006).
CAS Registry No. 904568-84-9 (Aug. 25, 2006).
CAS Registry No. 904569-62-6 (Aug. 25, 2006).
CAS Registry No. 904635-15-0 (Aug. 25, 2006).
CAS Registry No. 904635-23-0 (Aug. 25, 2006).
CAS Registry No. 904635-49-0 (Aug. 25, 2006).
CAS Registry No. 904635-57-0 (Aug. 25, 2006).
CAS Registry No. 904635-61-6 (Aug. 25, 2006).
CAS Registry No. 904635-67-2 (Aug. 25, 2006).
CAS Registry No. 904644-90-2 (Aug. 25, 2006).
CAS Registry No. 904644-93-5 (Aug. 25, 2006).
CAS Registry No. 904645-01-8 (Aug. 25, 2006).
CAS Registry No. 904645-03-0 (Aug. 25, 2006).
CAS Registry No. 904645-27-8 (Aug. 25, 2006).
CAS Registry No. 904645-29-0 (Aug. 25, 2006).
CAS Registry No. 904645-35-2 (Aug. 25, 2006).
CAS Registry No. 904645-35-8 (Aug. 25, 2006).
CAS Registry No. 904645-37-0 (Aug. 25, 2006).
CAS Registry No. 904645-47-2 (Aug. 25, 2006).
CAS Registry No. 904652-55-1 (Aug. 25, 2006).
CAS Registry No. 904652-68-2 (Aug. 25, 2006).
CAS Registry No. 904653-05-0 (Aug. 25, 2006).
CAS Registry No. 904653-11-8 (Aug. 25, 2006).
CAS Registry No. 904653-15-2 (Aug. 25, 2006).
CAS Registry No. 904653-17-4 (Aug. 25, 2006).
CAS Registry No. 904653-21-0 (Aug. 25, 2006).
CAS Registry No. 904653-22-1 (Aug. 25, 2006).
EP Extended Search Report for EP App No. 16830836.9, dated Dec. 19, 2018 (7 pages).
EP Extended Search Report for EP App No. 16830837.7, dated Dec. 17, 2018 (9 pages).
EP Extended Search Report for EP App No. 16830838.5, dated Nov. 19, 2018 (7 pages).
JP Office Action for App No. JP 2018-503804, dated Dec. 18, 2018 (with English Translation) (4 pages).
JP Office Action for App No. JP 2018-504720, dated Jan. 8, 2019 (with English Translation) (7 pages).
JP Office Action for App No. JP 2018-504096, dated Dec. 18, 2018 (with English Translation) (5 pages).
NZ Office Action for App No. NZ 739211, dated Jun. 14, 2019 (3 pages).
Rossi et al., *4-N-Hydroxy-4-[1-( sulfonyl )piperidin-4-yl ]-butyramides as HDAC inhibitors*, Bioorganic & Medicinal Chemistry Letters, 21:6767-6769 (2011).
RU Office Action for App. No. RU 2018106877, dated Oct. 18, 2018 (with English translation) (16 pages).
RU Office Action for App. No. RU 2018106904, dated Sep. 20, 2018 (with English translation) (14 pages).
RU Office Action for App. No. RU 2018106914, dated Nov. 15, 2018 (with English translation) (14 pages).
AU Examination Report No. 1 for App No. AU201603891, dated Nov. 16, 2019 (7 pages).
CA Office Action for App No. CA 2993929, dated Dec. 4, 2018 (4 pages.
CAS Registry No. 1384673-31-7 [Entered STN: Jul. 27, 2012] (Year: 2012).
CAS Registry No. 1436149-02-8 [Entered STN: Jun. 9, 2013] (Year: 2013).
CAS Registry No. 904635-69-4 (Aug. 25, 2006).
CAS Registry No. 904652-71-7 (Aug. 25, 2006).
CAS Registry No. 904653-13-0 (Aug. 25, 2006).
EP Suppl Search Report for App No. EP 16833369, dated Apr. 1, 2019 (6 pages).
CAS Registry No. 904548-10-3 (Aug. 25, 2006).
AU Examination Report No. 1 for App No. AU2016303891, dated Nov. 16, 2018 (7 pages).
CAS Registry No. 904645-39-2 Database Registry [Online] retrieved from STN, searched on Nov. 14, 2018.
CAS Registry No. 904652-59-1 Database Registry [Online] retrieved from STN, searched on Nov. 14, 2018.
Gamal Ei-Din. et, al, Synthesis and in vitro antiproliferative activity of new 1,3,4-oxadiazole derivatives possessing sulfonamide moiety, European Journal of Medicinal Chemistry, 90:45-52, (Jan. 27, 2015).
IN Office Action for App No. 201727037873, dated May 21, 2019 (7 pages).
IN Office Action for App No. 201817006324, dated Jun. 27, 2019 (6 pages).
Othman et al., *1,3,4-Oxadiazole, 1,3,4-thiadiazole and 1,2,4-triazole derivatives as potential antibacterial agents*, Arabian Journal of Chemistry (2014) https://doi.org/10.1016/j.arabjc.2014.09.003 (16 pages).

\* cited by examiner

1,3,4-OXADIAZOLE AMIDE DERIVATIVE COMPOUND AS HISTONE DEACETYLASE 6 INHIBITOR, AND PHARMACEUTICAL COMPOSITION CONTAINING SAME

TECHNICAL FIELD

The present invention relates to 1,3,4-oxadiazole amide derivative compounds having histone deacetylase 6 (HDAC6) inhibitory activity, stereoisomers thereof, or pharmaceutically acceptable salts thereof; uses thereof for the preparation of therapeutic medicaments; methods of treating diseases using the same; pharmaceutical compositions comprising the same; and methods for preparing the same.

BACKGROUND ART

Post-translational modifications such as acetylation are very crucial regulatory modules at the heart of biological processes in the cells and are tightly regulated by a multitude of enzymes. Histones are the chief protein components of chromatin and act as spools around which DNA strands to assist in DNA condensation. Also, the balance of histone acetylation and deacetylation is a critical role in the regulation of gene expression.

Histone deacetylases (HDACs) are enzymes that remove acetyl groups from lysine residues on histone proteins of chromatin, and are known to be associated with gene silencing and induce cell cycle arrest, angiogenic inhibition, immune regulation, cell death, etc. (Hassig et al., Curr. Opin. Chem. Biol. 1997, 1, 300-308). In addition, it was reported that the inhibition of enzymatic function of HDACs induces the apoptosis of cancer cells in vivo by reducing the activity of cancer cell survival-associated factors and activating cancer cell apoptosis-associated factors (Warrell et al, J. Natl. Cancer Inst. 1998, 90, 1621-1625).

In humans, 18 HDACs have been identified and are subdivided into four classes based on their homology to yeast HDACs. Among them, 11 HDACs use zinc as a cofactor and can be divided into three groups: Class I (HDAC1, 2, 3 and 8), Class II (IIa: HDAC4, 5, 7 and 9; IIb: HDAC6 and 10), Class IV (HDAC 11). Additionally, 7 HDACs of Class III (SIRT 1-7) require NAD+ instead of zinc as a cofactor (Bolden et al., Nat. Rev. Drug Discov. 2006, 5(9), 769-784).

Various HDAC inhibitors are in preclinical or clinical development, but to date, only non-selective HDAC inhibitors have been identified as anticancer agents, and only vorinostat (SAHA) and romidepsin (FK228) have been approved for the treatment of cutaneous T-cell lymphoma and panobinostat (LBH-589) have been approved for the treatment of multiple meyeloma. However, non-selective HDAC inhibitors are known to cause side effects such as fatigue and nausea, generally at high doses (Piekarz et al., Pharmaceuticals 2010, 3, 2751-2767). Such side effects have been reported to be due to the inhibition of class I HDACs. Due to such side effects, the use of non-selective HDAC inhibitors in the development of drugs other than anticancer drugs has been limited (Witt et al., Cancer Letters, 2009, 277, 8-21).

Meanwhile, it was reported that the selective inhibition of class II HDACs would not show toxicity shown in the inhibition of class I HDACs. Also, when selective HDAC inhibitors are developed, side effects such as toxicity, which are caused by the non-selective HDAC inhibition, can be overcome. Thus, selective HDAC inhibitors have potential to be developed as therapeutic agents effective for the treatment of various diseases (Matthias et al., Mol. Cell. Biol. 2008, 28, 1688-1701).

It is known that HDAC6, a member of Class IIb HDACs, is present mainly in the cytoplasm and is involved in the deacetylation of a number of non-histone substrates (HSP90, cortactin, etc.), including tubulin (Yao et al., Mol. Cell 2005, 18, 601-607). HDAC6 has two catalytic domains, and the zinc finger domain of C-terminal can bind to ubiquitinated proteins. It is known that HDAC6 has a number of non-histone proteins as substrates, and thus plays an important role in various diseases, including cancer, inflammatory diseases, autoimmune diseases, neurological diseases and neurodegenerative disorders (Santo et al., Blood 2012 119: 2579-258; Vishwakarma et al., International Immunopharmacology 2013, 16, 72-78; Hu et al., J. Neurol. Sci. 2011, 304, 1-8).

The common structural characteristic of various HDAC inhibitors is a structure consisting of a cap group, a linker and a zinc-binding group (ZBG), as shown in the following Vorinostat structure. Many researchers have conducted studies on enzyme inhibitory activity and selectivity by structurally modifying the cap group and the linker. Among these groups, the zinc-binding group is known to play a more important role in enzyme inhibitory activity and selectivity (Wiest et al., J. Org. Chem. 2013 78: 5051-5065; Methot et al., Bioorg. Med. Chem. Lett. 2008, 18, 973-978).

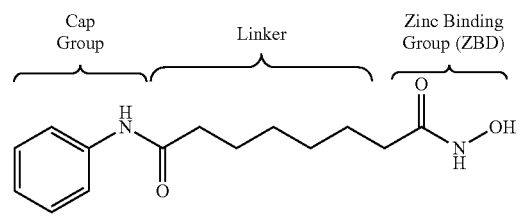 [SMILES: O=C(CCCCCCC(=O)Nc1ccccc1)NO]

The zinc-binding group is generally a hydroxamic acid or benzamide derivative. Herein, the hydroxamic acid derivative exhibits a potent HDAC inhibitory effect, but has problems of low bioavailability and severe off-target activity. In addition, the benzamide derivative has a problem in that it can produce toxic metabolites in vivo, because it contains aniline (Woster et al., Med. Chem. Commun. 2015, online publication).

Accordingly, there is a need for the development of selective HDAC 6 inhibitors for treatment of diseases such as cancer, inflammatory diseases, autoimmune diseases, neurological diseases and neurodegenerative disorders, which have a zinc-binding group with improved bioavailability and, at the same time, cause no side effects, unlike non-selective inhibitors that cause side effects.

DISCLOSURE

Technical Problem

It is an object of the present invention to provide 1,3,4-oxadiazole amide derivative compounds having selective HDAC6 inhibitory activity, stereoisomers thereof, or pharmaceutically acceptable salts thereof.

Another object of the present invention is to provide pharmaceutical compositions containing 1,3,4-oxadiazole amide derivative compounds having selective HDAC6 inhibitory activity, stereoisomers thereof, or pharmaceutically acceptable salts thereof.

Still another object of the present invention is to provide methods for preparing the novel compounds.

Still another object of the present invention is to provide pharmaceutical compositions for prevention or treatment of HDAC6 activity-associated diseases, including infectious diseases; neoplasms; endocrine, nutritional and metabolic diseases; mental and behavioral disorders; neurological diseases; diseases of the eye and adnexa; cardiovascular diseases; respiratory diseases; digestive diseases; diseases of the skin and subcutaneous tissue; diseases of the musculoskeletal system and connective tissue; or congenital malformations, deformations and chromosomal abnormalities, which contain the above-described compounds.

Still another object of the present invention is to provide the use of the compounds for the preparation of therapeutic medicaments against HDAC6 activity-associated diseases.

Yet another object of the present invention is to provide methods for treating HDAC6 activity-associated diseases, which comprise administering a therapeutically effective amount of the pharmaceutical compositions containing the compounds.

Technical Solution

The present inventors have discovered 1,3,4-oxadiazole amide derivative compounds, which have histone deacetylase 6 (HDAC6) inhibitory activity, and have found that these compounds can be used for the inhibition or treatment of histone deacetylase 6 (HDAC6) activity-associated diseases, thereby completing the present invention.

1,3,4-oxadiazole Amide Derivative Compounds

To achieve the above objects, the present invention provides an 1,3,4-oxadiazole amide derivative compound represented by the following formula I, a stereoisomer thereof, or a pharmaceutically acceptable salt thereof:

[Formula I]

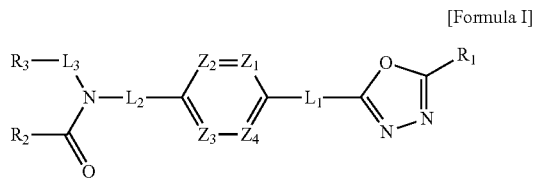

wherein $L_1$, $L_2$ and $L_3$ are each independently —($C_0$-$C_2$ alkyl)—;

$Z_1$ to $Z_4$ are each independently N or $CR^z$, wherein three or more of $Z_1$ to $Z_4$ may not be simultaneously N, and $R^z$ is —H or —X;

$R_1$ is —$CX_2H$ or —$CX_3$;

$R_2$ is —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_3$-$C_6$ cycloalkyl), -aryl, -heteroaryl,

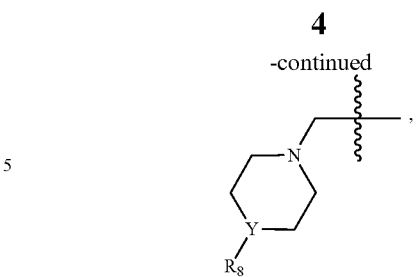

wherein at least one H of the —($C_3$-$C_6$ cycloalkyl), -aryl or -heteroaryl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —$CF_3$, Y is —N—, —O— or —S(=O)$_2$—, when Y is —N—, $R_4$ and $R_8$ are each independently —H, —($C_1$-$C_4$ alkyl), —C(=O)—($C_1$-$C_4$ alkyl), —C(=O)—($C_3$-$C_6$ cycloalkyl), —C(=O)—O($C_1$-$C_4$ alkyl), —C(=O)—$CF_3$, —S(=O)$_2$—($C_1$-$C_4$ alkyl), —($C_2$-$C_6$ heterocycloalkyl), benzyl or amine protecting group, wherein the —($C_2$-$C_6$ heterocycloalkyl) may contain an N, O or S atom in the ring, and when Y is —O— or —S(=O)$_2$—, $R_4$ and $R_8$ are null, $R_5$ to $R_8$ are each independently —H, —($C_1$-$C_4$ alkyl), —OH, —$CH_2OH$ or —C(=O)—$NH_2$, and a to c are each independently an integer of 1, 2 or 3;

$R_3$ is —H, —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_3$-$C_6$ cycloalkyl), -aryl, -heteroaryl,

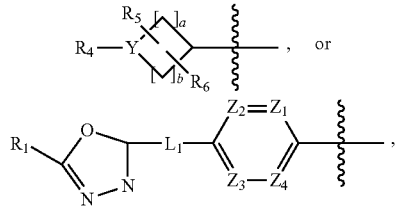

wherein at least one H of the —($C_3$-$C_6$ cycloalkyl), -aryl or -heteroaryl may be independently substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —$CF_3$, and $R_4$, $R_5$, $R_6$, Y, a, b, $R_1$, $L_1$, $Z_1$, $Z_2$, $Z_3$ and $Z_4$ are as defined above; and X is F, Cl, Br or I.

According to preferable embodiment of the present invention, $L_1$ and $L_3$ are each independently —($C_0$ alkyl)—;

$L_2$ is —($C_1$-$C_2$ alkyl)—;

$Z_1$ to $Z_4$ are each independently N or $CR^z$, wherein two or more of $Z_1$ to $Z_4$ may not be simultaneously N, and $R^z$ is —H or —X;

$R_1$ is —$CX_2H$ or —$CX_3$;

$R_2$ is —($C_1$-$C_4$ alkyl), —($C_3$-$C_6$ cycloalkyl), -aryl, -heteroaryl,

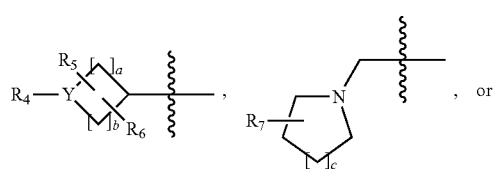

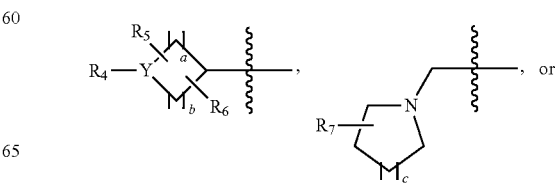

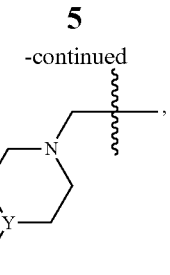

wherein at least one H of the —($C_3$-$C_6$ cycloalkyl), -aryl or -heteroaryl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —$CF_3$, Y is —N—, —O— or —S(=O)$_2$—, when Y is —N—, $R_4$ and $R_8$ are each independently —H, —($C_1$-$C_4$ alkyl), —C(=O)—($C_1$-$C_4$ alkyl), —C(=O)—$CF_3$, —S(=O)$_2$—($C_1$-$C_4$ alkyl), —($C_2$-$C_6$ heterocycloalkyl), —C(=O)—($C_3$-$C_6$ cycloalkyl), benzyl or amine protecting group, wherein the —($C_2$-$C_6$ heterocycloalkyl) may contain an O atom in the ring, and when Y is —O— or —S(=O)$_2$—, $R_4$ and $R_8$ are null, $R_5$ to $R_8$ are each independently —H, —($C_1$-$C_4$ alkyl), —OH, —$CH_2OH$ or —C(=O)—$NH_2$, and a to c are each independently an integer of 1, 2 or 3;

$R_3$ is -aryl or -heteroaryl, wherein at least one H of the -aryl or -heteroaryl may be independently substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —$CF_3$; and X is F, Cl, Br or I.

According to more preferable embodiment of the present invention, $L_1$ and $L_3$ are each independently —($C_0$ alkyl)—;

$L_2$ is —($C_1$ alkyl)—;

$Z_1$ to $Z_4$ are each independently N or $CR^z$, wherein two or more of $Z_1$ to $Z_4$ may not be simultaneously N, and $R^z$ is —H or —X;

$R_1$ is —$CF_2H$ or —$CF_3$;

$R_2$ is —($C_1$-$C_4$ alkyl), -pyridinyl or

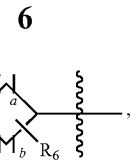

wherein at least one H of the pyridinyl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —$CF_3$, Y is —N—, $R_4$ is —($C_1$-$C_4$ alkyl), —C(=O)—($C_1$-$C_4$ alkyl) or —S(=O)$_2$—($C_1$-$C_4$ alkyl), $R_5$ and $R_6$ are each independently —H or —($C_1$-$C_4$ alkyl), and a and b are each independently an integer of 1 or 2;

$R_3$ is -aryl, wherein at least one H of the aryl may be substituted with —X; and X is F, Cl, Br or I.

According to particularly preferable embodiment of the present invention, $L_1$ and $L_3$ are each independently —($C_0$ alkyl)—;

$L_2$ is —($C_1$ alkyl)—;

$Z_1$ to $Z_4$ are each independently N or $CR^z$, wherein two or more of $Z_1$ to $Z_4$ may not be simultaneously N, and $R^z$ is —H or —X;

$R_1$ is —$CF_2H$ or —$CF_3$;

$R_2$ is -pyridinyl or

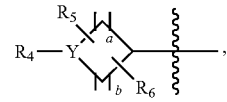

wherein at least one H of the pyridinyl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —$CF_3$, Y is —N—, $R_4$ is —($C_1$-$C_4$ alkyl), —C(=O)—($C_1$-$C_4$ alkyl) or —S(=O)$_2$—($C_1$-$C_4$ alkyl), $R_5$ or $R_6$ are each independently —H, and a and b are each independently an integer of 1 or 2;

$R_3$ is -aryl, wherein at least one H of the aryl may be substituted with —X; and X is F, Cl, Br or I.

The specific compounds represented by formula I are shown in Table 1 below:

TABLE 1

| Ex. | Comp. | Structure |
|---|---|---|
| 1 | 11022 | 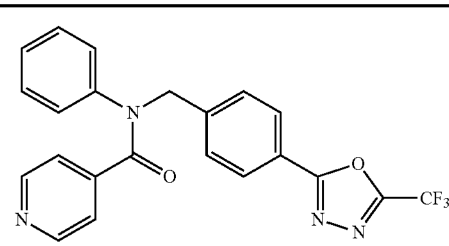 |

TABLE 1-continued

| Ex. | Comp. | Structure |
|---|---|---|
| 2 | 11105 | N-phenyl-N-(4-(5-(trifluoromethyl)-1,3,4-oxadiazol-2-yl)benzyl)acetamide |
| 3 | 11106 | N-phenyl-N-(4-(5-(trifluoromethyl)-1,3,4-oxadiazol-2-yl)benzyl)cyclohexanecarboxamide |
| 4 | 11107 | N-phenyl-N-(4-(5-(trifluoromethyl)-1,3,4-oxadiazol-2-yl)benzyl)benzamide |
| 5 | 11108 | N-(4-(5-(difluoromethyl)-1,3,4-oxadiazol-2-yl)benzyl)-N-phenylisonicotinamide |
| 6 | 11109 | N-(2-fluoro-4-(5-(trifluoromethyl)-1,3,4-oxadiazol-2-yl)benzyl)-N-phenylisonicotinamide |
| 7 | 11110 | N-(4-(5-(difluoromethyl)-1,3,4-oxadiazol-2-yl)-2-fluorobenzyl)-N-phenylisonicotinamide |

TABLE 1-continued

| Ex. | Comp. | Structure |
|---|---|---|
| 8 | 11134 | *N-Boc azetidine-3-carboxamide, N-phenyl, N-(4-(5-(trifluoromethyl)-1,3,4-oxadiazol-2-yl)benzyl)* |
| 9 | 11135 | *N-Boc piperidine-4-carboxamide, N-phenyl, N-(4-(5-(trifluoromethyl)-1,3,4-oxadiazol-2-yl)benzyl)* |
| 10 | 11136 | *Azetidine-3-carboxamide·HCl, N-phenyl, N-(4-(5-(trifluoromethyl)-1,3,4-oxadiazol-2-yl)benzyl)* |
| 11 | 11137 | *Piperidine-4-carboxamide·HCl, N-phenyl, N-(4-(5-(trifluoromethyl)-1,3,4-oxadiazol-2-yl)benzyl)* |
| 12 | 11138 | *1-Methylazetidine-3-carboxamide, N-phenyl, N-(4-(5-(trifluoromethyl)-1,3,4-oxadiazol-2-yl)benzyl)* |
| 13 | 11139 | *1-Ethylazetidine-3-carboxamide, N-phenyl, N-(4-(5-(trifluoromethyl)-1,3,4-oxadiazol-2-yl)benzyl)* |

TABLE 1-continued
| Ex. | Comp. | Structure |
|---|---|---|
| 14 | 11140 | 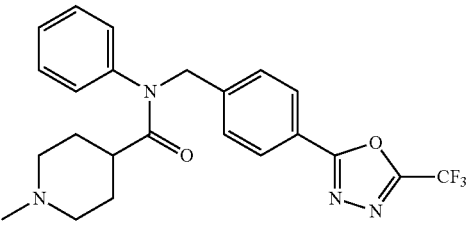 [SMILES: CN1CCC(C(=O)N(Cc2ccc(-c3nnc(C(F)(F)F)o3)cc2)c2ccccc2)CC1] |
| 15 | 11141 | 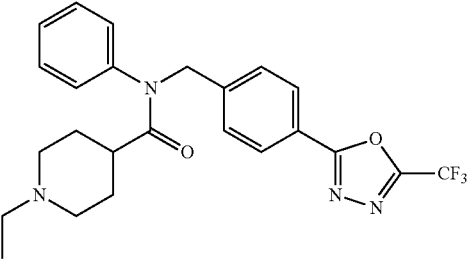 [SMILES: CCN1CCC(C(=O)N(Cc2ccc(-c3nnc(C(F)(F)F)o3)cc2)c2ccccc2)CC1] |
| 16 | 11142 | 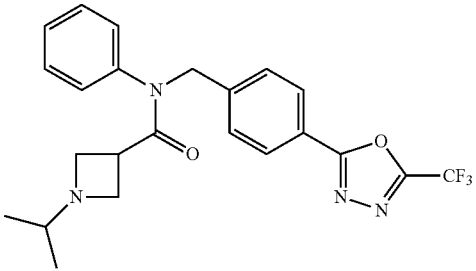 [SMILES: CC(C)N1CC(C(=O)N(Cc2ccc(-c3nnc(C(F)(F)F)o3)cc2)c2ccccc2)C1] |
| 17 | 11143 | 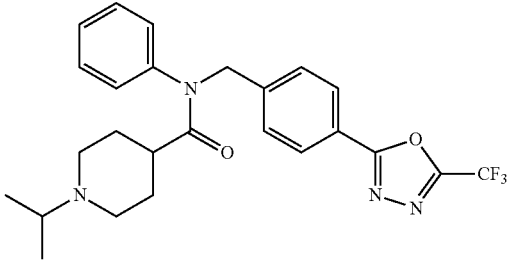 [SMILES: CC(C)N1CCC(C(=O)N(Cc2ccc(-c3nnc(C(F)(F)F)o3)cc2)c2ccccc2)CC1] |
| 18 | 11157 | 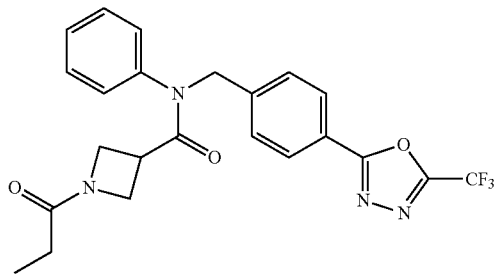 [SMILES: CCC(=O)N1CC(C(=O)N(Cc2ccc(-c3nnc(C(F)(F)F)o3)cc2)c2ccccc2)C1] |

TABLE 1-continued
| Ex. | Comp. | Structure |
|---|---|---|
| 19 | 11158 | 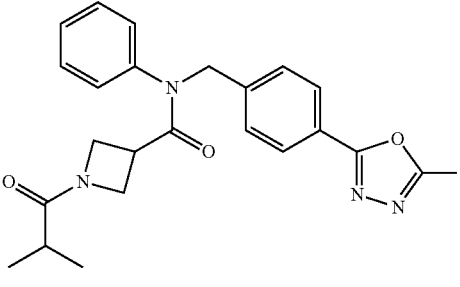 |
| 20 | 11159 | 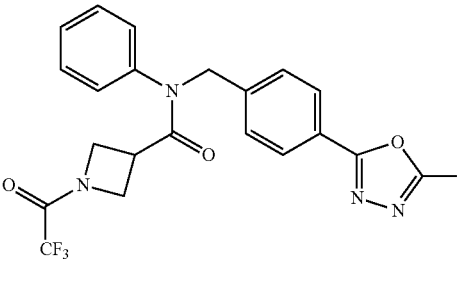 |
| 21 | 11160 | 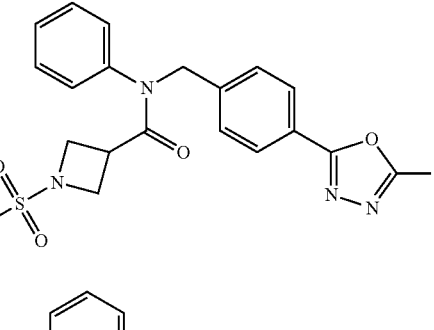 |
| 22 | 11161 | 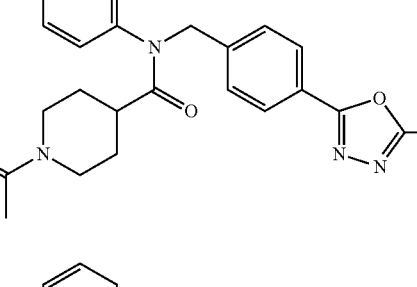 |
| 23 | 11162 | 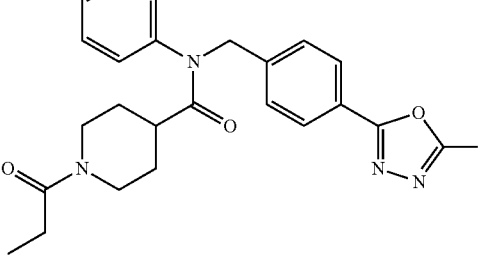 |

TABLE 1-continued

| Ex. | Comp. | Structure |
|---|---|---|
| 24 | 11163 | 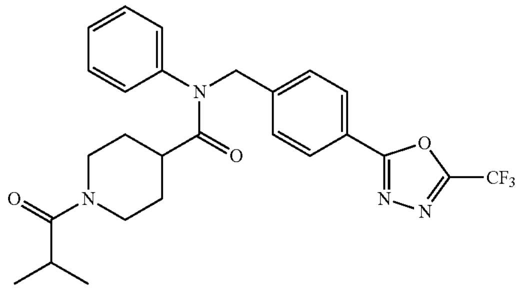 [SMILES: CC(C)C(=O)N1CCC(C(=O)N(Cc2ccc(-c3nnc(C(F)(F)F)o3)cc2)c2ccccc2)CC1] |
| 25 | 11164 | 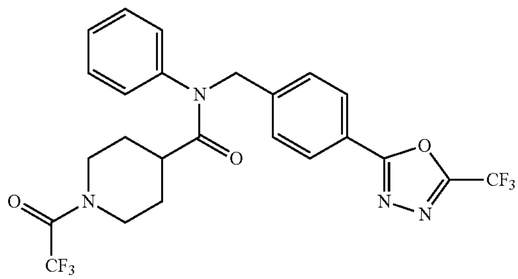 [SMILES: O=C(C1CCN(C(=O)C(F)(F)F)CC1)N(Cc1ccc(-c2nnc(C(F)(F)F)o2)cc1)c1ccccc1] |
| 26 | 11165 | 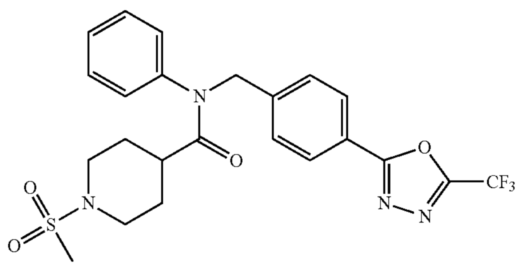 [SMILES: CS(=O)(=O)N1CCC(C(=O)N(Cc2ccc(-c3nnc(C(F)(F)F)o3)cc2)c2ccccc2)CC1] |
| 27 | 11166 | 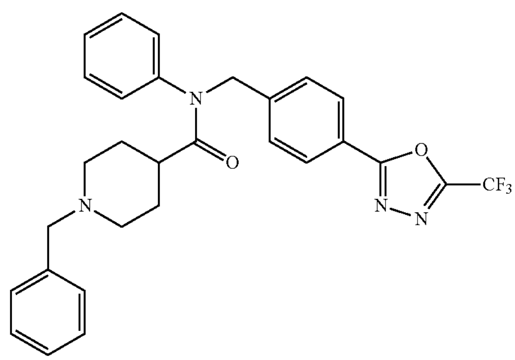 [SMILES: O=C(C1CCN(Cc2ccccc2)CC1)N(Cc1ccc(-c2nnc(C(F)(F)F)o2)cc1)c1ccccc1] |
| 28 | 11187 | 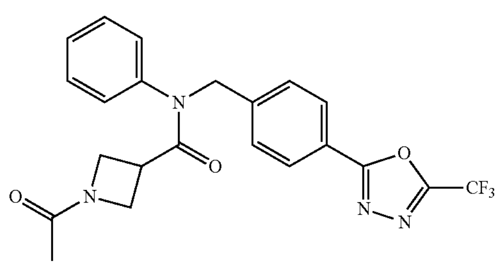 [SMILES: CC(=O)N1CC(C(=O)N(Cc2ccc(-c3nnc(C(F)(F)F)o3)cc2)c2ccccc2)C1] |

TABLE 1-continued

| Ex. | Comp. | Structure |
|---|---|---|
| 29 | 11188 | 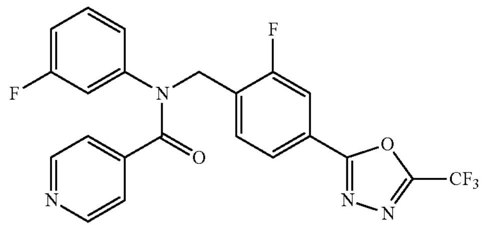 [SMILES: O=C(c1ccncc1)N(Cc1ccc(-c2nnc(C(F)(F)F)o2)cc1F)c1cccc(F)c1] |
| 30 | 11189 | 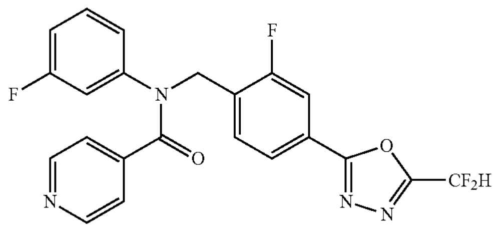 |
| 31 | 11200 | 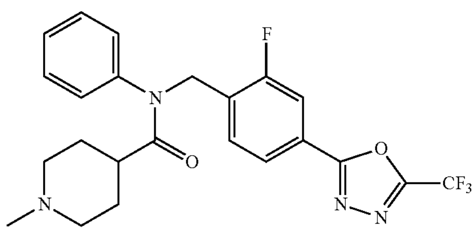 [SMILES: CN1CCC(C(=O)N(Cc2ccc(-c3nnc(C(F)(F)F)o3)cc2F)c2ccccc2)CC1] |
| 32 | 11201 | 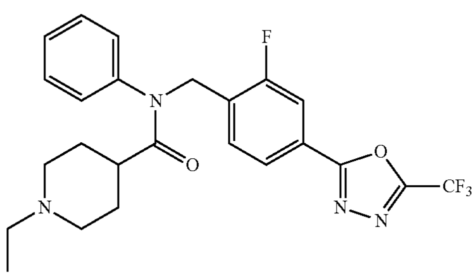 [SMILES: CCN1CCC(C(=O)N(Cc2ccc(-c3nnc(C(F)(F)F)o3)cc2F)c2ccccc2)CC1] |
| 33 | 11202 | 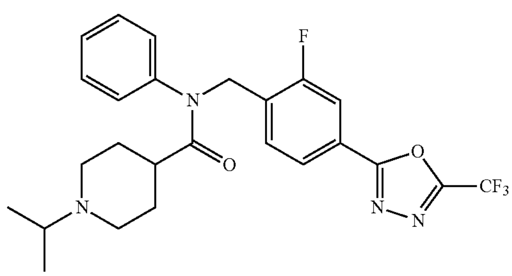 [SMILES: CC(C)N1CCC(C(=O)N(Cc2ccc(-c3nnc(C(F)(F)F)o3)cc2F)c2ccccc2)CC1] |
| 34 | 11203 | 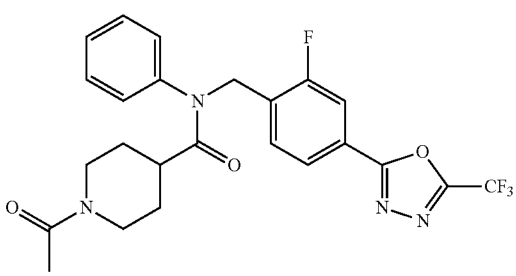 [SMILES: CC(=O)N1CCC(C(=O)N(Cc2ccc(-c3nnc(C(F)(F)F)o3)cc2F)c2ccccc2)CC1] |

TABLE 1-continued
| Ex. | Comp. | Structure |
|---|---|---|
| 35 | 11204 | 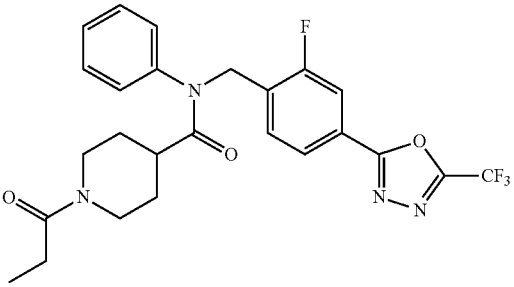 [SMILES: CCC(=O)N1CCC(C(=O)N(Cc2ccc(-c3nnc(C(F)(F)F)o3)cc2F)c2ccccc2)CC1] |
| 36 | 11205 | 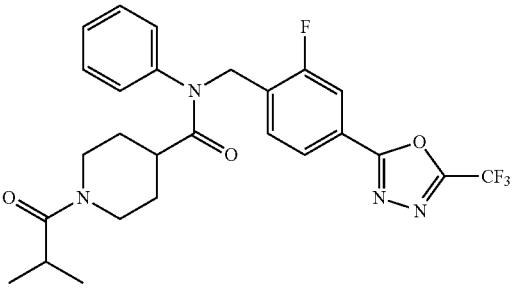 [SMILES: CC(C)C(=O)N1CCC(C(=O)N(Cc2ccc(-c3nnc(C(F)(F)F)o3)cc2F)c2ccccc2)CC1] |
| 37 | 11206 | 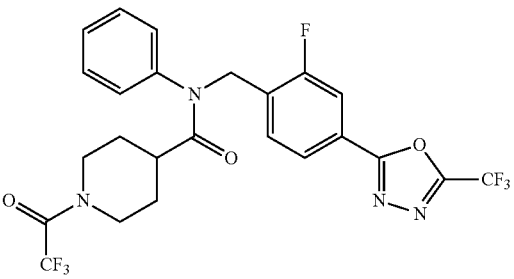 [SMILES: O=C(C1CCN(C(=O)C(F)(F)F)CC1)N(Cc1ccc(-c2nnc(C(F)(F)F)o2)cc1F)c1ccccc1] |
| 38 | 11207 | 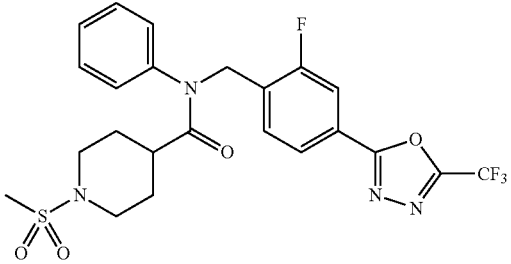 [SMILES: CS(=O)(=O)N1CCC(C(=O)N(Cc2ccc(-c3nnc(C(F)(F)F)o3)cc2F)c2ccccc2)CC1] |
| 39 | 11208 | 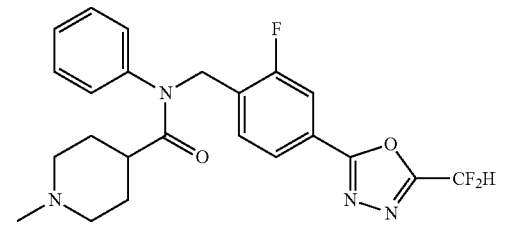 [SMILES: CN1CCC(C(=O)N(Cc2ccc(-c3nnc(C(F)F)o3)cc2F)c2ccccc2)CC1] |

TABLE 1-continued

| Ex. | Comp. | Structure |
|---|---|---|
| 40 | 11209 | 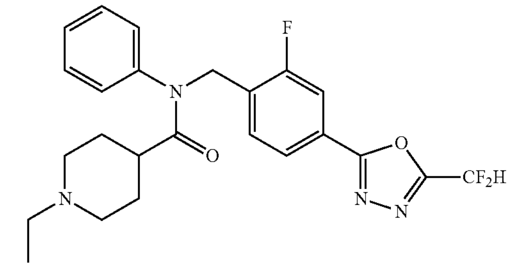 [SMILES: CCN1CCC(C(=O)N(Cc2ccc(-c3nnc(C(F)F)o3)cc2F)c2ccccc2)CC1] |
| 41 | 11210 | 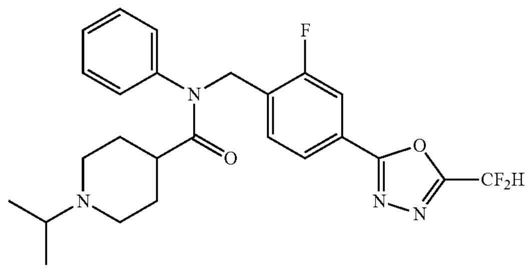 [SMILES: CC(C)N1CCC(C(=O)N(Cc2ccc(-c3nnc(C(F)F)o3)cc2F)c2ccccc2)CC1] |
| 42 | 11211 | 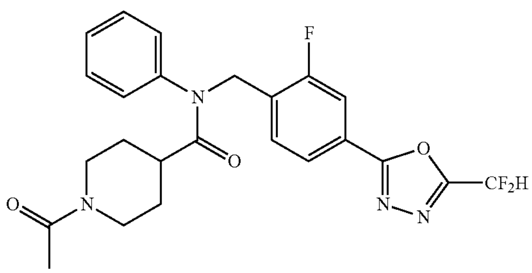 [SMILES: CC(=O)N1CCC(C(=O)N(Cc2ccc(-c3nnc(C(F)F)o3)cc2F)c2ccccc2)CC1] |
| 43 | 11212 | 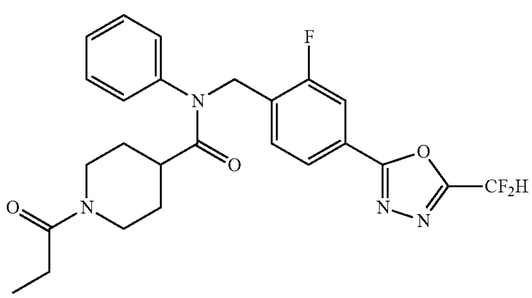 [SMILES: CCC(=O)N1CCC(C(=O)N(Cc2ccc(-c3nnc(C(F)F)o3)cc2F)c2ccccc2)CC1] |
| 44 | 11213 | 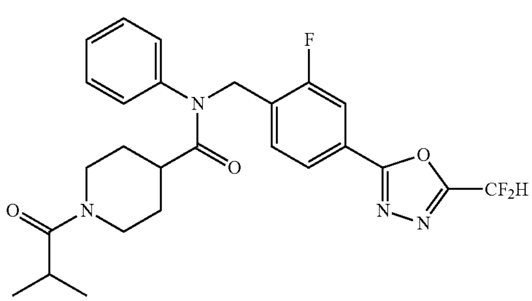 [SMILES: CC(C)C(=O)N1CCC(C(=O)N(Cc2ccc(-c3nnc(C(F)F)o3)cc2F)c2ccccc2)CC1] |

TABLE 1-continued
| Ex. | Comp. | Structure |
|---|---|---|
| 45 | 11214 | 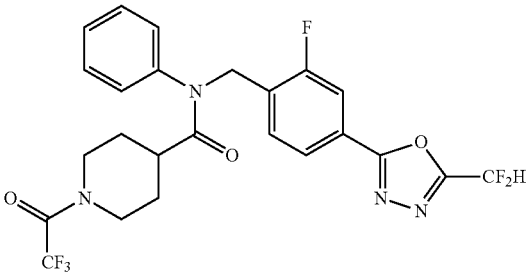 [SMILES: O=C(C1CCN(C(=O)C(F)(F)F)CC1)N(Cc1ccc(-c2nnc(C(F)F)o2)cc1F)c1ccccc1] |
| 46 | 11215 | 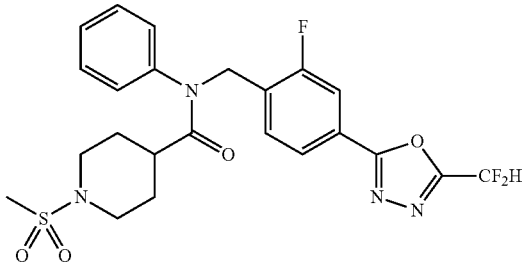 [SMILES: CS(=O)(=O)N1CCC(C(=O)N(Cc2ccc(-c3nnc(C(F)F)o3)cc2F)c2ccccc2)CC1] |
| 47 | 11232 | 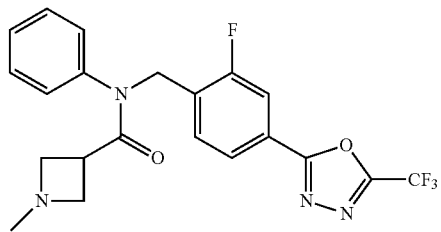 [SMILES: CN1CC(C(=O)N(Cc2ccc(-c3nnc(C(F)(F)F)o3)cc2F)c2ccccc2)C1] |
| 48 | 11233 | 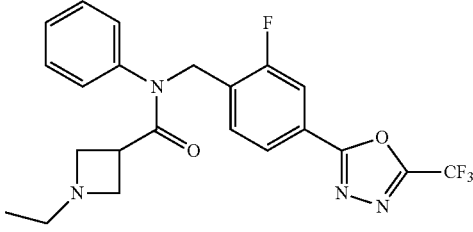 [SMILES: CCN1CC(C(=O)N(Cc2ccc(-c3nnc(C(F)(F)F)o3)cc2F)c2ccccc2)C1] |
| 49 | 11234 | 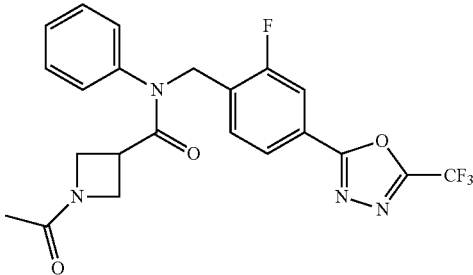 [SMILES: CC(=O)N1CC(C(=O)N(Cc2ccc(-c3nnc(C(F)(F)F)o3)cc2F)c2ccccc2)C1] |

TABLE 1-continued

| Ex. | Comp. | Structure |
|---|---|---|
| 50 | 11235 | 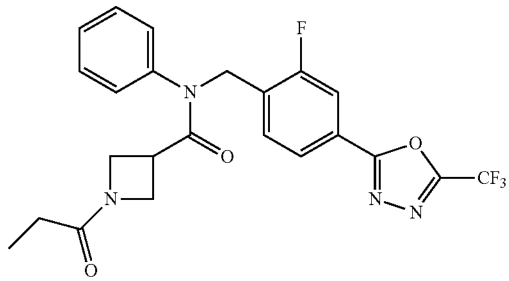 [SMILES: CCC(=O)N1CC(C(=O)N(Cc2ccc(-c3nnc(C(F)(F)F)o3)cc2F)c2ccccc2)C1] |
| 51 | 11236 | 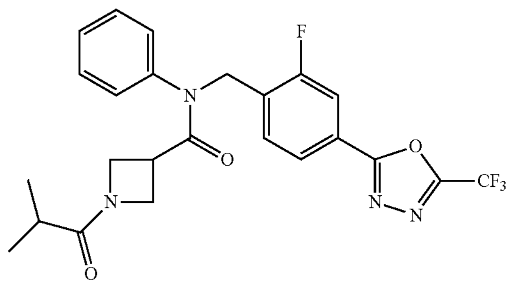 [SMILES: CC(C)C(=O)N1CC(C(=O)N(Cc2ccc(-c3nnc(C(F)(F)F)o3)cc2F)c2ccccc2)C1] |
| 52 | 11237 | 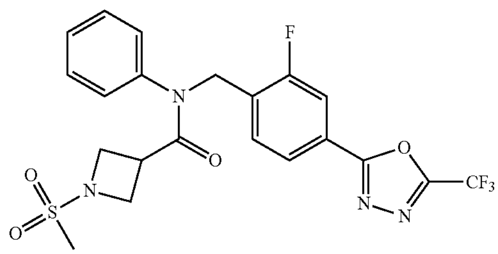 [SMILES: CS(=O)(=O)N1CC(C(=O)N(Cc2ccc(-c3nnc(C(F)(F)F)o3)cc2F)c2ccccc2)C1] |
| 53 | 11238 | 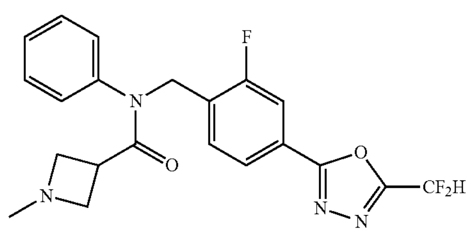 [SMILES: CN1CC(C(=O)N(Cc2ccc(-c3nnc(C(F)F)o3)cc2F)c2ccccc2)C1] |
| 54 | 11239 | 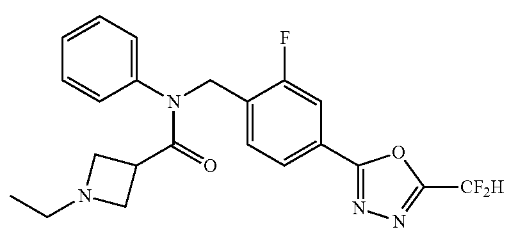 [SMILES: CCN1CC(C(=O)N(Cc2ccc(-c3nnc(C(F)F)o3)cc2F)c2ccccc2)C1] |
| 55 | 11240 | 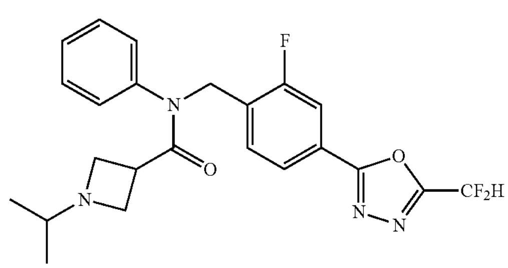 [SMILES: CC(C)N1CC(C(=O)N(Cc2ccc(-c3nnc(C(F)F)o3)cc2F)c2ccccc2)C1] |

TABLE 1-continued

| Ex. | Comp. | Structure |
|---|---|---|
| 56 | 11241 | 1-acetylazetidine-3-carboxamide with N-phenyl, N-[2-fluoro-4-(5-(difluoromethyl)-1,3,4-oxadiazol-2-yl)benzyl] |
| 57 | 11242 | 1-propionylazetidine-3-carboxamide with N-phenyl, N-[2-fluoro-4-(5-(difluoromethyl)-1,3,4-oxadiazol-2-yl)benzyl] |
| 58 | 11243 | 1-isobutyrylazetidine-3-carboxamide with N-phenyl, N-[2-fluoro-4-(5-(difluoromethyl)-1,3,4-oxadiazol-2-yl)benzyl] |
| 59 | 11244 | 1-(trifluoroacetyl)azetidine-3-carboxamide with N-phenyl, N-[2-fluoro-4-(5-(difluoromethyl)-1,3,4-oxadiazol-2-yl)benzyl] |
| 60 | 11245 | 1-(methylsulfonyl)azetidine-3-carboxamide with N-phenyl, N-[2-fluoro-4-(5-(difluoromethyl)-1,3,4-oxadiazol-2-yl)benzyl] |
| 61 | 11246 | N-phenyl-N-[2-fluoro-4-(5-(trifluoromethyl)-1,3,4-oxadiazol-2-yl)benzyl]acetamide |

TABLE 1-continued

| Ex. | Comp. | Structure |
|---|---|---|
| 62 | 11247 | 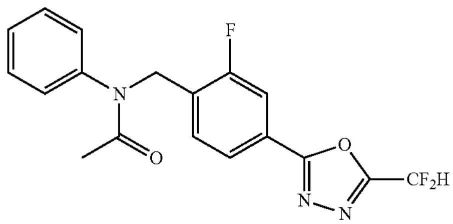 [SMILES: CC(=O)N(Cc1ccc(-c2nnc(C(F)F)o2)cc1F)c1ccccc1] |
| 63 | 11325 | 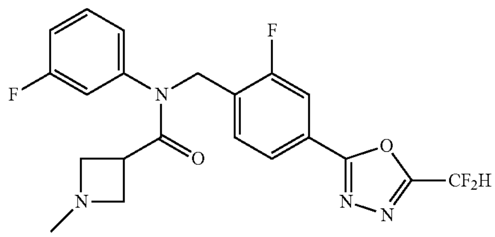 |
| 64 | 11326 | 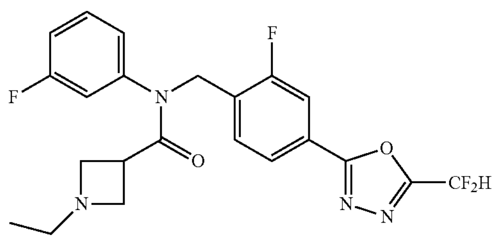 [SMILES: CCN1CC(C(=O)N(Cc2ccc(-c3nnc(C(F)F)o3)cc2F)c2cccc(F)c2)C1] |
| 65 | 11327 | 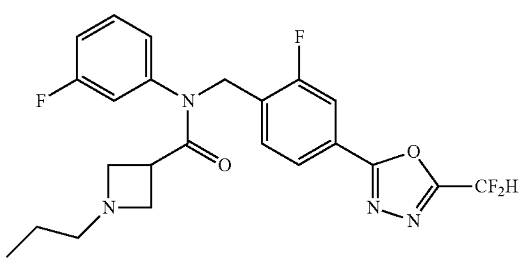 [SMILES: CCCN1CC(C(=O)N(Cc2ccc(-c3nnc(C(F)F)o3)cc2F)c2cccc(F)c2)C1] |
| 66 | 11328 | 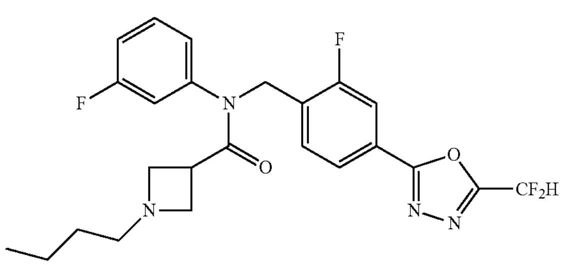 [SMILES: CCCCN1CC(C(=O)N(Cc2ccc(-c3nnc(C(F)F)o3)cc2F)c2cccc(F)c2)C1] |
| 67 | 11329 | 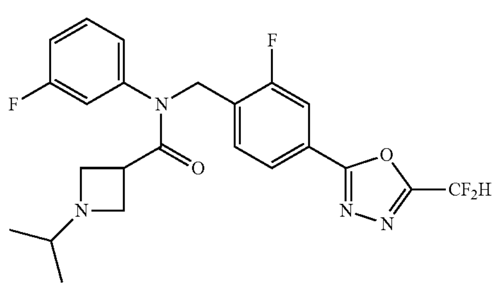 |

TABLE 1-continued

| Ex. | Comp. | Structure |
|---|---|---|
| 68 | 11330 | 1-acetylazetidine-3-carboxamide with N-(3-fluorophenyl)-N-[[2-fluoro-4-[5-(difluoromethyl)-1,3,4-oxadiazol-2-yl]phenyl]methyl] |
| 69 | 11331 | 1-propanoylazetidine-3-carboxamide with N-(3-fluorophenyl)-N-[[2-fluoro-4-[5-(difluoromethyl)-1,3,4-oxadiazol-2-yl]phenyl]methyl] |
| 70 | 11332 | 1-isobutyrylazetidine-3-carboxamide with N-(3-fluorophenyl)-N-[[2-fluoro-4-[5-(difluoromethyl)-1,3,4-oxadiazol-2-yl]phenyl]methyl] |
| 71 | 11333 | 1-(methylsulfonyl)azetidine-3-carboxamide with N-(3-fluorophenyl)-N-[[2-fluoro-4-[5-(difluoromethyl)-1,3,4-oxadiazol-2-yl]phenyl]methyl] |
| 72 | 11334 | 1-(ethylsulfonyl)azetidine-3-carboxamide with N-(3-fluorophenyl)-N-[[2-fluoro-4-[5-(difluoromethyl)-1,3,4-oxadiazol-2-yl]phenyl]methyl] |

TABLE 1-continued

| Ex. | Comp. | Structure |
|---|---|---|
| 73 | 11339 | 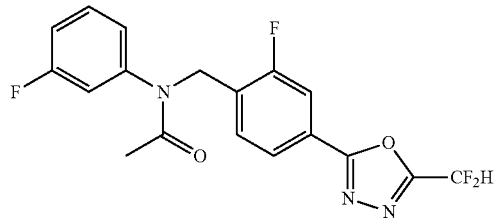 [SMILES: CC(=O)N(Cc1ccc(-c2nnc(C(F)F)o2)cc1F)c1cccc(F)c1] |
| 74 | 11340 | 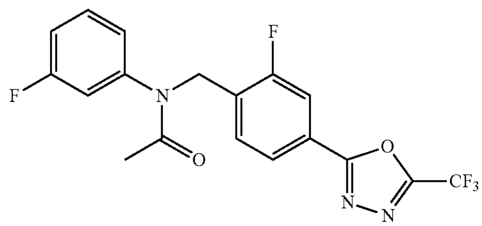 [SMILES: CC(=O)N(Cc1ccc(-c2nnc(C(F)(F)F)o2)cc1F)c1cccc(F)c1] |
| 75 | 11341 | 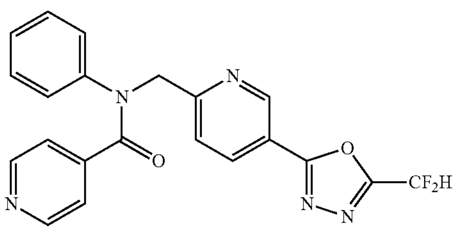 [SMILES: O=C(c1ccncc1)N(Cc1ccc(-c2nnc(C(F)F)o2)cn1)c1ccccc1] |
| 76 | 11356 | 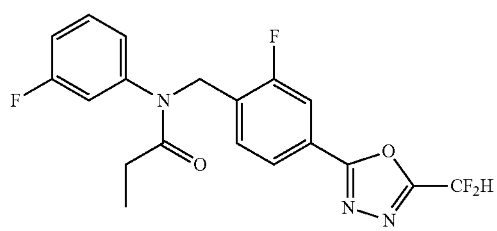 |
| 77 | 11357 | 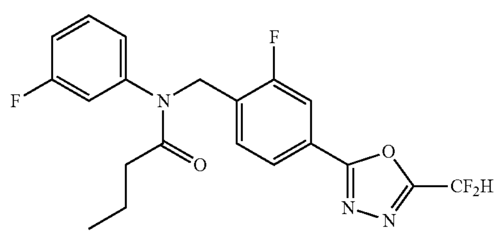 [SMILES: CCCC(=O)N(Cc1ccc(-c2nnc(C(F)F)o2)cc1F)c1cccc(F)c1] |
| 78 | 11358 | 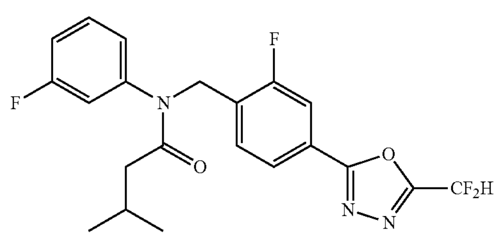 [SMILES: CC(C)CC(=O)N(Cc1ccc(-c2nnc(C(F)F)o2)cc1F)c1cccc(F)c1] |

TABLE 1-continued
| Ex. | Comp. | Structure |
|---|---|---|
| 79 | 11359 | 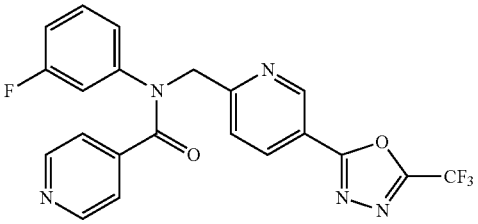 [SMILES: O=C(c1ccncc1)N(Cc1ccc(-c2nnc(C(F)(F)F)o2)cn1)c1cccc(F)c1] |
| 80 | 11360 | 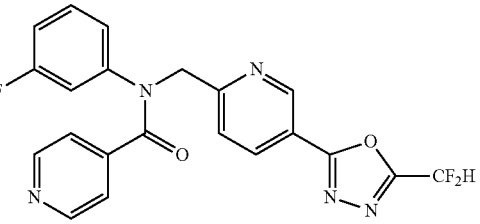 |
| 81 | 11376 | 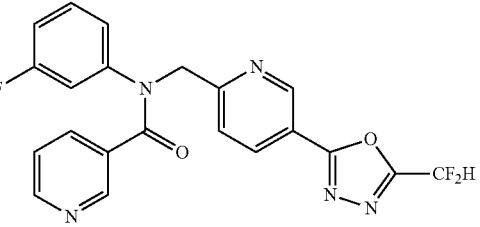 |
| 82 | 11414 | 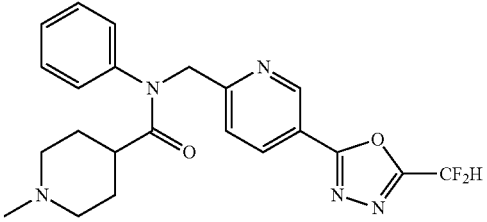 [SMILES: CN1CCC(C(=O)N(Cc2ccc(-c3nnc(C(F)F)o3)cn2)c2ccccc2)CC1] |
| 83 | 11418 | 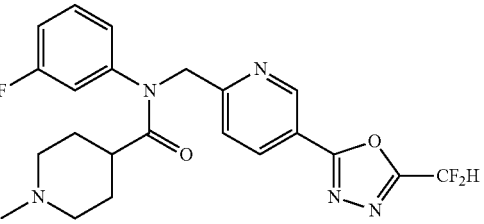 |
| 84 | 11419 | 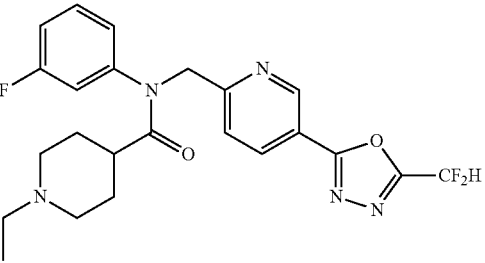 [SMILES: CCN1CCC(C(=O)N(Cc2ccc(-c3nnc(C(F)F)o3)cn2)c2cccc(F)c2)CC1] |

TABLE 1-continued

| Ex. | Comp. | Structure |
|---|---|---|
| 85 | 11534 | 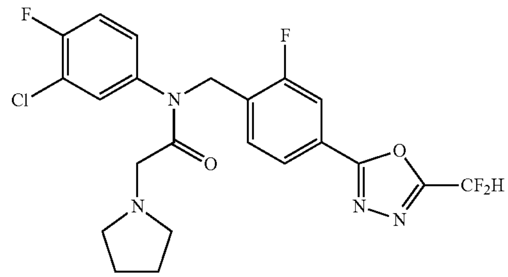 [SMILES: O=C(CN1CCCC1)N(Cc1ccc(-c2nnc(C(F)F)o2)cc1F)c1ccc(F)c(Cl)c1] |
| 86 | 11535 | 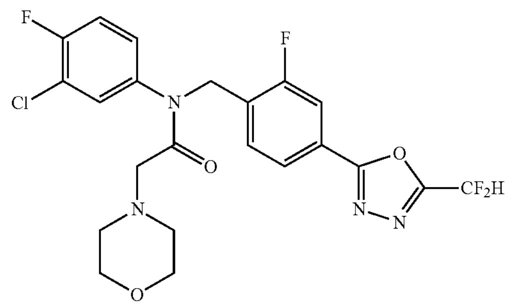 [SMILES: O=C(CN1CCOCC1)N(Cc1ccc(-c2nnc(C(F)F)o2)cc1F)c1ccc(F)c(Cl)c1] |
| 87 | 11536 | 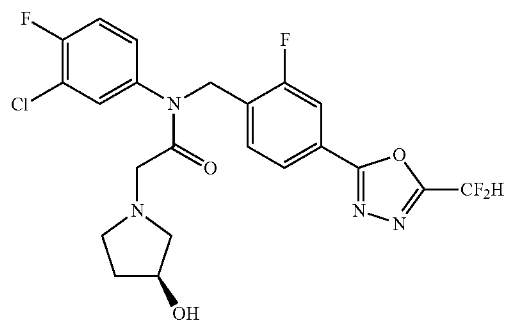 [SMILES: O=C(CN1CC[C@H](O)C1)N(Cc1ccc(-c2nnc(C(F)F)o2)cc1F)c1ccc(F)c(Cl)c1] |
| 88 | 11537 | 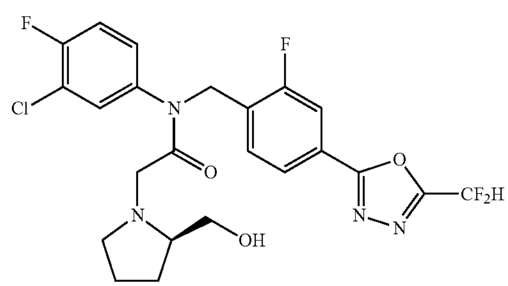 [SMILES: O=C(CN1CCC[C@@H]1CO)N(Cc1ccc(-c2nnc(C(F)F)o2)cc1F)c1ccc(F)c(Cl)c1] |
| 89 | 11538 | 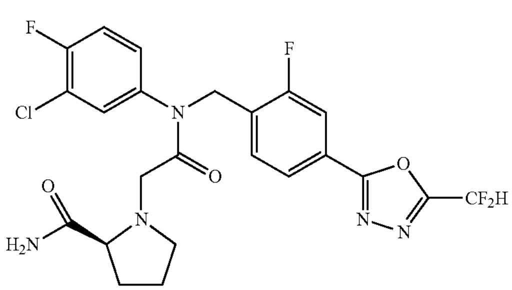 [SMILES: NC(=O)[C@@H]1CCCN1CC(=O)N(Cc1ccc(-c2nnc(C(F)F)o2)cc1F)c1ccc(F)c(Cl)c1] |

TABLE 1-continued
| Ex. | Comp. | Structure |
|---|---|---|
| 90 | 11584 | 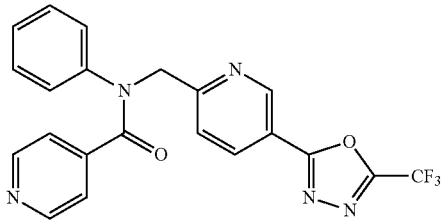 [SMILES: O=C(c1ccncc1)N(Cc1ccc(-c2nnc(C(F)(F)F)o2)cn1)c1ccccc1] |
| 91 | 11602 | 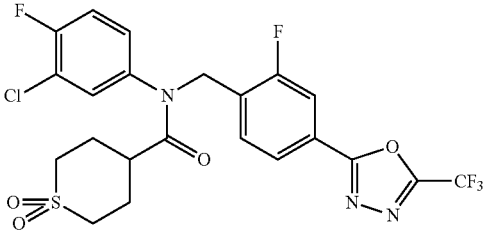 [SMILES: O=C(C1CCS(=O)(=O)CC1)N(Cc1ccc(-c2nnc(C(F)(F)F)o2)cc1F)c1ccc(F)c(Cl)c1] |
| 92 | 11603 | 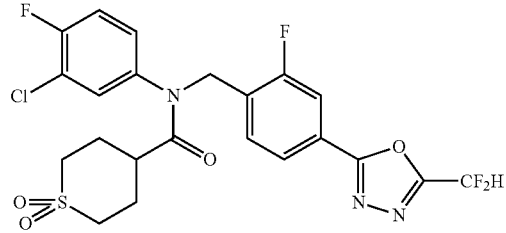 [SMILES: O=C(C1CCS(=O)(=O)CC1)N(Cc1ccc(-c2nnc(C(F)F)o2)cc1F)c1ccc(F)c(Cl)c1] |
| 93 | 11610 | 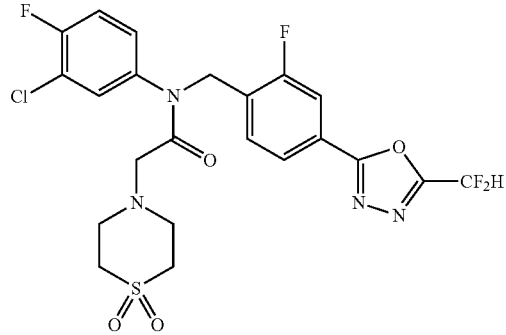 [SMILES: O=C(CN1CCS(=O)(=O)CC1)N(Cc1ccc(-c2nnc(C(F)F)o2)cc1F)c1ccc(F)c(Cl)c1] |
| 94 | 11611 | 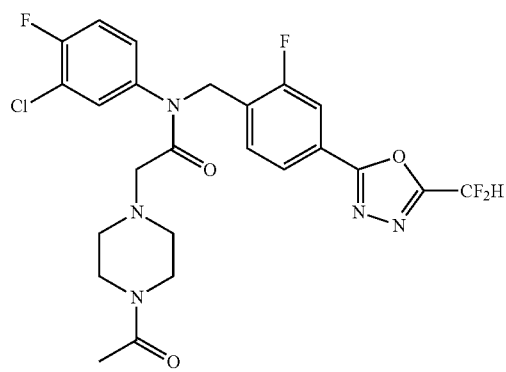 [SMILES: CC(=O)N1CCN(CC(=O)N(Cc2ccc(-c3nnc(C(F)F)o3)cc2F)c2ccc(F)c(Cl)c2)CC1] |

TABLE 1-continued

| Ex. | Comp. | Structure |
|---|---|---|
| 95 | 11612 | 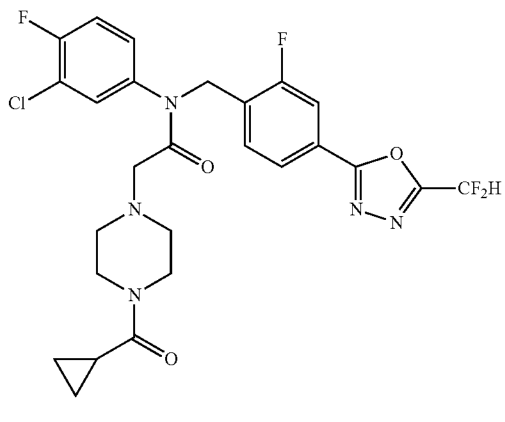 [SMILES: O=C(C1CC1)N1CCN(CC(=O)N(Cc2ccc(-c3nnc(C(F)F)o3)cc2F)c2ccc(F)c(Cl)c2)CC1] |
| 96 | 11613 | 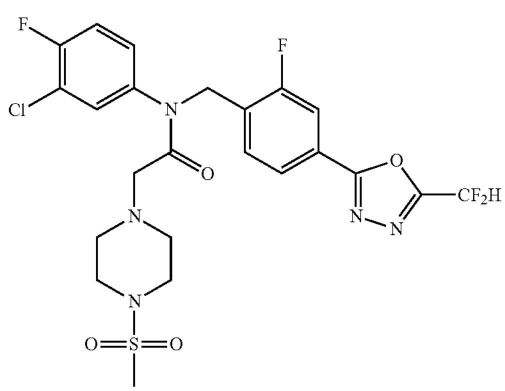 [SMILES: CS(=O)(=O)N1CCN(CC(=O)N(Cc2ccc(-c3nnc(C(F)F)o3)cc2F)c2ccc(F)c(Cl)c2)CC1] |
| 97 | 11614 | 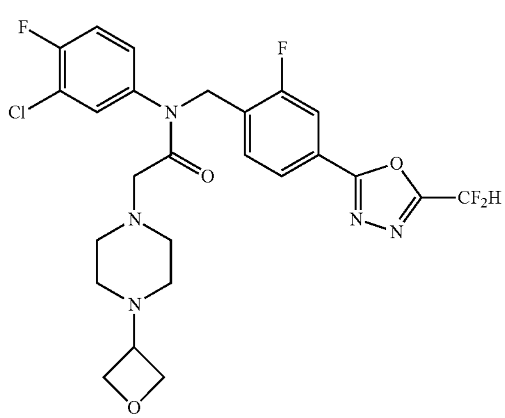 [SMILES: O=C(CN1CCN(C2COC2)CC1)N(Cc1ccc(-c2nnc(C(F)F)o2)cc1F)c1ccc(F)c(Cl)c1] |
| 98 | 11621 | 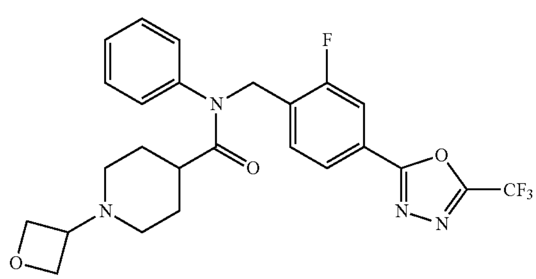 [SMILES: O=C(C1CCN(C2COC2)CC1)N(Cc1ccc(-c2nnc(C(F)(F)F)o2)cc1F)c1ccccc1] |

TABLE 1-continued

| Ex. | Comp. | Structure |
|---|---|---|
| 99 | 11622 | (structure shown) |

Preferably, the compounds represented by formula I, stereoisomers thereof or pharmaceutically acceptable salts thereof may be selected from the group consisting of compounds 11110, 11189, 11233, 11237, 11238, 11239, 11240, 11241, 11242, 11243, 11245, 11327, 11332, 11333, 11334, 11339, 11341, 11359, 11360, 11376, 11414, 11418 and 11419. More preferably, the compounds represented by formula I, stereoisomers thereof or pharmaceutically acceptable salts thereof may be selected from the group consisting of compounds 11189, 11233, 11239, 11241, 11242, 11243, 11333, 11334, 11341, 11359, 11360, 11376, 11414, 11418 and 11419.

As used herein, the term "pharmaceutically acceptable salt" means any salt that is generally used in the pharmaceutical field. Examples of the pharmaceutically acceptable salt include, but are not limited to, salts with inorganic ions such as calcium, potassium, sodium or magnesium ions, salts with inorganic acids such as hydrochloric acid, nitric acid, phosphoric acid, bromic acid, iodic acid, perchloric acid or sulfuric acid, salts with organic acids such as acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid or the like, salts with sulfonic acids such as methanesulfonic acid, ethanesulfonic acid, benzenesulfonic acid, p-toluenesulfonic acid or naphthalenesulfonic acid, salts with amino acids such as glycine, arginine or lysine, and salts with amines such as trimethylamine, triethylamine, ammonia, pyridine or picoline.

In the present invention, preferred salts include hydrochloride, phosphate, sulfate, trifluoroacetate, citrate, bromate, maleate or tartrate, and preferred examples of such compounds include 11022, 11136 and 11137 as disclosed herein.

The compounds represented by formula I may contain one or more asymmetrical carbon atoms, and thus may exist in the form of racemates, racemic mixtures, single enantiomers, diastereomeric mixtures, and individual diastereomers. The compounds of formula I can be separated into such isomers by methods known in the art, for example, column chromatography or HPLC. Alternatively, stereoisomers of the compounds of formula I may be synthesized by stereospecific synthesis using optically pure starting materials and/or reagents of known configuration.

Methods for Preparation of 1,3,4-oxadiazole Amide Derivative Compounds

The present invention provides methods for the preparation of the 1,3,4-oxadiazole amide derivative compounds presented by formula I, stereoisomers thereof, or pharmaceutically acceptable salts thereof.

Preferred methods for the preparation of the 1,3,4-oxadiazole amide derivative compounds presented by formula I, stereoisomers thereof, or pharmaceutically acceptable salts thereof are as shown in reaction schemes 1 to 5 below, and also include modifications obvious to those skilled in the art.

Reaction Scheme 1

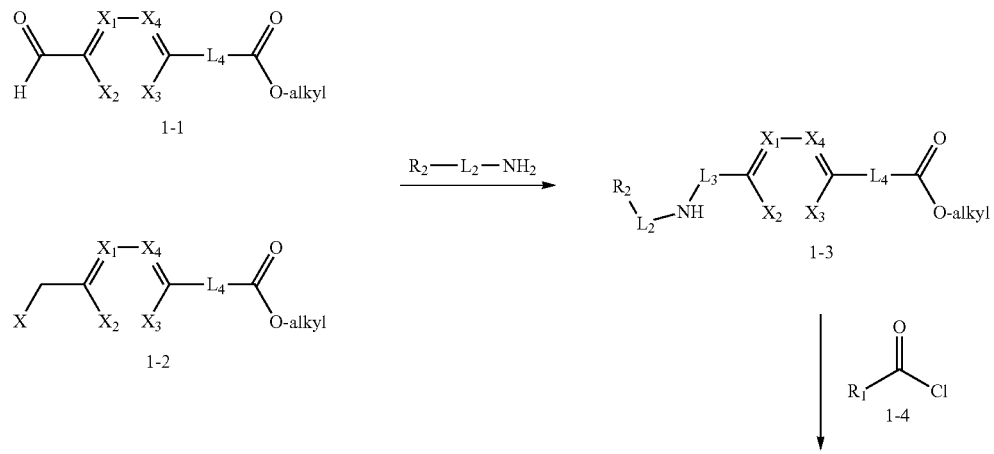

-continued

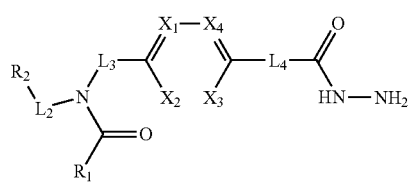

1-6

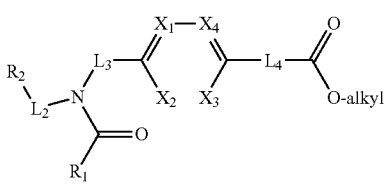

1-5

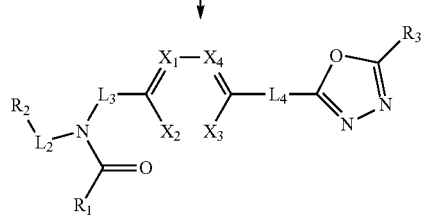

1-7

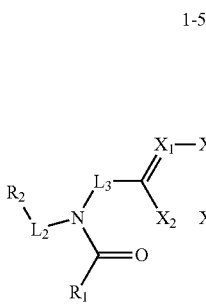

1-8

Reaction scheme 1 above shows a method for synthesis of compounds having an amide structure. As shown in reaction scheme 1, a compound of formula 1-1 is subjected to reductive amination with an amine compound, or a compound of formula 1-2 is subjected to a substitution reaction with an amine compound, thereby preparing a compound of formula 1-3. The compound of formula 1-3 is reacted with an acyl chloride of formula 1-4 to synthesize a compound of formula 1-5, which is then reacted with hydrazine, thereby preparing a compound of formula 1-6. The compound of formula 1-6 is reacted with trifluoroacetic anhydride or difluoroacetic anhydride to produce a compound of formula 1-7. When a compound of formula 1-8 in which an oxadiazole ring is not formed is obtained, it is reacted with 1-methoxy-N-triethylammoniosulfonyl-methanimidate (Burgess reagent) to obtain a compound of formula 1-8.

Compounds that are synthesized according to reaction scheme 1 are compounds 11022, 11105, 11106, 11107, 11108, 11109, 11110, 11188, 11189, 11246, 11247, 11339, 11340, 11341, 11356, 11357, 11358, 11359, 11360, 11376 and 11584.

Reaction Scheme 2

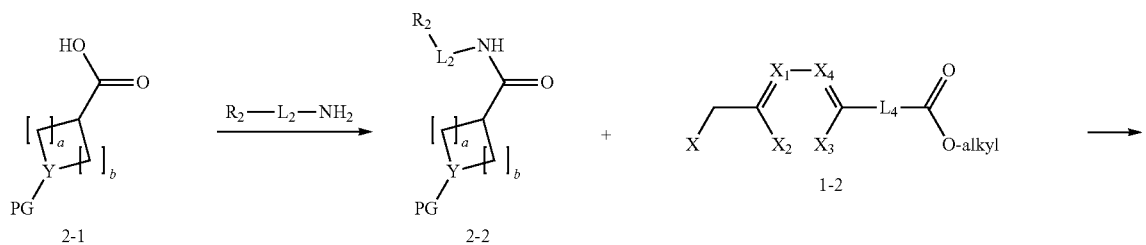

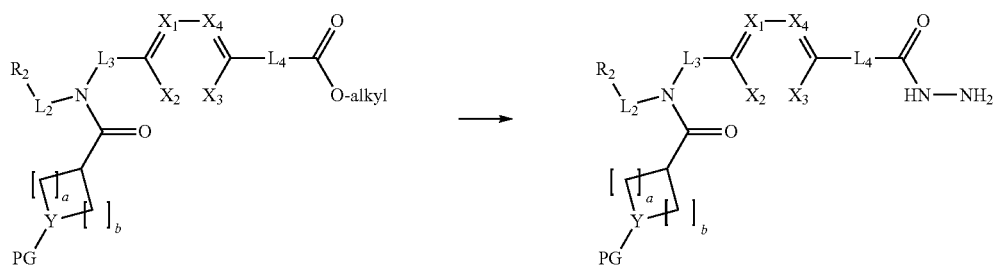

-continued

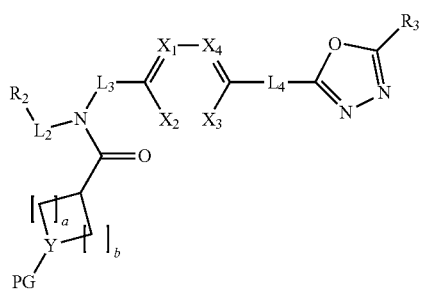

2-5

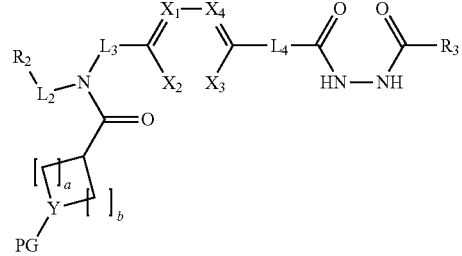

2-6

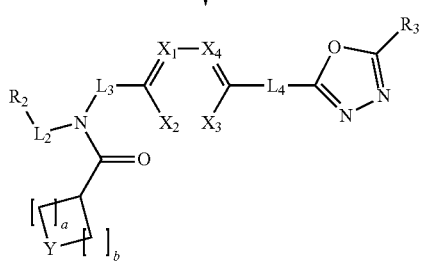

2-7

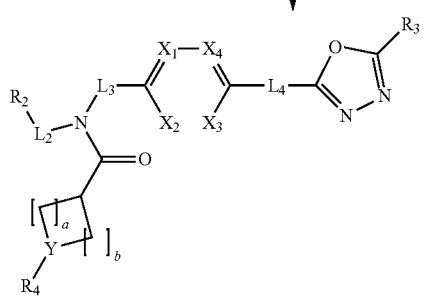

2-8

Reaction scheme 2 above shows a method for synthesis of compounds having a heterocycloalkyl amide structure. As shown in reaction scheme 2, a compound of formula 2-1 is reacted with an amine compound to synthesize a compound of formula 2-2, which is then subjected to a substitution reaction, thereby synthesizing a compound of formula 2-3. The compound of formula 2-3 is reacted with hydrazine to produce a compound of formula 2-4. The compound of formula 2-4 is reacted with trifluoroacetic anhydride or difluoroacetic anhydride to produce a compound of formula 2-5. When a compound of formula 2-6 in which an oxadiazole ring is not formed is obtained, it is reacted with 1-methoxy-N-triethylammoniosulfonyl-methanimidate (Burgess reagent) or methanesulfonyl chloride to obtain a compound of formula 2-5, which is then deprotected, thereby producing a compound of formula 2-7. The compound of formula 2-7 is reacted with aldehyde, acyl chloride, sulfonyl chloride, acetic anhydride, oxetan-3-one or the like, thereby synthesizing a compound of formula 2-8.

Compounds that are synthesized according to reaction scheme 2 above are compounds 11134, 11135, 11136, 11137, 11138, 11139, 11140, 11141, 11142, 11143, 11157, 11158, 11159, 11160, 11161, 11162, 11163, 11164, 11165, 11166, 11187, 11200, 11201, 11202, 11203, 11204, 11205, 11206, 11207, 11208, 11209, 11210, 11211, 11212, 11213, 11214, 11215, 11232, 11233, 11234, 11235, 11236, 11237, 11238, 11239, 11240, 11241, 11242, 11243, 11244, 11245, 11325, 11326, 11327, 11328, 11329, 11330, 11331, 11332, 11333, 11334, 11621 and 11622.

[Reaction Scheme 3]

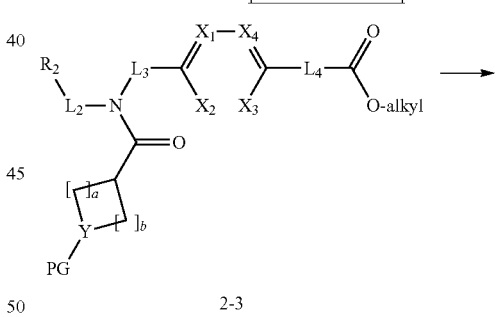

2-3

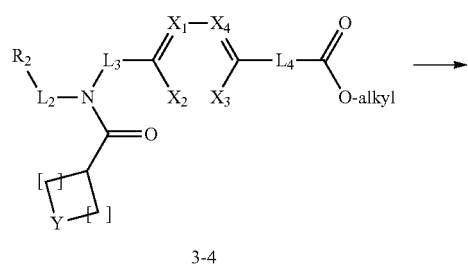

3-4

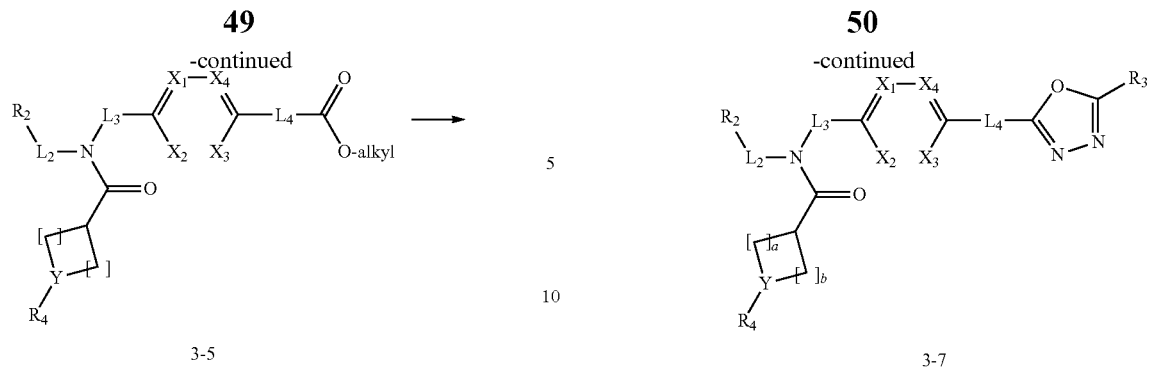

3-5

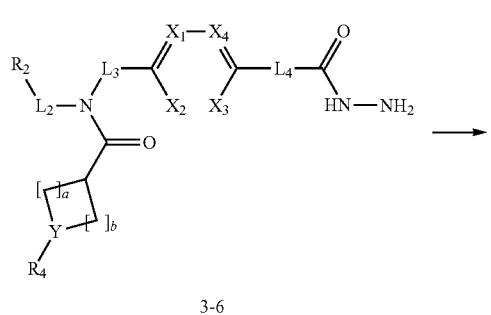

3-6

Reaction scheme 3 above shows a method for synthesis of compounds having a heterocycloalkyl amide structure. As shown in reaction scheme 3, a compound of formula 2-3 is deprotected to produce a compound of formula 3-4, which is then subjected to reductive amination, thereby preparing a compound of formula 3-5. The compound of formula 3-5 is reacted with hydrazine to produce a compound of formula 3-6. The compound of formula 3-6 is reacted with trifluoroacetic anhydride or difluoroacetic anhydride to synthesize a compound of formula 3-8.

Compounds that are synthesized according to reaction scheme 3 above are compounds 11414, 11418 and 11419.

Reaction Scheme 4

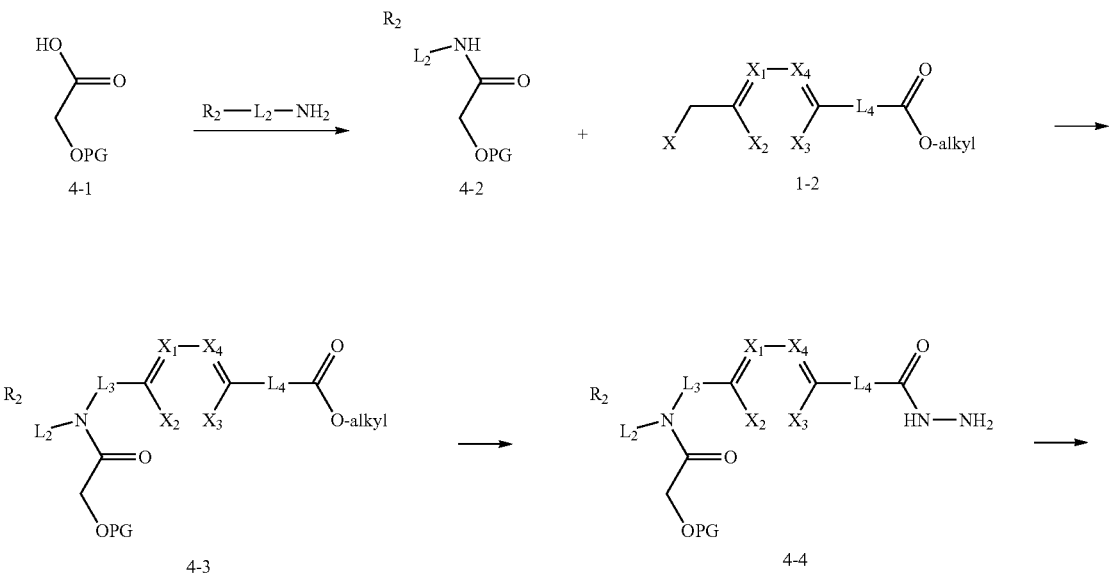

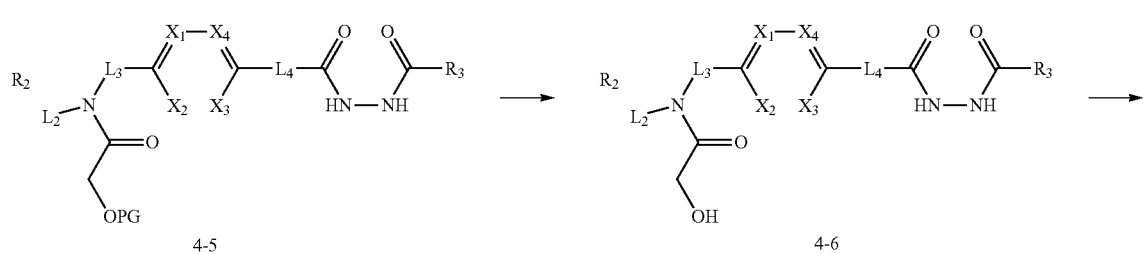

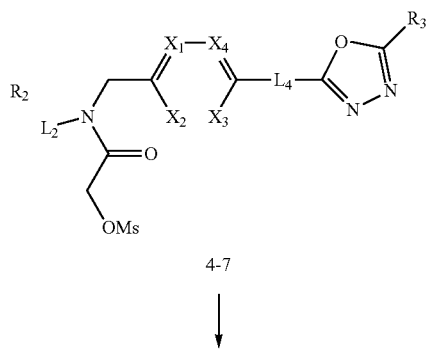

4-7

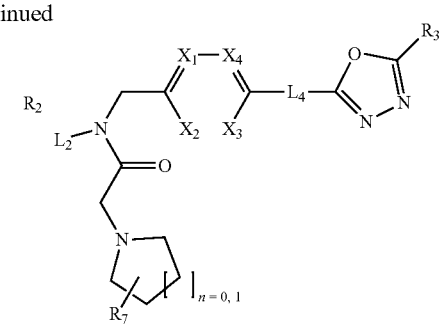

4-8

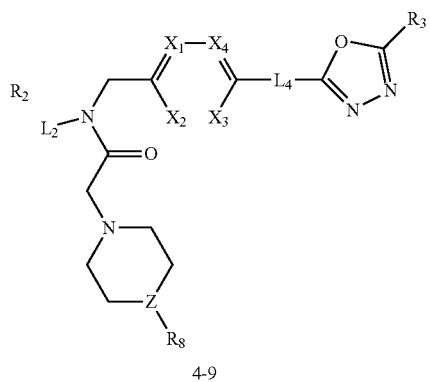

4-9

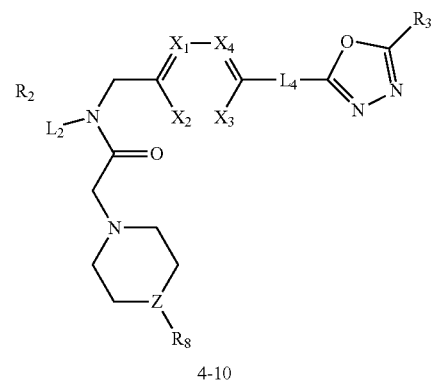

4-10

Reaction scheme 4 above shows a method for synthesis of compounds having a heterocycloalkyl amide structure. As shown in reaction scheme 4, a compound of formula 4-1 is reacted with an amine compound to obtain a compound of formula 4-2, which is then subjected to a substitution reaction, thereby synthesizing a compound of formula 4-3. The compound of formula 4-3 is reacted with hydrazine to produce a compound of formula 4-4. The compound of formula 4-4 is reacted with difluoroacetic anhydride to synthesize a compound of formula 4-5. The compound of formula 4-5 is deprotected to obtain a compound of formula 4-6, which is then reacted with methanesulfonyl chloride, thereby preparing a compound of formula 4-7. The compound of formula 4-7 is reacted with substituted cycloamine to produce a compound of formula 4-8. In addition, the compound of formula 4-7 is reacted with morpholine, thiomorpholine or piperazine derivative to synthesize a compound of formula 4-9. When the product is unsubstituted piperizine, it is reacted with sulfonyl chloride, acetic anhydride or oxetan-3-one to produce a compound of formula 4-10.

Compounds that are synthesized according to reaction scheme 4 above are compounds 11534, 11535, 11536, 11537, 11538, 11610, 11611, 11612, 11613 and 11614.

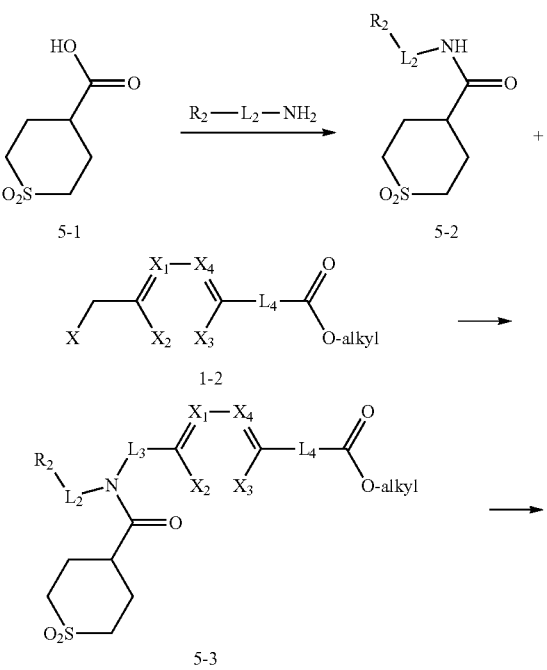

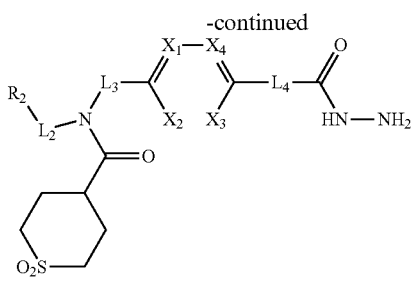

5-4

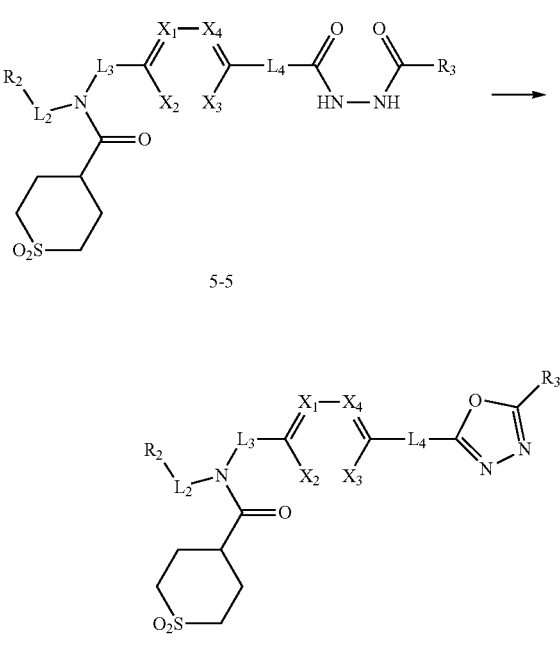

Reaction scheme 5 above shows a method for synthesis of compounds having a heterocycloalkyl amide structure. As shown in reaction scheme 5, a compound of formula 5-1 is reacted with an amine compound to obtain a compound of formula 5-2, which is then subjected to a substitution reaction to obtain a compound of formula 5-3. The compound of formula 5-3 is reacted with hydrazine to produce a compound of formula 5-4. The compound of formula 5-4 is reacted with trifluoroacetic anhydride or difluoroacetic anhydride to synthesize a compound of formula 5-5, which is then reacted with methanesulfonyl chloride, thereby synthesizing a compound of formula 5-6.

Compounds that are synthesized according to reaction scheme 5 above are compounds 11602 and 11603.

Compositions Comprising 1,3,4-oxadiazole Amide Derivative Compounds, the Use Thereof and the Method of Treating Diseases Using the Same The present invention provides a pharmaceutical composition for preventing or treating histone deacetylase 6 (HDAC6) activity-associated diseases, which contains, as an active ingredient, a compound represented by the following formula I, a stereoisomer thereof or a pharmaceutically acceptable salt thereof:

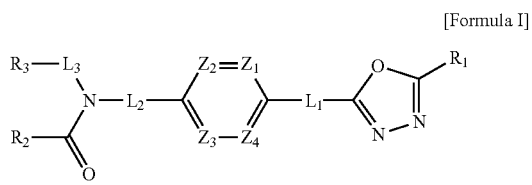

[Formula I]

wherein formula I is as defined above.

The pharmaceutical composition according to the present invention exhibits a remarkable effect on the prevention or treatment of histone deacetylase 6 activity-associated diseases by selectively inhibiting histone deacetylase 6.

The histone deacetylase 6 activity-associated diseases include infectious diseases such as prion disease; neoplasms such as benign tumor (e.g. myelodysplastic syndrome) or malignant tumor (e.g. multiple myeloma, lymphoma, leukemia, lung cancer, rectal cancer, colon cancer, prostate cancer, urothelial carcinoma, breast cancer, melanoma, skin cancer, liver cancer, brain cancer, gastric cancer, ovarian cancer, pancreatic cancer, head and neck cancer, oral cancer, or glioma); endocrine, nutritional and metabolic diseases such as Wilson's disease, amyloidosis or diabetes; mental and behavioral disorders such as depression or Rett's syndrome, and the like; neurological diseases such as atrophy of central nervous system (e.g. Huntington's disease, spinal muscular atrophy (SMA), spinocerebellar ataxia (SCA)), neurodegenerative disease (e.g. Alzheimer's disease), movement disorder (e.g. Parkinson's disease), neuropathy (e.g. hereditary neuropathy (Charcot-Marie-Tooth disease)), sporadic neuropathy, inflammatory neuropathy, drug-induced neuropathy), motor neuron diseases (amyotrophic lateral sclerosis (ALS)), or demyelinating diseases of the central nervous system (e.g. multiple sclerosis (MS)), and the like; diseases of the eye and adnexa, such as uveitis; cardiovascular diseases such as atrial fibrillation or stroke and the like; respiratory diseases such as asthma; digestive diseases such as alcoholic liver disease, inflammatory bowel disease, Crohn's disease or ulcerative bowel disease, and the like; diseases of the skin and subcutaneous tissue, such as psoriasis; diseases of the musculoskeletal system and connective tissue, such as rheumatoid arthritis, osteoarthritis or systemic lupus erythematosus (SLE), and the like; or congenital malformations, deformations and chromosomal abnormalities, such as autosomal dominant polycystic kidney disease, as well as disorders or diseases associated with the abnormal function of histone deacetylase.

The pharmaceutically acceptable salt is as described above with respect to a pharmaceutically acceptable salt of the compound represented by formula I according to the present invention.

For administration, the pharmaceutical composition according to the present invention may further contain at least one pharmaceutically acceptable carrier in addition to the compound of formula I, a stereoisomer thereof or a pharmaceutically acceptable salt thereof. The pharmaceutically acceptable carrier that is used in the present invention may be at least one of physiological saline, sterile water, Ringer solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, the composition may be formulated into injectable formulations such as solutions, suspensions, emulsions, etc., pills, capsules, granules or tablets using a diluent, a dispersing agent, a surfactant, a binder and a lubricant. Thus, the composition of the present invention may be in the form of patches, liquids, pills, capsules, granules, tablets, suppositories, etc. These formulations may be prepared either by conventional methods that are used for formulation in the art or by the method disclosed in Remington's Pharmaceutical Science (the latest edition), Mack Publishing Company, Easton Pa., and may be prepared depending on diseases or components.

The pharmaceutical composition of the present invention may be administered orally or parenterally (e.g., intravenously, subcutaneously, intraperitoneally or topically) depending on the intended use. The dose of the pharmaceutical composition varies depending on the patient's weight, age, sex, health conditions and diet, the time of administration, the mode of administration, excretion rate, the severity of the disease, and the like. The daily dose of the compound of formula I according to the present invention may be about 1 to 1000 mg/kg, preferably 5 to 100 mg/kg, and may be administered once to several times a day.

The pharmaceutical composition of the present invention may further contain, in addition to the compound represented by formula I, a stereoisomer thereof or a pharmaceutically acceptable salt thereof, one or more active ingredients that exhibit medicinal efficacy identical or similar thereto.

The present invention also provides a method for preventing or treating a histone deacetylase 6 activity-associated disease, which comprises administering a therapeutically effective amount of the compound represented by formula I, a stereoisomer thereof or a pharmaceutically acceptable salt thereof.

As used herein, the term "therapeutically effective amount" refers to the amount of the compound represented by formula I, which is effective for the prevention or treatment of histone deacetylase 6 activity-associated diseases.

The present invention also provides a method of selectively inhibiting HDAC6, which comprises administering the compound of formula I, a stereoisomer thereof or a pharmaceutically acceptable salt thereof to mammals including humans.

The method of preventing or treating histone deacetylase 6 activity-associated diseases according to the present invention includes inhibiting or averting the disease as well as addressing the disease itself, prior to the onset of symptoms by administering the compound represented by formula I. In the management of diseases, the magnitude of a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens may be readily selected by those skilled in the art with due consideration of such factors. In addition, the method of preventing or treating histone deacetylase 6 activity-associated diseases according to the present invention may further comprise administering a therapeutically effective amount of an additional active agent helpful for the treatment of the disease together with the compound represented by formula I, in which the additional active agent may exhibit a synergistic effect with the compound of formula I or an assistant effect.

The present invention is also intended to provide the use of the compound represented by formula I, a stereoisomer thereof or a pharmaceutically acceptable salt thereof, for the preparation of a medicament for treating histone deacetylase 6 activity-associated diseases. For the preparation of the medicament, the compound represented by formula I may be mixed with a pharmaceutically acceptable adjuvant, diluent, carrier or the like, and combined with other active agents such that the active ingredients can have synergistic effects.

The particulars mentioned in the use, composition and treatment method of the present invention may be appropriately combined unless contradictory to one another.

Advantageous Effects

The compounds represented by formula I according to the present invention, stereoisomers thereof or pharmaceutically acceptable salts thereof can selectively inhibit HDAC6, and thus exhibit excellent effects on the prevention or treatment of histone deacetylase 6 activity-associated diseases.

MODE FOR INVENTION

Hereinafter, the present invention will be described in further detail with reference to examples and experimental examples. However, these examples are for illustrative purposes only and are not intended to limit the scope of the present invention.

Preparation of 1,3,4-oxadiazole Amide Derivative Compounds

Specific methods for preparing the compounds of formula I are as follows.

EXAMPLE 1: Synthesis of Compound 11022, N-phenyl-N-(4-(5-(trifluoromethyl)-1,3,4-oxadiazol-2-yl)benzyl)isonicotinamide

[Step 1] Synthesis of methyl 4-((phenylamino)methyl)benzoate

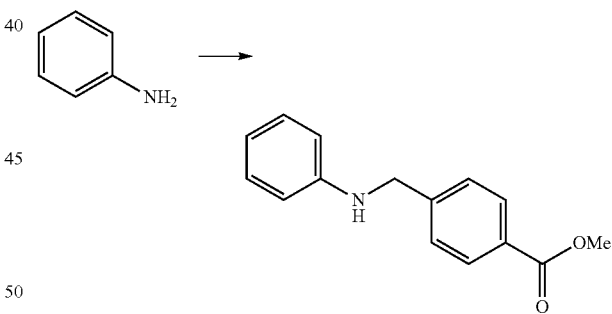

Aniline (1.961 mL, 21.475 mmol), methyl 4-formylbenzoate (4.230 g, 25.770 mmol) and acetic acid (0.614 mL, 10.738 mmol) were dissolved in methylene chloride (50 mL), and the solution was stirred at 0° C. for 10 minutes. Then, sodium triacetoxyborohydride (6.828 g, 32.213 mmol) was added to the stirred solution, followed by additional stirring at room temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (4.730 g, 91.3%) as colorless oil.

[Step 2] Synthesis of methyl 4-((N-phenylisonicotinamido)methyl)benzoate

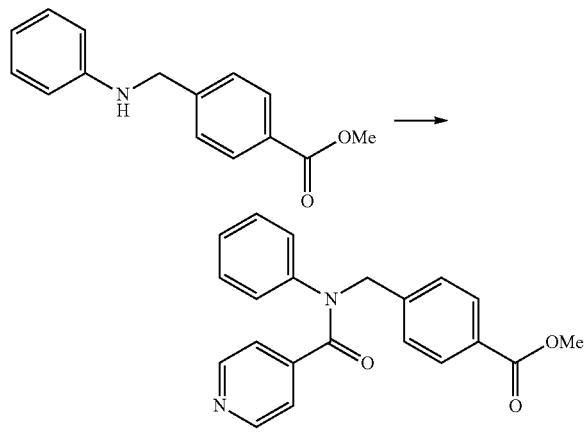

4-((phenylamino)methyl)benzoate (0.150 g, 0.622 mmol) synthesized in step 1, isonicotinoyl chloride hydrochloride (0.221 g, 1.243 mmol) and N,N-diisopropylethylamine (0.194 mL, 1.243 mmol) were dissolved in methylene chloride (10 mL) at room temperature, and the solution was stirred at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 50%) and concentrated to give the title compound (0.179 g, 83.1%) as a white solid.

[Step 3] Synthesis of N-(4-(hydrazinecarbonyl)benzyl)-N-phenylisonicotinamide

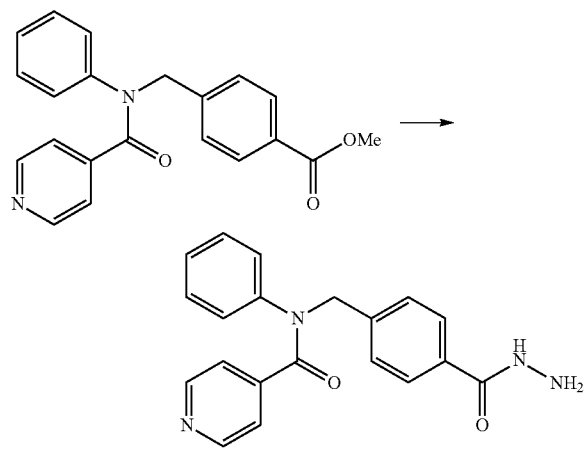

Methyl 4-((N-phenylisonicotinamido)methyl)benzoate (0.179 g, 0.517 mmol) synthesized in step 2, and hydrazine hydrate (0.488 mL, 10.335 mmol) were mixed in ethanol (10 mL), and the mixture was heated by microwave irradiation at 120° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/methylene chloride=from 0% to 15%) and concentrated to give the title compound (0.134 g, 74.9%) as a white solid.

[Step 4] Synthesis of Compound 11022

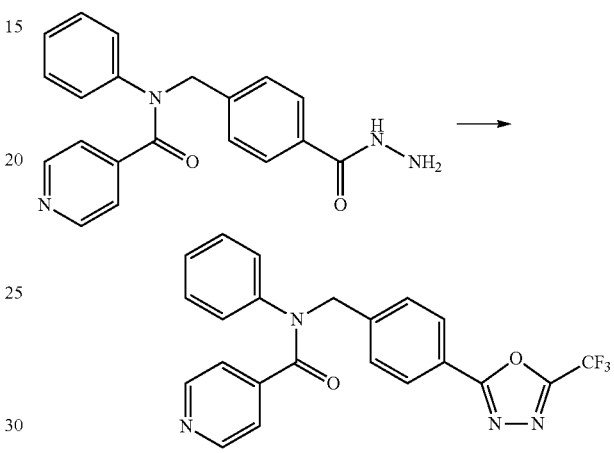

N-(4-(hydrazinecarbonyl)benzyl)-N-phenylisonicotinamide (0.105 g, 0.303 mmol) synthesized in step 3, trifluoroacetic anhydride (0.051 mL, 0.364 mmol) and triethylamine (0.084 mL, 0.606 mmol) were dissolved in methylene chloride (20 mL) at room temperature, and the solution was stirred at the same temperature. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/methylene chloride=from 0% to 30%) and concentrated to give the title compound (0.035 g, 26.1%) as a white foam solid.

$^1$H NMR (400 MHz, CDCl$_3$) δ 8.48 (d, 2H, J=5.8 Hz), 8.06 (d, 2H, J=8.3 Hz), 7.49 (d, 2H, J=8.2 Hz), 7.28-7.14 (m, 5H), 6.98-6.82 (m, 2H), 5.17 (d, 2H, J=19.0 Hz); LRMS (ES) m/z 425.2 (M$^+$+1).

[Step 5] Synthesis of Compound 11022 Hydrochloride

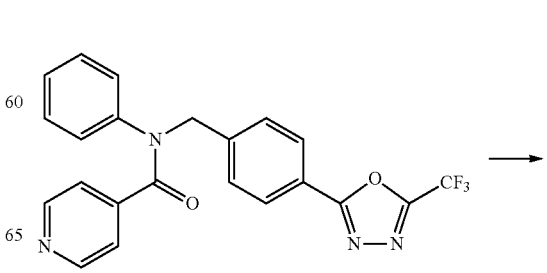

-continued

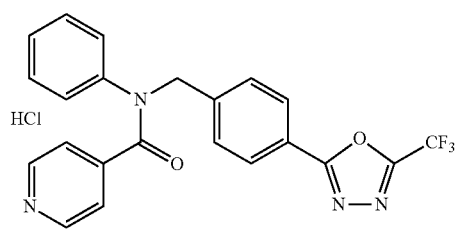

N-phenyl-N-(4-(5-(trifluoromethyl)-1,3,4-oxadizol-2-yl)benzyl)isonicotinamide (0.100 g, 0.236 mmol) synthesized in step 4 was dissolved in dichloromethane (10 mL) at room temperature, and hydrochloric acid (1.00 M solution in ethyl acetate, 0.259 mL, 0.259 mmol) was added to the solution, followed by stirring at the same temperature for 1 hour. The reaction mixture was concentrated under reduced pressure to remove the solvent, and ethyl acetate (2 mL) was added to the concentrate, followed by stirring. The precipitated solid was filtered, washed with ethyl acetate solution, and dried to give the title compound (0.108 g, 99.5%) as a white solid.

EXAMPLE 2: Synthesis of Compound 11105, N-phenyl-N-(4-(5-(trifluoromethyl)-1,3,4-oxadiazol-2-yl)benzyl)acetamide

[Step 1] Synthesis of methyl 4-((N-phenylacetamido)methyl)benzoate

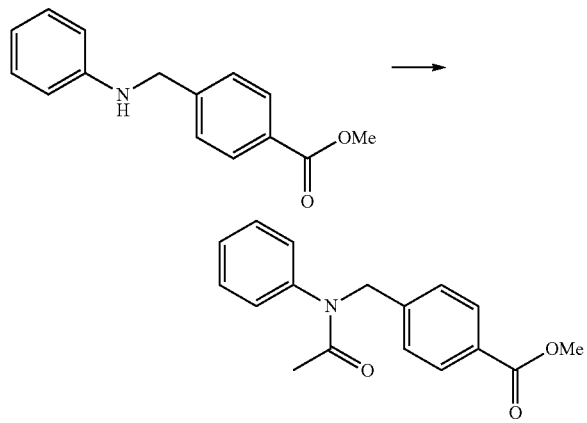

Methyl 4-((phenylamino)methyl)benzoate (0.200 g, 0.829 mmol) and diisopropylethylamine (0.290 mL, 1.658 mmol) were dissolved in methylene chloride (10 mL) at room temperature, and acetyl chloride (0.088 mL, 1.243 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.220 g, 93.7%) as a white solid.

[Step 2] Synthesis of N-(4-(hydrazinecarbonyl)benzyl)-N-phenylacetamide

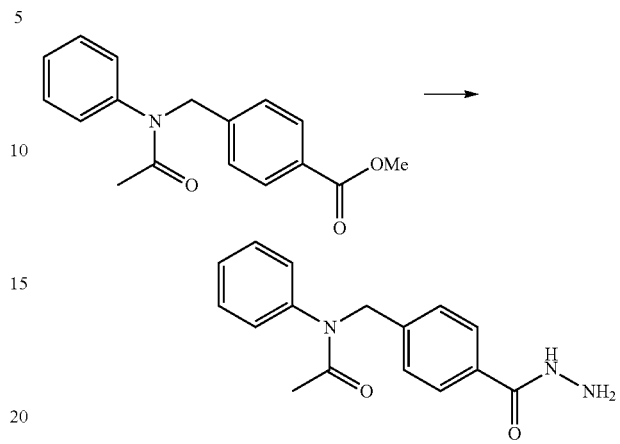

Methyl 4-((N-phenylacetamido)methyl)benzoate (0.220 g, 0.776 mmol) synthesized in step 1 and hydrazine hydrate (0.733 mL, 15.530 mmol) were mixed in ethanol (10 mL), and the mixture was heated by microwave irradiation at 120° C. for 2 hours, and then cooled down to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/methylene chloride=from 0% to 15%) and concentrated to give the title compound (0.145 g, 65.9%) as a white foam solid.

[Step 3] Synthesis of N-phenyl-N-(4-(2-(2,2,2-trifluoroacetyl)hydrazine-1-carbonyl)benzyl)acetamide

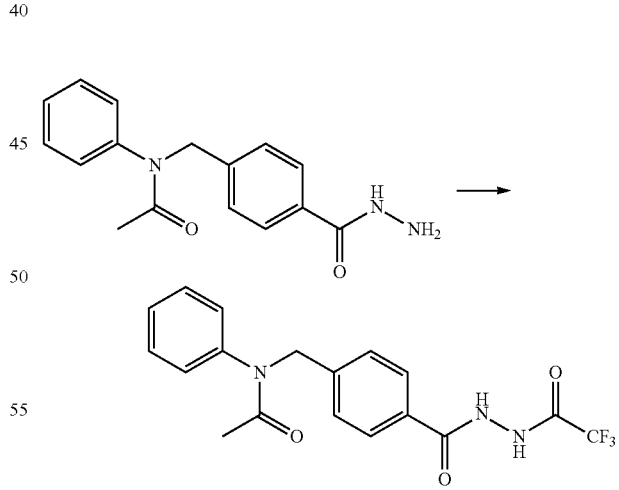

N-(4-(hydrazinecarbonyl)benzyl)-N-phenylacetamide (0.145 g, 0.512 mmol) synthesized in step 2 and triethylamine (0.142 mL, 1.024 mmol) were dissolved in methylene chloride (10 mL) at room temperature, and trifluoroacetic anhydride (0.087 mL, 0.614 mmol) was added to the solution, followed by stirring at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.180 g, 92.7%, yellow foam solid).

[Step 4] Synthesis of Compound 11105

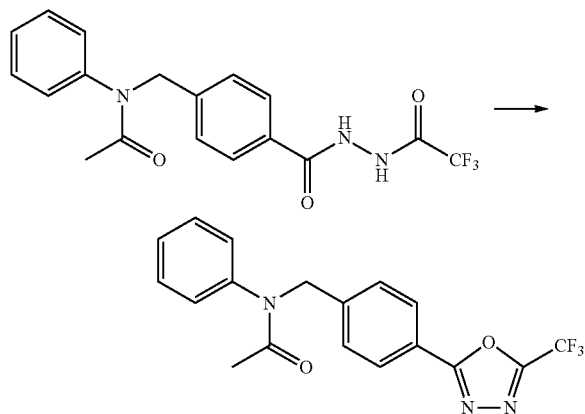

N-phenyl-N-(4-(2-(2,2,2-trifluoroacetyl)hydrazine-1-carbonyl)benzyl)acetamide (0.180 g, 0.475 mmol) synthesized in step 3 and 1-methoxy-N-triethylammoniosulfonyl-methanimidate (Burgess reagent, 0.170 g, 0.712 mmol) were mixed in tetrahydrofuran (10 mL), and the mixture was heated by microwave irradiation at 150° C. for 30 minutes and cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 50%) and concentrated to give the title compound (0.088 g, 51.3%) as light yellow oil.

$^1$H NMR (400 MHz, CDCl$_3$) δ 8.03 (d, 2H, J=8.3 Hz), 7.47-7.13 (m, 5H), 7.02 (dd, 2H, J=7.8, 1.5 Hz), 4.98 (s, 2H), 1.93 (s, 3H); LRMS (ES) m/z 362.3 (M$^+$+1).

EXAMPLE 3: Synthesis of Compound 11106, N-phenyl-N-(4-(5-(trifluoromethyl)-1,3,4-oxadiazol-2-yl)benzyl)cyclohexanecarboxamide

[Step 1] Synthesis of 4-((N-phenylcyclohexanecarboxamido)methyl)benzoate

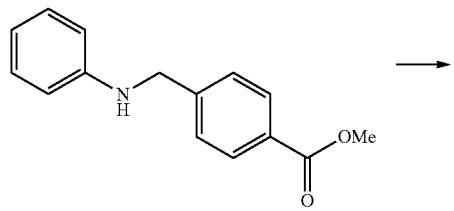

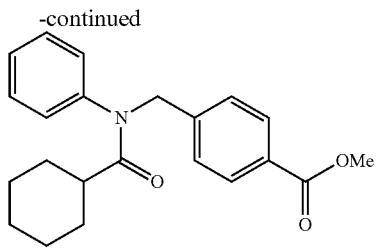

Methyl 4-((phenylamino)methyl)benzoate (0.200 g, 0.829 mmol) and N,N-diisopropylethylamine (0.290 mL, 1.658 mmol) were dissolved in methylene chloride (10 mL) at room temperature, and cyclohexanecarbonyl chloride (0.166 mL, 1.243 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 50%) and concentrated to give the title compound (0.285 g, 97.8%) as a white solid.

[Step 2] Synthesis of N-(4-(hydrazinecarbonyl)benzyl)-N-phenylcyclohexanecarboxamide

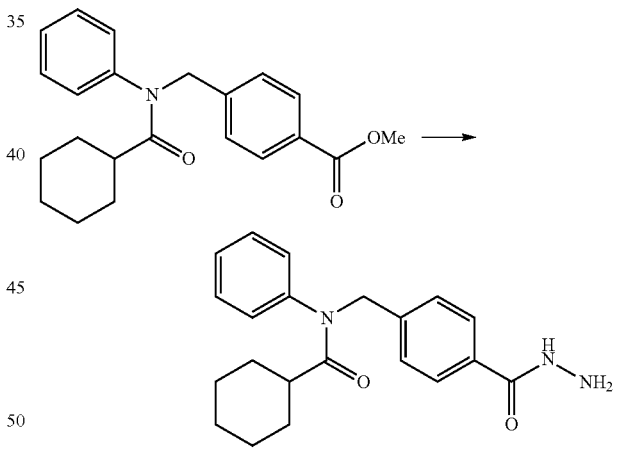

4-((N-phenylcyclohexanecarboxamido)methyl)benzoate (0.285 g, 0.811 mmol) synthesized in step 1 and hydrazine hydrate (0.766 mL, 16.219 mmol) were mixed in ethanol (10 mL), and the mixture was heated by microwave irradiation at 120° C. for 2 hours, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/methylene chloride=from 0% to 15%) and concentrated to give the title compound (0.239 g, 83.9%) as a white foam solid.

[Step 3] Synthesis of N-phenyl-N-(4-(2-(2,2,2-trifluoroacetyl)hydrazine-1-carbonyl)benzyl)cyclohexanecarboxamide

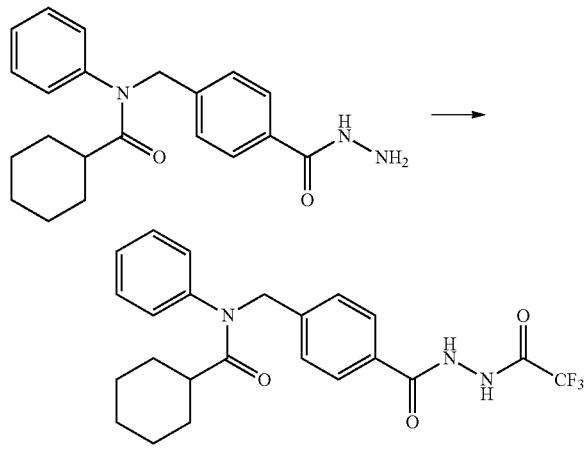

N-(4-(hydrazinecarbonyl)benzyl)-N-phenylcyclohexanecarboxamide (0.239 g, 0.680 mmol) synthesized in step 2 and triethylamine (0.189 mL, 1.360 mmol) were dissolved in methylene chloride (10 mL) at room temperature, and trifluoroacetic anhydride (0.115 mL, 0.816 mmol) was added to the solution, followed by stirring at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.300 g, 98.6%, white foam solid).

[Step 4] Synthesis of Compound 11106

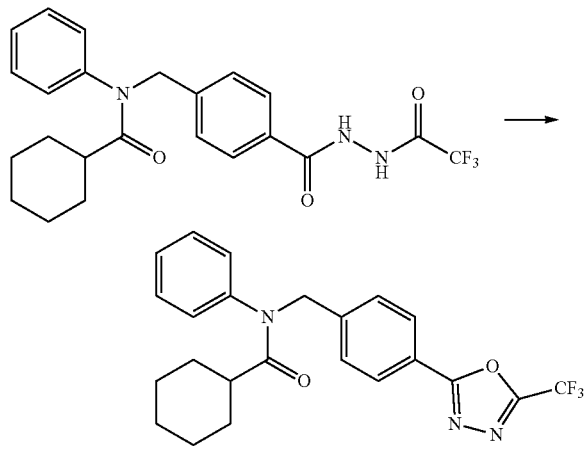

N-phenyl-N-(4-(2-(2,2,2-trifluoroacetyl)hydrazine-1-carbonyl)benzyl)cyclohexanecarboxamide (0.300 g, 0.670 mmol) synthesized in step 3 and 1-methoxy-N-triethylammoniosulfonyl-methanimidate (Burgess reagent, 0.240 g, 1.006 mmol) were mixed in tetrahydrofuran (10 mL), and the mixture was heated by microwave irradiation at 150° C. for 30 minutes and cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography ($SiO_2$, 4 g cartridge; methanol/dichloromethane=from 0% to 50%) and concentrated to give the title compound (0.096 g, 33.3%) as a white solid.

$^1$H NMR (400 MHz, $CDCl_3$) δ 8.02 (d, 2H, J=8.3 Hz), 7.44-7.31 (m, 5H), 7.07 (ddd, 2H, J=60.8, 5.1, 4.6 Hz), 4.94 (s, 2H), 2.18 (ddd, 1H, J=11.4, 7.3, 3.1 Hz), 1.74-1.48 (m, 7H), 1.32-1.08 (m, 1H), 1.08-0.40 (m, 2H); LRMS (ES) m/z 430.3 ($M^+$+1).

EXAMPLE 4: Synthesis of Compound 11107, N-phenyl-N-(4-(5-(trifluoromethyl)-1,3,4-oxadiazol-2-yl)benzyl)benzamide

[Step 1] Synthesis of methyl 4-((N-phenylbenzamido)methyl)benzoate

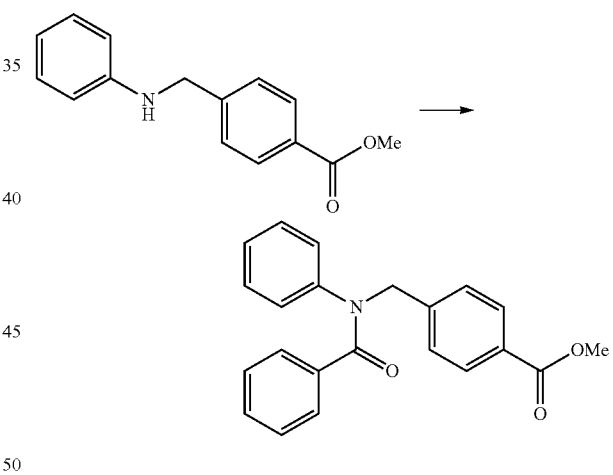

Methyl 4-((phenylamino)methyl)benzoate (0.200 g, 0.829 mmol) and N,N-diisopropylethylamine (0.290 mL, 1.658 mmol) were dissolved in methylene chloride (10 mL) at room temperature, and benzoyl chloride (0.175 g, 1.243 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography ($SiO_2$, 12 g cartridge; ethyl acetate/hexane=from 0% to 50%) and concentrated to give the title compound (0.264 g, 92.2%) as a white solid.

[Step 2] Synthesis of
N-(4-(hydrazinecarbonyl)benzyl)-N-phenylbenzamide

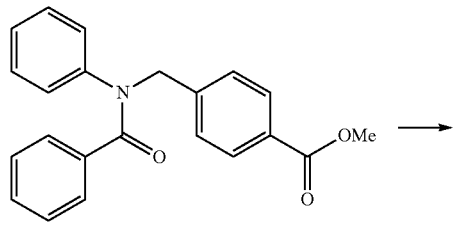

Methyl 4-((N-phenylbenzamido)methyl)benzoate (0.264 g, 0.764 mmol) synthesized in step 1 and hydrazine hydrate (0.722 mL, 15.287 mmol) were mixed in ethanol (10 mL), and the mixture was heated by microwave irradiation at 120° C. for 2 hours, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/methylene chloride=from 0% to 15%) and concentrated to give the title compound (0.222 g, 84.1%) as a white foam solid.

[Step 3] Synthesis of N-phenyl-N-(4-(2-(2,2,2-trifluoroacetyl)hydrazine-1-carbonyl)benzyl)benzamide

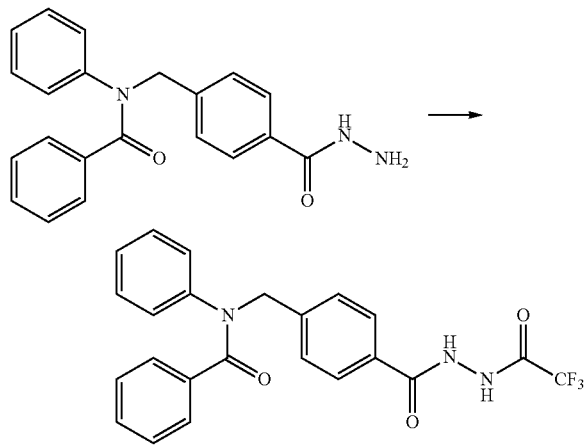

N-(4-(hydrazinecarbonyl)benzyl)-N-phenylbenzamide (0.364 g, 1.054 mmol) synthesized in step 2 and triethylamine (0.292 mL, 2.108 mmol) were dissolved in methylene chloride (10 mL) at room temperature, and trifluoroacetic anhydride (0.178 mL, 1.265 mmol) was added to the solution, followed by stirring at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.450 g, 96.7%, white foam solid).

[Step 4] Synthesis of Compound 11107

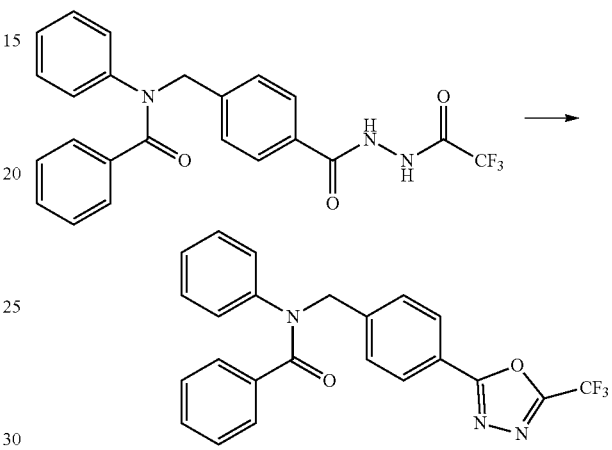

N-phenyl-N-(4-(2-(2,2,2-trifluoroacetyl)hydrazine-1-carbonyl)benzyl)benzamide (0.450 g, 1.019 mmol), synthesized in step 3, and 1-methoxy-N-triethylammoniosulfonyl-methanimidate (Burgess reagent, 0.364 g, 1.529 mmol), were mixed in tetrahydrofuran (10 mL), and the mixture was heated by microwave irradiation at 150° C. for 30 minutes, and cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.250 g, 57.9%) as light yellow solid.
$^1$H NMR (400 MHz, CDCl$_3$) δ 8.04 (d, 2H, J=8.3 Hz), 7.54 (t, 2H, J=9.9 Hz), 7.38-7.31 (m, 2H), 7.26-7.06 (m, 6H), 6.95 (dd, 2H, J=10.5, 9.1 Hz), 5.23 (s, 2H); LRMS (ES) m/z 430.3 (M$^+$+1)

EXAMPLE 5: Synthesis of Compound 11108,
N-(4-(5-(difluoromethyl)-1,3,4-oxadiazol-2-yl)benzyl)-N-phenylisonicotinamide

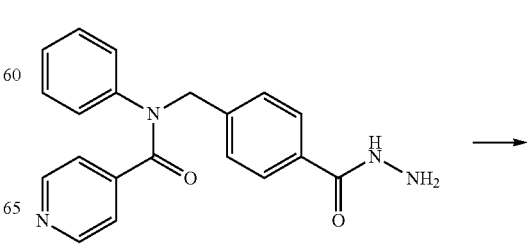

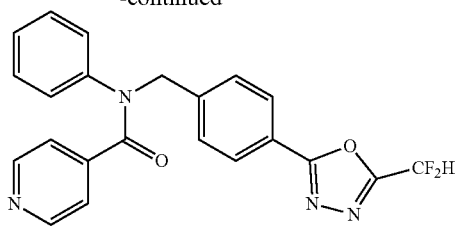

N-(4-(hydrazinecarbonyl)benzyl)-N-phenylisonicotinamide (0.200 g, 0.577 mmol) synthesized in step 3 of Example 1, 2,2-difluoroacetic anhydride (0.075 mL, 0.693 mmol) and triethylamine (0.160 mL, 1.155 mmol) were dissolved in N,N-dimethylformamide (10 mL) at room temperature, and the solution was stirred at 80° C. for 1 hour and cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.158 g, 67.3%) as a white solid.

$^1$H NMR (400 MHz, CDCl$_3$) δ 8.47 (d, 2H, J=4.5 Hz), 8.06 (d, 2H, J=8.2 Hz), 7.47 (d, 2H, J=8.1 Hz), 7.19 (d, 5H, J=5.1 Hz), 7.02 (d, 1H, J=15.5 Hz), 6.90 (d, 3H, J=5.8 Hz), 5.19 (s, 2H); LRMS (ES) m/z 407.3 (M$^+$+1).

EXAMPLE 6: Synthesis of Compound 11109, N-(2-fluoro-4-(5-(trifluoromethyl)-1,3,4-oxadiazol-2-yl)benzyl)-N-phenylisonicotinamide

[Step 1] Synthesis of methyl 3-fluoro-4-((N-phenylisonicotinamido)methyl)benzoate

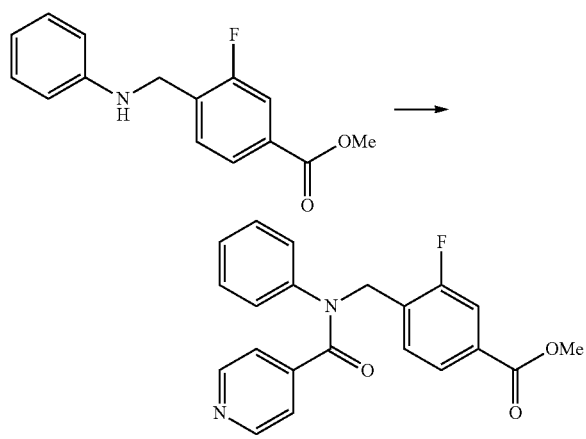

Methyl 3-fluoro-4-((phenylamino)methyl)benzoate (0.640 g, 2.468 mmol) and N,N-diisopropylethylamine (0.638 g, 4.937 mmol) were dissolved in methylene chloride (10 mL) at room temperature, and isonicotinoyl chloride hydrochloride (0.879 g, 4.937 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.840 g, 93.4%) as a yellow foam solid.

[Step 2] Synthesis of N-(2-fluoro-4-(hydrazinecarbonyl)benzyl)-N-phenylisonicotinamide

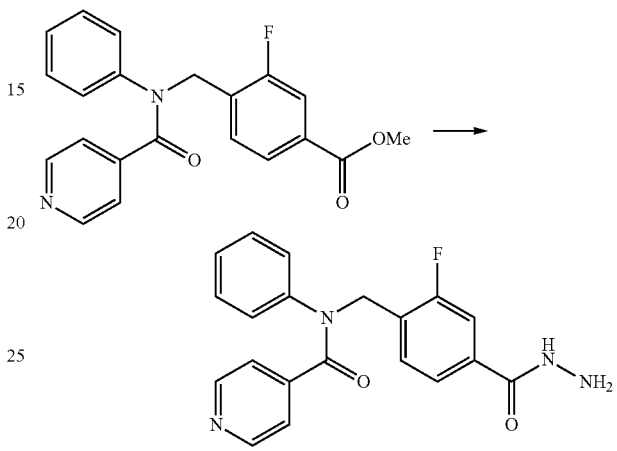

3-fluoro-4-((N-phenylisonicotinamido)methyl)benzoate (0.840 g, 2.305 mmol) synthesized in step 1 and hydrazine hydrate (2.177 mL, 46.106 mmol) were mixed in ethanol (10 mL), and the mixture was heated by microwave irradiation at 120° C. for 2 hours, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/methylene chloride=from 0% to 15%) and concentrated to give the title compound (0.814 g, 96.9%) as a white solid.

[Step 3] Synthesis of Compound 11109

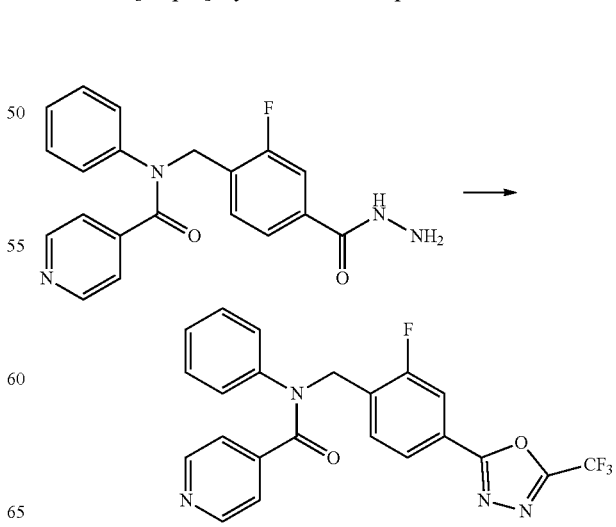

N-(2-fluoro-4-(hydrazinecarbonyl)benzyl)-N-phenylisonicotinamide (0.100 g, 0.274 mmol) synthesized in step 2 and triethylamine (0.076 mL, 0.549 mmol) were dissolved in N,N-dimethylformamide (10 mL) at room temperature, and trifluoroacetic anhydride (0.046 mL, 0.329 mmol) was added to the solution. The mixture was stirred at 80° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/methylene chloride=0% to 15%) and concentrated to give the title compound (0.060 g, 49.4%) as a white solid.

$^1$H NMR (400 MHz, CDCl$_3$) δ 8.49 (s, 2H), 7.89 (dd, 1H, J=8.0, 1.4 Hz), 7.79-7.64 (m, 2H), 7.25 (d, 1H, J=9.0 Hz), 7.29-7.03 (m, 5H), 7.03-6.89 (m, 2H), 5.27 (s, 2H); LRMS (ES) m/z 443.2 (M$^+$+1).

EXAMPLE 7: Synthesis of Compound 11110, N-(4-(5-(difluoromethyl)-1,3,4-oxadiazol-2-yl)-2-fluorobenzyl)-N-phenylisonicotinamide

[Step 1] Synthesis of N-(4-(2-(2,2-difluoroacetyl)hydrazine-1-carbonyl)-2-fluorobenzyl)-N-phenylisonicotinamide

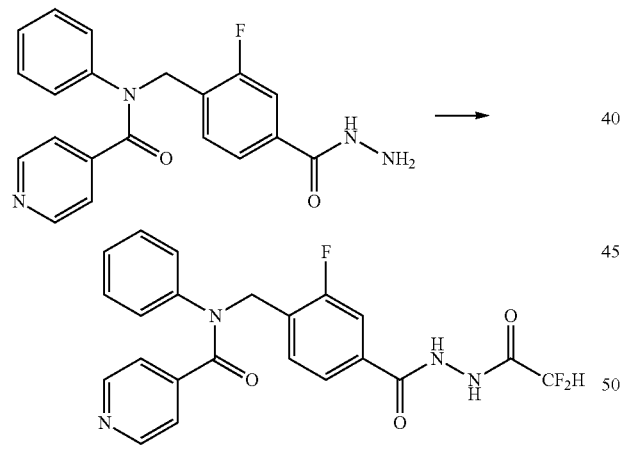

N-(2-fluoro-4-(hydrazinecarbonyl)benzyl)-N-phenylisonicotinamide (0.100 g, 0.274 mmol), synthesized in step 2 of Example 6, and triethylamine (0.076 mL, 0.549 mmol), were dissolved in methylene chloride (10 mL) at room temperature, and 2,2-difluoroacetic anhydride (0.057 g, 0.329 mmol) was added to the solution, followed by stirring at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.120 g, 98.8%, colorless oil).

[Step 2] Synthesis of Compound 11110

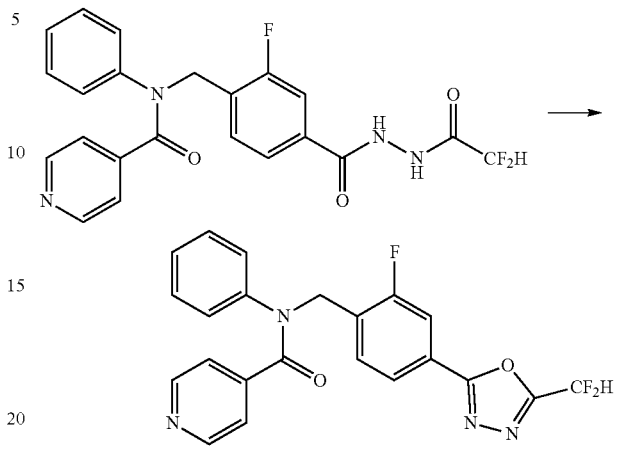

N-(4-(2-(2,2-difluoroacetyl)hydrazine-1-carbonyl)-2-fluorobenzyl)-N-phenylisonicotinamide (0.120 g, 0.271 mmol), synthesized in step 1, and 1-methoxy-N-triethylammoniosulfonyl-methanimidate (Burgess reagent, 0.097 g, 0.407 mmol), were mixed in tetrahydrofuran (10 mL), and the mixture was heated by microwave irradiation at 150° C. for 30 minutes, and cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.027 g, 23.5%) as a light yellow solid.

$^1$H NMR (400 MHz, CDCl$_3$) δ 8.49 (d, 2H, J=5.5 Hz), 7.91 (dd, 1H, J=8.0, 1.5 Hz), 7.90-7.57 (m, 2H), 7.29-7.07 (m, 5H), 6.95 (ddd, 3H, J=64.6, 48.3, 41.3 Hz), 5.27 (d, 2H, J=14.0 Hz); LRMS (ES) m/z 425.3 (M$^+$+1).

EXAMPLE 8: Synthesis of Compound 11134, tert-butyl 3-(phenyl(4-(5-(trifluoromethyl)-1,3,4-oxadiazol-2-yl)benzyl)carbamoyl)azetidine-1-carboxylate

[Step 1] Synthesis of tert-butyl 3-(phenylcarbamoyl)azetidine-1-carboxylate

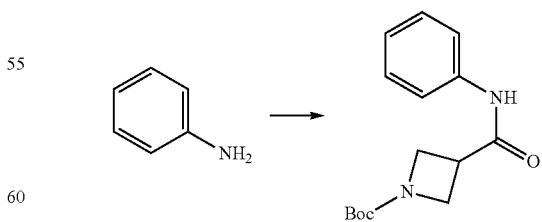

Aniline (1.961 mL, 21.475 mmol), 1-(tert-butoxycarbonyl)azetidine-3-carboxylic acid (4.321 g, 21.475 mmol), 1-ethyl-3-(3-dimethylaminopropyl)carbodiimide (EDC) (6.175 g, 32.213 mmol), 1H-benzo[d][1,2,3]triazol-1-ol (HOBt) (4.353 g, 32.213 mmol) and N,N-diisopropylethylamine (5.703 mL, 32.213 mmol) were dissolved in methylene chloride (150 mL) at room temperature, and the solution was stirred at the same temperature for 12 hours. Saturated aqueous ammonium chloride solution was added to the reaction mixture, followed by extraction with methylene chloride. The organic layer was washed with saturated aqueous sodium chloride solution, dried with magnesium sulfate anhydrous, filtered, and then concentrated under reduced pressure. The concentrate was purified by column chromatography (SiO$_2$, 120 g cartridge; ethyl acetate/hexane=from 5% to 50%) and concentrated to give the title compound (4.880 g, 82.2%) as a white solid.

[Step 2] Synthesis of tert-butyl 3-((4-(methoxycarbonyl)benzyl)(phenyl)carbamoyl)azetidine-1-carboxylate

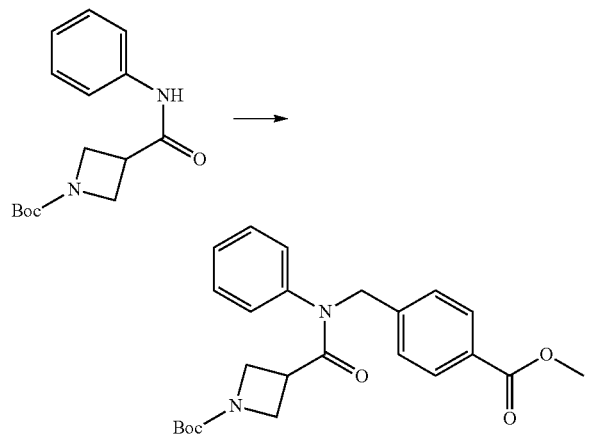

Tert-butyl 3-(phenylcarbamoyl)azetidine-1-carboxylate (1.000 g, 3.619 mmol) synthesized in step 1 was dissolved in tetrahydrofuran (70 mL), and sodium hydride (60.00%, 0.289 g, 7.237 mmol) was added slowly to the solution while the temperature was maintained at 0° C. The mixture was stirred for 20 minutes, and methyl 4-(bromomethyl)benzoate (0.829 g, 3.619 mmol) was added thereto, followed by additional stirring at 45° C. for 12 hours. The reaction mixture was cooled to room temperature, and then water (10 mL) was added to the reaction mixture at 0° C., followed by stirring for 5 minutes. After completion of the reaction, water was added to the reaction mixture, followed by extraction with ethyl acetate. The extract was filtered through a plastic filter to remove the solid residue and the aqueous layer, and then concentrated under reduced pressure. The concentrate was purified by column chromatography (SiO$_2$, 120 g cartridge; ethyl acetate/hexane=from 5% to 50%) and concentrated to give the title compound (1.200 g, 78.1%) as colorless oil.

[Step 3] Synthesis of tert-butyl 3-((4-(hydrazinecarbonyl)benzyl)(phenyl)carbamoyl)azetidine-1-carboxylate

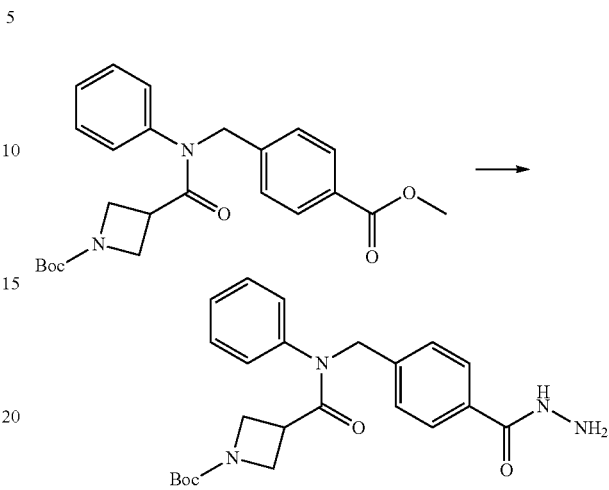

Tert-butyl3-((4-(methoxycarbonyl)benzyl)(phenyl)carbamoyl)azetidine-1-carboxylate (1.500 g, 3.534 mmol), synthesized in step 2, and hydrazine monohydrate (3.435 mL, 70.671 mmol), were mixed in ethanol (15 mL) at room temperature, and the mixture was heated by microwave irradiation at 120° C. for 1 hour, and then cooled to room temperature to terminate the reaction. The reaction mixture was concentrated under reduced pressure to remove the solvent, and water was added to concentrate, followed by extraction with methylene chloride. The organic layer was washed with saturated aqueous sodium chloride solution, dried with magnesium sulfate anhydrous, filtered, and then concentrated under reduced pressure. The title compound was used without further purification (1.400 g, 93.3%, white solid).

[Step 4] Synthesis of tert-butyl 3-(phenyl(4-(2-(2,2,2-trifluoroacetyl)hydrazine-1-carbonyl)benzyl)carbamoyl)azetidine-1-carboxylate

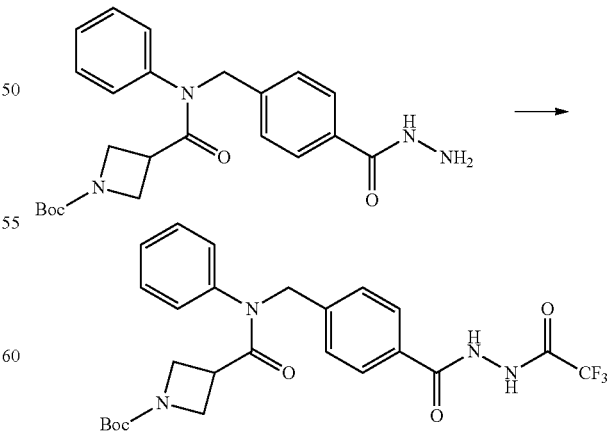

Tert-butyl3-((4-(hydrazinecarbonyl)benzyl)(phenyl)carbamoyl)azetidine-1-carboxylate (1.800 g, 4.240 mmol), synthesized in step 3, and triethylamine (0.710 mL, 5.088 mmol), were dissolved in N,N-dimethylformamide (30 mL) at room temperature, and trifluoroacetic anhydride (0.649 mL, 4.664 mmol) was added to the solution. The mixture was stirred at 90° C. for 12 hours, and then cooled to room temperature to terminate the reaction. Saturated aqueous ammonium chloride solution was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 5% to 60%) and concentrated to give the title compound (1.500 g, 68.0%) as a white solid.

[Step 5] Synthesis of Compound 11134

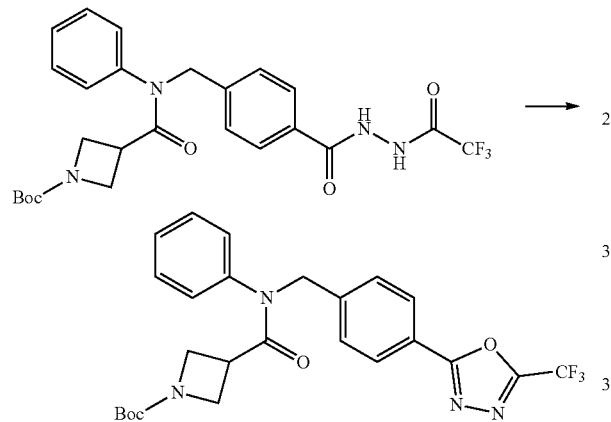

Tert-butyl3-(phenyl(4-(2-(2,2,2-trifluoroacetyl)hydrazine-1-carbonyl)benzyl)carbamoyl)azetidine-1-carboxylate (1.500 g, 2.882 mmol), synthesized in step 4, and 1-methoxy-N-triethylammoniosulfonyl-methanimidate (Burgess reagent, 1.030 g, 4.323 mmol) were mixed in tetrahydrofuran (15 mL) at room temperature, and the mixture was heated by microwave irradiation at 150° C. for 30 minutes, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 5% to 30%) and concentrated to give the title compound (1.200 g, 82.9%) as a white solid.

$^1$H NMR (700 MHz, CDCl$_3$) δ 8.02 (d, 2H, J=8.2 Hz), 7.44-7.31 (m, 5H), 6.97-6.86 (m, 2H), 4.97 (s, 2H), 4.11 (dd, 2H, J=9.9, 4.1 Hz), 3.65 (dd, 2H, J=11.2, 5.8 Hz), 3.34-3.14 (m, 1H), 1.40 (s, 9H); LRMS (ES) m/z 403.4 (M$^+$−100).

EXAMPLE 9: Synthesis of Compound 11135, tert-butyl 4-(phenyl(4-(5-(trifluoromethyl)-1,3,4-oxadiazol-2-yl)benzyl)carbamoyl)piperidine-1-carboxylate

[Step 1] Synthesis of tert-butyl 4-(phenylcarbamoyl)piperidine-1-carboxylate

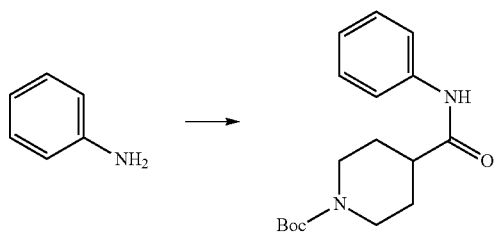 [SMILES: Nc1ccccc1 ; CC(C)(C)OC(=O)N1CCC(C(=O)Nc2ccccc2)CC1]

Aniline (1.961 mL, 21.475 mmol), 1-(tert-butoxycarbonyl)piperidine-4-carboxylic acid (4.924 g, 21.475 mmol), 1-ethyl-3-(3-dimethylaminopropyl)carbodiimide (EDC) (6.175 g, 32.213 mmol), 1H-benzo[d][1,2,3]triazol-1-ol (HOBt) (4.353 g, 32.213 mmol) and N,N-diisopropylethylamine (5.703 mL, 32.213 mmol) were dissolved in methylene chloride (150 mL) at room temperature, and the solution was stirred at the same temperature for 12 hours.

Saturated aqueous ammonium chloride solution was added to the reaction mixture, followed by extraction with methylene chloride. The organic layer was washed with saturated aqueous sodium chloride solution, dried with magnesium sulfate anhydrous, filtered, and then concentrated under reduced pressure. The concentrate was purified by column chromatography (SiO$_2$, 120 g cartridge; ethyl acetate/hexane=from 5% to 50%) and concentrated to give the title compound (5.040 g, 77.1%) as a white solid.

[Step 2] Synthesis of tert-butyl 4-((4-(methoxycarbonyl)benzyl)(phenyl)carbamoyl) piperidine-1-carboxylate

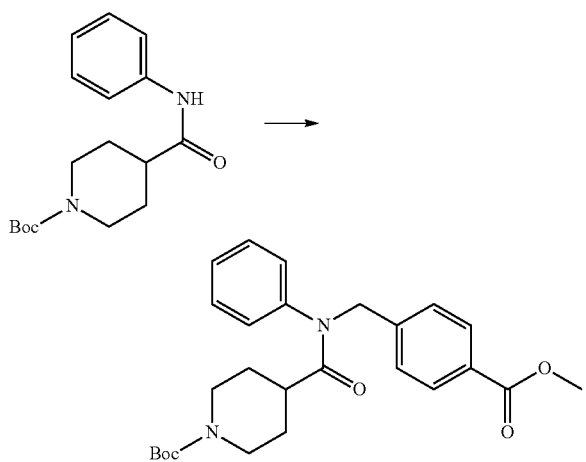

Tert-butyl 4-(phenylcarbamoyl)piperidine-1-carboxylate (1.000 g, 3.285 mmol) synthesized in step 1 was dissolved in tetrahydrofuran (70 mL), and sodium hydride (60.00%, 0.263 g, 6.571 mmol) was added slowly to the solution while the temperature was maintained at 0° C. The mixture was stirred for 20 minutes, and methyl 4-(bromomethyl)benzoate (0.753 g, 3.285 mmol) was added thereto, followed by additional stirring at 45° C. for 12 hours. The reaction mixture was cooled to room temperature, and then water (10 mL) was added to the reaction mixture at 0° C., followed by stirring for 5 minutes. After completion of the reaction, water was added to the reaction mixture, followed by extraction with ethyl acetate. The extract was filtered through a plastic filter to remove the solid residue and the aqueous layer, and then concentrated under reduced pressure. The concentrate was purified by column chromatography (SiO$_2$, 120 g cartridge; ethyl acetate/hexane=from 5% to 50%) and concentrated to give the title compound (1.300 g, 87.4%) as colorless oil.

[Step 3] Synthesis of tert-butyl 4-((4-(hydazinecarbonyl)benzyl)(phenyl)carbamoyl)piperidine-1-carboxylate

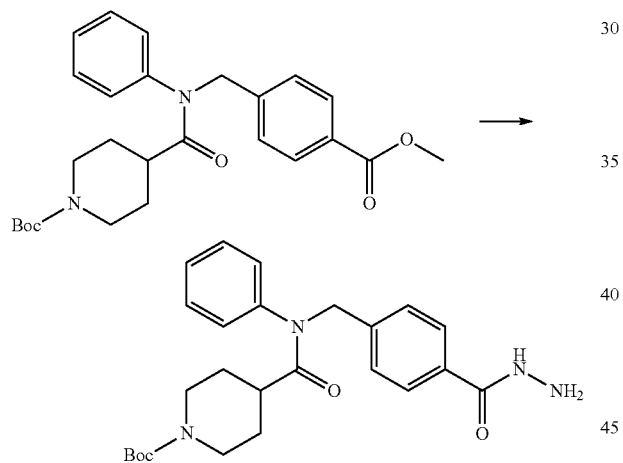

Tert-butyl 4-((4-(methoxycarbonyl)benzyl)(phenyl)carbamoyl)piperidine-1-carboxylate (1.500 g, 3.315 mmol), synthesized in step 2, and hydrazine monohydrate (3.319 g, 66.291 mmol), were mixed in ethanol (15 mL) at room temperature, and the mixture was heated at 120° C. for 1 hour, and then cooled to room temperature to terminate the reaction. The reaction mixture was concentrated under reduced pressure to remove the solvent, and water was added to the concentrate, followed by extraction with methylene chloride. The organic layer was washed with saturated aqueous sodium chloride solution, dried with magnesium sulfate anhydrous, filtered, and then concentrated under reduced pressure. The title compound was used without further purification (1.400 g, 93.3%, white solid).

[Step 4] Synthesis of tert-butyl 4-(phenyl(4-(2-(2,2,2-trifluoroacetyl)hydrazine-1-carbonyl)benzyl)carbamoyl)piperidine-1-carboxylate

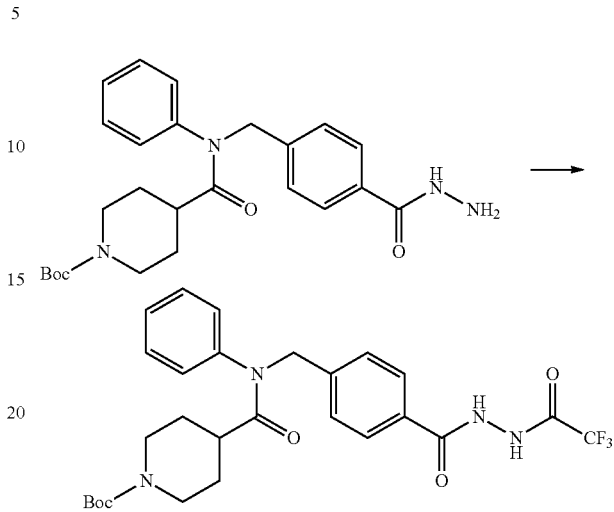

Tert-butyl 4-((4-(hydazinecarbonyl)benzyl)(phenyl)carbamoyl)piperidine-1-carboxylate (1.800 g, 3.977 mmol), synthesized in step 3, and triethylamine (0.666 mL, 4.773 mmol), were dissolved in N,N-dimethylformamide (30 mL) at room temperature, and trifluoroacetic anhydride (0.609 mL, 4.375 mmol) was added to the solution. The mixture was stirred at 90° C. for 12 hours, and then cooled to room temperature to terminate the reaction. Saturated aqueous ammonium chloride solution was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 5% to 60%) and concentrated to give the title compound (1.600 g, 73.3%) as a white solid.

[Step 5] Synthesis of Compound 11135

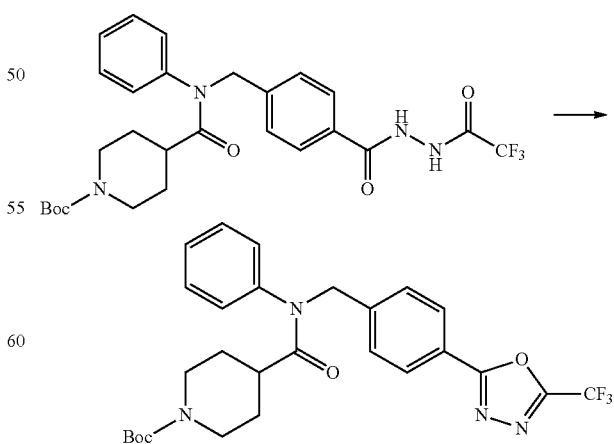

Tert-butyl 4-(phenyl(4-(2-(2,2,2-trifluoroacetyl)hydrazine-1-carbonyl)benzyl)carbamoyl)piperidine-1-carboxylate (1.600 g, 2.917 mmol), synthesized in step 4, and 1-methoxy-N-triethylammoniosulfonyl-methanimidate (Burgess reagent, 1.043 g, 4.375 mmol) were mixed in tetrahydrofuran (15 mL), and the mixture was heated by microwave irradiation at 150° C. for 30 minutes, and cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 5% to 30%) and concentrated to give the title compound (1.400 g, 90.5%) as a white solid.

$^1$H NMR (700 MHz, CDCl$_3$) δ 8.03 (d, 2H, J=8.0 Hz), 7.43-7.32 (m, 5H), 7.00 (d, 2H, J=7.1 Hz), 4.96 (d, 2H, J=20.2 Hz), 4.15-3.93 (m, 2H), 2.45 (s, 2H), 2.34 (t, 1H, J=11.3 Hz), 1.77 (qd, 2H, J=12.8, 4.0 Hz), 1.60 (d, 2H, J=12.7 Hz), 1.44 (s, 9H); LRMS (ES) m/z 531.4 (M$^+$+1).

EXAMPLE 10: Synthesis of Compound 11136, N-phenyl-N-(4-(5-(trifluoromethyl)-1,3,4-oxadiazol-2-yl)benzyl)azetidine-3-carboxamide hydrochloride

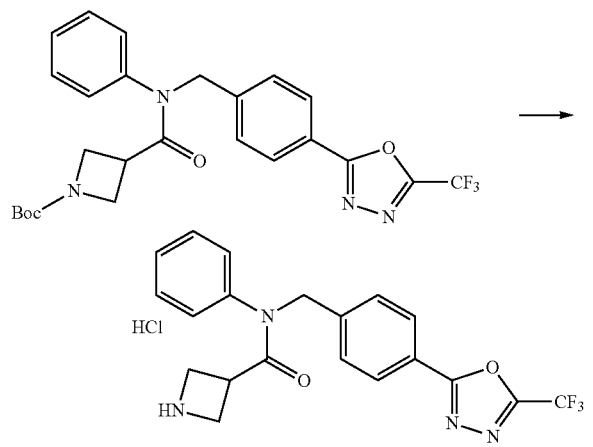

Tert-butyl 3-(phenyl(4-(5-(trifluoromethyl)-1,3,4-oxadiazol-2-yl)benzyl)carbamoyl)azetidine-1-carboxylate (1.100 g, 2.189 mmol) synthesized in Example 8 was dissolved in dichloromethane (50 mL), and hydrochloric acid (4.00 M solution in dioxane, 2.736 mL, 10.945 mmol) was added to the solution at 0° C., followed by stirring at room temperature for 12 hours. The reaction mixture was concentrated under reduced pressure to remove the solvent, and the concentrate was suspended in diethyl ether (50 mL) and filtered. The obtained solid was washed with diethyl ether and dried to give the title compound (0.920 g, 95.8%) as a white solid.

$^1$H NMR (700 MHz, CDCl$_3$+MeOD) δ 7.96 (dd, 2H, J=45.0, 36.1 Hz), 7.35 (ddd, 5H, J=40.2, 37.9, 10.0 Hz), 6.99 (d, 2H, J=77.6 Hz), 5.12-4.80 (m, 1H), 4.33 (s, 2H), 3.78 (d, 2H, J=25.5 Hz), 3.30 (d, 1H, J=120.8 Hz), 2.37 (s, 2H); LRMS (ES) m/z 403.0 (M$^+$+1).

EXAMPLE 11: Synthesis of Compound 11137, N-phenyl-N-(4-(5-(trifluoromethyl)-1,3,4-oxadiazol-2-yl)benzyl)piperidine-4-carboxamide hydrochloride

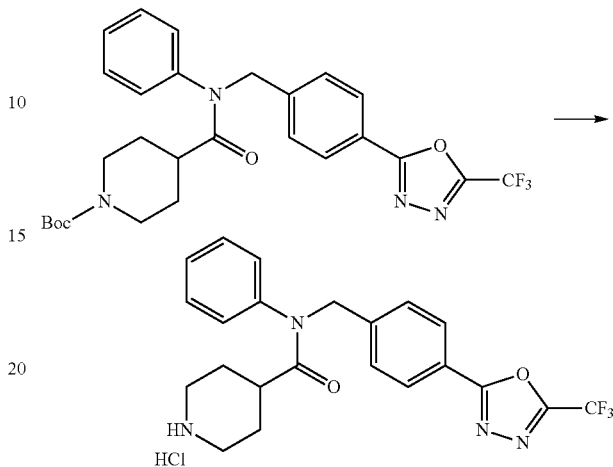

Tert-butyl 4-(phenyl(4-(5-(trifluoromethyl)-1,3,4-oxadiazol-2-yl)benzyl)carbamoyl)piperidine-1-carboxylate (1.300 g, 2.450 mmol) synthesized in Example 9 was dissolved in dichloromethane (50 mL), and hydrochloric acid (4.00 M solution in dioxane, 3.063 mL, 12.251 mmol) was added to the solution at 0° C., followed by stirring at room temperature for 12 hours. The reaction mixture was concentrated under reduced pressure to remove the solvent, and the concentrate was suspended in diethyl ether (50 mL) and filtered. The obtained solid was washed with diethyl ether and dried to give the title compound (1.080 g, 94.4%) as a white solid.

$^1$H NMR (700 MHz, CDCl$_3$+MeOD) δ 7.91 (dd, 2H, J=103.5, 50.3 Hz), 7.72-7.19 (m, 5H), 6.95 (s, 2H), 5.24-4.68 (m, 2H), 4.03-3.27 (m, 2H), 3.04-2.64 (m, 2H), 2.49 (s, 2H), 2.09 (s, 2H), 1.78 (d, 2H, J=93.2 Hz); LRMS (ES) m/z 431.4 (M$^+$+1).

EXAMPLE 12: Synthesis of Compound 11138, 1-methyl-N-phenyl-N-(4-(5-(trifluoromethyl)-1,3,4-oxadiazol-2-yl)benzyl)azetidine-3-carboxamide

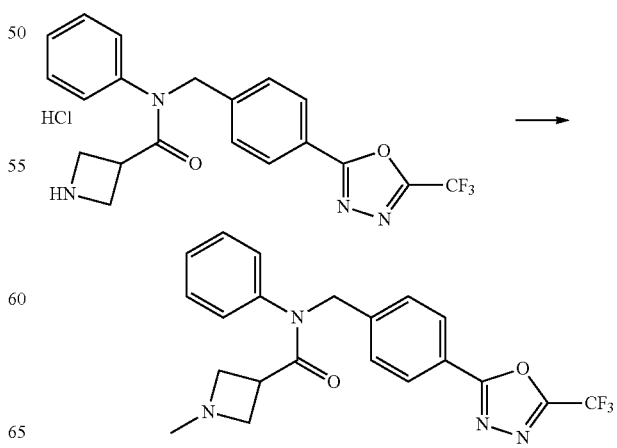

N-phenyl-N-(4-(5-(trifluoromethyl)-1,3,4-oxadiazol-2-yl)benzyl)azetidine-3-carboxamide hydrochloride (0.100 g, 0.228 mmol), synthesized in Example 10, and formaldehyde (37.00% solution in water, 0.025 mL, 0.342 mmol), were dissolved in dichloromethane (10 mL) at room temperature, and sodium triacetoxyborohydride (0.072 g, 0.342 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 15%) and concentrated to give the title compound (0.038 g, 40.0%) as a white solid.

$^1$H NMR (400 MHz, CDCl$_3$) δ 8.02 (d, 2H, J=8.2 Hz), 7.52-7.30 (m, 6H), 6.90 (dd, 2H, J=6.5, 2.8 Hz), 4.92 (d, 2H, J=19.3 Hz), 3.51-3.14 (m, 5H), 2.35 (s, 3H); LRMS (ES) m/z 417.3 (M$^+$+1).

EXAMPLE 13: Synthesis of Compound 11139, 1-ethyl-N-phenyl-N-(4-(5-(trifluoromethyl)-1,3,4-oxadiazol-2-yl)benzyl)azetidine-3-carboxamide

[Step 1] Synthesis of Compound 11139

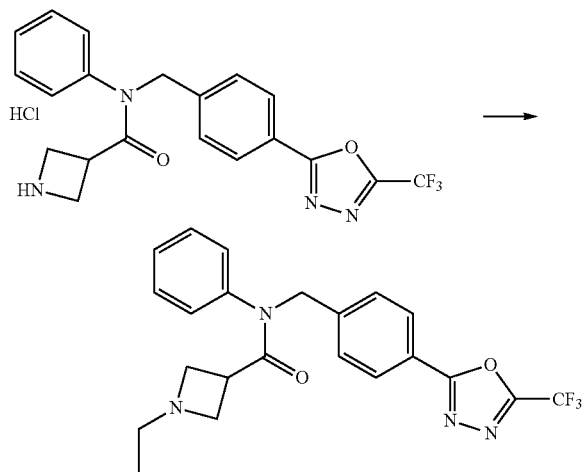

N-phenyl-N-(4-(5-(trifluoromethyl)-1,3,4-oxadiazol-2-yl)benzyl)azetidine-3-carboxamide hydrochloride (0.100 g, 0.228 mmol), synthesized in Example 10, and acetaldehyde (0.019 mL, 0.342 mmol) were dissolved in dichloromethane (10 mL) at room temperature, and sodium triacetoxyborohydride (0.072 g, 0.342 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 15%) and concentrated to give the title compound (0.042 g, 42.8%) as a white solid.

$^1$H NMR (400 MHz, CDCl$_3$) δ 8.07-7.97 (m, 2H), 7.34 (dt, 5H, J=22.3, 14.0 Hz), 6.95-6.83 (m, 2H), 4.92 (d, 2H, J=19.5 Hz), 3.55-3.08 (m, 5H), 2.58 (q, 2H, J=7.2 Hz), 0.96 (t, 3H, J=7.2 Hz); LRMS (ES) m/z 431.3 (M$^+$+1).

EXAMPLE 14: Synthesis of Compound 11140, 1-methyl-N-phenyl-N-(4-(5-(trifluoromethyl)-1,3,4-oxadiazol-2-yl)benzyl)piperidine-4-carboxamide

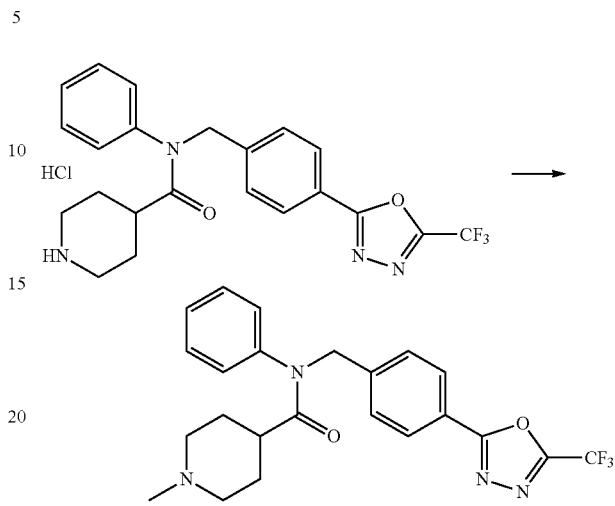

N-phenyl-N-(4-(5-(trifluoromethyl)-1,3,4-oxadiazol-2-yl)benzyl)piperidine-4-carboxamide hydrochloride (0.100 g, 0.214 mmol), synthesized in Example 11, and formaldehyde (37.00% solution in water, 0.024 mL, 0.321 mmol) were dissolved in dichloromethane (10 mL) at room temperature, and sodium triacetoxyborohydride (0.068 g, 0.321 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 15%) and concentrated to give the title compound (0.072 g, 75.6%) as a white solid.

$^1$H NMR (400 MHz, CDCl$_3$) δ 8.02 (d, 2H, J=8.3 Hz), 7.43-7.30 (m, 5H), 6.97 (dd, 2H, J=6.4, 3.2 Hz), 4.94 (s, 2H), 2.78 (d, 2H, J=113.6 Hz), 2.16 (dd, 4H, J=68.5, 23.5 Hz), 1.96 (dt, 3H, J=20.3, 13.8 Hz), 1.73 (s, 2H); LRMS (ES) m/z 431.3 (M$^+$+1).

EXAMPLE 15: Synthesis of Compound 11141, 1-ethyl-N-phenyl-N-(4-(5-(trifluoromethyl)-1,3,4-oxadiazol-2-yl)benzyl)piperidine-4-carboxamide

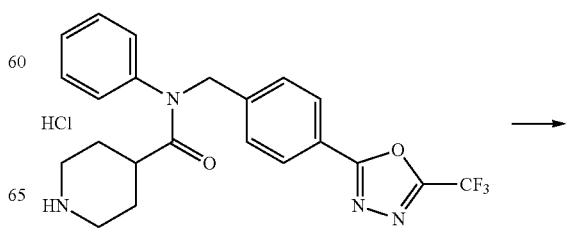

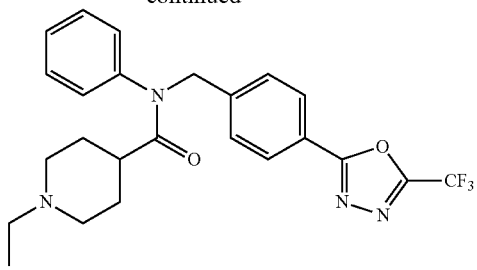

N-phenyl-N-(4-(5-(trifluoromethyl)-1,3,4-oxadiazol-2-yl)benzyl)piperidine-4-carboxamide hydrochloride (0.100 g, 0.214 mmol), synthesized in Example 11, and acetaldehyde (0.018 mL, 0.321 mmol) were dissolved in dichloromethane (10 mL) at room temperature, and sodium triacetoxyborohydride (0.068 g, 0.321 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 15%) and concentrated to give the title compound (0.065 g, 66.2%) as colorless oil.

$^1$H NMR (400 MHz, CDCl$_3$) δ 8.02 (d, 2H, J=8.3 Hz), 7.43-7.31 (m, 5H), 6.97 (dd, 2H, J=6.6, 2.9 Hz), 4.94 (s, 2H), 3.04 (s, 2H), 2.40 (d, 3H, J=75.4 Hz), 2.02-1.66 (m, 6H), 1.15 (dd, 3H, J=32.3, 25.8 Hz); LRMS (ES) m/z 459.34 (M$^+$+1)

EXAMPLE 16: Synthesis of Compound 11142, 1-isopropyl-N-phenyl-N-(4-(5-(trifluoromethyl)-1,3,4-oxadiazol-2-yl)benzyl)azetidine-3-carboxamide

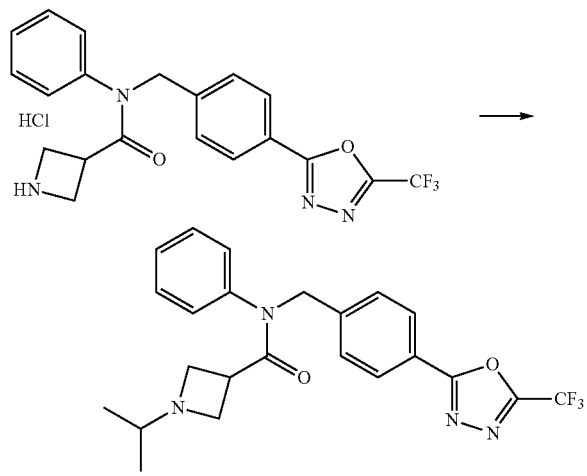

N-phenyl-N-(4-(5-(trifluoromethyl)-1,3,4-oxadiazol-2-yl)benzyl)azetidine-3-carboxamide hydrochloride (0.100 g, 0.228 mmol), synthesized in Example 10, and acetone (0.025 mL, 0.342 mmol) were dissolved in dichloromethane (10 mL) at room temperature, and sodium triacetoxyborohydride (0.072 g, 0.342 mmol) was added to the solution, followed by stirring at the same temperature. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.056 g, 55.3%) as a white solid.

$^1$H NMR (400 MHz, CDCl$_3$) δ 8.02 (d, 2H, J=8.2 Hz), 7.42-7.28 (m, 5H), 6.91 (dd, 2H, J=6.4, 3.1 Hz), 4.94 (s, 2H), 3.31 (d, 5H, J=21.1 Hz), 2.50 (s, 1H), 0.94 (d, 6H, J=6.1 Hz); LRMS (ES) m/z 445.3 (M$^+$+1).

EXAMPLE 17: Synthesis of Compound 11143, 1-isopropyl-N-phenyl-N-(4-(5-(trifluoromethyl)-1,3,4-oxadiazol-2-yl)benzyl)piperidine-4-carboxamide

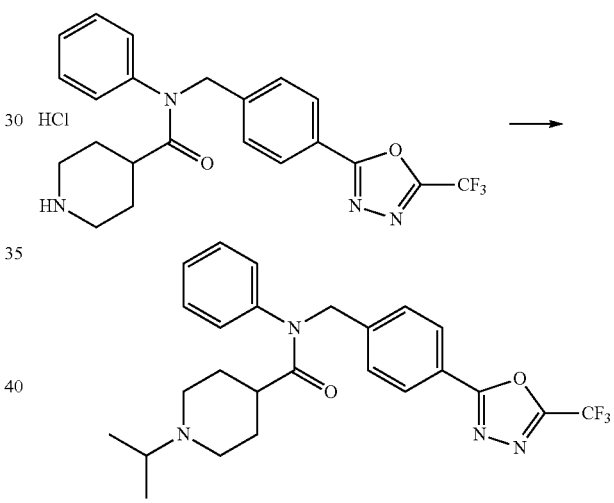

N-phenyl-N-(4-(5-(trifluoromethyl)-1,3,4-oxadiazol-2-yl)benzyl)piperidine-4-carboxamide hydrochloride (0.100 g, 0.214 mmol), synthesized in Example 11, and acetone (0.024 mL, 0.321 mmol) were dissolved in dichloromethane (10 mL) at room temperature, and sodium triacetoxyborohydride (0.068 g, 0.321 mmol) was added to the solution, followed by stirring at the same temperature. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.021 g, 20.8%) as a white solid.

$^1$H NMR (400 MHz, CDCl$_3$) δ 8.03 (d, 2H, J=8.3 Hz), 7.36 (dd, 5H, J=7.4, 4.2 Hz), 6.95 (dd, 2H, J=6.5, 3.1 Hz), 4.92 (s, 2H), 3.37 (d, 3H, J=63.0 Hz), 2.75 (d, 3H, J=67.4 Hz), 2.22 (s, 1H), 1.96 (s, 2H, J=30.4 Hz), 1.25 (s, 6H, J=169.3 Hz); LRMS (ES) m/z 473.3 (M$^+$+1).

EXAMPLE 18: Synthesis of Compound 11157, N-phenyl-1-propionyl-N-(4-(5-(trifluoromethyl)-1,3,4-oxadiazol-2-yl)benzyl)azetidine-3-carboxamide

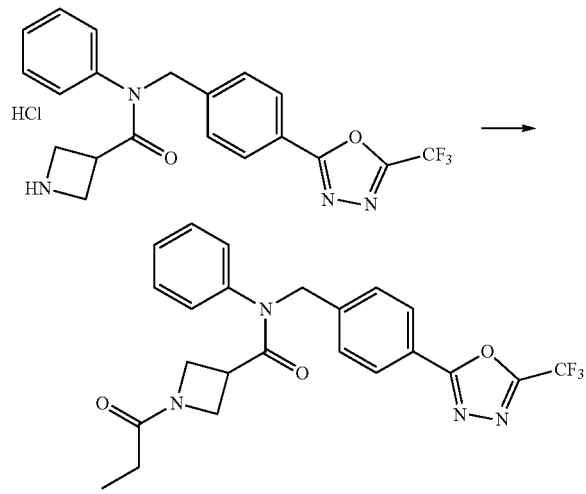

N-phenyl-N-(4-(5-(trifluoromethyl)-1,3,4-oxadiazol-2-yl)benzyl)azetidine-3-carboxamide hydrochloride (0.080 g, 0.182 mmol), synthesized in Example 10, and N,N-diisopropylethylamine (0.063 mL, 0.365 mmol) were dissolved in dichloromethane (10 mL) at room temperature, and propionyl chloride (0.018 mL, 0.201 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.008 g, 9.6%) as colorless oil.

$^1$H NMR (400 MHz, CDCl$_3$) δ 8.03 (d, 2H, J=8.2 Hz), 7.45-7.29 (m, 6H), 6.92 (dd, 2H, J=6.5, 2.8 Hz), 4.98 (s, 2H), 4.37-4.08 (m, 2H), 3.79 (d, 2H, J=6.7 Hz), 3.30 (ddd, 1H, J=15.1, 8.8, 6.4 Hz), 2.15-1.94 (m, 3H), 1.25 (s, 1H, J=20.0 Hz), 1.09 (t, 3H, J=7.5 Hz); LRMS (ES) m/z 459.3 (M$^+$+1).

EXAMPLE 19: Synthesis of Compound 11158, 1-isobutyryl-N-phenyl-N-(4-(5-(trifluoromethyl)-1,3,4-oxadiazol-2-yl)benzyl)azetidine-3-carboxamide

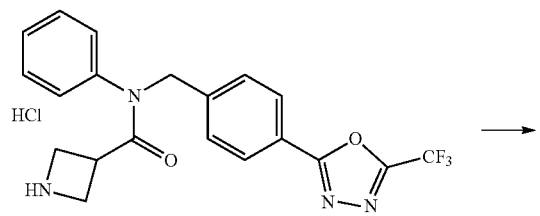

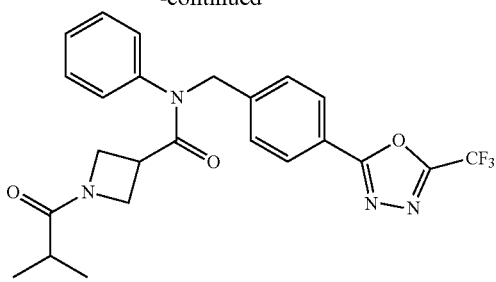

N-phenyl-N-(4-(5-(trifluoromethyl)-1,3,4-oxadiazol-2-yl)benzyl)azetidine-3-carboxamide hydrochloride (0.080 g, 0.182 mmol), synthesized in Example 10, and N,N-diisopropylethylamine (0.063 mL, 0.365 mmol) were dissolved in dichloromethane (10 mL) at room temperature, and isobutyryl chloride (0.021 mL, 0.201 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.025 g, 29.0%) as colorless oil.

$^1$H NMR (400 MHz, CDCl$_3$) δ 8.03 (d, 2H, J=8.3 Hz), 7.45-7.28 (m, 5H), 6.92 (dd, 2H, J=6.3, 3.2 Hz), 5.04-4.87 (m, 2H), 4.53-4.16 (m, 1H), 3.95-3.59 (m, 2H), 3.36-3.20 (m, 1H), 2.39 (td, 2H, J=13.6, 6.8 Hz), 1.07 (dd, 6H, J=16.3, 6.8 Hz); LRMS (ES) m/z 473.3 (M$^+$+1).

EXAMPLE 20: Synthesis of Compound 11159, N-phenyl-1-(2,2,2-trifluoroacetyl)-N-(4-(5-(trifluoromethyl)-1,3,4-oxadiazol-2-yl)benzyl)azetidine-3-carboxamide

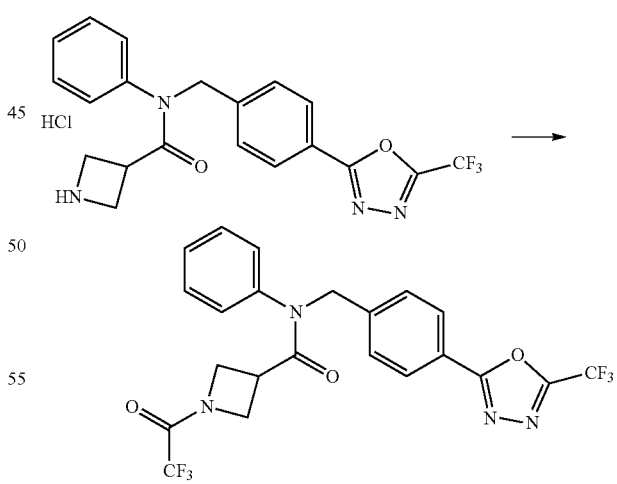

N-phenyl-N-(4-(5-(trifluoromethyl)-1,3,4-oxadiazol-2-yl)benzyl)azetidine-3-carboxamide hydrochloride (0.080 g, 0.182 mmol), synthesized in Example 10, and N,N-diisopropylethylamine (0.063 mL, 0.365 mmol) were dissolved in dichloromethane (10 mL) at room temperature, and 2,2,2-trifluoroacetic anhydride (0.028 mL, 0.201 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.013 g, 14.3%) as colorless oil.

$^1$H NMR (400 MHz, CDCl$_3$) δ 8.04 (d, 2H, J=8.2 Hz), 7.44-7.31 (m, 5H), 6.96-6.83 (m, 2H), 4.97 (t, 2H, J=8.2 Hz), 4.72-4.62 (m, 1H), 4.14 (dt, 2H, J=14.4, 8.2 Hz), 3.89-3.76 (m, 1H), 3.50-3.36 (m, 1H); LRMS (ES) m/z 499.3 (M$^+$+1).

EXAMPLE 21: Synthesis of Compound 11160, 1-(methylsulfonyl)-N-phenyl-N-(4-(5-(trifluoromethyl)-1,3,4-oxadiazol-2-yl)benzyl)azetidine-3-carboxamide

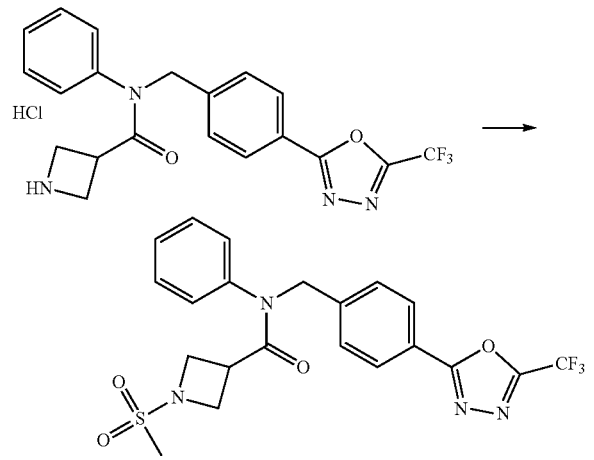

N-phenyl-N-(4-(5-(trifluoromethyl)-1,3,4-oxadiazol-2-yl)benzyl)azetidine-3-carboxamide hydrochloride (0.080 g, 0.182 mmol), synthesized in Example 10, and N,N-diisopropylethylamine (0.064 mL, 0.365 mmol) were dissolved in dichloromethane (10 mL) at room temperature, and methanesulfonyl chloride (0.016 mL, 0.201 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.018 g, 20.6%) as a white solid.

$^1$H NMR (400 MHz, CDCl$_3$) δ 8.08-7.98 (m, 2H), 7.43-7.31 (m, 5H), 6.91 (ddd, 2H, J=5.5, 4.6, 2.9 Hz), 4.96 (s, 2H), 4.12 (dd, 2H, J=15.2, 7.3 Hz), 3.72-3.62 (m, 2H), 3.38-3.26 (m, 1H), 2.89 (d, 3H, J=4.0 Hz); LRMS (ES) m/z 481.2 (M$^+$+1).

EXAMPLE 22: Synthesis of Compound 11161, 1-acetyl-N-phenyl-N-(4-(5-(trifluoromethyl)-1,3,4-oxadiazol-2-yl)benzyl)piperidine-4-carboxamide

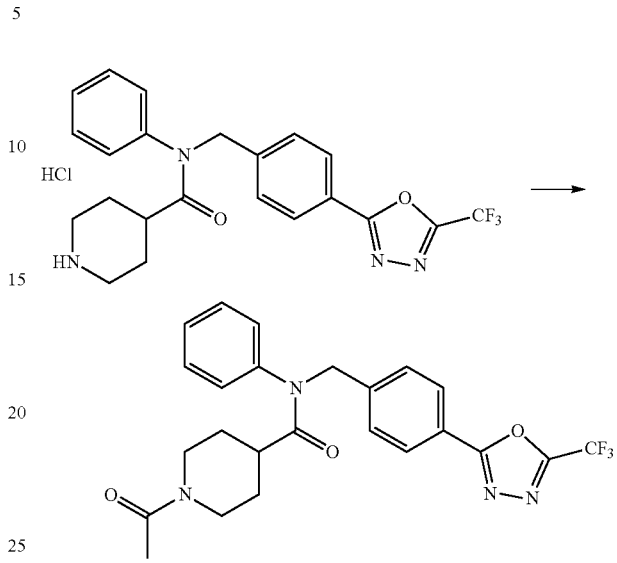

N-phenyl-N-(4-(5-(trifluoromethyl)-1,3,4-oxadiazol-2-yl)benzyl)piperidine-4-carboxamide hydrochloride (0.080 g, 0.171 mmol), synthesized in Example 11, and N,N-diisopropylethylamine (0.059 mL, 0.343 mmol) were dissolved in dichloromethane (10 mL) at room temperature, and acetyl chloride (0.013 mL, 0.188 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.052 g, 64.2%) as a white solid.

$^1$H NMR (400 MHz, CDCl$_3$) δ 8.02 (d, 2H, J=8.3 Hz), 7.37 (dd, 5H, J=5.4, 3.0 Hz), 6.99 (dd, 2H, J=6.6, 2.9 Hz), 4.94 (s, 2H), 4.51 (s, 1H), 3.77 (s, 1H), 2.80 (s, 1H), 2.38 (ddd, 2H, J=30.5, 20.3, 9.3 Hz), 2.04 (s, 3H, J=9.5, 4.9 Hz), 1.88-1.53 (m, 4H); LRMS (ES) m/z 473.3 (M$^+$+1).

EXAMPLE 23: Synthesis of Compound 11162, N-phenyl-1-propionyl-N-(4-(5-(trifluoromethyl)-1,3,4-oxadiazol-2-yl)benzyl)piperidine-4-carboxamide

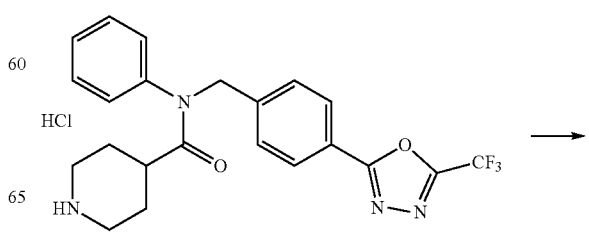

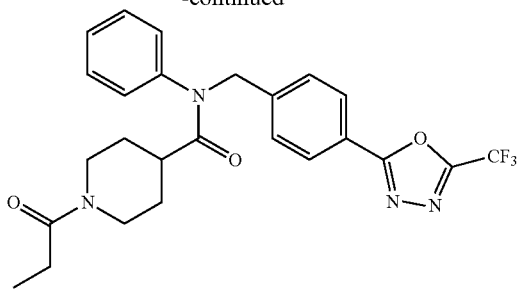

N-phenyl-N-(4-(5-(trifluoromethyl)-1,3,4-oxadiazol-2-yl)benzyl)piperidine-4-carboxamide hydrochloride (0.080 g, 0.171 mmol), synthesized in Example 11, and N,N-diisopropylethylamine (0.059 mL, 0.343 mmol) were dissolved in dichloromethane (10 mL) at room temperature, and propionyl chloride (0.016 mL, 0.188 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.061 g, 73.2%) as a white solid.

$^1$H NMR (400 MHz, CDCl$_3$) δ 8.02 (d, 2H, J=8.0 Hz), 7.37 (dd, 5H, J=5.0, 3.0 Hz), 6.99 (dd, 2H, J=6.2, 2.6 Hz), 4.94 (s, 2H), 4.51 (s, 1H), 3.85 (s, 1H), 2.36 (ddd, 4H, J=21.9, 14.8, 9.1 Hz), 1.90-1.52 (m, 5H), 1.12 (t, 3H, J=7.5 Hz); LRMS (ES) m/z 487.4 (M$^+$+1).

EXAMPLE 24: Synthesis of Compound 11163, 1-isobutyryl-N-phenyl-N-(4-(5-(trifluoromethyl)-1,3,4-oxadiazol-2-yl)benzyl)piperidine-4-carboxamide

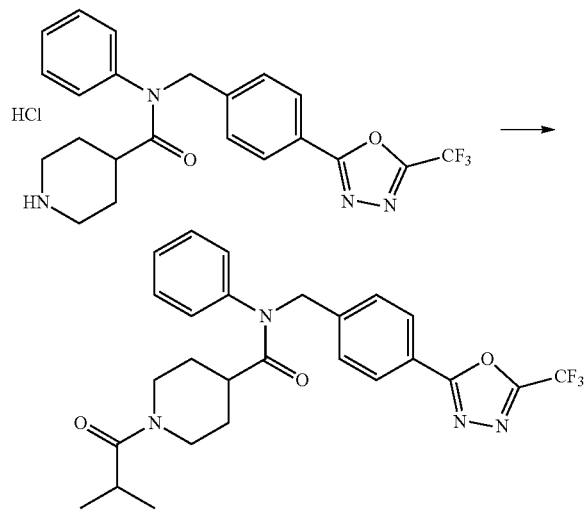

N-phenyl-N-(4-(5-(trifluoromethyl)-1,3,4-oxadiazol-2-yl)benzyl)piperidine-4-carboxamide hydrochloride (0.080 g, 0.171 mmol), synthesized in Example 11, and N,N-diisopropylethylamine (0.059 mL, 0.343 mmol) were dissolved in dichloromethane (10 mL) at room temperature, and isobutyryl chloride (0.020 mL, 0.188 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.064 g, 74.6%) as colorless oil.

$^1$H NMR (400 MHz, CDCl$_3$) δ 8.02 (d, 2H, J=8.3 Hz), 7.37 (dd, 5H, J=5.3, 3.1 Hz), 6.99 (dd, 2H, J=6.2, 3.2 Hz), 4.94 (s, 2H), 2.74 (dt, 2H, J=13.4, 6.7 Hz), 2.48-2.26 (m, 2H), 1.90-1.49 (m, 6H), 1.10 (t, 6H, J=11.3 Hz); LRMS (ES) m/z 501.3 (M$^+$+1).

EXAMPLE 25: Synthesis of Compound 11164, N-phenyl-1-(2,2,2-trifluoroacetyl)-N-(4-(5-(trifluoromethyl)-1,3,4-oxadiazol-2-yl)benzyl)piperidine-4-carboxamide

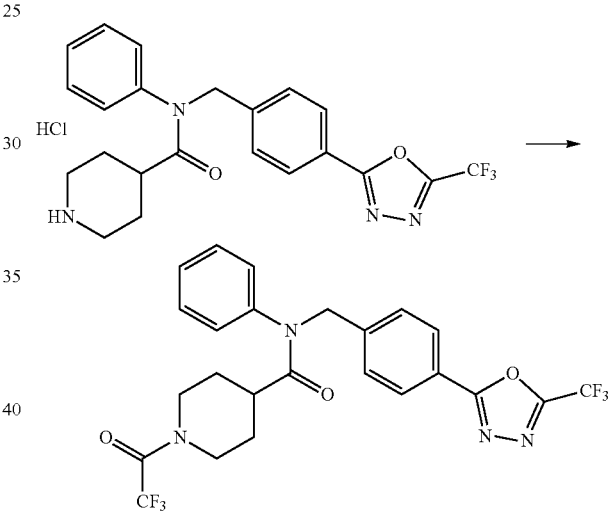

N-phenyl-N-(4-(5-(trifluoromethyl)-1,3,4-oxadiazol-2-yl)benzyl)piperidine-4-carboxamide hydrochloride (0.080 g, 0.171 mmol), synthesized in Example 11, and N,N-diisopropylethylamine (0.059 mL, 0.343 mmol) were dissolved in dichloromethane (10 mL) at room temperature, and 2,2,2-trifluoroacetic anhydride (0.027 mL, 0.188 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.061 g, 67.6%) as colorless oil.

$^1$H NMR (400 MHz, CDCl$_3$) δ 8.03 (d, 2H, J=8.2 Hz), 7.38 (t, 5H, J=7.1 Hz), 7.05-6.87 (m, 2H), 4.94 (q, 2H, J=14.5 Hz), 4.42 (d, 1H, J=13.2 Hz), 3.97 (d, 1H, J=14.3 Hz), 2.93 (t, 1H, J=13.1 Hz), 2.62 (t, 1H, J=12.0 Hz), 2.50 (dd, 1H, J=12.5, 8.5 Hz), 1.89 (dd, 2H, J=24.8, 13.1 Hz), 1.72 (d, 2H, J=14.0 Hz); LRMS (ES) m/z 527.3 (M$^+$+1).

EXAMPLE 26: Synthesis of Compound 11165, 1-(methylsulfonyl)-N-phenyl-N-(4-(5-(trifluoromethyl)-1,3,4-oxadiazol-2-yl)benzyl)piperidine-4-carboxamide

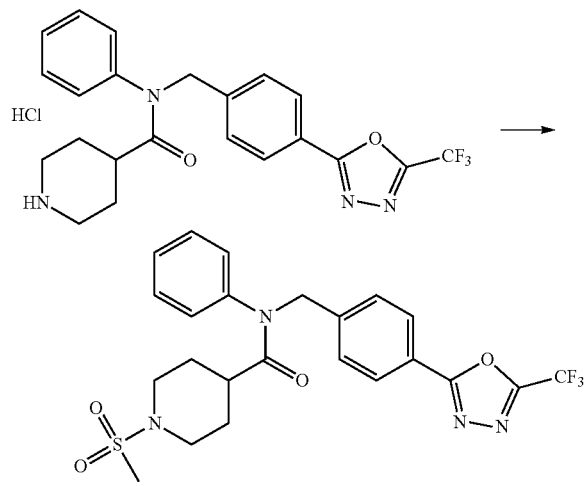

N-phenyl-N-(4-(5-(trifluoromethyl)-1,3,4-oxadiazol-2-yl)benzyl)piperidine-4-carboxamide hydrochloride (0.080 g, 0.171 mmol), synthesized in Example 11, and N,N-diisopropylethylamine (0.060 mL, 0.343 mmol) were dissolved in dichloromethane (10 mL) at room temperature, and methanesulfonyl chloride (0.015 mL, 0.188 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.070 g, 80.3%) as a white solid.

$^1$H NMR (400 MHz, CDCl$_3$) δ 8.02 (d, 2H, J=8.1 Hz), 7.37 (dd, 5H, J=5.3, 2.8 Hz), 6.98 (dd, 2H, J=6.3, 2.7 Hz), 4.94 (s, 2H), 3.80-3.62 (m, 2H), 2.72 (s, 3H), 2.51 (dd, 2H, J=16.4, 7.1 Hz), 2.38-2.22 (m, 1H), 2.02-1.84 (m, 2H), 1.78-1.66 (m, 2H); LRMS (ES) m/z 509.2 (M$^+$+1).

EXAMPLE 27: Synthesis of Compound 11166, 1-benzyl-N-phenyl-N-(4-(5-(trifluoromethyl)-1,3,4-oxadiazol-2-yl)benzyl)piperidine-4-carboxamide

[Step 1] Synthesis of Compound 11166

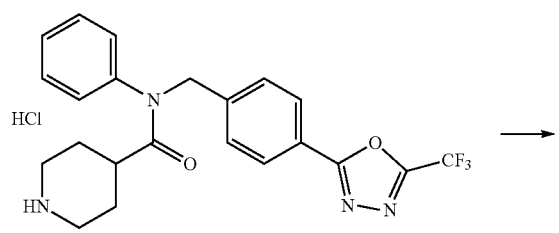

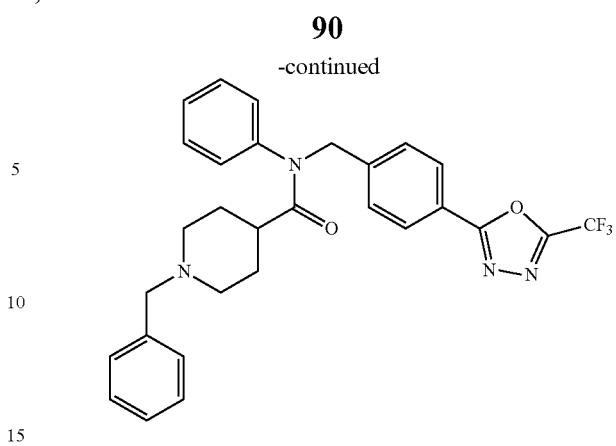

N-phenyl-N-(4-(5-(trifluoromethyl)-1,3,4-oxadiazol-2-yl)benzyl)piperidine-4-carboxamide hydrochloride (0.080 g, 0.171 mmol), synthesized in Example 11, and N,N-diisopropylethylamine (0.059 mL, 0.343 mmol) were dissolved in dichloromethane (10 mL) at room temperature, and (bromomethyl)benzene (0.024 mL, 0.206 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.060 g, 67.3%) as a white solid.

$^1$H NMR (400 MHz, CDCl$_3$) δ 8.01 (d, 2H, J=8.0 Hz), 7.44-7.24 (m, 10H), 7.02-6.84 (m, 2H), 4.94 (s, 2H), 3.41 (s, 2H), 2.83 (s, 2H), 2.17 (s, 1H), 1.93 (d, 2H, J=10.8 Hz), 1.64 (d, 5H, J=36.5 Hz); LRMS (ES) m/z 521.4 (M$^+$+1).

EXAMPLE 28: Synthesis of Compound 11187, N1-acetyl-N-phenyl-N-(4-(5-(trifluoromethyl)-1,3,4-oxadiazol-2-yl)benzyl)azetidine-3-carboxamide

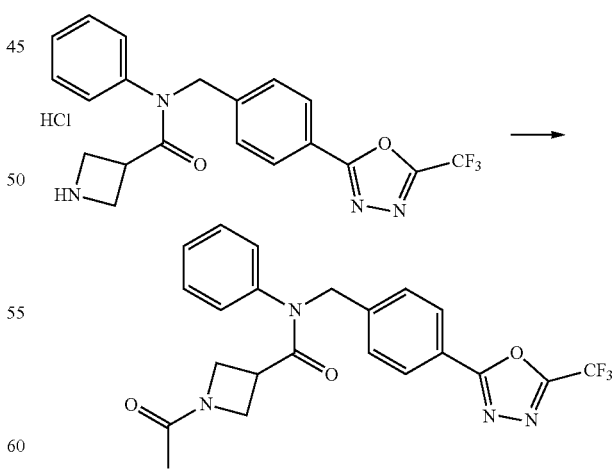

N-phenyl-N-(4-(5-(trifluoromethyl)-1,3,4-oxadiazol-2-yl)benzyl)azetidine-3-carboxamide hydrochloride (0.080 g, 0.182 mmol), synthesized in Example 10, and N,N-diisopropylethylamine (0.063 mL, 0.365 mmol) were dissolved in dichloromethane (10 mL) at room temperature, and acetyl chloride (0.014 mL, 0.201 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$ plate, 20×20×1 mm; 100%-aqueous ethyl acetate solution/hexane=100%)) and concentrated to give the title compound (0.020 g, 24.7%) as colorless oil.

$^1$H NMR (400 MHz, CDCl$_3$) δ 8.03 (d, 2H, J=8.1 Hz), 7.44-7.28 (m, 5H), 6.91 (dd, 2H, J=6.5, 2.4 Hz), 4.97 (s, 2H), 4.44 (s, 1H), 3.92 (dd, 3H, J=107.3, 55.1 Hz), 3.29 (ddd, 1H, J=15.2, 8.8, 6.3 Hz), 1.81 (d, 3H, J=6.8 Hz); LRMS (ES) m/z 445.3 (M$^+$+1).

EXAMPLE 29: Synthesis of Compound 11188, N-(2-fluoro-4-(5-(trifluoromethyl)-1,3,4-oxadiazol-2-yl)benzyl)-N-(3-fluorophenyl)isonicotinamide

[Step 1] Synthesis of methyl 3-fluoro-4-(((3-fluorophenyl)amino)methyl)benzoate

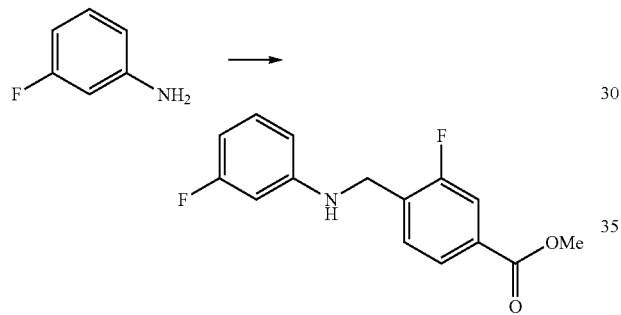

3-Fluoroaniline (0.200 g, 1.800 mmol), methyl 4-(bromomethyl)-3-fluorobenzoate (0.445 g, 1.800 mmol) and calcium carbonate (0.497 g, 3.600 mmol) were dissolved in acetonitrile (15 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 50%) and concentrated to give the title compound (0.324 g, 64.9%) as colorless oil.

[Step 2] Synthesis of methyl 3-fluoro-4-((N-(3-fluorophenyl)isonicotinamido)methyl)benzoate

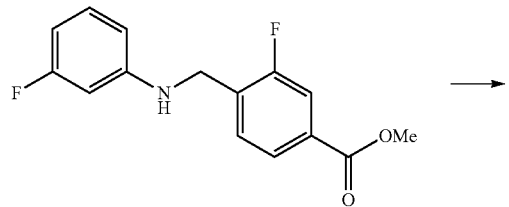

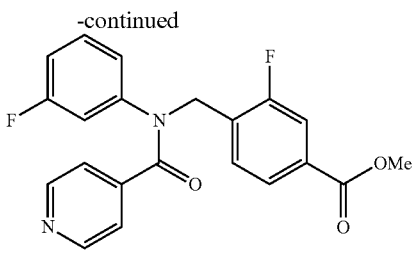

Methyl 3-fluoro-4-(((3-fluorophenyl)amino)methyl)benzoate (0.320 g, 1.154 mmol) synthesized in step 1, isonicotinoyl hydrochloride (0.247 g, 1.385 mmol) and N,N-diisopropylethylamine (0.398 mL, 2.308 mmol) were dissolved in dichloromethane (10 mL) at room temperature, and the solution was stirred at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 100%) and concentrated to give the title compound (0.300 g, 68.0%) as a yellow foam solid.

[Step 3] Synthesis of N-(2-fluoro-4-(hydrazinecarbonyl)benzyl)-N-(3-fluorophenyl)isonicotinamide

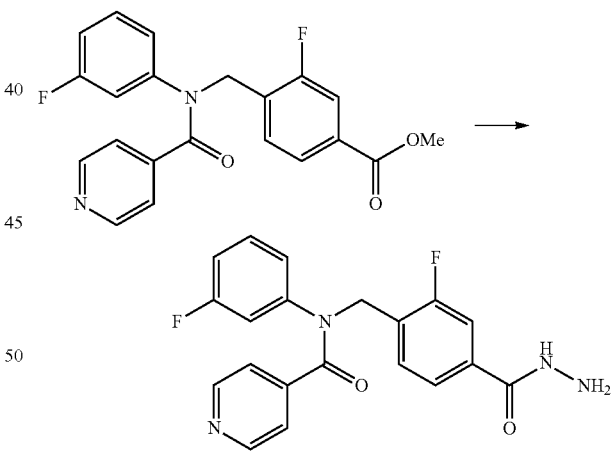

Methyl 3-fluoro-4-((N-(3-fluorophenyl)isonicotinamido)methyl)benzoate (0.300 g, 0.785 mmol), synthesized in step 2, and hydrazine hydrate (0.786 g, 15.692 mmol) were mixed in ethanol (20 mL), and the mixture was heated at reflux for 18 hours, and then cooled down to room temperature. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.250 g, 83.3%) as a yellow foam solid.

Step 4 Synthesis of N-(2-fluoro-4-(2-(2,2,2-trifluoroacetyl)hydrazine-1-carbonyl)benzyl)-N-(3-fluorophenyl) isonicotinamide

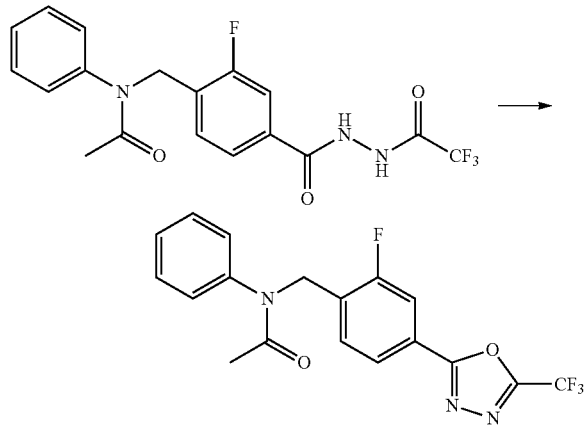

N-(2-fluoro-4-(hydrazinecarbonyl)benzyl)-N-(3-fluorophenyl)isonicotinamide (0.125 g, 0.327 mmol), synthesized in step 3, and triethylamine (0.091 mL, 0.654 mmol) were dissolved in dichloromethane (10 mL) at room temperature, and trifluoroacetic anhydride (0.055 mL, 0.392 mmol) was added to the solution, followed by stirring at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.145 g, 92.7%) as yellow foam solid.

[Step 5] Synthesis of Compound 11188

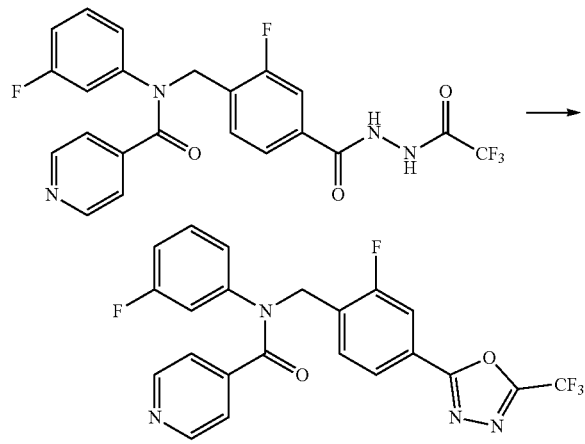

N-(2-fluoro-4-(2-(2,2,2-trifluoroacetyl)hydrazine-1-carbonyl)benzyl)-N-(3-fluorophenyl)isonicotinamide (0.160 g, 0.334 mmol), synthesized in step 4, and 1-methoxy-N-triethylammoniosulfonyl-methanimidate (Burgess reagent, 0.120 g, 0.502 mmol) were mixed in tetrahydrofuran (10 mL), and the mixture was heated by microwave irradiation at 150° C. for 30 minutes and cooled down to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.058 g, 37.7%) as a white solid.

$^1$H NMR (400 MHz, CDCl$_3$) δ 8.53 (s, 2H), 7.91 (dd, 1H, J=8.0, 1.5 Hz), 7.83-7.57 (m, 2H), 7.37-7.27 (m, 2H), 7.17 (dd, 1H, J=8.1, 6.3 Hz), 6.94 (td, 1H, J=8.1, 2.3 Hz), 6.78-6.62 (m, 2H), 5.23 (d, 2H, J=20.2 Hz); LRMS (ES) m/z 461.3 (M$^+$+1).

EXAMPLE 30: Synthesis of Compound 11189, N-(4-(5-(difluoromethyl)-1,3,4-oxadiazol-2-yl)-2-fluorobenzyl)-N-(3-fluorophenyl)isonicotinamide

[Step 1] Synthesis of N-(4-(2-(2,2-difluoroacetyl)hydrazine-1-carbonyl)-2-fluorobenzyl)-N-(3-fluorophenyl)isonicotinamide

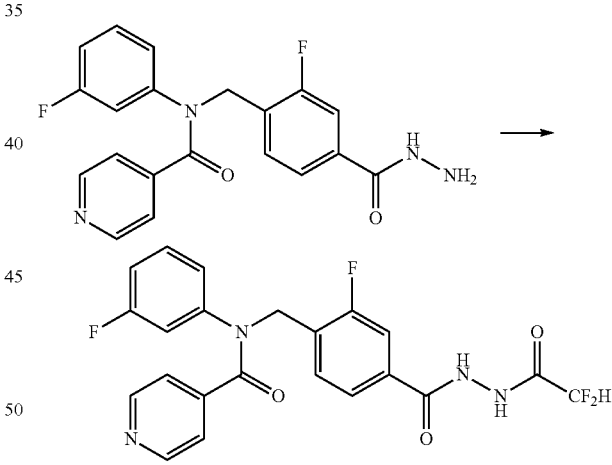

N-(2-fluoro-4-(hydrazinecarbonyl)benzyl)-N-(3-fluorophenyl)isonicotinamide (0.125 g, 0.327 mmol), synthesized in step 3 of Example 29, and triethylamine (0.091 mL, 0.654 mmol) were dissolved in dichloromethane (10 mL) at room temperature, and 2,2-difluoroacetic anhydride (0.043 mL, 0.392 mmol) was added to the solution, followed by stirring at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.135 g, 89.7%) as a yellow foam solid.

[Step 2] Synthesis of Compound 11189

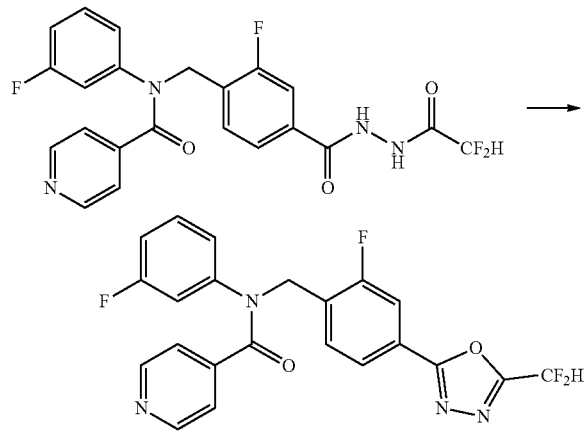

N-(4-(2-(2,2-difluoroacetyl)hydrazine-1-carbonyl)-2-fluorobenzyl)-N-(3-fluorophenyl)isonicotinamide (0.160 g, 0.348 mmol), synthesized in step 1, and 1-methoxy-N-triethylammoniosulfonyl-methanimidate (Burgess reagent, 0.124 g, 0.521 mmol) were mixed in tetrahydrofuran (10 mL), and the mixture was heated by microwave irradiation at 150° C. for 30 minutes and cooled down to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.089 g, 57.9%) as a white solid.

$^1$H NMR (400 MHz, CDCl$_3$) δ 8.54 (d, 2H, J=4.8 Hz), 7.91 (d, 1H, J=7.8 Hz), 7.77 (d, 1H, J=9.9 Hz), 7.68 (t, 1H, J=7.6 Hz), 7.32 (d, 2H, J=2.9 Hz), 7.17 (dd, 1H, J=14.7, 7.3 Hz), 7.05-6.83 (m, 2H), 6.83-6.61 (m, 2H), 5.33-5.12 (m, 2H); LRMS (ES) m/z 442.9 (M$^+$+1).

EXAMPLE 31: Synthesis of Compound 11200, N-(2-fluoro-4-(5-(trifluoromethyl)-1,3,4-oxadiazol-2-yl)benzyl)-1-methyl-N-phenylpiperidine-4-carboxamide

[Step 1] Synthesis of tert-butyl 4-((2-fluoro-4-(methoxycarbonyl)benzyl)(phenyl)carbamoyl)piperidine-1-carboxylate

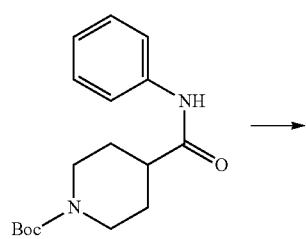

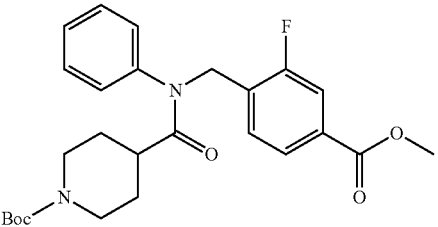

Tert-butyl 4-(phenylcarbamoyl)piperidine-1-carboxylate (2.000 g, 6.571 mmol) synthesized in step 1 of Example 9 was dissolved in tetrahydrofuran (80 mL), and sodium hydride (60.00%, 0.526 g, 13.141 mmol) was added slowly to the solution while the temperature was maintained at 0° C. The mixture was stirred for 20 minutes, and methyl 4-(bromomethyl)-3-fluorobenzoate (1.948 g, 7.885 mmol) was added thereto, followed by additional stirring at 50° C. for 12 hours. The reaction mixture was cooled down to room temperature, and then water (20 mL) was added to the reaction mixture at 0° C., followed by stirring for 5 minutes. After completion of the reaction, water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 80 g cartridge; ethyl acetate/hexane=from 5% to 50%) and concentrated to give the title compound (2.600 g, 84.1%) as colorless oil.

[Step 2] Synthesis of tert-butyl 4-((2-fluoro-4-(hydrazinecarbonyl)benzyl)(phenyl)carbamoyl)piperidine-1-carboxylate

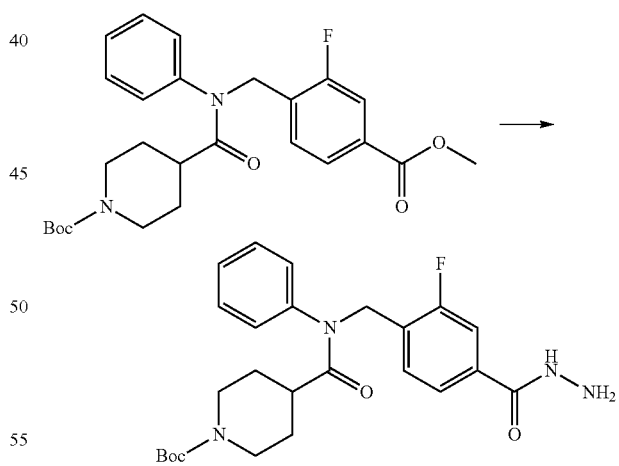

Tert-butyl 4-((2-fluoro-4-(methoxycarbonyl)benzyl)(phenyl)carbamoyl)piperidine-1-carboxylate (2.500 g, 5.313 mmol), synthesized in step 1, and hydrazine monohydrate (5.154 mL, 106.261 mmol) were mixed in ethanol (100 mL) at room temperature, and the mixture was heated at reflux for 12 hours and cooled down to room temperature. Then, the reaction mixture was concentrated under reduced pressure to remove the solvent. Water was added to the concentrate, followed by extraction with dichloromethane. The organic layer was washed with saturated aqueous sodium chloride solution, dried with magnesium sulfate anhydrous, filtered, and then concentrated under reduced pressure. The title compound was used without further purification (2.400 g, 96.0%) as white solid.

[Step 3] Synthesis of tert-butyl 4-((2-fluoro-4-(2-(2,2,2-trifluoroacetyl)hydrazine-1-carbonyl)benzyl)(phenyl)carbamoyl)piperidine-1-carboxylate

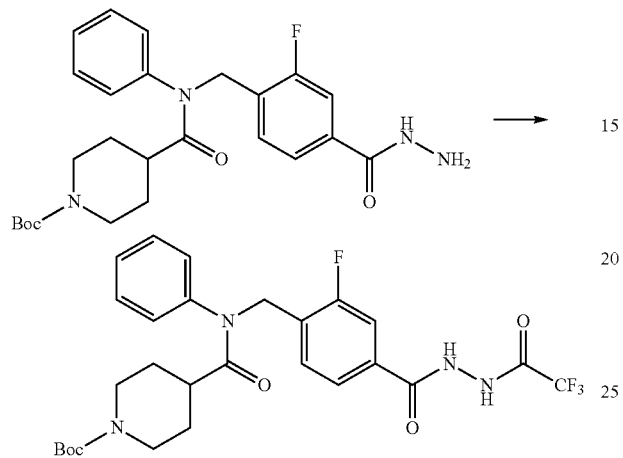

Tert-butyl 4-((2-fluoro-4-(hydrazinecarbonyl)benzyl)(phenyl)carbamoyl)piperidine-1-carboxylate (1.200 g, 2.550 mmol), synthesized in step 2, and triethylamine (0.427 mL, 3.060 mmol) were dissolved in dichloromethane (50 mL) at room temperature, and trifluoroacetic anhydride (0.390 mL, 2.805 mmol) was added to the solution, followed by stirring at the same temperature for 4 hours. Saturated aqueous ammonium chloride solution was added to the reaction mixture, followed by extraction with dichloromethane. The organic layer was washed with saturated aqueous sodium chloride solution, dried with magnesium sulfate anhydrous, filtered, and then concentrated under reduced pressure. The title compound was used without further purification (1.400 g, 96.9%) as colorless oil.

[Step 4] Synthesis of tert-butyl 4-((2-fluoro-4-(5-(trifluoromethyl)-1,3,4-oxadiazol-2-yl)benzyl)(phenyl)carbamoyl)piperidine-1-carboxylate

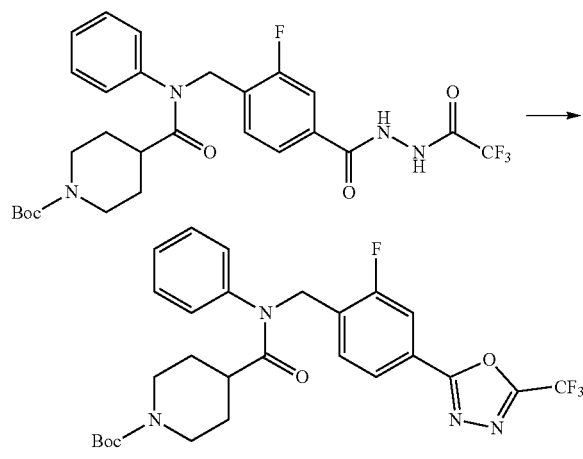

Tert-butyl 4-((2-fluoro-4-(2-(2,2,2-trifluoroacetyl)hydrazine-1-carbonyl)benzyl)(phenyl)carbamoyl)piperidine-1-carboxylate (1.400 g, 2.471 mmol), synthesized in step 3, and 1-methoxy-N-triethylammoniosulfonyl-methanimidate (Burgess reagent, 0.883 g, 3.707 mmol) were mixed in tetrahydrofuran (100 mL) at room temperature, and the mixture was heated under reflux for 12 hours, and then cooled down to room temperature. The reaction mixture was concentrated under reduced pressure to remove the solvent, and the concentrate was purified by column chromatography (SiO$_2$, 80 g cartridge; ethyl acetate/hexane=10% to 30%) and concentrated to give the title compound (0.740 g, 54.6%) as a white solid.

[Step 5] Synthesis of N-(2-fluoro-4-(5-(trifluoromethyl)-1,3,4-oxadiazol-2-yl)benzyl)-N-phenylpiperidine-4-carboxamide hydrochloride

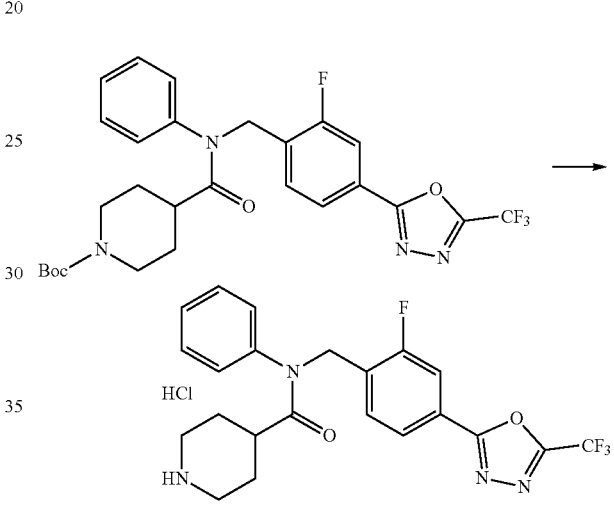

Tert-butyl 4-((2-fluoro-4-(5-(trifluoromethyl)-1,3,4-oxadiazol-2-yl)benzyl)(phenyl)carbamoyl)piperidine-1-carboxylate (0.740 g, 1.349 mmol) synthesized in step 4 was dissolved in dichloromethane (50 mL) at room temperature, and hydrochloric acid (4.00 M solution in dioxane, 1.686 mL, 6.745 mmol) was added to the solution. The mixture was stirred at the same temperature for 12 hours. The reaction mixture was concentrated under reduced pressure to remove the solvent, and the concentrate was suspended in diethyl ether (50 mL) and filtered. The obtained solid was washed with diethyl ether and dried to give the title compound (0.610 g, 93.3%) as a white solid.

[Step 6] Synthesis of Compound 11200

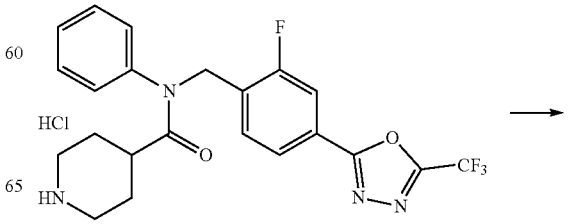

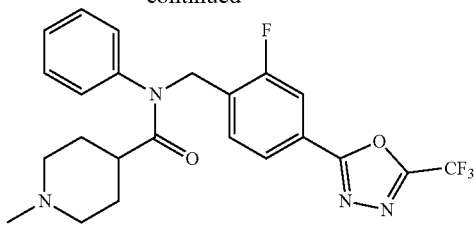

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol) synthesized in step 5, formaldehyde (37.00% solution in water, 0.012 mL, 0.155 mmol) and sodium triacetoxyborohydride (0.033 g, 0.155 mmol) were dissolved in dichloromethane (4 mL) at room temperature, and the solution was stirred at the same temperature for 12 hours. The reaction mixture was concentrated under reduced pressure to remove the solvent, and the concentrate was purified by column chromatography (SiO$_2$, 4 g cartridge; methanol/dichloromethane=from 0% to 15%) and concentrated to give the title compound (0.020 g, 41.9%) as a white solid.

$^1$H NMR (700 MHz, CDCl$_3$) δ 7.86 (d, 1H, J=7.8 Hz), 7.72 (d, 1H, J=9.4 Hz), 7.56 (t, 1H, J=7.0 Hz), 7.36 (d, 3H, J=12.4 Hz), 7.03 (t, 2H, J=13.6 Hz), 5.01 (d, 2H, J=22.8 Hz), 3.32-3.03 (m, 2H), 2.53-2.38 (m, 4H), 2.03 (dd, 4H, J=43.3, 40.1 Hz), 1.86 (d, 2H, J=48.6 Hz); LRMS (ES) m/z 463.3 (M$^+$+1).

EXAMPLE 32: Synthesis of Compound 11201, 1-ethyl-N-(2-fluoro-4-(5-trifluoromethyl)-1,3,4-oxadiazol-2-yl)benzyl)-N-phenylpiperidine-4-carboxamide

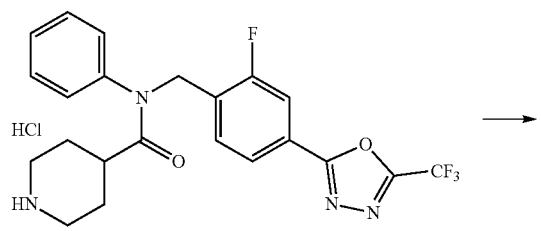

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol) synthesized in step 5 of Example 31, acetaldehyde (0.009 mL, 0.155 mmol) and sodium triacetoxyborohydride (0.033 g, 0.155 mmol) were dissolved in dichloromethane (4 mL) at room temperature, and the solution was stirred at the same temperature for 12 hours. The reaction mixture was concentrated under reduced pressure to remove the solvent, and the concentrate was purified by column chromatography (SiO$_2$, 4 g cartridge; methanol/dichloromethane=from 0% to 15%) and concentrated to give the title compound (0.025 g, 50.9%) as a white solid.

$^1$H NMR (700 MHz, CDCl$_3$) δ 7.85 (d, 1H, J=6.8 Hz), 7.71 (d, 1H, J=8.8 Hz), 7.53 (s, 1H), 7.36 (s, 3H), 7.01 (d, 2H, J=26.5 Hz), 5.11-4.94 (m, 2H), 3.26 (s, 3H), 2.77 (s, 2H), 2.48 (s, 3H), 2.05-2.00 (m, 3H, J=57.5 Hz), 1.22 (d, 3H, J=5.3 Hz); LRMS (ES) m/z 477.3 (M$^+$+1).

EXAMPLE 33: Synthesis of Compound 11202, N-(2-fluoro-4-(5-(trifluoromethyl)-1,3,4-oxadiazol-2-yl)benzyl)-1-isopropyl-N-phenylpiperidine-4-carboxamide

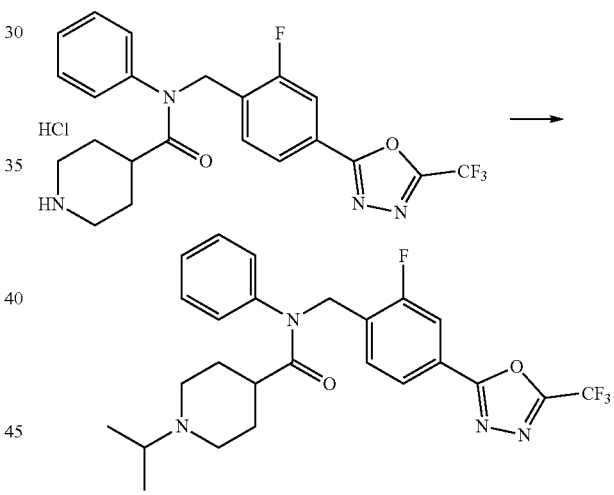

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol) synthesized in step 5 of Example 31, acetone (0.011 mL, 0.155 mmol) and sodium triacetoxyborohydride (0.033 g, 0.155 mmol) were dissolved in dichloromethane (4 mL) at room temperature, and the solution was stirred at the same temperature for 12 hours. The reaction mixture was concentrated under reduced pressure to remove the solvent, and the concentrate was purified by column chromatography (SiO$_2$, 4 g cartridge; methanol/dichloromethane=from 0% to 15%) and concentrated to give the title compound (0.020 g, 39.5%) as a white solid.

$^1$H NMR (700 MHz, CDCl$_3$) δ 7.86 (d, 1H, J=7.9 Hz), 7.73 (d, 1H, J=9.5 Hz), 7.55-7.48 (m, 1H), 7.40-7.33 (m, 3H), 7.05-6.98 (m, 2H), 5.02 (s, 2H), 3.40 (t, 3H, J=58.2 Hz), 2.78 (d, 2H, J=8.9 Hz), 2.60 (s, 1H), 2.11 (d, 2H, J=36.1 Hz), 2.00 (d, 4H, J=9.5 Hz), 1.30 (d, 4H, J=5.9 Hz); LRMS (ES) m/z 491.0 (M$^+$+1).

EXAMPLE 34: Synthesis of Compound 11203, 1-acetyl-N-(2-fluoro-4-(5-(trifluoromethyl)-1,3,4-oxadiazol-2-yl)benzyl)-N-phenylpiperidine-4-carboxamide

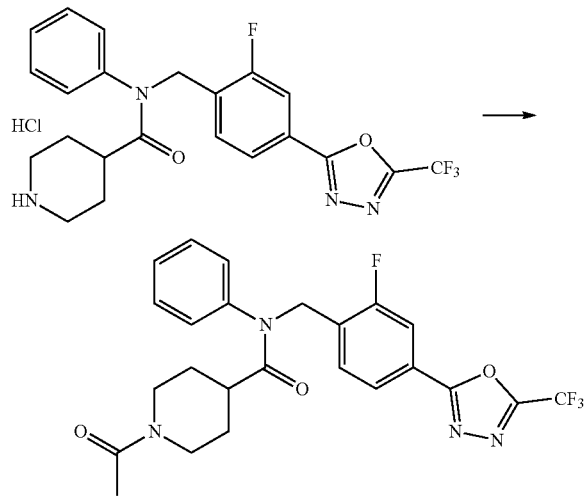

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol), synthesized in step 5 of Example 31, and N,N-diisopropylethylamine (0.036 mL, 0.206 mmol) were dissolved in dichloromethane (4 mL) at room temperature, and acetyl chloride (0.008 mL, 0.113 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.032 g, 63.3%) as colorless oil.

$^1$H NMR (700 MHz, CDCl$_3$) δ 7.87 (d, 1H, J=7.9 Hz), 7.72 (d, 1H, J=9.4 Hz), 7.62-7.55 (m, 1H), 7.39 (s, 3H), 7.12-7.02 (m, 2H), 5.04 (s, 2H), 4.53 (s, 1H), 3.79 (s, 1H), 2.84 (s, 1H), 2.51-2.42 (m, 1H), 2.34 (s, 1H), 2.06 (t, 4H, J=4.7 Hz), 1.78 (d, 3H, J=69.3 Hz); LRMS (ES) m/z 491.1 (M$^+$+1).

EXAMPLE 35: Synthesis of Compound 11204, N-(2-fluoro-4-(5-(trifluoromethyl)-1,3,4-oxadiazol-2-yl)benzyl)-N-phenyl-1-propionylpiperidine-4-carboxamide

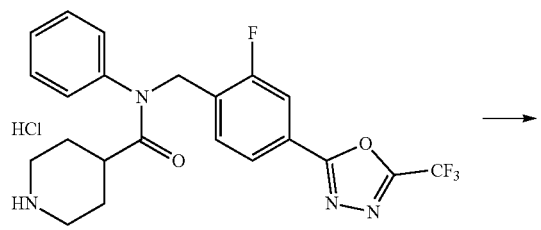

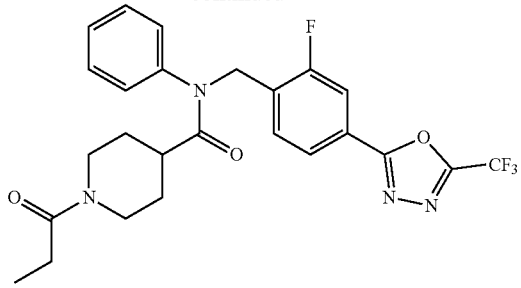

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol), synthesized in step 5 of Example 31, and N,N-diisopropylethylamine (0.036 mL, 0.206 mmol) were dissolved in dichloromethane (4 mL) at room temperature, and propionyl chloride (0.010 mL, 0.113 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 57.7%) as colorless oil.

$^1$H NMR (700 MHz, CDCl$_3$) δ 7.87 (t, 1H, J=6.2 Hz), 7.74-7.70 (m, 1H), 7.58 (d, 1H, J=6.7 Hz), 7.39 (d, 3H, J=4.5 Hz), 7.06 (s, 2H), 5.04 (s, 3H), 4.54 (s, 1H), 3.83 (s, 1H), 2.78 (s, 1H), 2.31 (s, 4H), 1.77 (s, 2H, J=67.0 Hz), 1.19-1.02 (m, 4H); LRMS (ES) m/z 505.3 (M$^+$+1).

EXAMPLE 36: Synthesis of Compound 11205, N-(2-fluoro-4-(5-(trifluoromethyl)-1,3,4-oxadiazol-2-yl)benzyl)-1-isobutyryl-N-phenylpiperidine-4-carboxamide

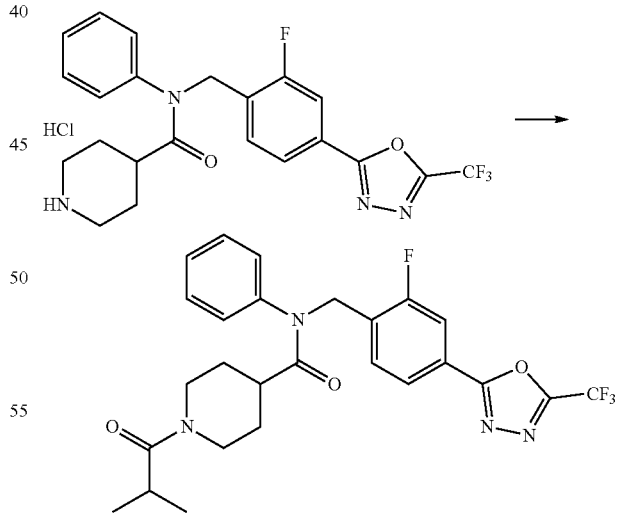

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol), synthesized in step 5 of Example 31, and N,N-diisopropylethylamine (0.036 mL, 0.206 mmol) were dissolved in dichloromethane (4 mL) at room temperature, and isobutyryl chloride (0.012 mL, 0.113 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 56.1%) as colorless oil.

$^1$H NMR (700 MHz, CDCl$_3$) δ 7.87 (d, 1H, J=8.0 Hz), 7.71 (t, 1H, J=11.3 Hz), 7.58 (t, 1H, J=7.5 Hz), 7.42-7.37 (m, 3H), 7.07 (d, 2H, J=7.7 Hz), 5.00 (d, 2H, J=39.7 Hz), 4.56 (s, 1H), 4.04-3.80 (m, 1H), 2.94-2.66 (m, 2H), 2.53-2.41 (m, 1H), 2.31 (dt, 1H, J=45.9, 23.1 Hz), 1.76 (dd, 2H, J=36.0, 30.1 Hz), 1.10 (d, 8H, J=6.8 Hz); LRMS (ES) m/z 519.5 (M$^+$+1).

EXAMPLE 37: Synthesis of Compound 11206, N-(2-fluoro-4-(5-(trifluoromethyl)-1,3,4-oxadiazol-2-yl)benzyl)-N-phenyl-1-(2,2,2-trifluoroacetyl)piperidine-4-carboxamide

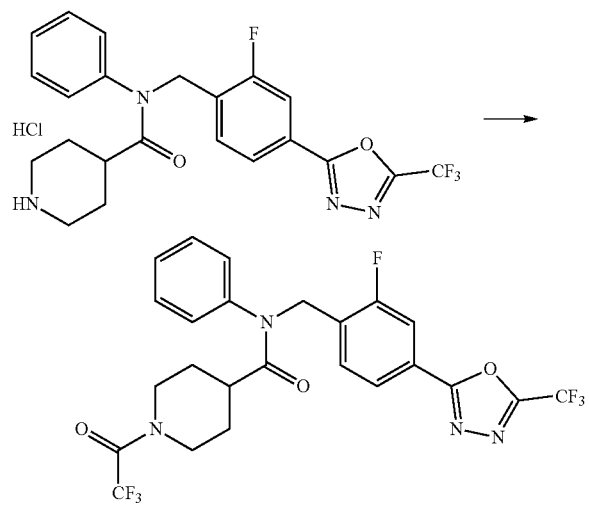

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol), synthesized in step 5 of Example 31, and N,N-diisopropylethylamine (0.036 mL, 0.206 mmol) were dissolved in dichloromethane (4 mL) at room temperature, and trifluoroacetic anhydride (0.016 mL, 0.113 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 53.4%) as colorless oil.

$^1$H NMR (700 MHz, CDCl$_3$) δ 7.87 (d, 1H, J=8.0 Hz), 7.73 (d, 1H, J=9.6 Hz), 7.57 (t, 1H, J=7.4 Hz), 7.41 (d, 3H, J=5.4 Hz), 7.07 (d, 2H, J=6.9 Hz), 5.10-4.98 (m, 2H), 4.43 (d, 1H, J=13.4 Hz), 3.98 (d, 1H, J=13.8 Hz), 2.96 (t, 1H, J=12.8 Hz), 2.74-2.58 (m, 1H), 2.54 (t, 1H, J=10.5 Hz), 1.96-1.81 (m, 2H), 1.75 (d, 2H, J=13.0 Hz); LRMS (ES) m/z 545.4 (M$^+$+1).

EXAMPLE 38: Synthesis of Compound 11207, N-(2-fluoro-4-(5-(trifluoromethyl)-1,3,4-oxadiazol-2-yl)benzyl)-1-(methylsulfonyl)-N-phenylpiperidine-4-carboxamide

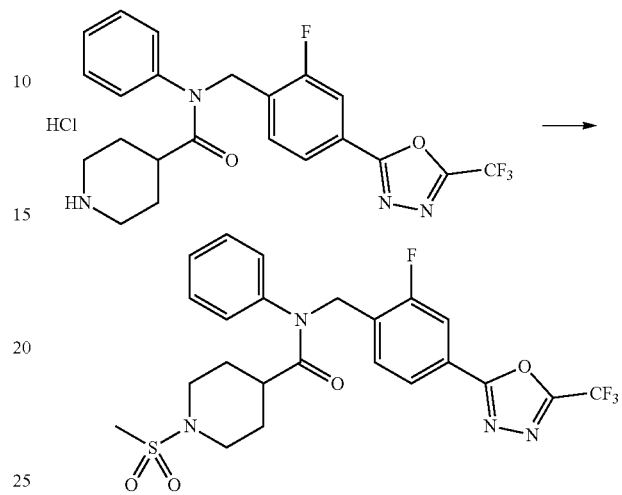

N-(2-fluoro-4-(5-(trifluoromethyl)-1,3,4-oxadiazol-2-yl)benzyl)-N-phenylpiperidine-4-carboxamide hydrochloride (0.050 g, 0.103 mmol), synthesized in step 5 of Example 31, and N,N-diisopropylethylamine (0.036 mL, 0.206 mmol) were dissolved in dichloromethane (4 mL) at room temperature, and methanesulfonyl chloride (0.009 mL, 0.113 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 55.3%) as a white solid.

$^1$H NMR (700 MHz, CDCl$_3$) δ 7.87 (d, 1H, J=7.8 Hz), 7.73 (d, 1H, J=9.4 Hz), 7.58 (t, 1H, J=6.4 Hz), 7.39 (s, 3H), 7.06 (d, 2H, J=5.7 Hz), 5.04 (s, 2H), 3.74 (d, 2H, J=10.1 Hz), 2.74 (d, 3H, J=2.1 Hz), 2.54 (t, 2H, J=11.7 Hz), 2.36 (dd, 1H, J=10.1, 7.7 Hz), 1.95 (dd, 2H, J=23.6, 11.6 Hz), 1.75 (d, 2H, J=13.2 Hz); LRMS (ES) m/z 527.3 (M$^+$+1).

EXAMPLE 39: Synthesis of Compound 11208, N-(4-(5-(difluoromethyl)-1,3,4-oxadiazol-2-yl)-2-fluorobenzyl)-1-methyl-N-phenylpiperidine-4-carboxamide

[Step 1] Synthesis of tert-butyl 4-((4-(2-(2,2-difluoroacetyl)hydrazine-1-carbonyl)-2-fluorobenzyl)(phenyl)carbamoyl)piperidine-1-carboxylate

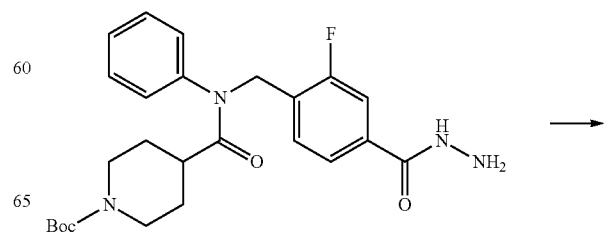

-continued

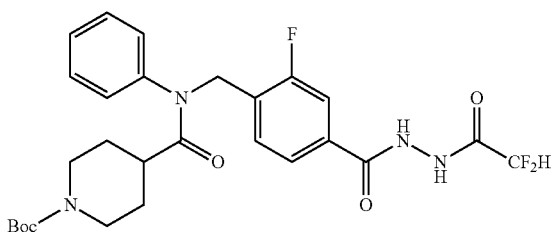

Tert-butyl 4-((2-fluoro-4-(hydrazinecarbonyl)benzyl)(phenyl)carbamoyl)piperidine-1-carboxylate (1.200 g, 2.550 mmol), synthesized in step 2 of Example 31, and triethylamine (0.427 mL, 3.060 mmol) were dissolved in dichloromethane (50 mL) at room temperature, and difluoroacetic anhydride (0.349 mL, 2.805 mmol) was added to the solution. The mixture was stirred at the same temperature for 4 hours. Saturated aqueous ammonium chloride solution was added to the reaction mixture, followed by extraction with dichloromethane. The organic layer was washed with saturated aqueous sodium chloride solution, dried with magnesium sulfate anhydrous, filtered, and then concentrated under reduced pressure. The title compound was used without further purification (1.350 g, 96.5%) as colorless oil.

[Step 2] Synthesis of tert-butyl 4-((4-(5-(difluoromethyl)-1,3,4-oxadiazol-2-yl)-2-fluorobenzyl)(phenyl)carbamoyl)piperidine-1-carboxylate

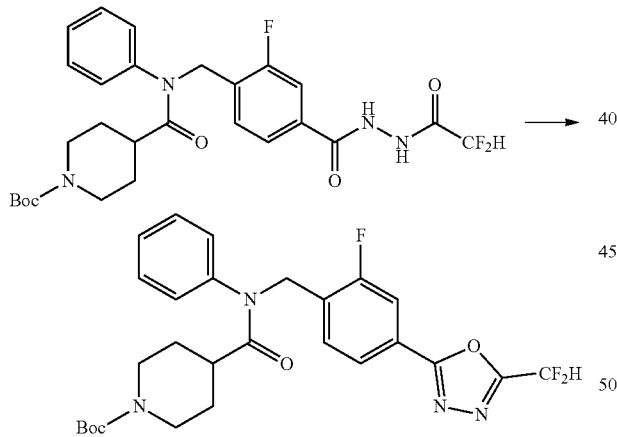

Tert-butyl 4-((4-(2-(2,2-difluoroacetyl)hydrazine-1-carbonyl)-2-fluorobenzyl)(phenyl)carbamoyl)piperidine-1-carboxylate (1.350 g, 2.461 mmol), synthesized in step 1, and 1-methoxy-N-triethylammoniosulfonyl-methanimidate (Burgess reagent, 0.880 g, 3.691 mmol) were mixed in tetrahydrofuran (100 mL) at room temperature, and the mixture was heated at reflux for 12 hours, and then cooled down to room temperature. The reaction mixture was concentrated under reduced pressure to remove the solvent, and the concentrate was purified by column chromatography (SiO$_2$, 80 g cartridge; ethyl acetate/hexane=from 10% to 30%) and concentrated to give the title compound (0.800 g, 61.3%) as a white solid.

[Step 3] Synthesis of N-(4-(5-(difluoromethyl)-1,3,4-oxadiazol-2-yl)-2-fluorobenzyl)-N-phenylpiperidine-4-carboxamide hydrochloride

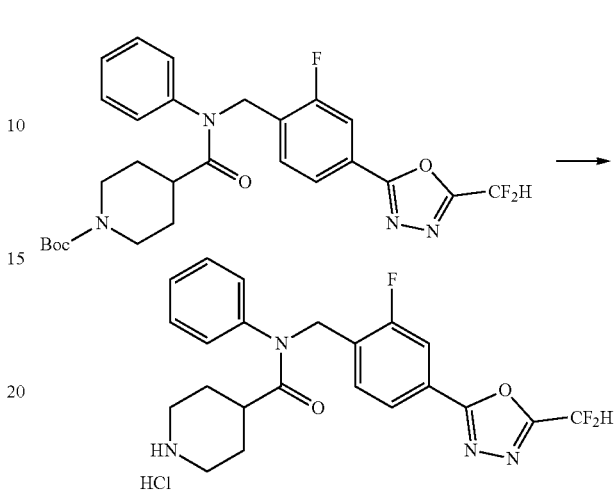

Tert-butyl 4-((4-(5-(difluoromethyl)-1,3,4-oxadiazol-2-yl)-2-fluorobenzyl)(phenyl)carbamoyl)piperidine-1-carboxylate (0.800 g, 1.508 mmol) synthesized in step 2 was dissolved in dichloromethane (50 mL) at room temperature, and hydrochloric acid (4.00 M solution in dioxane, 1.885 mL, 7.539 mmol) was added to the solution. The mixture was stirred at the same temperature for 12 hours. The reaction mixture was concentrated under reduced pressure, and the concentrate was suspended in diethyl ether (50 mL) and filtered. The obtained solid was washed with diethyl ether and dried to give the title compound (0.660 g, 93.7%) as a white solid.

[Step 4] Synthesis of Compound 11208

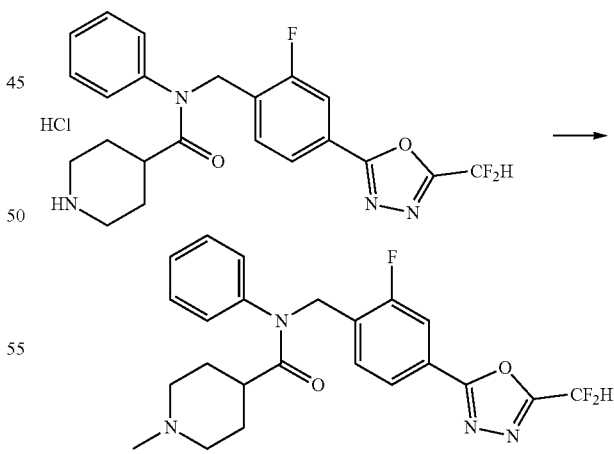

N-(4-(5-(difluoromethyl)-1,3,4-oxadiazol-2-yl)-2-fluorobenzyl)-N-phenylpiperidine-4-carboxamide hydrochloride (0.050 g, 0.107 mmol) synthesized in step 3, formaldehyde (37.00% solution in water, 0.012 mL, 0.161 mmol) and sodium triacetoxyborohydride (0.034 g, 0.161 mmol) were dissolved in dichloromethane (4 mL) at room temperature, and the solution was stirred at the same temperature for 12 hours. The reaction mixture was concentrated under reduced pressure to remove the solvent, and the concentrate was purified by column chromatography (SiO$_2$, 4 g cartridge; methanol/dichloromethane=from 0% to 15%) and concentrated to give the title compound (0.022 g, 46.2%) as a white solid.

$^1$H NMR (700 MHz, CDCl$_3$) δ 7.86 (t, 1H, J=13.4 Hz), 7.72 (d, 1H, J=9.7 Hz), 7.55 (t, 1H, J=7.5 Hz), 7.41-7.33 (m, 3H), 7.09-7.02 (m, 2H), 6.92 (t, 1H, J=51.7 Hz), 5.07-4.94 (m, 2H), 3.16-3.02 (m, 2H), 2.38 (s, 1H), 2.24 (s, 3H), 1.97 (d, 3H, J=9.6 Hz), 1.81 (d, 3H, J=9.7 Hz); LRMS (ES) m/z 445.3 (M$^+$+1).

EXAMPLE 40: Synthesis of Compound 11209, N-(4-(5-(difluoromethyl)-1,3,4-oxadiazol-2-yl)-2-fluorobenzyl)-1-ethyl-N-phenylpiperidine-4-carboxamide

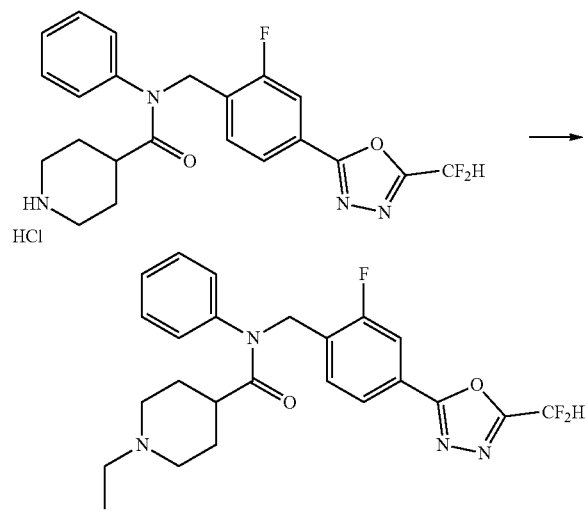

N-(4-(5-(difluoromethyl)-1,3,4-oxadiazol-2-yl)-2-fluorobenzyl)-N-phenylpiperidine-4-carboxamide hydrochloride (0.050 g, 0.107 mmol) synthesized in step 3 of Example 39, acetaldehyde (0.009 mL, 0.161 mmol) and sodium triacetoxyborohydride (0.034 g, 0.161 mmol) were dissolved in dichloromethane (4 mL) at room temperature, and the solution was stirred at the same temperature for 12 hours. The reaction mixture was concentrated under reduced pressure to remove the solvent, and the concentrate was purified by column chromatography (SiO$_2$, 4 g cartridge; methanol/dichloromethane=from 0% to 15%) and concentrated to give the title compound (0.025 g, 50.9%) as a white solid.

$^1$H NMR (700 MHz, CDCl$_3$) δ 7.86 (d, 1H, J=6.0 Hz), 7.73 (d, 1H, J=6.7 Hz), 7.52 (s, 1H), 7.37 (s, 3H), 7.03 (s, 2H), 6.88 (d, 1H, J=51.6 Hz), 5.02 (s, 2H), 3.48 (d, 2H, J=5.4 Hz), 3.25 (s, 3H), 2.77 (s, 3H), 2.50 (s, 2H), 1.25 (s, 4H); LRMS (ES) m/z 459.2 (M$^+$+1).

EXAMPLE 41: Synthesis of Compound 11210, N-(4-(5-(difluoromethyl)-1,3,4-oxadiazol-2-yl)-2-fluorobenzyl)-1-isopropyl-N-phenylpiperidine-4-carboxamide

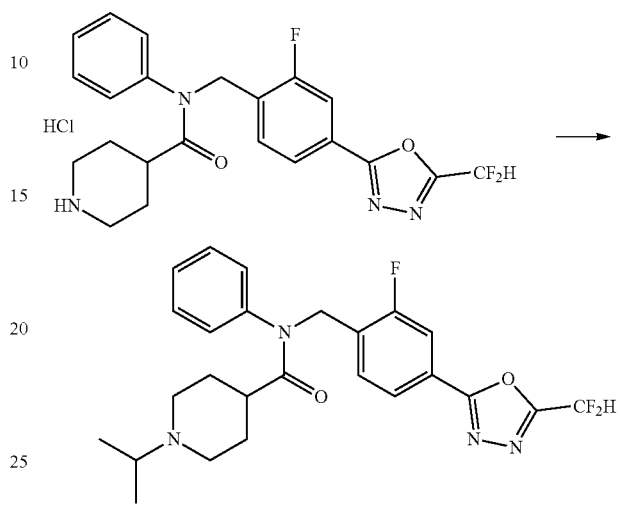

N-(4-(5-(difluoromethyl)-1,3,4-oxadiazol-2-yl)-2-fluorobenzyl)-N-phenylpiperidine-4-carboxamide hydrochloride (0.050 g, 0.107 mmol) synthesized in step 3 of Example 39, acetone (0.012 mL, 0.161 mmol) and sodium triacetoxyborohydride (0.034 g, 0.161 mmol) were dissolved in dichloromethane (4 mL) at room temperature, and the solution was stirred at the same temperature for 12 hours. The reaction mixture was concentrated under reduced pressure to remove the solvent, and the concentrate was purified by column chromatography (SiO$_2$, 4 g cartridge; methanol/dichloromethane=from 0% to 15%) and concentrated to give the title compound (0.020 g, 39.5%) as a white solid.

$^1$H NMR (700 MHz, CDCl$_3$) δ 7.85 (t, 1H, J=17.4 Hz), 7.75 (d, 1H, J=9.5 Hz), 7.46 (d, 1H, J=25.1 Hz), 7.38 (d, 3H, J=2.9 Hz), 7.01 (d, 2H, J=2.6 Hz), 6.97-6.81 (m, 1H), 5.08-4.98 (m, 2H), 3.59 (s, 1H), 3.38 (d, 1H, J=17.5 Hz), 2.87 (d, 2H, J=199.2 Hz), 2.30 (d, 3H, J=82.5 Hz), 1.95 (d, 3H, J=47.9 Hz), 1.40 (s, 6H); LRMS (ES) m/z 473.1 (M$^+$+1).

EXAMPLE 42: Synthesis of Compound 11211, 1-acetyl-N-(4-(5-(difluoromethyl)-1,3,4-oxadiazol-2-yl)-2-fluorobenzyl)-N-phenylpiperidine-4-carboxamide

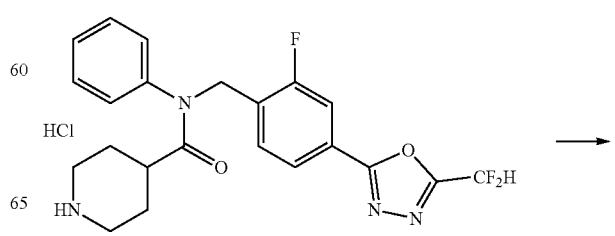

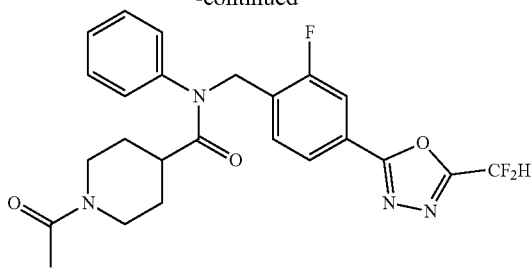

N-(4-(5-(difluoromethyl)-1,3,4-oxadiazol-2-yl)-2-fluorobenzyl)-N-phenylpiperidine-4-carboxamide hydrochloride (0.050 g, 0.107 mmol), synthesized in step 3 of Example 39, and N,N-diisopropylethylamine (0.037 mL, 0.214 mmol) were dissolved in dichloromethane (4 mL) at room temperature, and acetyl chloride (0.008 mL, 0.118 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 59.3%) as colorless oil.

$^1$H NMR (700 MHz, CDCl$_3$) δ 7.87 (d, 1H, J=7.8 Hz), 7.72 (d, 1H, J=9.5 Hz), 7.56 (t, 1H, J=7.2 Hz), 7.39 (s, 3H), 7.06 (d, 2H, J=6.1 Hz), 6.92 (t, 1H, J=51.6 Hz), 5.03 (t, 2H, J=11.0 Hz), 4.54 (d, 1H, J=11.3 Hz), 3.75 (t, 1H, J=41.8 Hz), 2.83 (d, 1H, J=11.1 Hz), 2.41 (ddd, 3H, J=79.6, 32.3, 14.8 Hz), 1.85 (d, 2H, J=10.1 Hz), 1.79-1.62 (m, 4H); LRMS (ES) m/z 473.4 (M$^+$+1).

EXAMPLE 43: Synthesis of Compound 11212, N-(4-(5-(difluoromethyl)-1,3,4-oxadiazol-2-yl)-2-fluorobenzyl)-N-phenyl-1-propionylpiperidine-4-carboxamide

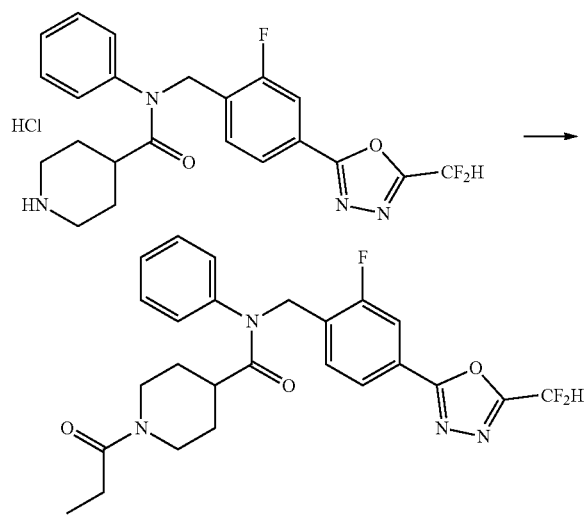

N-(4-(5-(difluoromethyl)-1,3,4-oxadiazol-2-yl)-2-fluorobenzyl)-N-phenylpiperidine-4-carboxamide hydrochloride (0.050 g, 0.107 mmol), synthesized in step 3 of Example 39, and N,N-diisopropylethylamine (0.037 mL, 0.214 mmol) were dissolved in dichloromethane (4 mL) at room temperature, and propionyl chloride (0.010 mL, 0.118 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 57.6%) as colorless oil.

$^1$H NMR (700 MHz, CDCl$_3$) δ 7.87 (d, 1H, J=7.8 Hz), 7.72 (d, 1H, J=9.5 Hz), 7.56 (t, 1H, J=7.1 Hz), 7.39 (d, 3H, J=5.5 Hz), 7.05 (t, 2H, J=13.9 Hz), 6.92 (t, 1H, J=51.7 Hz), 5.02 (d, 3H, J=27.7 Hz), 4.55 (s, 1H), 3.92-3.68 (m, 1H), 2.96-2.66 (m, 2H), 2.45 (t, 2H, J=10.5 Hz), 1.78 (d, 4H, J=56.0 Hz), 1.13 (t, 3H, J=7.1 Hz); LRMS (ES) m/z 487.2 (M$^+$+1).

EXAMPLE 44: Synthesis of Compound 11213, N-(4-(5-(difluoromethyl)-1,3,4-oxadiazol-2-yl)-2-fluorobenzyl)-1-isobutyryl-N-phenylpiperidine-4-carboxamide

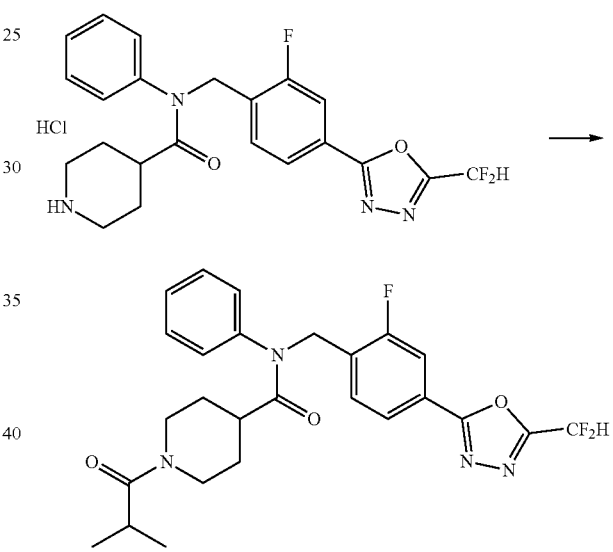

N-(4-(5-(difluoromethyl)-1,3,4-oxadiazol-2-yl)-2-fluorobenzyl)-N-phenylpiperidine-4-carboxamide hydrochloride (0.050 g, 0.107 mmol), synthesized in step 3 of Example 39, and N,N-diisopropylethylamine (0.037 mL, 0.214 mmol) were dissolved in dichloromethane (4 mL) at room temperature, and isobutyryl chloride (0.012 mL, 0.118 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 56.0%) as colorless oil.

$^1$H NMR (700 MHz, CDCl$_3$) δ 7.90-7.82 (m, 1H), 7.72 (t, 1H, J=10.3 Hz), 7.56 (d, 1H, J=6.6 Hz), 7.39 (d, 3H, J=4.7 Hz), 7.06 (d, 2H, J=3.0 Hz), 6.99-6.82 (m, 1H), 5.01 (d, 3H, J=32.5 Hz), 4.56 (s, 1H), 3.91 (s, 1H), 2.76 (dd, 3H, J=23.9, 18.5 Hz), 2.46 (d, 2H, J=6.7 Hz), 2.31 (s, 1H), 1.82 (s, 1H), 1.29-1.20 (m, 2H), 1.13-1.09 (m, 4H); LRMS (ES) m/z 501.3 (M$^+$+1).

EXAMPLE 45: Synthesis of Compound 11214, N-(4-(5-(difluoromethyl)-1,3,4-oxadiazol-2-yl)-2-fluorobenzyl)-N-phenyl-1-(2,2,2-trifluoroacetyl)piperidine-4-carboxamide

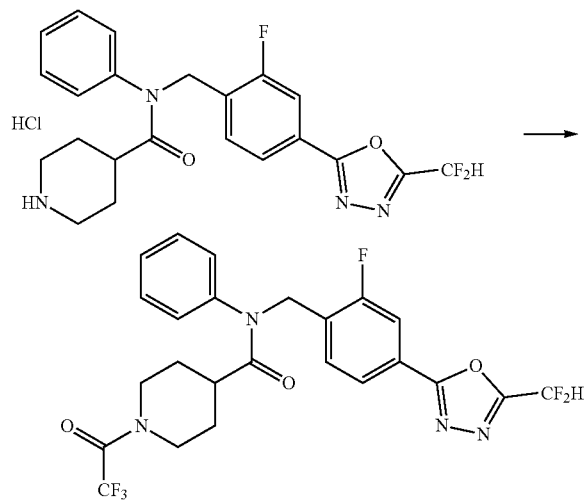

N-(4-(5-(difluoromethyl)-1,3,4-oxadiazol-2-yl)-2-fluorobenzyl)-N-phenylpiperidine-4-carboxamide hydrochloride (0.050 g, 0.107 mmol), synthesized in step 3 of Example 39, and N,N-diisopropylethylamine (0.037 mL, 0.214 mmol) were dissolved in dichloromethane (4 mL) at room temperature, and trifluoroacetic anhydride (0.017 mL, 0.118 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=from 5% to 70%) and concentrated to give the title compound (0.030 g, 53.2%) as colorless oil.

$^1$H NMR (700 MHz, CDCl$_3$) δ 7.88 (d, 1H, J=8.0 Hz), 7.72 (t, 1H, J=20.1 Hz), 7.55 (dd, 1H, J=20.6, 13.1 Hz), 7.42 (dd, 3H, J=16.5, 7.5 Hz), 7.07 (d, 2H, J=7.6 Hz), 7.01-6.85 (m, 1H), 5.04 (q, 2H, J=14.8 Hz), 4.43 (d, 1H, J=13.5 Hz), 3.97 (t, 1H, J=24.0 Hz), 2.96 (t, 1H, J=12.7 Hz), 2.65 (t, 1H, J=12.3 Hz), 2.54 (dt, 1H, J=16.1, 7.8 Hz), 1.97-1.83 (m, 2H), 1.75 (d, 2H, J=13.3 Hz); LRMS (ES) m/z 527.3 (M$^+$+1).

EXAMPLE 46: Synthesis of Compound 11215, N-(4-(5-(difluoromethyl)-1,3,4-oxadiazol-2-yl)-2-fluorobenzyl)-1-(methylsulfonyl)-N-phenylpiperidine-4-carboxamide

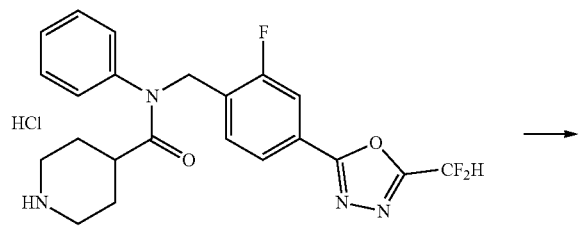

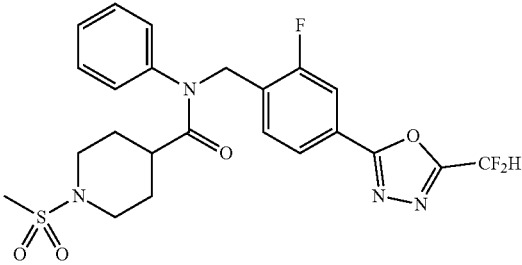

N-(4-(5-(difluoromethyl)-1,3,4-oxadiazol-2-yl)-2-fluorobenzyl)-N-phenylpiperidine-4-carboxamide hydrochloride (0.050 g, 0.107 mmol), synthesized in step 3 of Example 39, and N,N-diisopropylethylamine (0.037 mL, 0.214 mmol) were dissolved in dichloromethane (4 mL) at room temperature, and methanesulfonyl chloride (0.009 mL, 0.118 mmol) was added to the solution. The mixture was stirred at the same temperature for 12 hours. The reaction mixture was concentrated under reduced pressure to remove the solvent, and the concentrate was purified by column chromatography (SiO$_2$, 4 g cartridge; ethyl acetate/hexane=5% to 70%) and concentrated to give the title compound (0.030 g, 55.1%) as a white solid.

$^1$H NMR (700 MHz, CDCl$_3$) δ 7.88 (d, 1H, J=7.2 Hz), 7.73 (d, 1H, J=9.2 Hz), 7.56 (t, 1H, J=6.1 Hz), 7.39 (s, 3H), 7.06 (s, 2H), 6.93 (td, 1H, J=51.6, 2.2 Hz), 5.03 (d, 2H, J=14.7 Hz), 3.75 (d, 2H, J=9.6 Hz), 2.74 (d, 3H, J=2.3 Hz), 2.55 (t, 2H, J=11.7 Hz), 2.36 (dd, 1H, J=10.0, 7.3 Hz), 1.95 (dd, 2H, J=23.5, 11.5 Hz), 1.75 (d, 2H, J=13.3 Hz); LRMS (ES) m/z 509.3 (M$^+$+1).

EXAMPLE 47: Synthesis of Compound 11232, N-(2-fluoro-4-(5-(trifluoromethyl)-1,3,4-oxadiazol-2-yl)benzyl)-1-methyl-N-phenylazetidine-3-carboxamide

[Step 1] Synthesis of tert-butyl 3-((2-fluoro-4-(methoxycarbonyl)benzyl)carbamoyl)azetidine-1-carboxylate

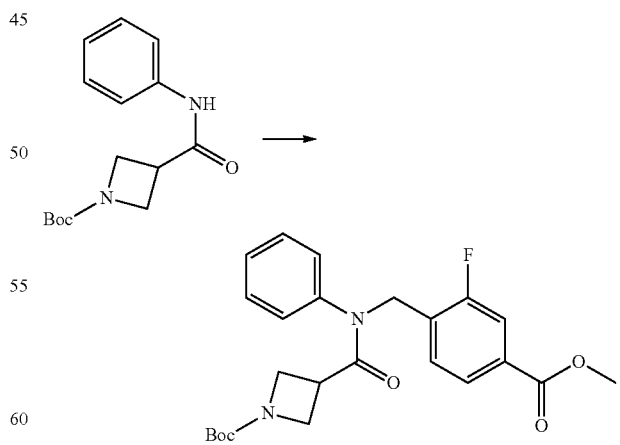

Tert-butyl 3-(phenylcarbamoyl)azetidine-1-carboxylate (2.000 g, 7.237 mmol) synthesized in step 1 of Example 8 was dissolved in tetrahydrofuran (80 mL), and sodium hydride (60.00%, 0.579 g, 14.475 mmol) was added slowly to the solution while the temperature was maintained at 0°

C. The mixture was stirred for 20 minutes, and then methyl 4-(bromomethyl)-3-fluorobenzoate (2.146 g, 8.685 mmol) was added thereto, followed by additional stirring at 50° C. for 12 hours. Then, the reaction mixture was cooled down to room temperature, and water (20 mL) was added to the reaction mixture at 0° C., followed by stirring for 5 minutes. After completion of the reaction, water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 80 g cartridge; ethyl acetate/hexane=from 5% to 50%) and concentrated to give the title compound (2.800 g, 87.4%) as colorless oil.

[Step 2] Synthesis of tert-butyl 3-((2-fluoro-4-(hydrazinecarbonyl)benzyl)(phenyl)carbamoyl)azetidine-1-carboxylate

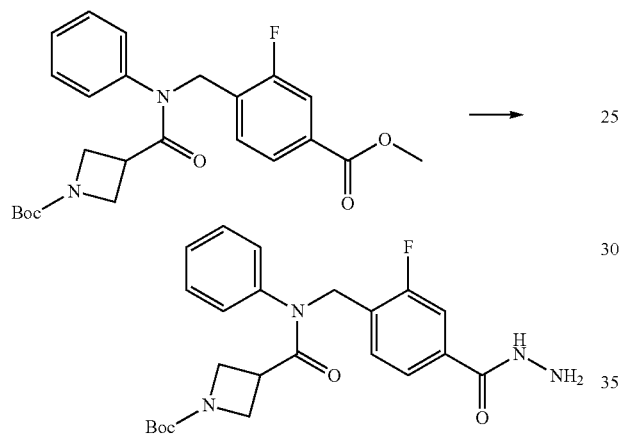

Tert-butyl 3-((2-fluoro-4-(methoxycarbonyl)benzyl)(phenyl)carbamoyl)azetidine-1-carboxylate (2.500 g, 5.650 mmol), synthesized in step 1, and hydrazine monohydrate (5.481 mL, 112.997 mmol) were mixed in ethanol (100 mL) at room temperature, and the mixture was heated at reflux for 12 hours and cooled down to room temperature. The reaction mixture was concentrated under reduced pressure to remove the solvent, and water was added to the concentrate, followed by extraction with dichloromethane. The organic layer was washed with saturated aqueous sodium chloride solution, dried with magnesium sulfate anhydrous, filtered, and then concentrated under reduced pressure. The title compound was used without further purification (2.400 g, 96.0%) as a white solid.

[Step 3] Synthesis of tert-butyl 3-((2-fluoro-4-(2-(2,2,2-trifluoroacetyl)hydrazine-1-carbonyl)benzyl)(phenyl)carbamoyl)azetidine-1-carboxylate

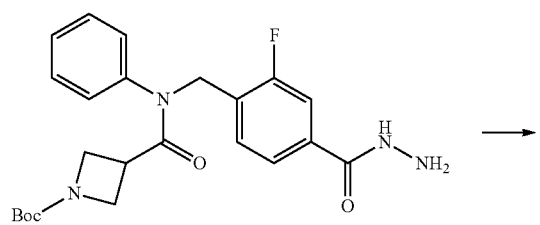

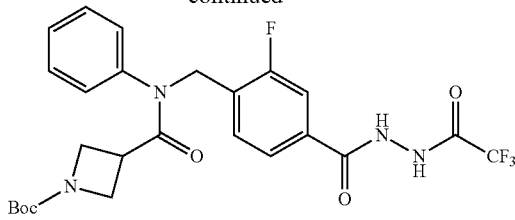

Tert-butyl 3-((2-fluoro-4-(hydrazinecarbonyl)benzyl)(phenyl)carbamoyl) azetidine-1-carboxylate (1.200 g, 2.712 mmol), synthesized in step 2, and triethylamine (0.454 mL, 3.254 mmol) were dissolved in dichloromethane (50 mL) at room temperature, and trifluoroacetic anhydride (0.415 mL, 2.983 mmol) was added to the solution. The mixture was stirred at the same temperature for 4 hours. Saturated aqueous ammonium chloride solution was added to the reaction mixture, followed by extraction with dichloromethane. The organic layer was washed with saturated aqueous sodium chloride solution, dried with magnesium sulfate anhydrous, filtered, and then concentrated under reduced pressure. The title compound was used without further purification (1.400 g, 95.9%) as colorless oil.

[Step 4] Synthesis of tert-butyl 3-((2-fluoro-4-(5-(trifluoromethyl)-1,3,4-oxadiazol-2-yl)benzyl)(phenyl)carbamoyl)azetidine-1-carboxylate

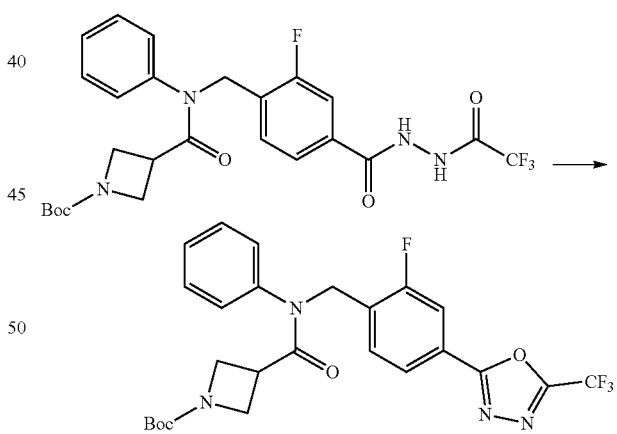

Tert-butyl 3-((2-fluoro-4-(2-(2,2,2-trifluoroacetyl)hydrazine-1-carbonyl)benzyl)(phenyl)carbamoyl)azetidine-1-carboxylate (1.400 g, 2.600 mmol), synthesized in step 3, and 1-methoxy-N-triethylammoniosulfonyl-methanimidate (Burgess reagent, 0.929 g, 3.900 mmol) were mixed in tetrahydrofuran (100 mL) at room temperature. The mixture was heated at reflux for 12 hours, and then cooled down to room temperature. The reaction mixture was concentrated under reduced pressure, and the concentrate was purified by column chromatography (SiO$_2$, 80 g cartridge; ethyl acetate/hexane=from 10% to 30%) and concentrated to give the title compound (0.800 g, 59.1%) as a white solid.

[Step 5] Synthesis of N-(2-fluoro-4-(5-(trifluoromethyl)-1,3,4-oxadiazol-2-yl)benzyl)-N-phenylazetidine-3-carboxamide hydrochloride

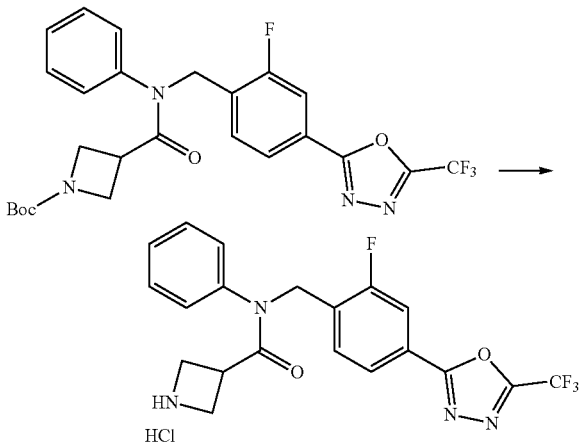

Tert-butyl 3-((2-fluoro-4-(5-(trifluoromethyl)-1,3,4-oxadiazol-2-yl)benzyl)(phenyl)carbamoyl)azetidine-1-carboxylate (0.800 g, 1.537 mmol) synthesized in step 4 was dissolved in dichloromethane (50 mL) at room temperature, and hydrochloric acid (4.00 M solution in dioxane, 1.921 mL, 7.685 mmol) was added to the solution. The mixture was stirred at the same temperature for 12 hours. The reaction mixture was concentrated under reduced pressure to remove the solvent, and the concentrate was suspended in diethyl ether (50 mL) and filtered. The obtained solid was washed with diethyl ether and dried to give the title compound (0.600 g, 85.4%) as a white solid.

[Step 6] Synthesis of Compound 11232

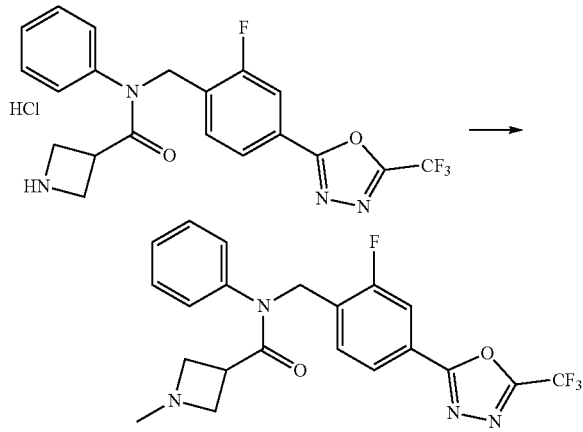

N-(2-fluoro-4-(5-(trifluoromethyl)-1,3,4-oxadiazol-2-yl)benzyl)-N-phenylazetidine-3-carboxamide hydrochloride (0.050 g, 0.109 mmol), synthesized in step 5, and formaldehyde (37.00% solution in water, 0.012 mL, 0.164 mmol) were dissolved in dichloromethane (10 mL) at room temperature, and sodium triacetoxyborohydride (0.035 g, 0.164 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 20%) and concentrated to give the title compound (0.017 g, 35.8%) as a yellow solid.

$^1$H NMR (CDCl$_3$, 700 MHz) δ 7.92-7.84 (m, 1H), 7.73 (t, 1H, J=15.4 Hz), 7.60-7.51 (m, 1H), 7.37 (d, 3H, J=14.7 Hz), 6.93 (dd, 2H, J=32.2, 3.1 Hz), 5.11-5.00 (m, 2H), 3.84-3.58 (m, 4H), 3.49-3.40 (m, 1H), 2.66-2.51 (m, 3H); LRMS (ES) m/z 435.2 (M$^+$+1).

EXAMPLE 48: Synthesis of Compound 11233, 1-ethyl-N-(2-fluoro-4-(5-(trifluoromethyl)-1,3,4-oxadiazol-2-yl)benzyl)-N-phenylazetidine-3-carboxamide

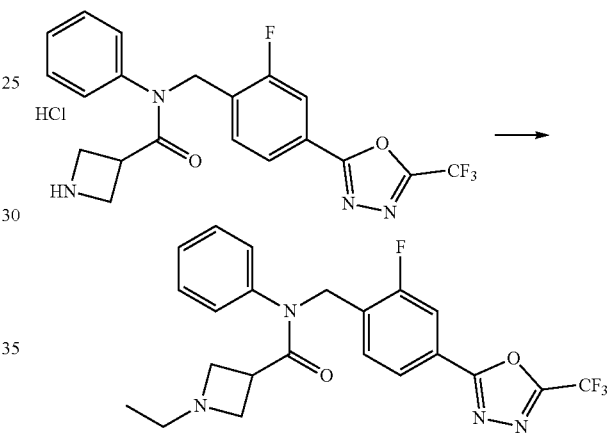

N-(2-fluoro-4-(5-(trifluoromethyl)-1,3,4-oxadiazol-2-yl)benzyl)-N-phenylazetidine-3-carboxamide hydrochloride (0.050 g, 0.109 mmol), synthesized in step 5 of Example 47, and acetaldehyde (0.009 mL, 0.164 mmol) were dissolved in dichloromethane (10 mL) at room temperature, and sodium triacetoxyborohydride (0.035 g, 0.164 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.015 g, 30.6%) as a brown solid.

$^1$H NMR (CDCl$_3$, 700 MHz) δ 7.88 (d, 1H, J=7.7 Hz), 7.72 (t, 1H, J=15.3 Hz), 7.58 (t, 1H, J=6.9 Hz), 7.40 (d, 3H, J=39.7 Hz), 6.96 (t, 2H, J=20.0 Hz), 5.11-4.95 (m, 2H), 3.40 (d, 5H, J=67.9 Hz), 2.62 (d, 2H, J=4.5 Hz), 0.95 (d, 3H, J=71.5 Hz); LRMS (ES) m/z 449.3 (M$^+$+1).

EXAMPLE 49: Synthesis of Compound 11234, 1-acetyl-N-(2-fluoro-4-(5-(trifluoromethyl)-1,3,4-oxadiazol-2-yl)benzyl)-N-phenylazetidine-3-carboxamide

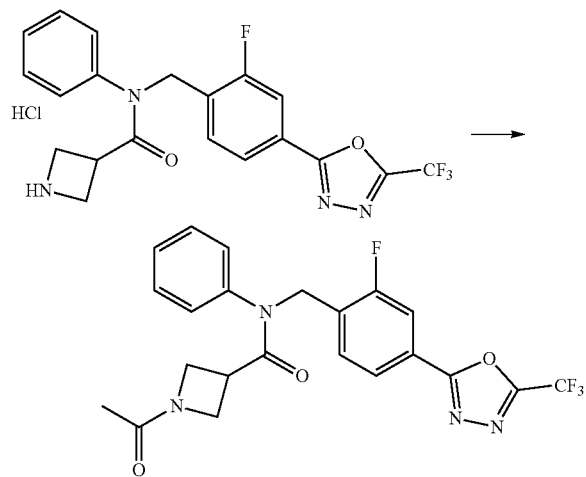

N-(2-fluoro-4-(5-(trifluoromethyl)-1,3,4-oxadiazol-2-yl)benzyl)-N-phenylazetidine-3-carboxamide hydrochloride (0.050 g, 0.109 mmol), synthesized in step 5 of Example 47, and N,N-diisopropylethylamine (0.038 mL, 0.219 mmol) were dissolved in dichloromethane (10 mL) at room temperature, and acetyl chloride (0.009 mL, 0.120 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; dichloromethane/methanol=0% to 20%) and concentrated to give the title compound (0.027 g, 53.3%) as a yellow solid.

$^1$H NMR (CDCl$_3$, 700 MHz) δ 7.94-7.83 (m, 1H), 7.75 (t, 1H, J=9.4 Hz), 7.62-7.54 (m, 1H), 7.39 (s, 3H), 6.99 (d, 2H, J=5.4 Hz), 5.08 (s, 2H), 4.47 (t, 1H, J=7.0 Hz), 4.08-4.01 (m, 1H), 3.94 (t, 1H, J=8.4 Hz), 3.70 (t, 1H, J=9.5 Hz), 3.38-3.27 (m, 1H), 1.84 (s, 3H); LRMS (ES) m/z 463.3 (M$^+$+1).

EXAMPLE 50: Synthesis of Compound 11235, N-(2-fluoro-4-(5-(trifluoromethyl)-1,3,4-oxadiazol-2-yl)benzyl)-N-phenyl-1-propionylazetidine-3-carboxamide

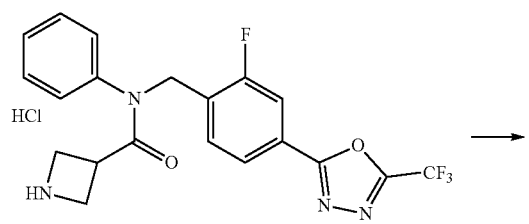

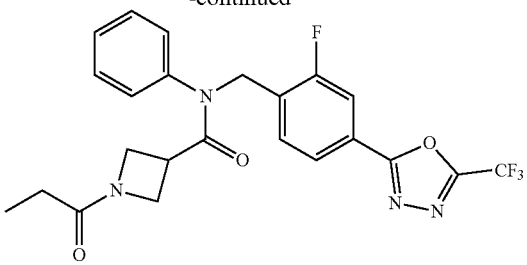

N-(2-fluoro-4-(5-(trifluoromethyl)-1,3,4-oxadiazol-2-yl)benzyl)-N-phenylazetidine-3-carboxamide hydrochloride (0.050 g, 0.109 mmol), synthesized in step 5 of Example 47, and N,N-diisopropylethylamine (0.038 mL, 0.219 mmol) were dissolved in dichloromethane (10 mL) at room temperature, and propionyl chloride (0.011 mL, 0.120 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.012 g, 23.0%) as a white solid.

$^1$H NMR (CDCl$_3$, 700 MHz) δ 7.87 (dd, 1H, J=23.0, 10.1 Hz), 7.75 (d, 1H, J=9.5 Hz), 7.61 (dt, 1H, J=15.0, 7.6 Hz), 7.44-7.34 (m, 3H), 7.00 (d, 2H, J=5.7 Hz), 5.13-5.02 (m, 2H), 4.41 (d, 1H, J=76.8 Hz), 3.92 (dd, 2H, J=97.6, 59.0 Hz), 3.69 (dd, 1H, J=59.2, 21.2 Hz), 3.40-3.28 (m, 1H), 2.11 (d, 2H, J=51.5 Hz), 1.13-1.05 (m, 3H); LRMS (ES) m/z 477.2 (M$^+$+1).

EXAMPLE 51: Synthesis of Compound 11236, N-(2-fluoro-4-(5-(trifluoromethyl)-1,3,4-oxadiazol-2-yl)benzyl)-1-isobutyryl-N-phenylazetidine-3-carboxamide

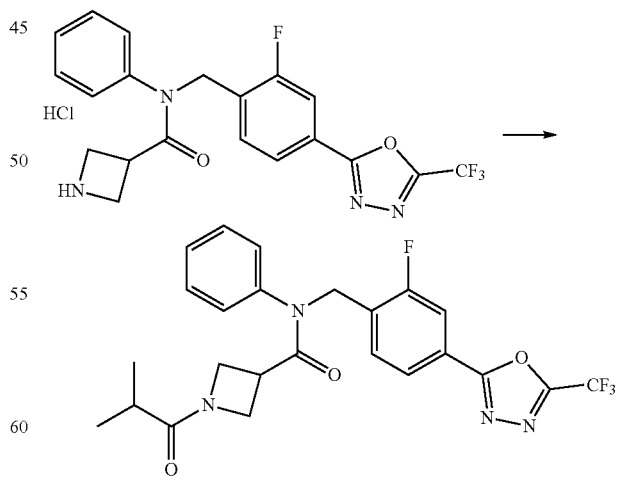

N-(2-fluoro-4-(5-(trifluoromethyl)-1,3,4-oxadiazol-2-yl)benzyl)-N-phenylazetidine-3-carboxamide hydrochloride (0.050 g, 0.109 mmol), synthesized in step 5 of Example 47, and N,N-diisopropylethylamine (0.038 mL, 0.219 mmol)

were dissolved in dichloromethane (10 mL) at room temperature, and isobutyryl chloride (0.013 mL, 0.120 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.036 g, 67.1%) as a white solid.

$^1$H NMR (CDCl$_3$, 700 MHz) δ 7.87 (t, 1H, J=10.4 Hz), 7.74 (d, 1H, J=9.6 Hz), 7.61 (dt, 1H, J=29.5, 7.6 Hz), 7.45-7.33 (m, 3H), 6.98 (dd, 2H, J=28.1, 7.6 Hz), 5.15-4.97 (m, 2H), 4.38 (dd, 1H, J=60.8, 56.4 Hz), 4.14-3.57 (m, 3H), 3.39-3.28 (m, 1H), 2.45-2.32 (m, 1H), 1.07 (s, 6H); LRMS (ES) m/z 491.3 (M$^+$+1).

EXAMPLE 52: Synthesis of Compound 11237, N-(2-fluoro-4-(5-(trifluoromethyl)-1,3,4-oxadiazol-2-yl)benzyl)-1-(methanesulfonyl)-N-phenylazetidine-3-carboxamide

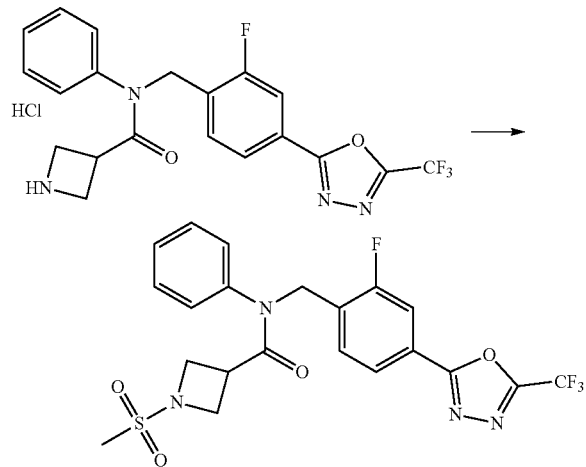

N-(2-fluoro-4-(5-(trifluoromethyl)-1,3,4-oxadiazol-2-yl)benzyl)-N-phenylazetidine-3-carboxamide hydrochloride (0.050 g, 0.109 mmol), synthesized in step 5 of Example 47, and N,N-diisopropylethylamine (0.038 mL, 0.219 mmol) were dissolved in dichloromethane (10 mL) at room temperature, and methanesulfonyl chloride (0.009 mL, 0.120 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.026 g, 47.7%) as a white solid.

$^1$H NMR (CDCl$_3$, 700 MHz) δ 7.89 (t, 1H, J=9.1 Hz), 7.75 (d, 1H, J=9.4 Hz), 7.57 (t, 1H, J=7.5 Hz), 7.40 (d, 3H, J=1.5 Hz), 6.98 (d, 2H, J=3.7 Hz), 5.08 (s, 2H), 4.13 (t, 2H, J=7.5 Hz), 3.70 (t, 2H, J=8.3 Hz), 3.36 (p, 1H, J=7.9 Hz), 2.91 (s, 3H); LRMS (ES) m/z 499.2 (M$^+$+1).

EXAMPLE 53: Synthesis of Compound 11238, N-(4-(5-(difluoromethyl)-1,3,4-oxadiazol-2-yl)-2-fluorobenzyl)-1-methyl-N-phenylazetidine-3-carboxamide

[Step 1] Synthesis of tert-butyl 3-((4-(2-(2,2-difluoroacetyl)hydrazine-1-carbonyl)-2-fluorobenzyl)(phenyl)carbamoyl)azetidine-1-carboxylate

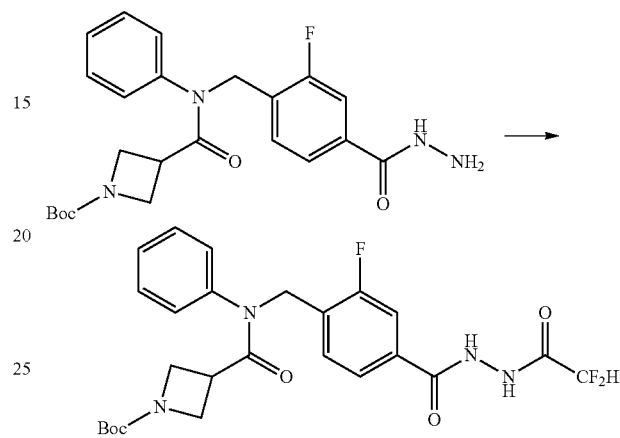

Tert-butyl 3-((2-fluoro-4-(hydrazinecarbonyl)benzyl)(phenyl)carbamoyl)aztidine-1-carboxylate (1.200 g, 2.712 mmol), synthesized in step 2 of Example 47, and triethylamine (0.454 mL, 3.254 mmol) were dissolved in dichloromethane (50 mL) at room temperature, and difluoroacetic anhydride (0.371 mL, 2.983 mmol) was added to the solution. The mixture was stirred at the same temperature for 4 hours. Saturated aqueous ammonium chloride solution was added to the reaction mixture, followed by extraction with dichloromethane. The organic layer was washed with saturated aqueous sodium chloride solution, dried with magnesium sulfate anhydrous, filtered, and then concentrated under reduced pressure. The title compound was used without further purification (1.400 g, 99.2%) as colorless oil.

[Step 2] Synthesis of tert-butyl 3-((4-(5-(difluoromethyl)-1,3,4-oxadiazol-2-yl)-2-fluorobenzyl)(phenyl)carbamoyl)azetidine-1-carboxylate

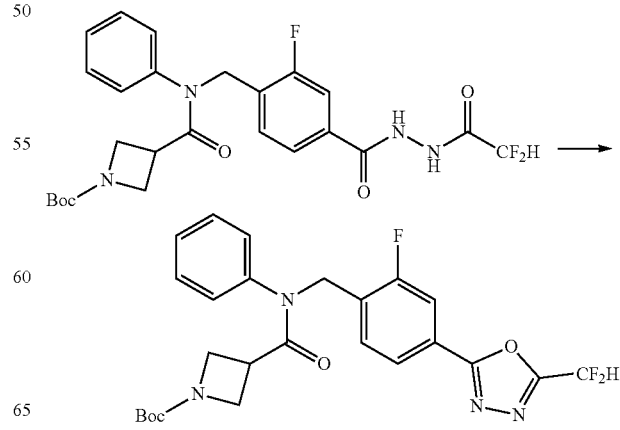

Tert-butyl 3-((4-(2-(2,2-difluoroacetyl)hydrazine-1-carbonyl)-2-fluorobenzyl)(phenyl)carbamoyl)azetidine-1-carboxylate (1.400 g, 2.690 mmol), synthesized in step 1, and 1-methoxy-N-triethylammoniosulfonyl-methanimidate (Burgess reagent, 0.961 g, 4.035 mmol) were mixed in tetrahydrofuran (100 mL), and the mixture was heated under reflux for 12 hours and cooled down to room temperature. The reaction mixture was concentrated under reduced pressure to remove the solvent, and the concentrate was purified by column chromatography (SiO$_2$, 80 g cartridge; ethyl acetate/hexane=from 10% to 30%) to give the title compound (0.700 g, 51.8%) as a white solid.

[Step 3] Synthesis of N-(4-(5-(difluoromethyl)-1,3,4-oxadiazol-2-yl)-2-fluorobenzyl)-N-phenylazetidine-3-carboxamide hydrochloride

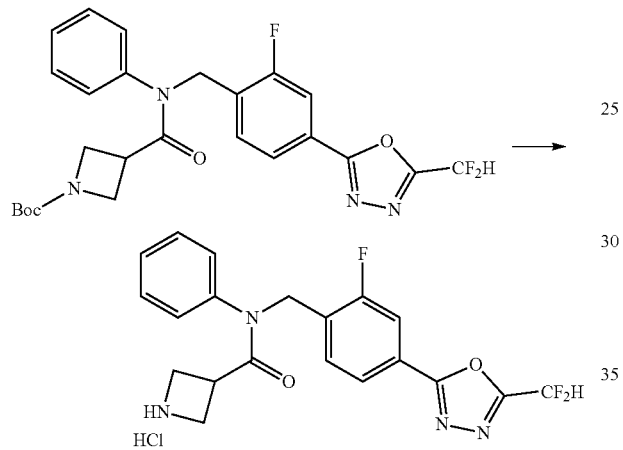

Tert-butyl 3-((4-(5-(difluoromethyl)-1,3,4-oxadiazol-2-yl)-2-fluorobenzyl)(phenyl)carbamoyl)azetidine-1-carboxylate (0.700 g, 1.393 mmol) synthesized in step 2 was dissolved in dichloromethane (50 mL) at room temperature, and hydrochloric acid (4.00 M solution in dioxane, 1.741 mL, 6.965 mmol) was added to the solution. The mixture was stirred at the same temperature for 12 hours. The reaction mixture was concentrated under reduced pressure to remove the solvent, and the concentrate was suspended in diethyl ether (50 mL) and filtered. The obtained solid was washed with diethyl ether and dried to give the title compound (0.600 g, 98.1%) as a white solid.

[Step 4] Synthesis of Compound 11238

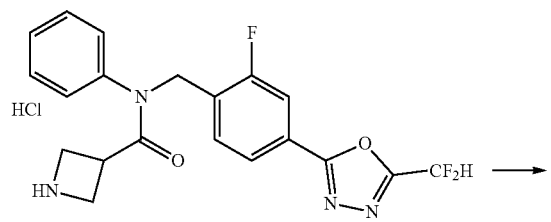

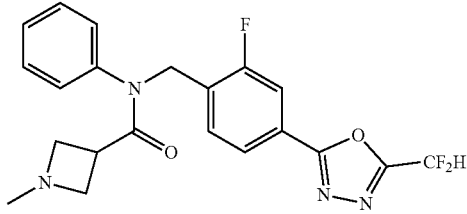

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3, and formaldehyde (37.00% solution in water, 0.013 mL, 0.171 mmol) were dissolved in dichloromethane (10 mL) at room temperature, and sodium triacetoxyborohydride (0.036 g, 0.171 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.010 g, 21.1%) as a white solid.

$^1$H NMR (CDCl$_3$, 700 MHz) δ 7.88 (d, 1H, J=7.8 Hz), 7.73 (d, 1H, J=9.6 Hz), 7.61-7.53 (m, 1H), 7.35 (t, 3H, J=9.7 Hz), 7.15 (d, 1H, J=6.8 Hz), 6.97 (dd, 2H, J=29.0, 22.5 Hz), 5.11-4.97 (m, 2H), 3.24 (dd, 4H, J=67.4, 30.6 Hz), 2.32 (s, 3H), 2.00-1.68 (m, 1H); LRMS (ES) m/z 417.3 (M$^+$+1).

EXAMPLE 54: Synthesis of Compound 11239, N-(4-(5-(difluoromethyl)-1,3,4-oxadiazol-2-yl)-2-fluorobenzyl)-1-ethyl-N-phenylazetidine-3-carboxamide

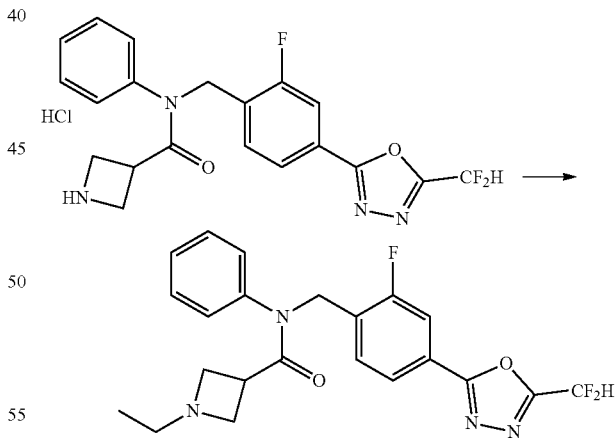

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3 of Example 53, and acetaldehyde (0.010 mL, 0.171 mmol) were dissolved in dichloromethane (10 mL) at room temperature, and sodium triacetoxyborohydride (0.036 g, 0.171 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.017 g, 34.7%) as a yellow solid.

$^1$H NMR (CDCl$_3$, 700 MHz) δ 7.91-7.83 (m, 1H), 7.74 (d, 1H, J=9.7 Hz), 7.57-7.49 (m, 1H), 7.44-7.34 (m, 3H), 7.02-6.83 (m, 3H), 5.10-4.99 (m, 2H), 3.71-3.59 (m, 2H), 3.52 (dd, 2H, J=19.3, 11.2 Hz), 3.49-3.37 (m, 1H), 2.84-2.72 (m, 2H), 1.13-1.00 (m, 3H); LRMS (ES) m/z 431.3 (M$^+$+1).

EXAMPLE 55: Synthesis of Compound 11240, N-(4-(5-(difluoromethyl)-1,3,4-oxadiazol-2-yl)-2-fluorobenzyl)-1-isopropyl-N-phenylazetidine-3-carboxamide

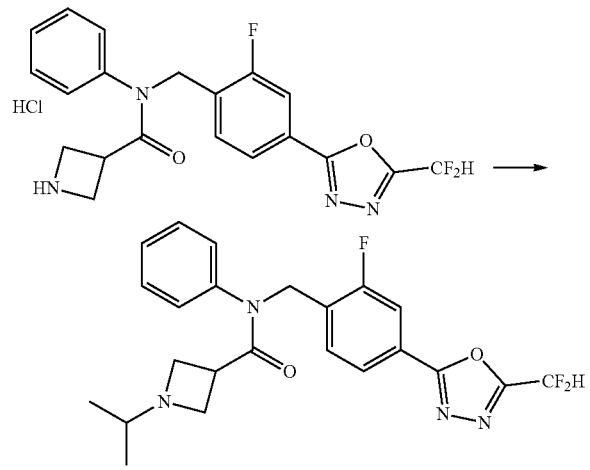

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3 of Example 53, and acetone (0.013 mL, 0.171 mmol) were dissolved in dichloromethane (10 mL) at room temperature, and sodium triacetoxyborohydride (0.036 g, 0.171 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.025 g, 49.4%) as a yellow solid.

$^1$H NMR (CDCl$_3$, 700 MHz) δ 7.92-7.82 (m, 1H), 7.73 (t, 1H, J=8.8 Hz), 7.54 (t, 1H, J=7.5 Hz), 7.38 (d, 3H, J=5.3 Hz), 7.04-6.82 (m, 3H), 5.03 (d, 2H, J=21.2 Hz), 3.63-3.34 (m, 5H), 2.80-2.67 (m, 1H), 1.03 (t, 6H, J=7.8 Hz); LRMS (ES) m/z 445.3 (M$^+$+1).

EXAMPLE 56: Synthesis of Compound 11241, 1-acetyl-N-(4-(5-(difluoromethyl)-1,3,4-oxadiazol-2-yl)-2-fluorobenzyl)-N-phenylazetidine-3-carboxamide

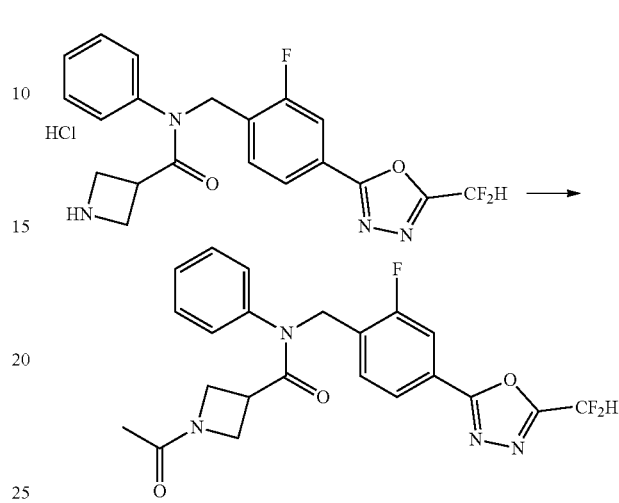

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3 of Example 53, and N,N-diisopropylethylamine (0.039 mL, 0.228 mmol) were dissolved in dichloromethane (10 mL) at room temperature, and acetyl chloride (0.009 mL, 0.125 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.014 g, 27.6%) as a yellow solid.

$^1$H NMR (CDCl$_3$, 700 MHz) δ 7.88 (d, 1H, J=7.9 Hz), 7.73 (t, 1H, J=12.4 Hz), 7.58 (t, 1H, J=7.5 Hz), 7.39 (d, 3H, J=5.2 Hz), 7.01-6.82 (m, 3H), 5.10-5.05 (m, 2H), 4.48 (t, 1H, J=7.1 Hz), 4.09-4.01 (m, 1H), 3.94 (t, 1H, J=8.3 Hz), 3.70 (t, 1H, J=9.3 Hz), 3.36-3.27 (m, 1H), 1.50-1.43 (m, 3H); LRMS (ES) m/z 445.3 (M$^+$+1).

EXAMPLE 57: Synthesis of Compound 11242, N-(4-(5-(difluoromethyl)-1,3,4-oxadiazol-2-yl)-2-fluorobenzyl)-N-phenyl-1-propionylazetidine-3-carboxamide

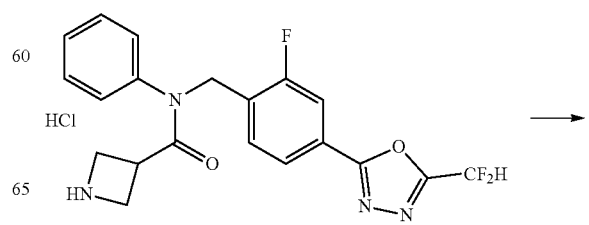

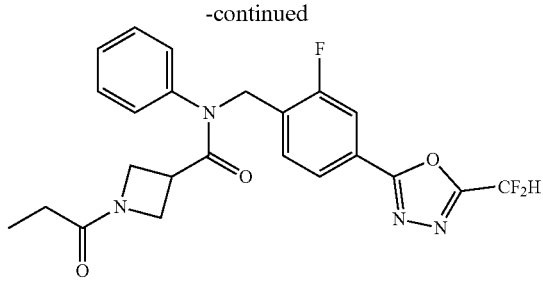

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3 of Example 53, and N,N-diisopropylethylamine (0.039 mL, 0.228 mmol) were dissolved in dichloromethane (10 mL) at room temperature, and propionyl chloride (0.011 mL, 0.125 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.017 g, 32.5%) as a yellow solid.

$^1$H NMR (CDCl$_3$, 700 MHz) δ 7.88 (d, 1H, J=7.9 Hz), 7.74 (d, 1H, J=9.7 Hz), 7.57 (dd, 1H, J=19.2, 11.7 Hz), 7.40 (dd, 3H, J=16.9, 7.9 Hz), 7.03-6.83 (m, 3H), 5.08 (s, 2H), 4.56-4.32 (m, 1H), 4.03 (ddd, 4H, J=153.6, 33.8, 26.6 Hz), 3.36-3.28 (m, 1H), 2.89-2.80 (m, 1H), 2.07 (d, 2H, J=8.1 Hz), 1.10 (t, 3H, J=7.6 Hz); LRMS (ES) m/z 459.3 (M$^+$+1).

EXAMPLE 58: Synthesis of Compound 11243, N-(4-(5-(difluoromethyl)-1,3,4-oxadiazol-2-yl)-2-fluorobenzyl)-1-isobutyryl-N-phenylazetidine-3-carboxamide

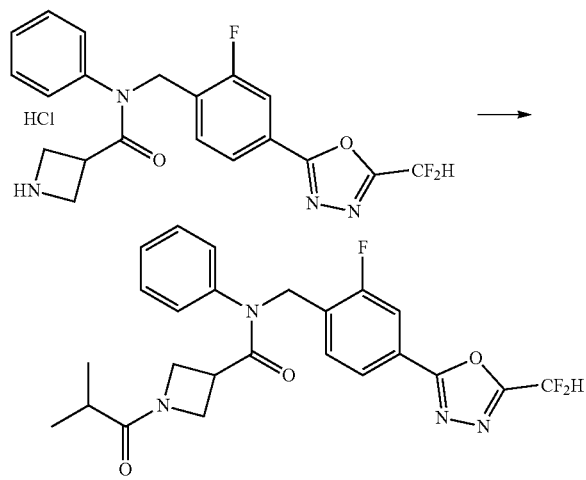

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3 of Example 53, and N,N-diisopropylethylamine (0.039 mL, 0.228 mmol) were dissolved in dichloromethane (10 mL) at room temperature, and isobutyryl chloride (0.013 mL, 0.125 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.023 g, 42.7%) as a white solid.

$^1$H NMR (CDCl$_3$, 700 MHz) δ 7.88 (dd, 1H, J=8.0, 1.2 Hz), 7.74 (dd, 1H, J=9.7, 1.1 Hz), 7.61-7.54 (m, 1H), 7.39 (dt, 3H, J=11.8, 4.2 Hz), 7.02-6.83 (m, 3H), 5.14-4.97 (m, 2H), 4.50 (s, 1H), 4.00 (d, 2H, J=56.0 Hz), 3.74-3.61 (m, 1H), 3.38-3.24 (m, 1H), 2.43-2.34 (m, 1H), 1.07 (d, 6H, J=25.4 Hz); LRMS (ES) m/z 473.3 (M$^+$+1).

EXAMPLE 59: Synthesis of Compound 11244, N-(4-(5-(difluoromethyl)-1,3,4-oxadiazol-2-yl)-2-fluorobenzyl)-N-phenyl-1-(2,2,2-trifluoroacetyl) azetidine-3-carboxamide

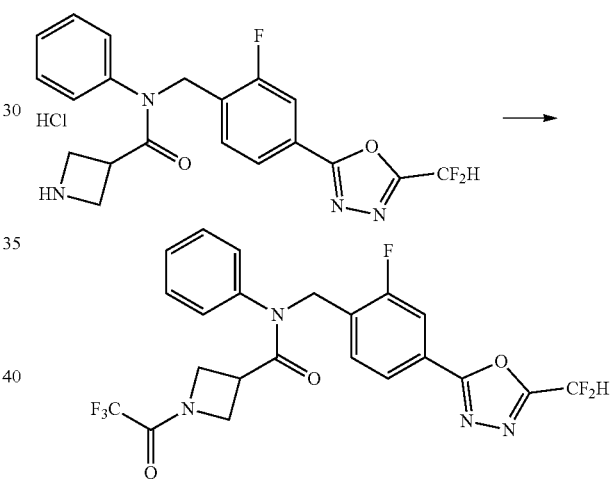

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3 of Example 53, and N,N-diisopropylethylamine (0.039 mL, 0.228 mmol) were dissolved in dichloromethane (10 mL) at room temperature, and 2,2,2-trifluoroacetic anhydride (0.018 mL, 0.125 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$ plate, 20×20×1 mm; methanol/dichloromethane=10%) and concentrated to give the title compound (0.005 g, 8.8%) as a white solid.

$^1$H NMR (CDCl$_3$, 700 MHz) δ 7.89 (d, 1H, J=7.9 Hz), 7.76 (d, 1H, J=9.6 Hz), 7.57 (dd, 1H, J=15.6, 8.0 Hz), 7.42 (d, 3H, J=3.2 Hz), 7.02-6.83 (m, 3H), 5.13-5.07 (m, 2H), 4.74-4.67 (m, 1H), 4.30-4.24 (m, 1H), 4.19 (t, 1H, J=9.1 Hz), 3.87 (t, 1H, J=9.8 Hz), 3.47 (dt, 1H, J=22.3, 7.9 Hz); LRMS (ES) m/z 499.1 (M$^+$+1).

EXAMPLE 60: Synthesis of Compound 11245, N-(4-(5-(difluoromethyl)-1,3,4-oxadiazol-2-yl)-2-fluorobenzyl)-1-(methylsulfonyl)-N-phenylazetidine-3-carboxamide

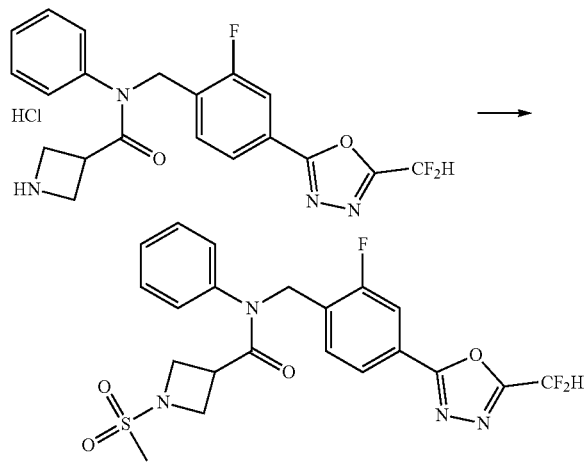

N-(4-(5-(difluoromethyl)-1,3,4-oxadiazol-2-yl)-2-fluorobenzyl)-N-phenylazetidine-3-carboxamide hydrochloride (0.050 g, 0.114 mmol), synthesized in step 3 of Example 53, and N,N-diisopropylethylamine (0.040 mL, 0.228 mmol) were dissolved in dichloromethane (10 mL) at room temperature, and methanesulfonyl chloride (0.010 mL, 0.125 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.013 g, 23.7%) as a white solid.

$^1$H NMR (CDCl$_3$, 700 MHz) δ 7.88 (d, 1H, J=7.9 Hz), 7.75 (d, 1H, J=9.6 Hz), 7.55 (dd, 1H, J=18.1, 10.7 Hz), 7.40 (d, 3H, J=1.6 Hz), 7.02-6.84 (m, 3H), 5.07 (d, 2H, J=14.4 Hz), 4.14 (t, 2H, J=7.5 Hz), 3.71 (t, 2H, J=8.3 Hz), 3.39-3.32 (m, 1H), 2.91 (s, 3H); LRMS (ES) m/z 481.2 (M$^+$+1).

EXAMPLE 61: Synthesis of Compound 11246, N-(2-fluoro-4-(5-(trifluoromethyl)-1,3,4-oxadiazol-2-yl)benzyl)-N-phenylacetamide

[Step 1] Synthesis of methyl 3-fluoro-4-((N-phenylacetamido)methyl)benzoate

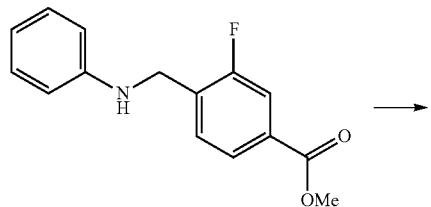

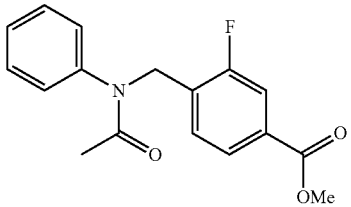

Methyl 3-fluoro-4-((phenylamino)methyl)benzoate (0.150 g, 0.579 mmol) and N,N-diisopropylamine (0.199 mL, 1.157 mmol) were dissolved in dichloromethane (10 mL) at room temperature, and acetyl chloride (0.045 mL, 0.636 mmol) was added to the solution, followed by stirring at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.158 g, 90.6%) as colorless oil.

[Step 2] Synthesis of N-(2-fluoro-4-(hydrazinecarbonyl)benzyl)-N-phenylacetamide

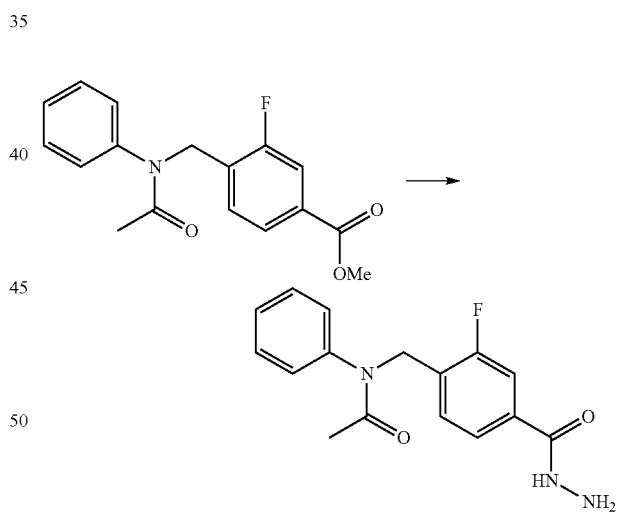

Methyl 3-fluoro-4-((N-phenylacetamido)methyl)benzoate (0.158 g, 0.524 mmol), synthesized in step 1, and nitrogen oxide (0.495 mL, 10.487 mmol) were mixed in ethanol (10 mL) at room temperature, and the mixture was heated under reflux for 5 hours and cooled down to room temperature. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.150 g, 94.9%) as colorless oil.

[Step 3] Synthesis of N-(2-fluoro-4-(2-(2,2,2-trifluoroacetyl)hydrazine-1-carbonyl)benzyl)-N-phenylacetamide

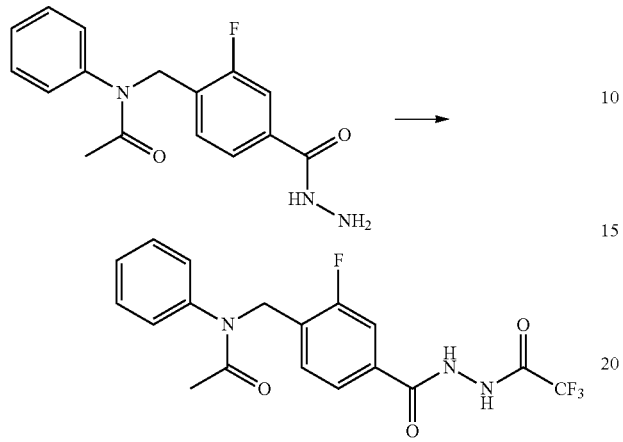

N-(2-fluoro-4-(hydrazinecarbonyl)benzyl)-N-phenylacetamide (0.075 g, 0.249 mmol), synthesized in step 2, and triethylamine (0.069 mL, 0.498 mmol) were dissolved in dichloromethane (10 mL) at room temperature, and trifluoroacetic anhydride (0.042 mL, 0.299 mmol) was added to the solution. The mixture was stirred at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.090 g, 91.0%) as colorless oil.

[Step 4] Synthesis of Compound 11246

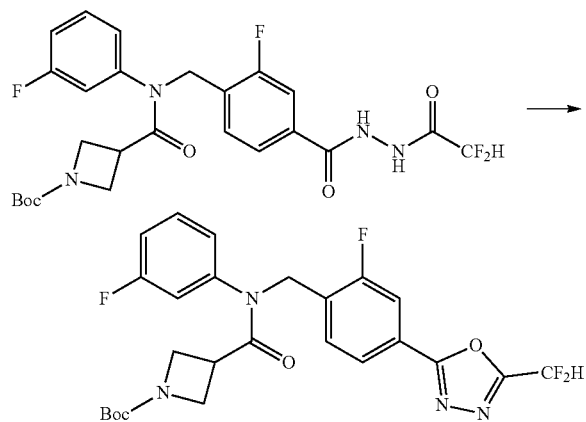

N-(2-fluoro-4-(2-(2,2,2-trifluoroacetyl)hydrazine-1-carbonyl)benzyl)-N-phenylacetamide (0.090 g, 0.227 mmol), synthesized in step 3, and 1-methoxy-N-triethylammoniosulfonyl-methanimidate (Burgess reagent, 0.081 g, 0.340 mmol) were mixed with dichloromethane (10 mL), and the mixture was heated by microwave irradiation at 150° C. for 30 minutes, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.004 g, 4.7%) as colorless oil.

$^1$H NMR (CDCl$_3$, 400 MHz) δ 7.84 (dd, 1H, J=8.0, 1.6 Hz), 7.68 (dd, 1H J=9.7, 1.4 Hz), 7.60 (t, J=7.6 Hz, 1H), 7.36-7.28 (m, 3H), 7.05 (dd, 2H, J=7.9, 1.4 Hz), 5.03 (s, 2H), 1.91 (s, 3H); LRMS (ES) m/z 380.2 (M$^+$+1)

EXAMPLE 62: Synthesis of Compound 11247, N-(4-(5-(difluoromethyl)-1,3,4-oxadiazol-2-yl)-2-fluorobenzyl)-N-phenylacetamide

[Step 1] N-(4-(2-(2,2-difluoroacetyl)hydrazine-1-carbonyl)-2-fluorobenzyl)-N-phenylacetamide

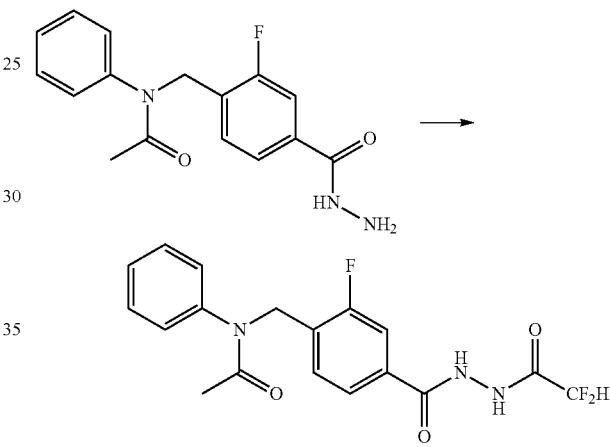

N-(2-fluoro-4-(hydrazinecarbonyl)benzyl)-N-phenylacetamide (0.075 g, 0.249 mmol), synthesized in step 2 of Example 61, and triethylamine (0.069 mL, 0.498 mmol) were dissolved in dichloromethane (10 mL) at room temperature, and 2,2-difluoroacetic anhydride (0.032 mL, 0.299 mmol) was added to the solution. The mixture was stirred at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.093 g, 98.5%) as colorless oil.

[Step 2] Synthesis of Compound 11247

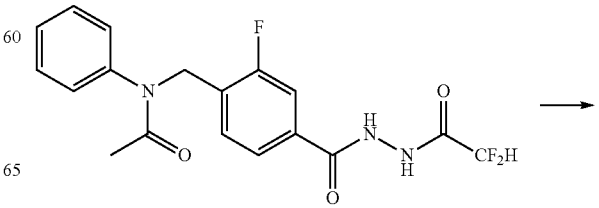

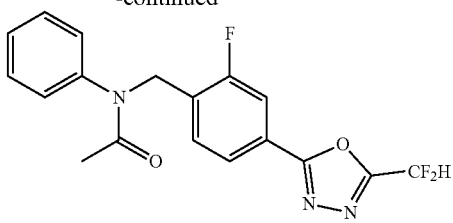

N-(4-(2-(2,2-difluoroacetyl)hydrazine-1-carbonyl)-2-fluorobenzyl)-N-phenylacetamide (0.093 g, 0.245 mmol), synthesized in step 1, 1-methoxy-N-triethylammoniosulfonyl-methanimidate (Burgess reagent, 0.088 g, 0.368 mmol) were mixed in dichloromethane (10 mL), and the mixture was heated by microwave irradiation at 150° C. for 30 minutes, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.005 g, 5.6%) as colorless oil.

$^1$H NMR (CDCl$_3$, 400 MHz) δ 7.84 (dd, J=8.0, 1.6 Hz, 1H), 7.69 (dd, J=9.8, 1.5 Hz, 1H), 7.58 (t, J=7.6 Hz, 1H), 7.37-7.30 (m, 3H), 7.06-7.03 (m, 2H), 6.90 (t, J=48.6 Hz, 1H), 5.04 (s, 2H), 1.93 (s, 3H); LRMS (ES) m/z 362.2 (M$^+$+1).

EXAMPLE 63: Synthesis of Compound 11325, N-(4-(5-(difluoromethyl)-1,3,4-oxadiazol-2-yl)-2-fluorobenzyl)-N-(3-fluorophenyl)-1-methylazetidine-3-carboxamide

[Step 1] Synthesis of tert-butyl 3-((2-fluoro-4-(methoxycarbonyl)benzyl)(3-fluorophenyl)carbamoyl)azetidine-1-carboxylate

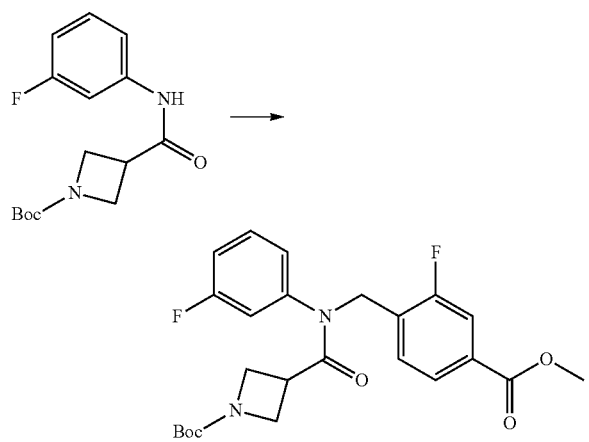

Tert-butyl 3-((3-fluorophenyl)carbamoyl)azetidine-1-carboxylate (0.550 g, 1.869 mmol) was dissolved in tetrahydrofuran (80 mL), and sodium hydride (60.00%, 0.149 g, 3.737 mmol) was added slowly to the solution while the temperature was maintained at 0° C. The mixture was stirred for 20 minutes, and then methyl 4-(bromomethyl)-3-fluorobenzoate (0.508 g, 2.056 mmol) was added thereto. The reaction mixture was further stirred at 50° C. for 12 hours and cooled to room temperature. Then, water (20 mL) was added to the reaction mixture at 0° C., followed by stirring for 5 minutes. After completion of the reaction, water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 80 g cartridge; ethyl acetate/hexane=from 5% to 50%) and concentrated to give the title compound (0.700 g, 81.4%) as a white solid.

[Step 2] Synthesis of tert-butyl 3-((2-fluoro-4-(hydrazinecarbonyl)benzyl)(3-fluorophenyl)carbamoyl)azetidine-1-carboxylate

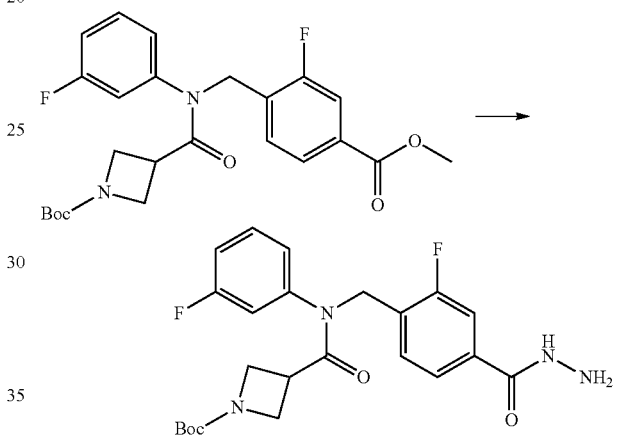

Tert-butyl 3-((2-fluoro-4-(methoxycarbonyl)benzyl)(3-fluorophenyl)carbamoyl)azetidine-1-carboxylate (0.700 g, 1.520 mmol), synthesized in step 1, and hydrazine monohydrate (1.475 mL, 30.403 mmol) were mixed in ethanol (50 mL) at room temperature, and the mixture was heated under reflux for 12 hours, and then cooled to room temperature. The reaction mixture was concentrated under reduced pressure to remove the solvent, and water was added to the concentrate, followed by extraction with dichloromethane. The organic layer was washed with saturated aqueous sodium chloride solution, dried with magnesium sulfate anhydrous, filtered, and then concentrated under reduced pressure. The title compound was used without further purification (0.600 g, 85.7%) as white solid.

[Step 3] Synthesis of tert-butyl 3-((4-(2-(2,2-difluoroacetyl)hydrazine-1-carbonyl)-2-fluorobenzyl)(3-fluorophenyl)carbamoyl)azetidine-1-carboxylate

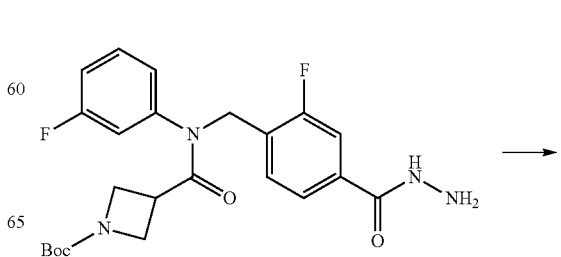

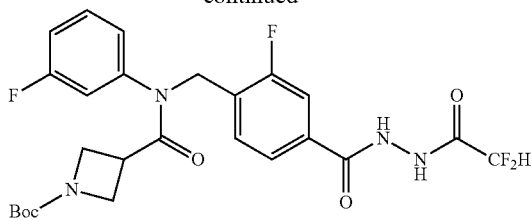

Tert-butyl 3-((2-fluoro-4-(hydrazinecarbonyl)benzyl)(3-fluorophenyl)carbamoyl)azetidine-1-carboxylate (0.600 g, 1.303 mmol), synthesized in step 2, and triethylamine (0.218 mL, 1.564 mmol) were dissolved in dichloromethane (50 mL) at room temperature, and difluoroacetic anhydride (0.178 mL, 1.433 mmol) was added to the solution. The mixture was stirred at the same temperature for 4 hours. Saturated aqueous ammonium chloride solution was added to the reaction mixture, followed by extraction with dichloromethane. The organic layer was washed with saturated aqueous sodium chloride solution, dried with magnesium sulfate anhydrous, filtered, and then concentrated under reduced pressure. The title compound was used without further purification (0.600 g, 85.5%) as colorless oil.

[Step 4] Synthesis of tert-butyl 3-((4-(5-(difluoromethyl)-1,3,4-oxadiazol-2-yl)-2-fluorobenzyl)(3-fluorophenyl)carbamoyl)azetidine-1-carboxylate

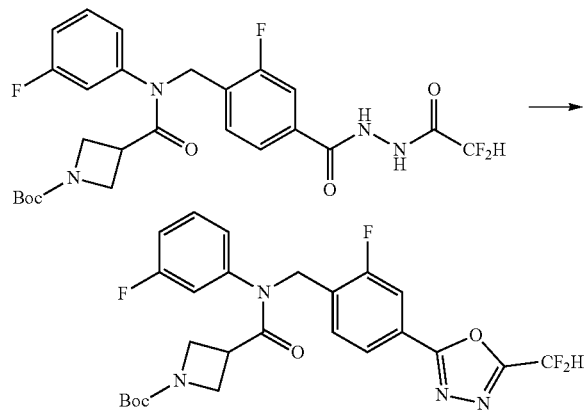

Tert-butyl 3-((4-(2-(2,2-difluoroacetyl)hydrazine-1-carbonyl)-2-fluorobenzyl)(3-fluorophenyl)carbamoyl)azetidine-1-carboxylate (0.600 g, 1.114 mmol), synthesized in step 3, and 1-methoxy-N-triethylammoniosulfonyl-methanimidate (Burgess reagent, 0.398 g, 1.671 mmol) were mixed in tetrahydrofuran (15 mL) at room temperature. The mixture was heated by microwave irradiation at 150° C. for 30 minutes, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 5% to 30%) and concentrated to give the title compound (0.500 g, 86.2%) as a white solid.

[Step 5] Synthesis of N-(4-(5-(difluoromethyl)-1,3,4-oxadiazol-2-yl)-2-fluorobenzyl)-N-(3-fluorophenyl)azetidine-3-carboxamide hydrochloride

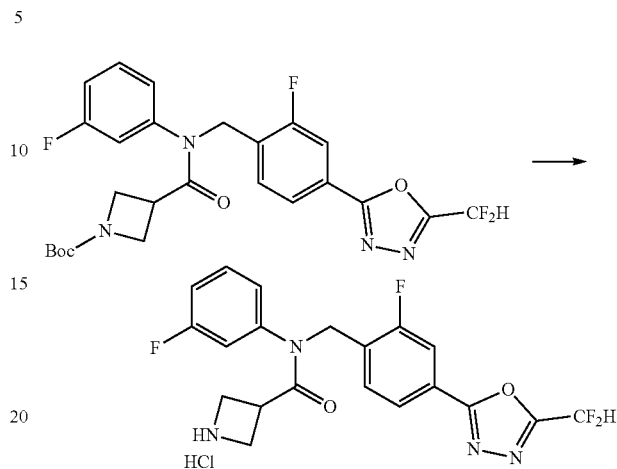

Tert-butyl 3-((4-(5-(difluoromethyl)-1,3,4-oxadiazol-2-yl)-2-fluorobenzyl)(3-fluorophenyl)carbamoyl)azetidine-1-carboxylate (0.500 g, 0.961 mmol) synthesized in step 4 was dissolved in dichloromethane (50 mL) at room temperature, and hydrochloric acid (4.00 M solution in dioxane, 1.201 mL, 4.803 mmol) was added to the solution. The mixture was stirred at the same temperature for 12 hours. The reaction mixture was concentrated under reduced pressure to remove the solvent, and the concentrate was suspended in diethyl ether (50 mL) and filtered. The obtained solid was washed with diethyl ether and dried to afford the title compound (0.430 g, 98.0%) as a white solid.

[Step 6] Synthesis of Compound 11325

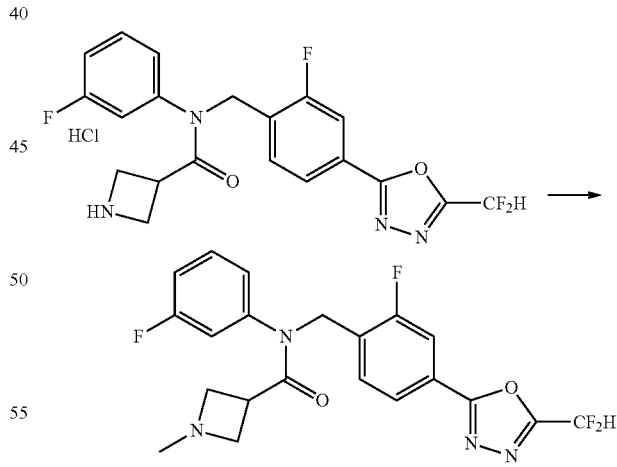

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5, and formaldehyde (37.00% solution in water, 0.012 mL, 0.164 mmol) were dissolved in dichloromethane (10 mL) at room temperature, and sodium triacetoxyborohydride (0.035 g, 0.164 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.007 g, 14.7%) as colorless oil.

$^1$H NMR (400 MHz, CDCl$_3$) δ 7.87 (dd, 1H, J=8.0, 1.6 Hz), 7.74 (dd, 1H, J=9.8, 1.5 Hz), 7.53 (t, 1H, J=7.6 Hz), 7.34 (td, 1H, J=8.2, 6.4 Hz), 7.09 (td, 1H, J=8.3, 2.3 Hz), 6.93 (dd, 1H, J=68.9, 34.4 Hz), 6.76-6.66 (m, 2H), 4.99 (d, 2H, J=19.7 Hz), 3.60 (dd, 2H, J=18.8, 10.8 Hz), 3.46 (t, 2H, J=8.0 Hz), 3.35 (dt, 1H, J=16.2, 8.1 Hz), 2.44 (d, 3H, J=13.4 Hz); LRMS (ES) m/z 435.2 (M$^+$+1).

EXAMPLE 64: Synthesis of Compound 11326, N-(4-(5-(difluoromethyl)-1,3,4-oxadiazol-2-yl)-2-fluorobenzyl)-1-ethyl-N-(3-fluorophenyl)azetidine-3-carboxamide

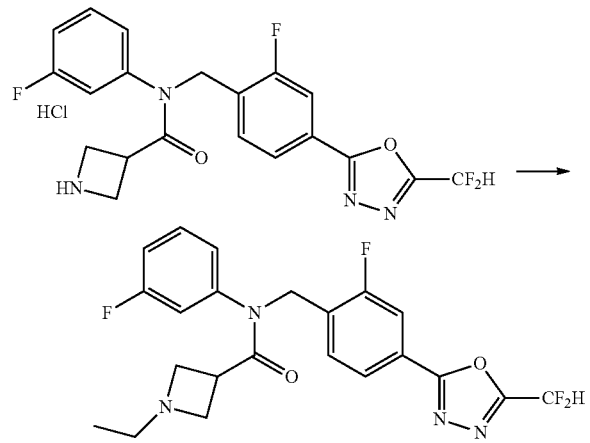

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and acetaldehyde (0.009 mL, 0.164 mmol) were dissolved in dichloromethane (10 mL) at room temperature, and sodium triacetoxyborohydride (0.035 g, 0.164 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.007 g, 14.3%) as yellow oil.

$^1$H NMR (400 MHz, CDCl$_3$) δ 7.87 (dd, 1H, J=8.0, 1.5 Hz), 7.73 (dd, 1H, J=9.8, 1.5 Hz), 7.54 (t, 1H, J=7.6 Hz), 7.33 (td, 1H, J=8.1, 6.4 Hz), 7.08 (td, 1H, J=8.3, 1.9 Hz), 6.93 (dd, 1H, J=69.2, 34.1 Hz), 6.78-6.69 (m, 2H), 4.99 (d, 2H, J=19.8 Hz), 3.50-3.18 (m, 5H), 2.59 (q, 2H, J=7.2 Hz), 0.96 (t, 3H, J=7.2 Hz); LRMS (ES) m/z 449.3 (M$^+$+1).

EXAMPLE 65: Synthesis of Compound 11327, N-(4-(5-(difluoromethyl)-1,3,4-oxadiazol-2-yl)-2-fluorobenzyl)-N-(3-fluorophenyl)-1-propylazetidine-3-carboxamide

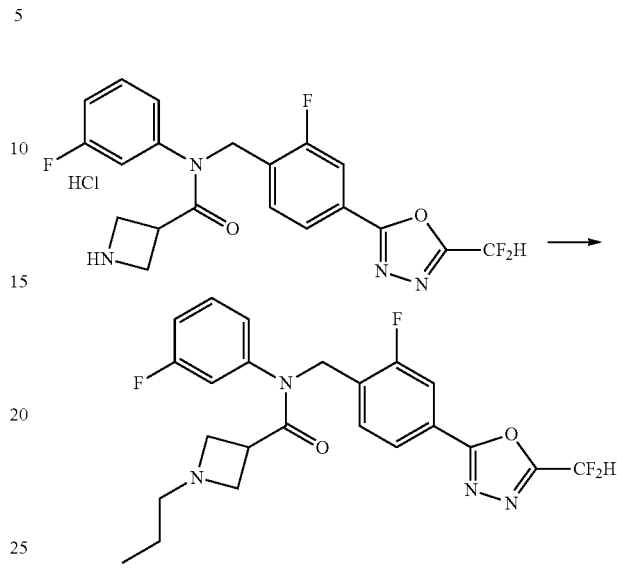

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and propionaldehyde (0.010 g, 0.164 mmol) were dissolved in dichloromethane (10 mL) at room temperature, and sodium triacetoxyborohydride (0.035 g, 0.164 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.017 g, 33.6%) as colorless oil.

$^1$H NMR (400 MHz, CDCl$_3$) δ 7.86 (dd, 1H, J=8.0, 1.5 Hz), 7.72 (dd, 1H, J=9.8, 1.5 Hz), 7.51 (dd, 1H, J=15.7, 8.0 Hz), 7.32 (tt, 1H, J=11.9, 5.9 Hz), 7.07 (td, 1H, J=8.1, 2.1 Hz), 6.90 (dd, 1H, J=58.6, 44.7 Hz), 6.77-6.68 (m, 2H), 4.99 (d, 2H, J=16.3 Hz), 3.61-3.47 (m, 2H), 3.47-3.31 (m, 3H), 2.57 (dd, 2H, J=18.4, 10.5 Hz), 1.39 (dq, 2H, J=14.9, 7.4 Hz), 0.90-0.81 (m, 3H); LRMS (ES) m/z 463.2 (M$^+$+1).

EXAMPLE 66: Synthesis of Compound 11328, 1-butyl-N-(4-(5-(difluoromethyl)-1,3,4-oxadiazol-2-yl)-2-fluorobenzyl)-N-(3-fluorophenyl)azetidine-3-carboxamide

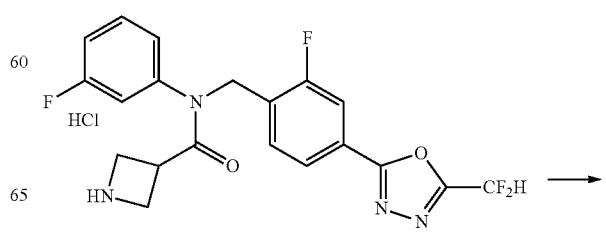

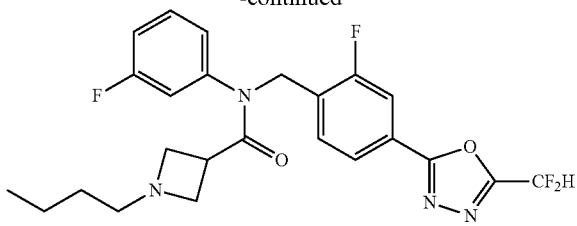

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and butyraldehyde (0.012 g, 0.164 mmol) were dissolved in dichloromethane (10 mL) at room temperature, and sodium triacetoxyborohydride (0.035 g, 0.164 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.020 g, 38.4%) as colorless oil.

$^1$H NMR (400 MHz, CDCl$_3$) δ 7.86 (dd, 1H, J=8.0, 1.5 Hz), 7.73 (dd, 1H, J=9.8, 1.5 Hz), 7.51 (t, 1H, J=7.6 Hz), 7.34 (dt, 1H, J=14.2, 6.5 Hz), 7.13-7.05 (m, 1H), 6.90 (dd, 1H, J=58.6, 44.7 Hz), 6.77-6.64 (m, 2H), 4.99 (d, 2H, J=13.6 Hz), 3.71-3.56 (m, 2H), 3.56-3.38 (m, 3H), 2.67 (dd, 2H, J=19.4, 11.4 Hz), 1.42-1.21 (m, 4H), 0.92-0.79 (m, 3H); LRMS (ES) m/z 477.3 (M$^+$+1).

EXAMPLE 67: Synthesis of Compound 11329, N-(4-(5-(difluoromethyl)-1,3,4-oxadiazol-2-yl)-2-fluorobenzyl)-N-(3-fluorophenyl)-1-isopropylazetidine-3-arboxamide

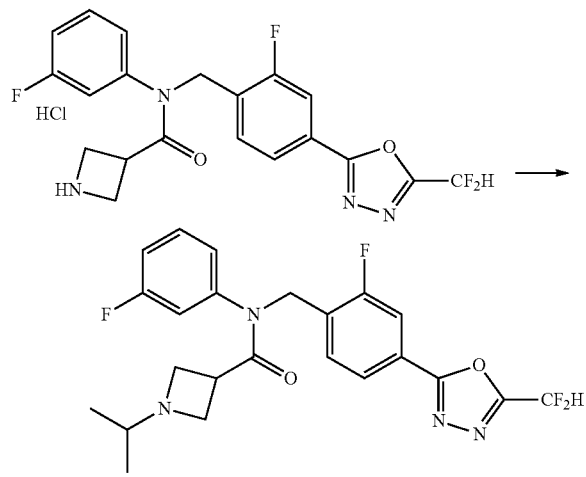

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and acetone (0.012 mL, 0.164 mmol) were dissolved in dichloromethane (10 mL) at room temperature, and sodium triacetoxyborohydride (0.035 g, 0.164 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 20%) and concentrated to give the title compound (0.010 g, 19.8%) as a white solid.

$^1$H NMR (400 MHz, CDCl$_3$) δ 7.87 (dd, 1H, J=8.0, 1.5 Hz), 7.73 (dd, 1H, J=9.8, 1.5 Hz), 7.54 (t, 1H, J=7.5 Hz), 7.33 (tt, 1H, J=12.4, 6.2 Hz), 7.07 (td, 1H, J=8.2, 2.0 Hz), 7.05-6.77 (m, 1H), 6.78-6.68 (m, 2H), 4.98 (d, 2H, J=19.6 Hz), 3.43 (s, 2H), 3.37-3.22 (m, 3H), 2.61-2.48 (m, 1H), 1.02-0.92 (m, 6H); LRMS (ES) m/z 463.2 (M$^+$+1).

EXAMPLE 68: Synthesis of Compound 11330, 1-acetyl-N-(4-(5-(difluoromethyl)-1,3,4-oxadiazol-2-yl)-2-fluorobenzyl)-N-(3-fluorophenyl)azetidine-3-carboxamide

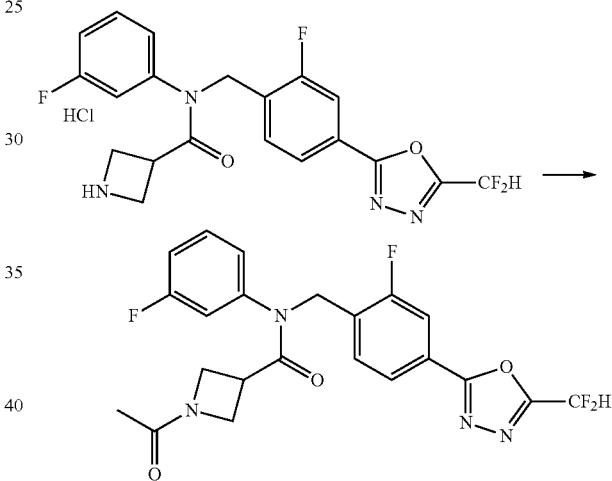

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and N,N-diisopropylethylamine (0.038 mL, 0.219 mmol) were dissolved in dichloromethane (10 mL) at room temperature, and acetyl chloride (0.009 mL, 0.120 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 90%) and concentrated to give the title compound (0.016 g, 31.6%) as colorless oil.

$^1$H NMR (400 MHz, CDCl$_3$) δ 7.87 (dd, 1H, J=8.0, 1.6 Hz), 7.74 (dd, 1H, J=9.8, 1.6 Hz), 7.60-7.51 (m, 1H), 7.40-7.30 (m, 1H), 7.09 (td, 1H, J=8.2, 2.4 Hz), 7.06-6.78 (m, 1H), 6.74 (dt, 2H, J=7.9, 6.8 Hz), 5.02 (d, 2H, J=19.1 Hz), 4.45 (s, 1H), 3.99 (d, 2H, J=33.8 Hz), 3.79-3.68 (m, 1H), 3.31 (tt, 1H, J=8.8, 6.3 Hz), 1.82 (s, 3H); LRMS (ES) m/z 463.2 (M$^+$+1).

EXAMPLE 69: Synthesis of Compound 11331, N-(4-(5-(difluoromethyl)-1,3,4-oxadiazol-2-yl)-2-fluorobenzyl)-N-(3-fluorophenyl)-1-propionylazetidine-3-carboxamide

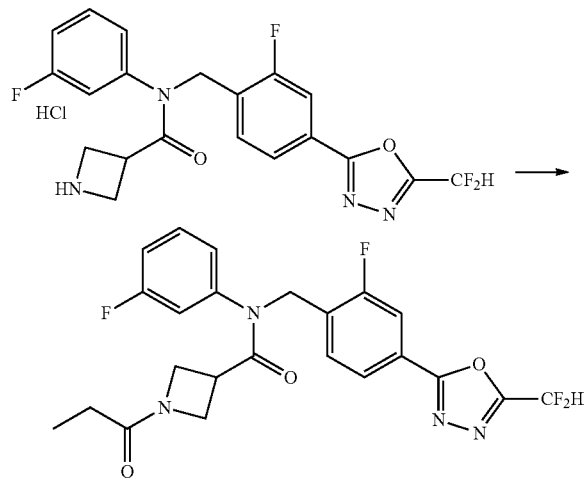

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and N,N-diisopropylethylamine (0.038 mL, 0.219 mmol) were dissolved in dichloromethane (10 mL) at room temperature, and propionyl chloride (0.011 mL, 0.120 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 90%) and concentrated to give the title compound (0.018 g, 34.5%) as a white solid.

$^1$H NMR (400 MHz, CDCl$_3$) δ 7.87 (dd, 1H, J=8.0, 1.5 Hz), 7.73 (dd, 1H, J=9.8, 1.4 Hz), 7.54 (dd, 1H, J=16.0, 8.3 Hz), 7.35 (dd, 1H, J=14.4, 8.1 Hz), 7.13-7.05 (m, 1H), 7.05-6.77 (m, 1H), 6.74 (dd, 2H, J=7.5, 5.3 Hz), 5.07-4.99 (m, 2H), 4.35 (dd, 1H, J=24.2, 19.7 Hz), 4.14-3.79 (m, 2H), 3.79-3.65 (m, 1H), 3.32 (tt, 1H, J=8.9, 6.4 Hz), 2.11-1.94 (m, 2H), 1.08 (dd, 3H, J=10.0, 5.1 Hz); LRMS (ES) m/z 477.3 (M$^+$+1).

EXAMPLE 70: Synthesis of Compound 11332, N-(4-(5-(difluoromethyl)-1,3,4-oxadiazol-2-yl)-2-fluorobenzyl)-N-(3-fluorophenyl)-1-isobutyrylazetidine-3-carboxamide

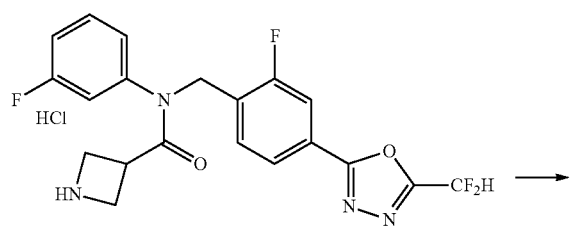

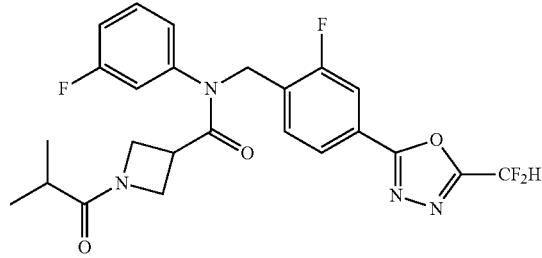

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and N,N-diisopropylethylamine (0.038 mL, 0.219 mmol) were dissolved in dichloromethane (10 mL) at room temperature, and isobutyryl chloride (0.013 mL, 0.120 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 90%) and concentrated to give the title compound (0.021 g, 39.1%) as colorless oil.

$^1$H NMR (400 MHz, CDCl$_3$) δ 7.87 (dd, 1H, J=8.0, 1.4 Hz), 7.72 (dt, 1H, J=15.7, 7.8 Hz), 7.54 (dd, 1H, J=15.6, 8.0 Hz), 7.36 (dd, 1H, J=8.3, 6.3 Hz), 7.15-7.05 (m, 1H), 7.05-6.78 (m, 1H), 6.78-6.68 (m, 2H), 5.02 (d, 2H, J=19.0 Hz), 4.47 (s, 1H), 4.07-3.62 (m, 3H), 3.38-3.25 (m, 1H), 2.48-2.30 (m, 1H), 1.11-0.95 (m, 6H); LRMS (ES) m/z 491.2 (M$^+$+1).

EXAMPLE 71: Synthesis of Compound 11333, N-(4-(5-(difluoromethyl)-1,3,4-oxadiazol-2-yl)-2-fluorobenzyl)-N-(3-fluorophenyl)-1-(methylsulfonyl)azetidine-3-carboxamide

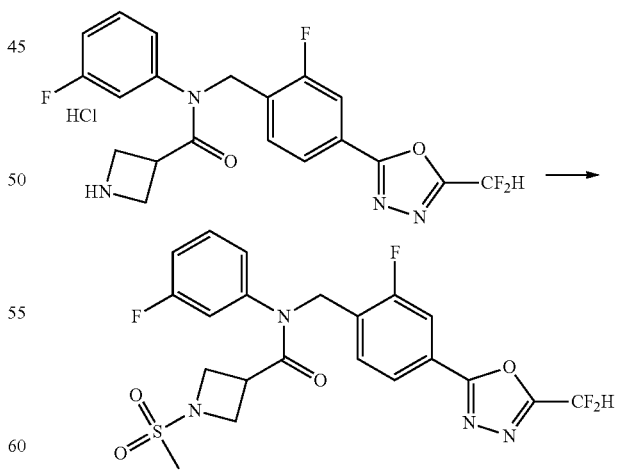

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and N,N-diisopropylethylamine (0.038 mL, 0.219 mmol) were dissolved in dichloromethane (10 mL) at room temperature, and methanesulfonyl chloride (0.009 mL, 0.120 mmol) was added to the solution. The mixture was stirred at the same temperature for 18 hours. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 90%) and concentrated to give the title compound (0.012 g, 22.0%) as a white solid.

$^1$H NMR (400 MHz, CDCl$_3$) δ 7.87 (dd, 1H, J=8.0, 1.5 Hz), 7.74 (dd, 1H, J=9.8, 1.4 Hz), 7.52 (dd, 1H, J=15.1, 7.5 Hz), 7.36 (dd, 1H, J=11.1, 5.0 Hz), 7.14-7.07 (m, 1H), 7.05-6.78 (m, 1H), 6.78-6.69 (m, 2H), 5.08-4.98 (m, 2H), 4.16-4.07 (m, 2H), 3.77-3.68 (m, 2H), 3.41-3.28 (m, 1H), 2.89 (d, 3H, J=5.3 Hz); LRMS (ES) m/z 499.2 (M$^+$+1).

EXAMPLE 72: Synthesis of Compound 11334, N-(4-(5-(difluoromethyl)-1,3,4-oxadiazol-2-yl)-2-fluorobenzyl)-1-(ethylsulfonyl)-N-(3-fluorophenyl)azetidine-3-carboxamide

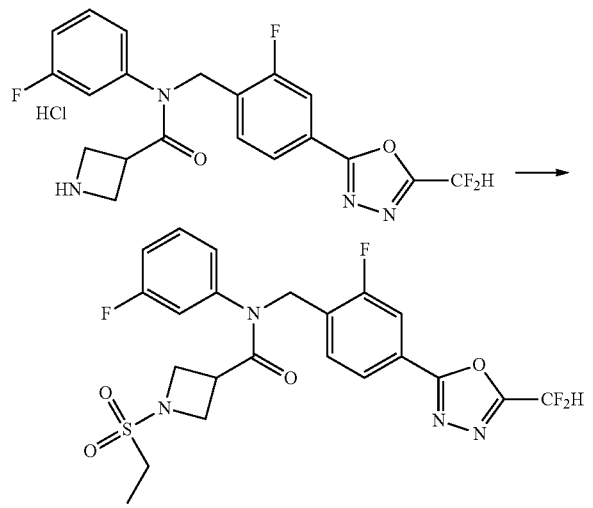

N-(4-(5-(difluoromethyl)-1,3,4-oxadiazol-2-yl)-2-fluorobenzyl)-N-(3-fluorophenyl)azetidine-3-carboxamide hydrochloride (0.050 g, 0.109 mmol), synthesized in step 5 of Example 63, and N,N-diisopropylethylamine (0.038 mL, 0.219 mmol) were dissolved in dichloromethane (10 mL) at room temperature, and ethanesulfonyl chloride (0.015 mL, 0.120 mmol) was added to the solution. The mixture was stirred at the same temperature for 1 hour. Water was added to the reaction mixture, followed by extraction with dichloromethane. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 90%) and concentrated to give the title compound (0.020 g, 35.7%) as colorless oil.

$^1$H NMR (400 MHz, CDCl$_3$) δ 7.87 (dd, 1H, J=8.0, 1.6 Hz), 7.79-7.70 (m, 1H), 7.56 (dd, 1H, J=15.7, 8.1 Hz), 7.35 (td, 1H, J=8.1, 6.4 Hz), 7.10 (td, 1H, J=8.1, 2.1 Hz), 7.07-6.78 (m, 1H), 6.78-6.70 (m, 2H), 5.10-4.98 (m, 2H), 4.22-4.10 (m, 2H), 3.74-3.61 (m, 2H), 3.41-3.30 (m, 1H), 3.00-2.90 (m, 2H), 1.34 (q, 3H, J=7.4 Hz); LRMS (ES) m/z 513.2 (M$^+$+1).

EXAMPLE 73: Synthesis of Compound 11339, N-(4-(5-(difluoromethyl)-1,3,4-oxadiazol-2-yl)-2-fluorobenzyl)-N-(3-fluorophenyl)acetamide

[Step 1] Synthesis of methyl 4-(bromomethyl)-3-fluorobenzoate

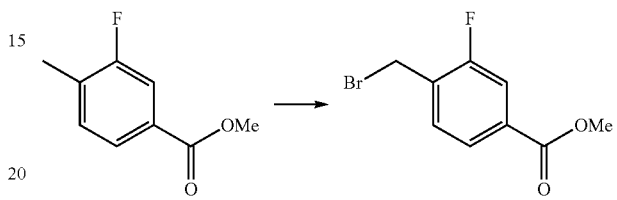

Methyl 3-fluoro-4-methylbenzoate (8.500 g, 50.544 mmol), 1-bromopyrolidin-2,5-one (NBS, 9.446 g, 53.071 mmol) and azobisisobutyronitrile (AIBN, 0.415 g, 2.527 mmol) were mixed in dichloromethane (150 mL) at room temperature, and the mixture was heated under reflux for 18 hours, and then cooled to room temperature. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 0% to 50%) and concentrated to give the title compound (7.600 g, 60.9%) as a white solid.

[Step 2] Synthesis of methyl 3-fluoro-4-(((3-fluorophenyl)amino)methyl)benzoate

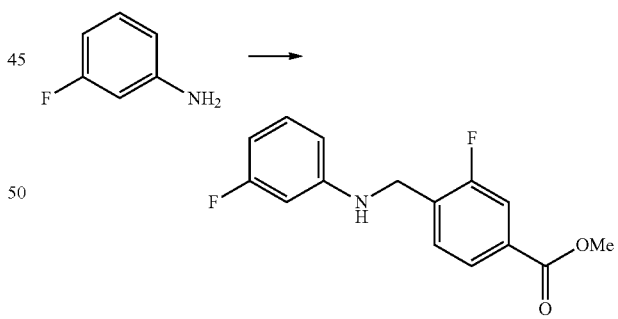

3-Fluoroaniline (1.000 g, 8.999 mmol), methyl 4-(bromomethyl)-3-fluorobenzoate (2.446 g, 9.899 mmol) synthesized in step 1, and N,N-diisopropylethylamine (3.102 mL, 17.999 mmol) were dissolved in acetonitrile (50 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 24 g cartridge; ethyl acetate/hexane=from 0% to 80%) and concentrated to give the title compound (2.170 g, 87.0%) as colorless oil.

[Step 3] Synthesis of methyl 3-fluoro-4-((N-(3-fluorophenyl)acetamido)methyl)benzoate

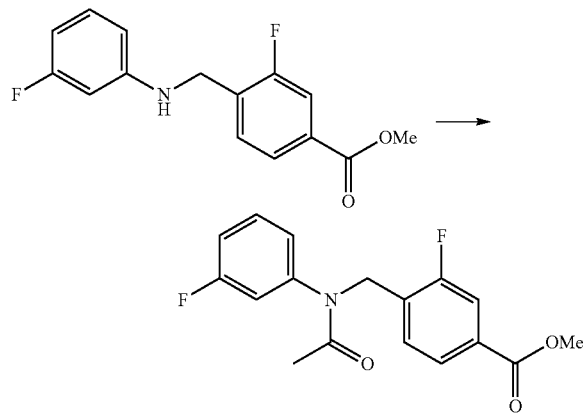

Methyl 3-fluoro-4-(((3-fluorophenyl)amino)methyl)benzoate (0.200 g, 0.721 mmol), synthesized in step 2, and N,N-diisopropylethylamine (0.251 mL, 1.443 mmol) were dissolved in dichloromethane (10 mL) at room temperature, and acetyl chloride (0.061 mL, 0.866 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.210 g, 91.2%) as yellow oil.

[Step 4] Synthesis of N-(2-fluoro-4-(hydrazinecarbonyl)benzyl)-N-(3-fluorophenyl)acetamide

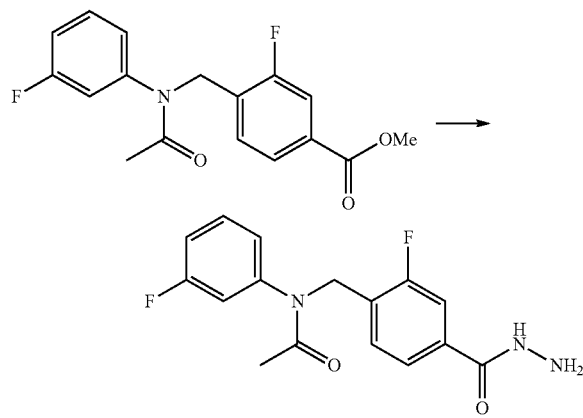

Methyl 3-fluoro-4-((N-(3-fluorophenyl)acetamido)methyl)benzoate (0.210 g, 0.658 mmol), synthesized in step 3, and hydrazine hydrate (0.658 g, 13.153 mmol) were mixed in ethanol (10 mL) at room temperature, and the mixture was heated under reflux for 18 hours, and then cooled to room temperature. Then, water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.187 g, 89.0%) as white foam solid.

[Step 5] Synthesis of Compound 11339

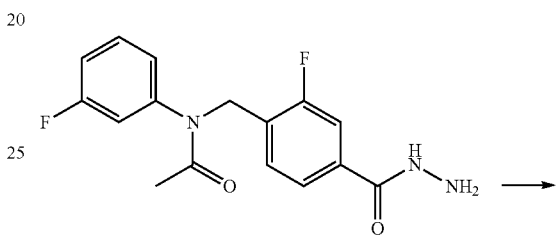

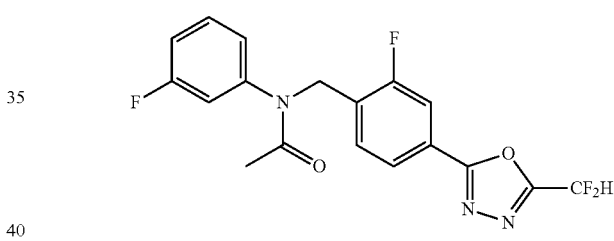

N-(2-fluoro-4-(hydrazinecarbonyl)benzyl)-N-(3-fluorophenyl)acetamide (0.090 g, 0.282 mmol), synthesized in step 4, and triethylamine (0.079 mL, 0.564 mmol) were dissolved in dichloromethane (10 mL) at room temperature, and 2,2-difluoroacetic anhydride (0.037 mL, 0.338 mmol) was added to the solution. The mixture was stirred at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.071 g, 66.4%) as colorless oil.

$^1$H NMR (400 MHz, CDCl$_3$) δ 7.85 (dt, 1H, J=13.6, 6.8 Hz), 7.75-7.66 (m, 1H), 7.63-7.52 (m, 1H), 7.32 (tt, 1H, J=12.0, 6.0 Hz), 7.10-7.01 (m, 1H), 6.94-6.75 (m, 3H), 5.02 (s, 2H), 1.95 (s, 3H); LRMS (ES) m/z 380.2 (M$^+$+1).

EXAMPLE 74: Synthesis of Compound 11340, N-(2-fluoro-4-(5-(trifluoromethyl)-1,3,4-oxadiazol-2-yl)benzyl)-N-(3-fluorophenyl)acetamide

[Step 1] N-(2-fluoro-4-(2-(2,2,2-trifluoroacetyl)hydrazine-1-carbonyl)benzyl)-N-(3-fluorophenyl)acetamide

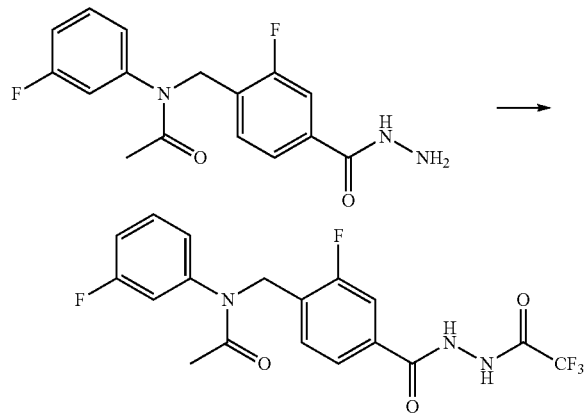

N-(2-fluoro-4-(hydrazinecarbonyl)benzyl)-N-(3-fluorophenyl)acetamide (0.090 g, 0.282 mmol), synthesized in step 4 of Example 73, and triethylamine (0.079 mL, 0.564 mmol) were dissolved in dichloromethane (10 mL) at room temperature, and trifluoroacetic anhydride (0.048 mL, 0.338 mmol) was added to the solution. The mixture was stirred at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.112 g, 95.7%) as yellow oil.

[Step 2] Synthesis of Compound 11340

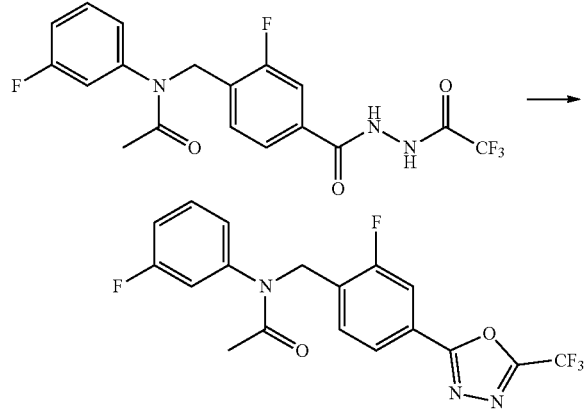

N-(2-fluoro-4-(2-(2,2,2-trifluoroacetyl)hydrazine-1-carbonyl)benzyl)-N-(3-fluorophenyl)acetamide (0.120 g, 0.289 mmol), synthesized in step 1, and 1-methoxy-N-triethylammoniosulfonyl-methanimidate (Burgess reagent, 0.103 g, 0.433 mmol) were mixed in tetrahydrofuran (10 mL), and the mixture was heated by microwave irradiation at room temperature for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.029 g, 25.3%) as colorless oil.

$^1$H NMR (400 MHz, CDCl$_3$) δ 7.87 (dd, 1H, J=8.0, 1.4 Hz), 7.73 (d, 1H, J=9.7 Hz), 7.61 (t, 1H, J=7.6 Hz), 7.34 (td, 1H, J=8.1, 6.5 Hz), 7.05 (td, 1H, J=8.3, 2.1 Hz), 6.84 (dd, 2H, J=22.0, 8.5 Hz), 5.03 (s, 2H), 1.95 (s, 3H); LRMS (ES) m/z 398.1 (M$^+$+1).

EXAMPLE 75: Synthesis of Compound 11341, N-((5-(5-(difluoromethyl)-1,3,4-oxadiazol-2-yl)pyridin-2-yl)methyl)-N-phenylisonicotinamide

[Step 1] Synthesis of methyl 6-((N-phenylisonicotinamido)methyl)nicotinate

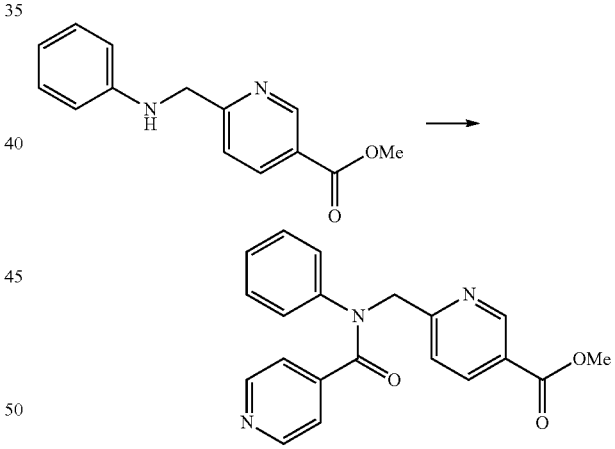

Methyl 6-((phenylamino)methyl)nicotinate (0.050 g, 0.206 mmol) and triethylamine (0.058 mL, 0.413 mmol) were dissolved in dichloromethane (10 mL) at room temperature, and isonicotinoyl chloride hydrochloride (0.044 g, 0.248 mmol) was added to the solution, followed by stirring at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 80%) and concentrated to give the title compound (0.071 g, 99.0%) as colorless oil.

[Step 2] Synthesis of N-((5-(hydrazinecarbonyl)pyridin-2-yl)methyl)-N-phenylisonicotinamide

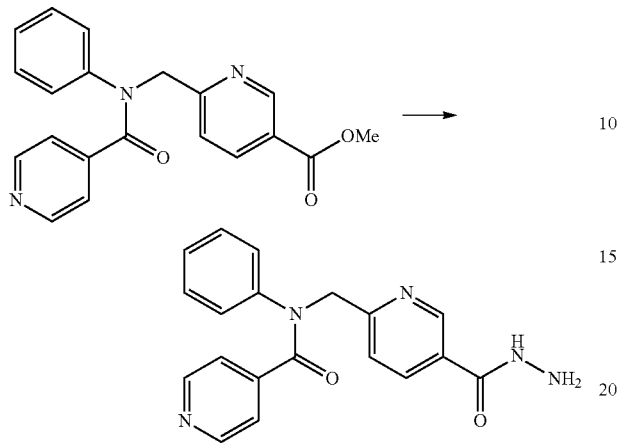

Methyl 6-((N-phenylisonicotinamido)methyl)nicotinate (0.071 g, 0.204 mmol), synthesized in step 1, and hydrazine hydrate (0.199 mL, 4.088 mmol) were dissolved in ethanol (10 mL) at 90° C., and the solution was stirred at the same temperature for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.070 g, 98.6%) as colorless oil.

[Step 3] Synthesis of Compound 11341

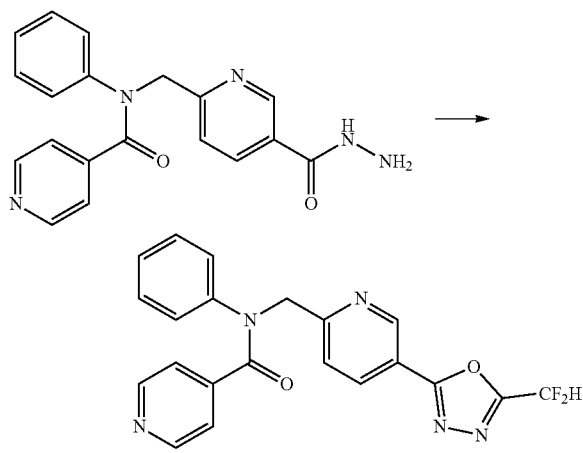

N-((5-(hydrazinecarbonyl)pyridin-2-yl)methyl)-N-phenylisonicotinamide (0.070 g, 0.202 mmol), synthesized in step 2, and triethylamine (0.056 mL, 0.403 mmol) were dissolved in dichloromethane (10 mL) at room temperature, and 2,2-difluoroacetic anhydride (0.028 mL, 0.262 mmol) was added to the solution. The mixture was stirred at the same temperature for 1 hour. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 100%) and concentrated to give the title compound (0.045 g, 54.8%) as colorless oil.

$^1$H NMR (400 MHz, CDCl$_3$) δ 9.29 (d, 1H, J=1.7 Hz), 8.47 (d, 2H, J=5.3 Hz), 8.38 (dd, 1H, J=8.2, 2.2 Hz), 7.63 (d, 1H, J=8.2 Hz), 7.25-7.16 (m, 5H), 7.16-7.09 (m, 2H), 7.09-6.79 (m, 1H), 5.28 (d, 2H, J=21.7 Hz); LRMS (ES) m/z 408.3 (M$^+$+1).

EXAMPLE 76: Synthesis of Compound 11356, N-(4-(5-(difluoromethyl)-1,3,4-oxadiazol-2-yl)-2-fluorobenzyl)-N-(3-fluorophenyl)propionamide

[Step 1] Synthesis of methyl 3-fluoro-4-((N-(3-fluorophenyl)propionamido)methyl)benzoate

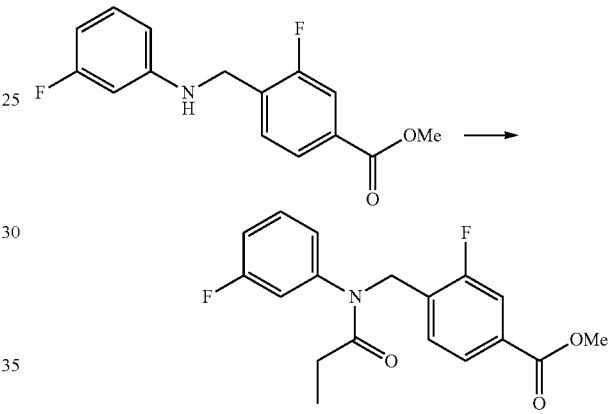

Methyl 3-fluoro-4-(((3-fluorophenyl)amino)methyl)benzoate (0.100 g, 0.361 mmol), synthesized in step 2 of Example 73, and N,N-diisopropylethylamine (0.126 mL, 0.721 mmol) were dissolved in dichloromethane (10 mL) at room temperature, and propionyl chloride (0.041 mL, 0.469 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.100 g, 83.2%) as colorless oil.

[Step 2] Synthesis of N-(2-fluoro-4-(hydrazinecarbonyl)benzyl)-N-(3-fluorophenyl)propionamide

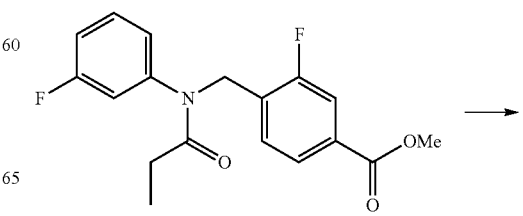

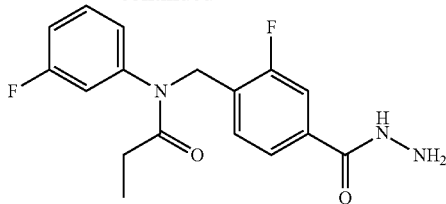

Methyl 3-fluoro-4-((N-(3-fluorophenyl)propionamido)methyl)benzoate (0.100 g, 0.300 mmol), synthesized in step 1, and hydrazine monohydrate (0.292 mL, 6.000 mmol) were mixed in ethanol (6 mL) at room temperature, and the mixture was heated under reflux for 18 hours, and then cooled to room temperature. The reaction mixture was concentrated under reduced pressure to remove the solvent. The title compound was used without further purification (0.098 g, 98.0%) as colorless oil.

[Step 3] Synthesis of N-(4-(2-(2,2-difluoroacetyl)hydrazine-1-carbonyl)-2-fluorobenzyl)-N-(3-fluorophenyl)propionamide

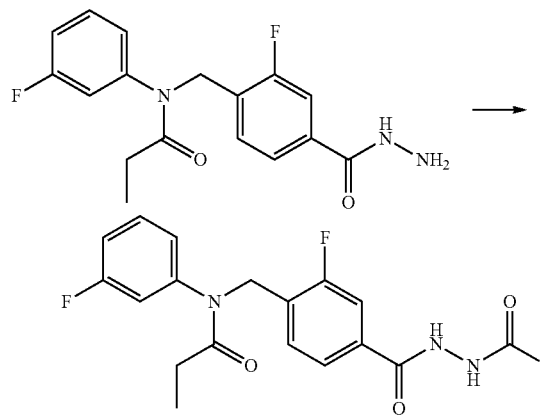

N-(2-fluoro-4-(hydrazinecarbonyl)benzyl)-N-(3-fluorophenyl)propionamide (0.098 g, 0.294 mmol), synthesized in step 2, and triethylamine (0.082 mL, 0.588 mmol) were dissolved in dichloromethane (10 mL) at room temperature, and 2,2-difluoroacetic anhydride (0.038 mL, 0.353 mmol) was added to the solution. The mixture was stirred at the same temperature for 2 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.120 g, 99.2%) as colorless oil.

[Step 4] Synthesis of Compound 11356

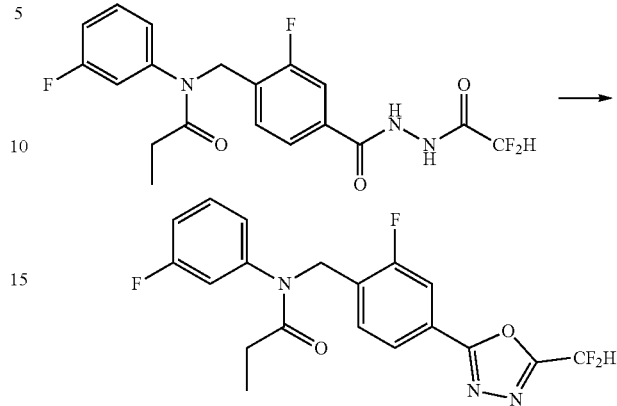

N-(4-(2-(2,2-difluoroacetyl)hydrazine-1-carbonyl)-2-fluorobenzyl)-N-(3-fluorophenyl)propionamide (0.120 g, 0.292 mmol), synthesized in step 3, and 1-methoxy-N-triethylammoniosulfonyl-methanimidate (Burgess reagent, 0.104 g, 0.438 mmol) were mixed in tetrahydrofuran (10 mL), and the mixture was heated by microwave irradiation at 150° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.018 g, 15.7%) as colorless oil.

$^1$H NMR (400 MHz, CDCl$_3$) δ 9.29 (d, 1H, J=1.7 Hz), 8.47 (d, 2H, J=5.3 Hz), 8.38 (dd, 1H, J=8.2, 2.2 Hz), 7.63 (d, 1H, J=8.2 Hz), 7.25-7.16 (m, 5H), 7.16-7.09 (m, 2H), 7.09-6.79 (m, 1H), 5.28 (d, 2H, J=21.7 Hz); LRMS (ES) m/z 408.3 (M$^+$+1).

EXAMPLE 77: Synthesis of Compound 11357, N-(4-(5-(difluoromethyl)-1,3,4-oxadiazol-2-yl)-2-fluorobenzyl)-N-(3-fluorophenyl)butyramide

[Step 1] Synthesis of methyl 3-fluoro-4-((N-(3-fluorophenyl)butyramido)methyl)benzoate

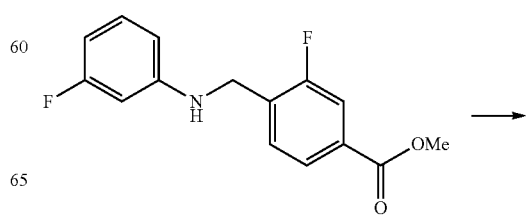

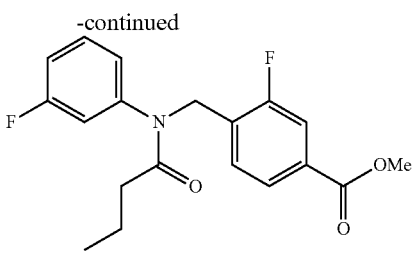

Methyl 3-fluoro-4-(((3-fluorophenyl)amino)methyl)benzoate (0.100 g, 0.361 mmol), synthesized in step 2 of Example 73, and N,N-diisopropylethylamine (0.126 mL, 0.721 mmol) were dissolved in dichloromethane (10 mL) at room temperature, and butyryl chloride (0.049 mL, 0.469 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.103 g, 82.2%) as colorless oil.

[Step 2] Synthesis of N-(2-fluoro-4-(hydrazinecarbonyl)benzyl)-N-(3-fluorophenyl)butyramide

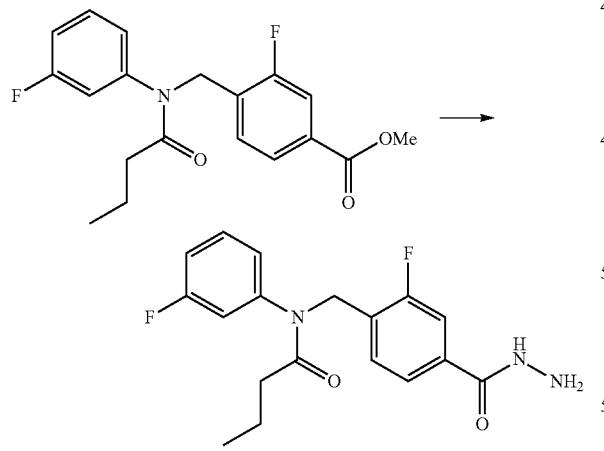

Methyl 3-fluoro-4-((N-(3-fluorophenyl)butyramido)methyl)benzoate (0.103 g, 0.297 mmol), synthesized in step 1, and hydrazine monohydrate (0.288 mL, 5.930 mmol) were mixed in ethanol (6 mL) at room temperature, and the mixture was heated under reflux for 18 hours, and then cooled to room temperature. The reaction mixture was concentrated under reduced pressure to remove the solvent. The title compound was used without further purification (0.100 g, 97.1%) as colorless oil.

[Step 3] Synthesis of N-(4-(2-(2,2-difluoroacetyl)hydrazine-1-carbonyl)-2-fluorobenzyl)-N-(3-fluorophenyl)butyramide

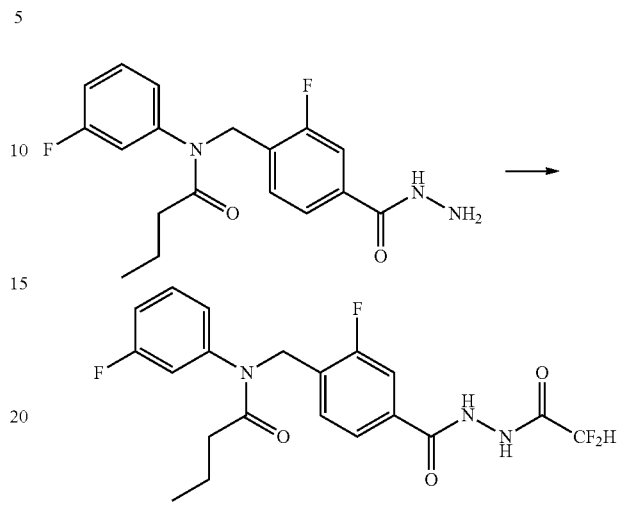

N-(2-fluoro-4-(hydrazinecarbonyl)benzyl)-N-(3-fluorophenyl)butyramide (0.100 g, 0.288 mmol), synthesized in step 2, and triethylamine (0.080 mL, 0.576 mmol) were dissolved in dichloromethane (10 mL) at room temperature, and 2,2-difluoroacetic anhydride (0.038 mL, 0.345 mmol) was added to the solution. The mixture was stirred at the same temperature for 2 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.120 g, 98.0%) as colorless oil.

[Step 4] Synthesis of Compound 11357

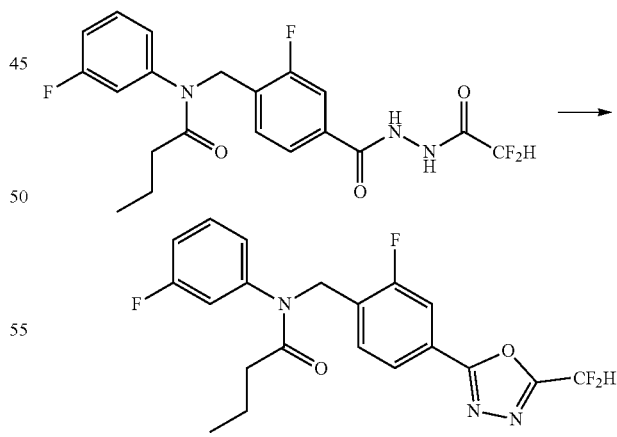

N-(4-(2-(2,2-difluoroacetyl)hydrazine-1-carbonyl)-2-fluorobenzyl)-N-(3-fluorophenyl)butyramide (0.120 g, 0.282 mmol), synthesized in step 3, and 1-methoxy-N-triethylammoniosulfonyl-methanimidate (Burgess reagent, 0.101 g, 0.423 mmol) were mixed in tetrahydrofuran (10 mL), and the mixture was heated by microwave irradiation at 150° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.012 g, 10.4%) as colorless oil.

$^1$H NMR (400 MHz, CDCl$_3$) δ 7.87 (dd, 1H, J=8.1, 1.7 Hz), 7.72 (dd, 1H, J=9.8, 1.7 Hz), 7.59 (t, 1H, J=7.6 Hz), 7.33 (td, 1H, J=8.1, 6.3 Hz), 7.11-7.01 (m, 1H), 6.93-6.75 (m, 3H), 5.02 (s, 2H), 2.10 (t, 2H, J=7.4 Hz), 1.64 (h, 2H, J=7.4 Hz), 0.86 (t, 3H, J=7.4 Hz); LRMS (ES) m/z 408.2 (M$^+$+1).

EXAMPLE 78: Synthesis of Compound 11358, N-(4-(5-(difluoromethyl)-1,3,4-oxadiazol-2-yl)-2-fluorobenzyl)-N-(3-fluorophenyl)-3-methylbutanamide

[Step 1] Synthesis of methyl 3-fluoro-4-((N-(3-fluorophenyl)-3-methylbutanamido)methyl)benzoate

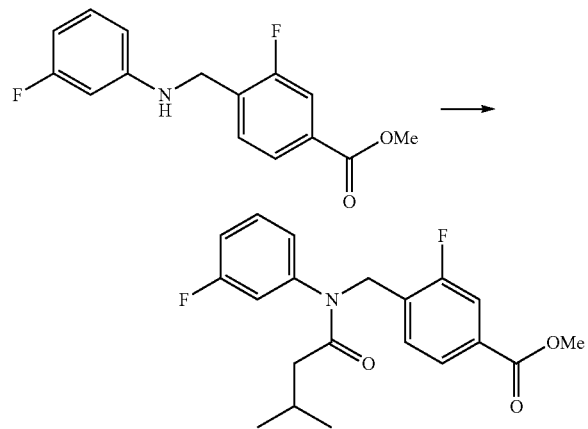

Methyl 3-fluoro-4-(((3-fluorophenyl)amino)methyl)benzoate (0.100 g, 0.361 mmol), synthesized in step 2 of Example 73, and N,N-diisopropylethylamine (0.126 mL, 0.721 mmol) were dissolved in dichloromethane (10 mL) at room temperature, and 3-methylbutanoyl chloride (0.057 mL, 0.469 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 50%) and concentrated to give the title compound (0.115 g, 88.2%) as colorless oil.

[Step 2] Synthesis of N-(2-fluoro-4-(hydrazinecarbonyl)benzyl)-N-(3-fluorophenyl)-3-methylbutanamide

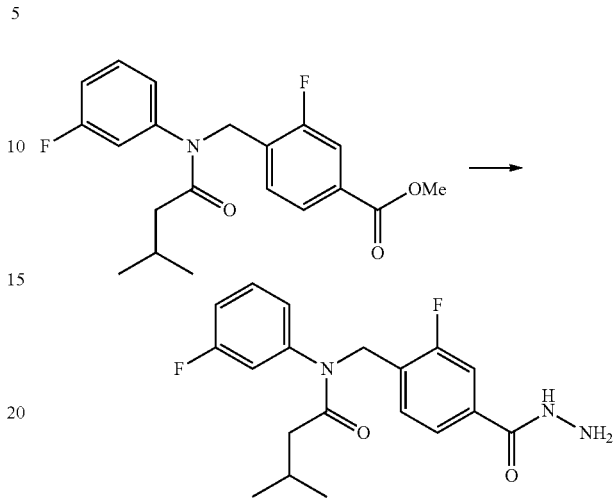

Methyl 3-fluoro-4-((N-(3-fluorophenyl)-3-methylbutanamido)methyl)benzoate (0.115 g, 0.318 mmol), synthesized in step 1, and hydrazine monohydrate (0.309 mL, 6.364 mmol) were mixed in ethanol (6 mL) at room temperature, and the mixture was heated under reflux for 18 hours, and then cooled to room temperature. The reaction mixture was concentrated under reduced pressure to remove the solvent. The title compound was used without further purification (0.105 g, 91.3%) as colorless oil.

[Step 3] N-(4-(2-(2,2-difluoroacetyl)hydrazine-1-carbonyl)-2-fluorobenzyl)-N-(3-fluorophenyl)-3-methylbutanamide

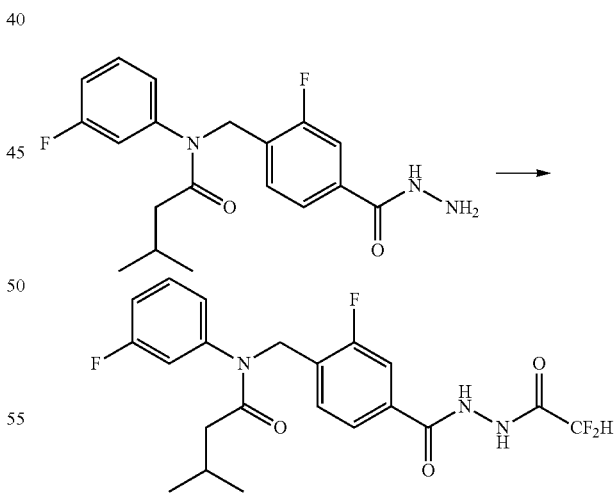

N-(2-fluoro-4-(hydrazinecarbonyl)benzyl)-N-(3-fluorophenyl)-3-methylbutanamide (0.105 g, 0.291 mmol), synthesized in step 2, and triethylamine (0.081 mL, 0.581 mmol) were dissolved in dichloromethane (10 mL) at room temperature, and 2,2-difluoroacetic anhydride (0.038 mL, 0.349 mmol) was added to the solution. The mixture was stirred at the same temperature for 2 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.122 g, 95.6%) as colorless oil.

[Step 4] Synthesis of Compound 11358

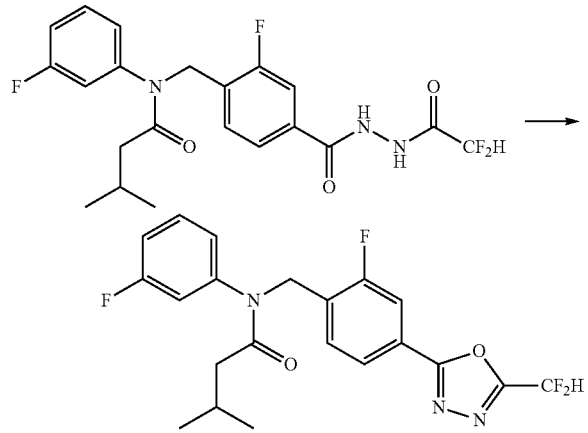

N-(4-(2-(2,2-difluoroacetyl)hydrazine-1-carbonyl)-2-fluorobenzyl)-N-(3-fluorophenyl)-3-methylbutanamide (0.140 g, 0.319 mmol), synthesized in step 3, and 1-methoxy-N-triethylammoniosulfonyl-methanimidate (Burgess reagent, 0.114 g, 0.478 mmol) were mixed in tetrahydrofuran (10 mL), and the mixture was heated by microwave irradiation at 150° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO₂, 4 g cartridge; ethyl acetate/hexane=from 0% to 50%) and concentrated to give the title compound (0.011 g, 8.2%) as colorless oil.

¹H NMR (400 MHz, CDCl₃) δ 7.87 (dd, 1H, J=8.0, 1.7 Hz), 7.72 (dd, 1H, J=9.8, 1.7 Hz), 7.60 (t, 1H, J=7.6 Hz), 7.33 (td, 1H, J=8.1, 6.3 Hz), 7.10-7.02 (m, 1H), 6.93-6.74 (m, 3H), 5.03 (s, 2H), 2.18 (dq, 1H, J=13.5, 6.7 Hz), 2.01 (d, 2H, J=7.0 Hz), 0.87 (d, 6H, J=6.6 Hz); LRMS (ES) m/z 422.3 (M⁺+1).

EXAMPLE 79: Synthesis of Compound 11359, N-(3-fluorophenyl)-N-((5-(5-(trifluoromethyl)-1,3,4-oxadiazol-2-yl)pyridin-2-yl)methyl)isonicotinamide

[Step 1] Synthesis of methyl 6-((N-(3-fluorophenyl)isonicotinamido)methyl)nicotinate

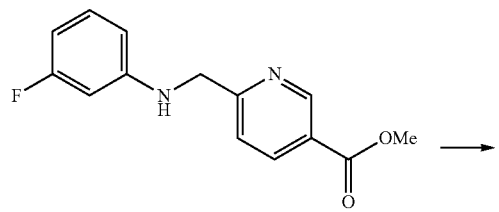

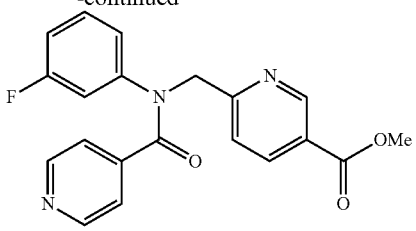

Methyl 6-(((3-fluorophenyl)amino)methyl)nicotinate (0.200 g, 0.768 mmol) and N,N-diisopropylethylamine (0.268 mL, 1.537 mmol) were dissolved in dichloromethane (10 mL) at room temperature, and isonicotinoyl chloride hydrochloride (0.178 g, 0.999 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO₂, 12 g cartridge; ethyl acetate/hexane=from 0% to 100%) and concentrated to give the title compound (0.277 g, 98.7%) as colorless oil.

[Step 2] Synthesis of N-(3-fluorophenyl)-N-((5-(hydrazinecarbonyl)pyridin-2-yl)methyl)isonicotinamide

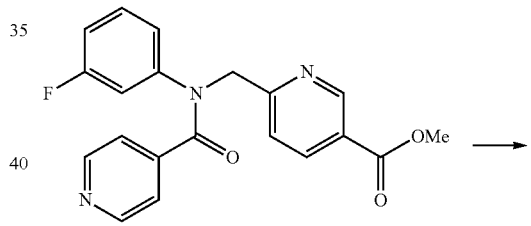

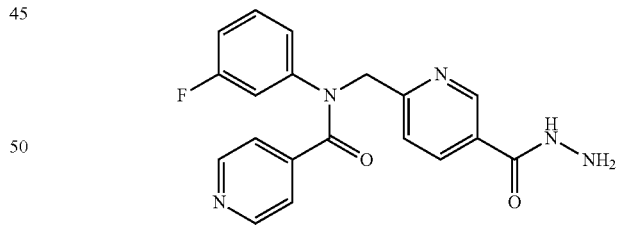

Methyl 6-((N-(3-fluorophenyl)isonicotinamido)methyl)nicotinate (0.277 g, 0.758 mmol), synthesized in step 1, and hydrazine monohydrate (0.737 mL, 15.163 mmol) were mixed in ethanol (10 mL), and the mixture was heated by microwave irradiation at 120° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.220 g, 79.4%) as white foam solid.

[Step 3] Synthesis of N-(3-fluorophenyl)-N-((5-(2-(2,2,2-trifluoroacetyl)hydrazine-1-carbonyl)pyridin-2-yl)methyl)isonicotinamide

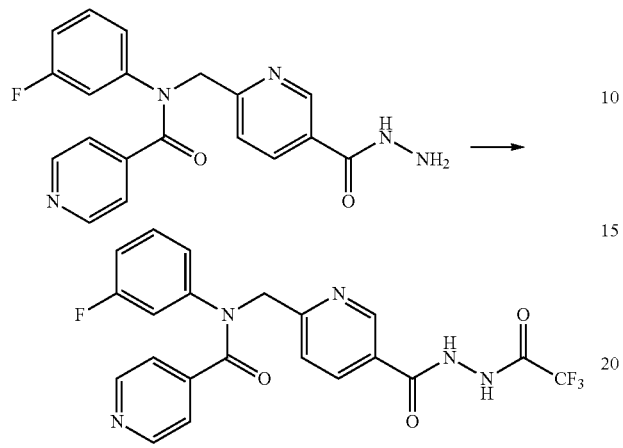

N-(3-fluorophenyl)-N-((5-(hydrazinecarbonyl)pyridin-2-yl)methyl)isonicotinamide (0.100 g, 0.274 mmol), synthesized in step 2, and triethylamine (0.076 mL, 0.547 mmol) were dissolved in dichloromethane (10 mL) at room temperature, and trifluoroacetic anhydride (0.050 mL, 0.356 mmol) was added to the solution. The mixture was stirred at the same temperature for 1 hour. The reaction mixture was concentrated under reduced pressure to remove the solvent. The title compound was used without further purification (0.121 g, 95.8%) as colorless oil.

[Step 4] Synthesis of Compound 11359

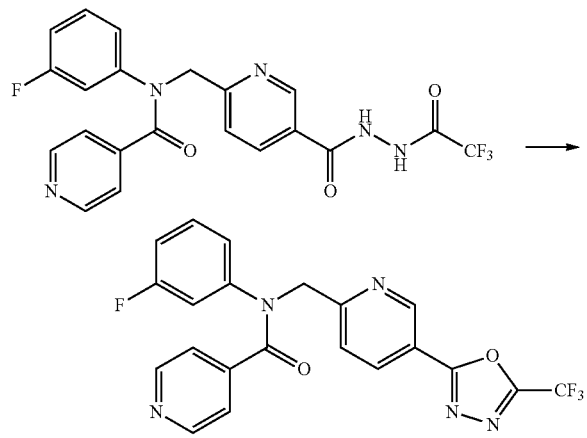

N-(3-fluorophenyl)-N-((5-(2-(2,2,2-trifluoroacetyl)hydrazine-1-carbonyl)pyridin-2-yl)methyl)isonicotinamide (0.130 g, 0.282 mmol), synthesized in step 3, and 1-methoxy-N-triethylammoniosulfonyl-methanimidate (Burgess reagent, 0.101 g, 0.423 mmol) were mixed in tetrahydrofuran (10 mL), and the mixture was heated by microwave irradiation at 150° C. for 30 minutes, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; ethyl acetate/hexane=from 0% to 100%) and concentrated to give the title compound (0.024 g, 19.2%) as yellow oil.

$^1$H NMR (400 MHz, CDCl$_3$) δ 9.37-9.26 (m, 1H), 8.61-8.48 (m, 2H), 8.40 (dd, 1H, J=8.2, 2.2 Hz), 7.63 (d, 1H, J=8.2 Hz), 7.32-7.27 (m, 2H), 7.18 (td, 1H, J=8.2, 6.2 Hz), 7.02 (dt, 1H, J=9.4, 2.3 Hz), 6.96-6.87 (m, 2H), 5.28 (s, 2H); LRMS (ES) m/z 444.3 (M$^+$+1).

EXAMPLE 80: Synthesis of Compound 11360, N-((5-(5-(difluoromethyl)-1,3,4-oxadiazol-2-yl)pyridin-2-yl)methyl)-N-(3-fluorophenyl)isonicotinamide

[Step 1] Synthesis of N-((5-(2-(2,2-difluoroacetyl)hydrazine-1-carbonyl)pyridin-2-yl)methyl)-N-(3-fluorophenyl)isonicotinamide

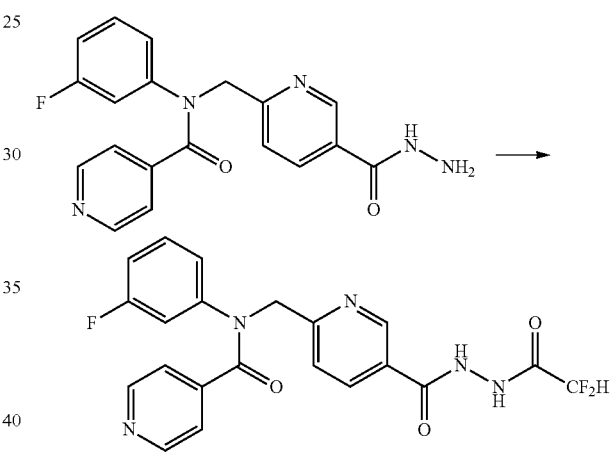

N-(3-fluorophenyl)-N-((5-(hydrazinecarbonyl)pyridin-2-yl)methyl)isonicotinamide (0.120 g, 0.328 mmol), synthesized in step 2 of Example 79, and triethylamine (0.092 mL, 0.657 mmol) were dissolved in dichloromethane (10 mL) at room temperature, and 2,2-difluoroacetic anhydride (0.046 mL, 0.427 mmol) was added to the solution. The mixture was stirred at the same temperature for 1 hour. The reaction mixture was concentrated under reduced pressure to remove the solvent. The title compound was used without further purification (0.140 g, 96.1%) as colorless oil.

[Step 2] Synthesis of Compound 11360

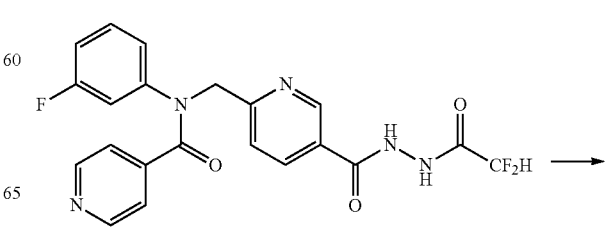

-continued

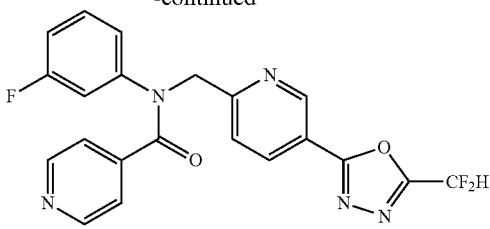

N-((5-(2-(2,2-difluoroacetyl)hydrazine-1-carbonyl)pyridin-2-yl)methyl)-N-(3-fluorophenyl)isonicotinamide (0.140 g, 0.316 mmol), synthesized in step 1, and 1-methoxy-N-triethylammoniosulfonyl-methanimidate (Burgess reagent, 0.113 g, 0.474 mmol) were mixed in tetrahydrofuran (10 mL), and the mixture was heated by microwave irradiation at 150° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 100%) and concentrated to give the title compound (0.021 g, 15.6%) as brown oil.

$^1$H NMR (400 MHz, CDCl$_3$) δ 9.35-9.24 (m, 1H), 8.57-8.48 (m, 2H), 8.40 (dd, 1H, J=8.2, 2.2 Hz), 7.62 (d, 1H, J=8.2 Hz), 7.24 (d, 2H, J=1.5 Hz), 7.18 (td, 1H, J=8.2, 6.3 Hz), 7.08-6.98 (m, 1H), 6.95-6.80 (m, 3H), 5.27 (s, 2H); LRMS (ES) m/z 426.3 (M$^+$+1).

EXAMPLE 81: Synthesis of Compound 11376, N-((5-(5-(difluoromethyl)-1,3,4-oxadiazol-2-yl)pyridin-2-yl)methyl)-N-(3-fluorophenyl)nicotinamide

[Step 1] Synthesis of methyl 6-(((3-fluorophenyl)amino)methyl)nicotinate

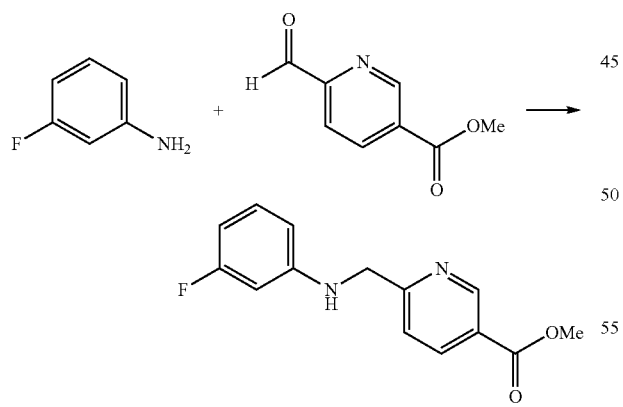

3-Fluoroaniline (1.500 g, 13.499 mmol) and methyl 6-formylnicotinate (2.452 g, 14.849 mmol) were dissolved in dichloromethane (10 mL) at room temperature, and sodium triacetoxyborohydride (4.291 g, 20.248 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 0% to 80%) and concentrated to give the title compound (2.830 g, 80.5%) as a yellow solid.

[Step 2] Synthesis of methyl 6-((N-(3-fluorophenyl)nicotinamido)methyl)nicotinate

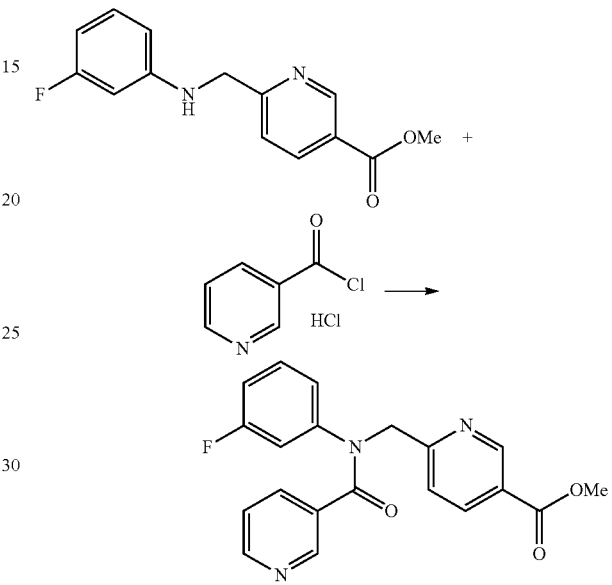

Methyl 6-(((3-fluorophenyl)amino)methyl)nicotinate (0.100 g, 0.384 mmol), synthesized in step 1, and triethylamine (0.107 mL, 0.768 mmol) were dissolved in dichloromethane (10 mL) at room temperature, and nicotinoyl chloride hydrochloride (0.103 g, 0.576 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.111 g, 79.1%) as yellow oil.

[Step 3] Synthesis of N-(3-fluorophenyl)-N-((5-(hydrazinecarbonyl)pyridin-2-yl)methyl)nicotinamide

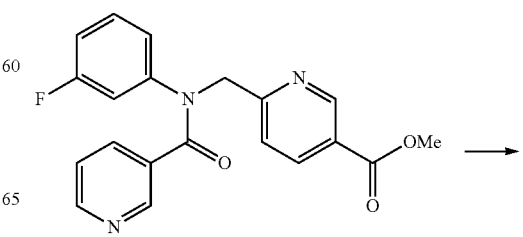

-continued

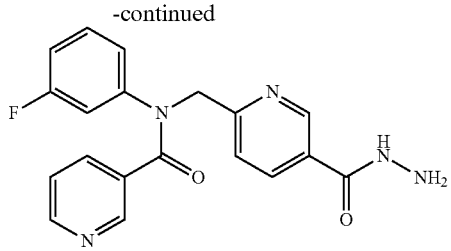

Methyl 6-((N-(3-fluorophenyl)nicotinamido)methyl)nicotinate (0.111 g, 0.304 mmol), synthesized in step 2, and hydrazine monohydrate (0.295 mL, 6.076 mmol) were mixed in ethanol (10 mL) at room temperature, and the mixture was heated under reflux for 18 hours, and then cooled to room temperature. The reaction mixture was concentrated under reduced pressure to remove the solvent. The title compound was used without further purification (0.108 g, 97.3%) as yellow oil.

[Step 4] Synthesis of N-((5-(2-(2,2-difluoroacetyl)hydrazine-1-carbonyl)pyridin-2-yl)methyl)-N-(3-fluorophenyl)nicotinamide

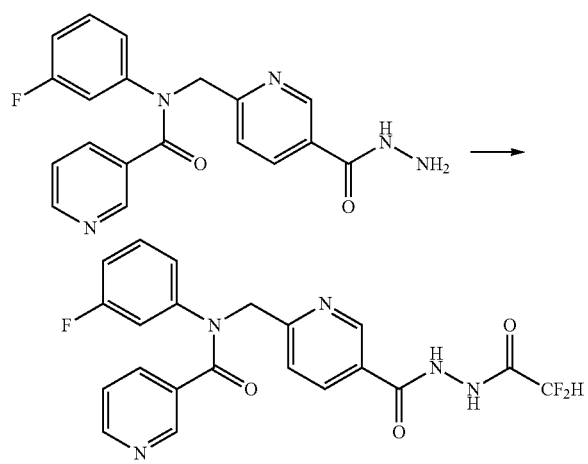

N-(3-fluorophenyl)-N-((5-(hydrazinecarbonyl)pyridin-2-yl)methyl)nicotinamide (0.111 g, 0.304 mmol), synthesized in step 3, and triethylamine (0.085 mL, 0.608 mmol) were dissolved in tetrahydrofuran (10 mL) at room temperature, and 2,2-difluoroacetic anhydride (0.050 mL, 0.456 mmol) was added to the solution. The mixture was stirred at 80° C. for 18 hours, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (0.133 g, 98.7%) as colorless oil.

[Step 5] Synthesis of Compound 11376

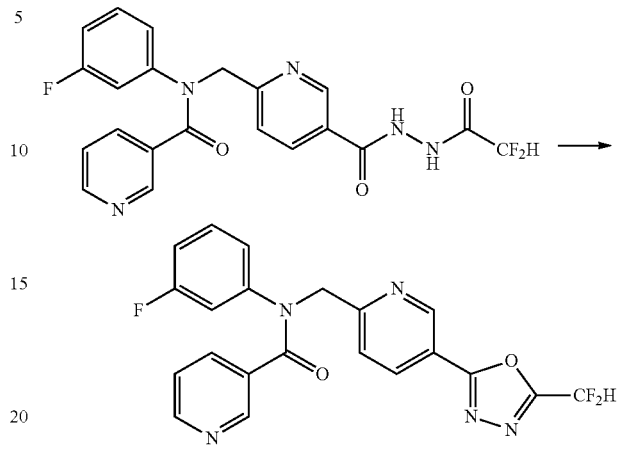

N-((5-(2-(2,2-difluoroacetyl)hydrazine-1-carbonyl)pyridin-2-yl)methyl)-N-(3-fluorophenyl)nicotinamide (0.140 g, 0.316 mmol), synthesized in step 4, and 1-methoxy-N-triethylammoniosulfonyl-methanimidate (Burgess reagent, 0.226 g, 0.947 mmol) were mixed in tetrahydrofuran (10 mL), and the mixture was heated by microwave irradiation at 150° C. for 1 hour, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography ($SiO_2$, 4 g cartridge; ethyl acetate/hexane=from 0% to 80%) and concentrated to give the title compound (0.018 g, 13.4%) as brown oil.

$^1$H NMR (400 MHz, $CDCl_3$) δ 9.35-9.24 (m, 2H), 8.81 (d, 1H, J=5.1 Hz), 8.64-8.51 (m, 2H), 8.41 (ddd, 1H, J=8.3, 3.6, 2.3 Hz), 7.81-7.62 (m, 2H), 7.26-7.15 (m, 2H), 6.88-6.42 (m, 2H), 5.32 (d, 2H, J=2.8 Hz); LRMS (ES) m/z 426.4 ($M^+$+1).

EXAMPLE 82: Synthesis of Compound 11414, N-((5-(5-(difluoromethyl)-1,3,4-oxadiazol-2-yl)pyridin-2-yl)methyl)-1-methyl-N-phenylpipetidine-4-carboxamide

[Step 1] Synthesis of methyl 6-((1-(tert-butoxycarbonyl)-N-phenylpiperidine-4-carboxamido)methyl)nicotinate

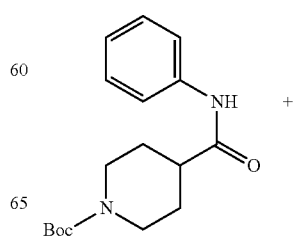

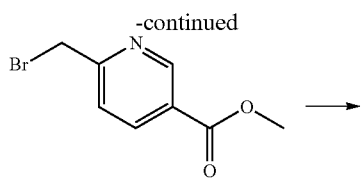

Tert-butyl 4-(phenylcarbamoyl)piperidine-1-carboxylate (0.400 g, 1.314 mmol) was dissolved in tetrahydrofuran (30 mL), and sodium hydride (60.00%, 0.079 g, 1.971 mmol) was added slowly to the solution while the temperature was maintained at 0° C. The mixture was stirred for 20 minutes. Methyl 6-(bromomethyl)nicotinate (0.333 g, 1.446 mmol) was added to the reaction solution, followed by additional stirring at room temperature for 12 hours. Then, water (2 mL) was added to the reaction mixture at 0° C., followed by stirring for 5 minutes. After completion of the reaction, water was added to the reaction mixture, followed by extraction with dichloromethane. The extract was filtered through a plastic filter to remove the solid residue and the aqueous layer, and then concentrated under reduced pressure. The concentrate was purified by column chromatography (SiO₂, 40 g cartridge; ethyl acetate/hexane=from 5% to 40%) and concentrated to give the title compound (0.390 g, 65.4%) as a foam solid.

[Step 2] Synthesis of methyl 6-((N-phenylpiperidine-4-carboxamido)methyl)nicotinate hydrochloride

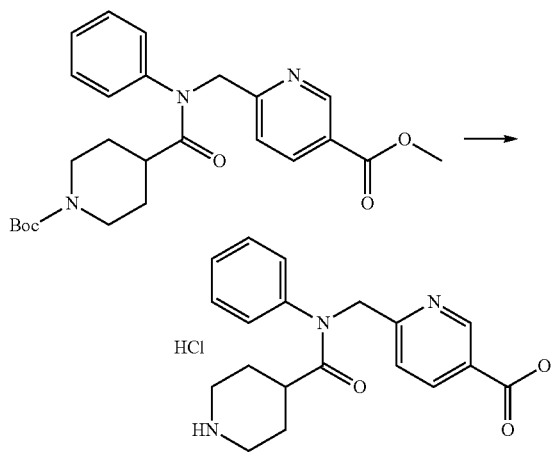

Methyl 6-((1-(tert-butoxycarbonyl)-N-phenylpiperidine-4-carboxamido)methyl)nicotinate (0.390 g, 0.860 mmol), synthesized in step 1, was dissolved in dichloromethane (30 mL), and hydrochloric acid (4.00 M solution in dioxane, 2.150 mL, 8.599 mmol) was added to the solution at 0° C. The mixture was stirred at room temperature for 12 hours. The reaction mixture was concentrated under reduced pressure to remove the solvent. The title compound was used without further purification (0.330 g, 98.4%) as white solid.

[Step 3] Synthesis of methyl 6-((1-methyl-N-phenylpiperidine-4-carboxamido)methyl)nicotinate

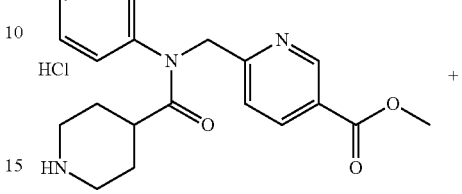

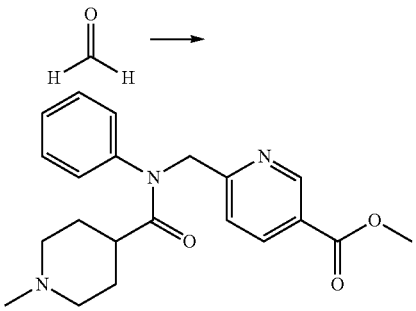

Methyl 6-((N-phenylpiperidine-4-carboxamido)methyl) nicotinate hydrochloride (0.150 g, 0.385 mmol) synthesized in step 2, formaldehyde (37.00% solution in water, 0.143 mL, 1.924 mmol) and sodium triacetoxyborohydride (0.204 g, 0.962 mmol) were dissolved in dichloromethane (20 mL) at room temperature, and the solution was stirred at the same temperature for 18 hours. Water was added to the reaction mixture, followed by extraction with dichloromethane. The extract was filtered through a plastic filter to remove the solid residue and the aqueous layer, and then concentrated under reduced pressure. The concentrate was purified by column chromatography (SiO₂, 12 g cartridge; methanol/dichloromethane=from 0% to 10%) and concentrated to give the title compound (0.120 g, 84.9%) as a foam solid.

[Step 4] Synthesis of N-((5-(hydrazinecarbonyl)pyridin-2-yl)methyl)-1-methyl-N-phenylpiperidine-4-carboxamide

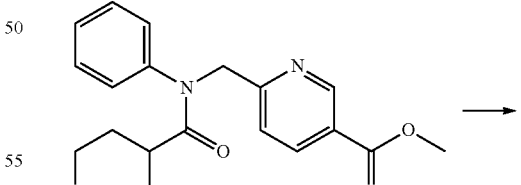

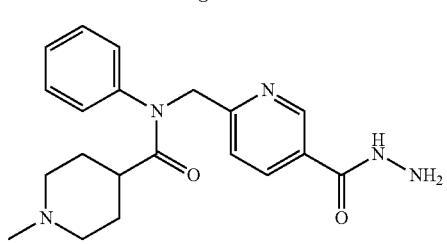

Methyl 6-((1-methyl-N-phenylpiperidine-4-carboxamido)methyl)nicotinate (0.120 g, 0.327 mmol), synthesized in step 3, and hydrazine monohydrate (0.079 mL, 1.633 mmol) were dissolved in ethanol (10 mL) at room temperature, and the solution was heated under reflux for 12 hours, and then cooled to room temperature to terminate the reaction. The reaction mixture was concentrated under reduced pressure to remove the solvent, and the concentrate was purified by column chromatography (SiO$_2$, 4 g cartridge; methanol/dichloromethane=from 5% to 30%) and concentrated to give the title compound (0.115 g, 95.8%) as a foam solid.

[Step 5] Synthesis of Compound 11414

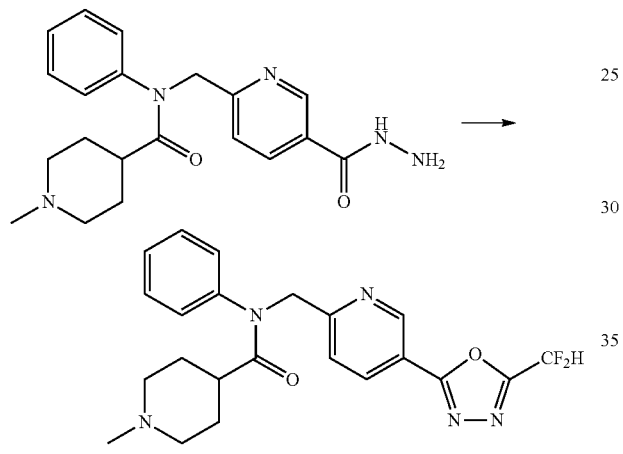

N-((5-(hydrazinecarbonyl)pyridin-2-yl)methyl)-1-methyl-N-phenylpiperidine-4-carboxamide (0.200 g, 0.544 mmol) synthesized in step 4, 2,2-difluoroacetic anhydride (0.178 mL, 1.633 mmol) and triethylamine (0.152 mL, 1.089 mmol) were dissolved in tetrahydrofuran (10 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$ plate, 20×20×1 mm; methanol/dichloromethane=20%) and concentrated to give the title compound (0.002 g, 0.9%) as a white solid.

$^1$H NMR (400 MHz, CDCl$_3$) δ 9.30-9.24 (m, 1H), 8.36 (dd, 1H, J=8.2, 2.2 Hz), 7.58-7.33 (m, 5H), 7.25-7.22 (m, 1H), 7.10-6.80 (m, 1H), 5.05 (s, 2H), 3.46 (d, 2H, J=11.1 Hz), 3.26 (d, 2H, J=11.8 Hz), 2.91 (s, 2H), 2.74 (d, 3H, J=4.1 Hz), 2.36 (s, 1H), 1.96 (d, 2H, J=14.7 Hz); LRMS (ES) m/z 428.5 (M$^+$+1).

EXAMPLE 83: Synthesis of Compound 11418, N-((5-(5-(difluoromethyl)-1,3,4-oxadiazol-2-yl)pyridin-2-yl)methyl)-N-(3-fluorophenyl)-1-methylpiperidine-4-carboxamide

[Step 1] Synthesis of methyl 6-((1-(tert-butoxycarbonyl)-N-(3-fluorophenyl)piperidine-4-carboxamido)methyl)nicotinate

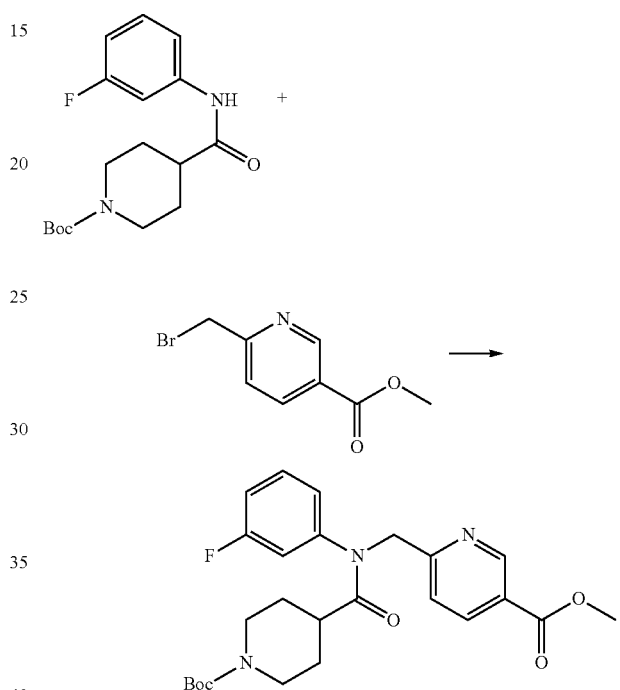

Tert-butyl 4-((3-fluorophenyl)carbamoyl)piperidine-1-carboxylate (0.400 g, 1.241 mmol) was dissolved in tetrahydrofuran (30 mL), and sodium hydride (60.00%, 0.074 g, 1.861 mmol) was added slowly to the solution while the temperature was maintained at 0° C. The reaction mixture was stirred for 20 minutes. Then, methyl 6-(bromomethyl)nicotinate (0.314 g, 1.365 mmol) was added to the reaction solution, followed by additional stirring at room temperature for 12 hours. Then, water (2 mL) was added to the reaction mixture at 0° C., followed by stirring for 5 minutes. After completion of the reaction, water was added to the reaction mixture, followed by extraction with dichloromethane. The extract was filtered through a plastic filter to remove the solid residue and the aqueous layer, and then concentrated under reduced pressure. The concentrate was purified by column chromatography (SiO$_2$, 40 g cartridge; ethyl acetate/hexane=from 5% to 40%) and concentrated to give the title compound (0.400 g, 68.4%) as a foam solid.

[Step 2] Synthesis of methyl 6-((N-(3-fluorophenyl)piperidine-4-carboxamido)methyl)nicotinate hydrochloride

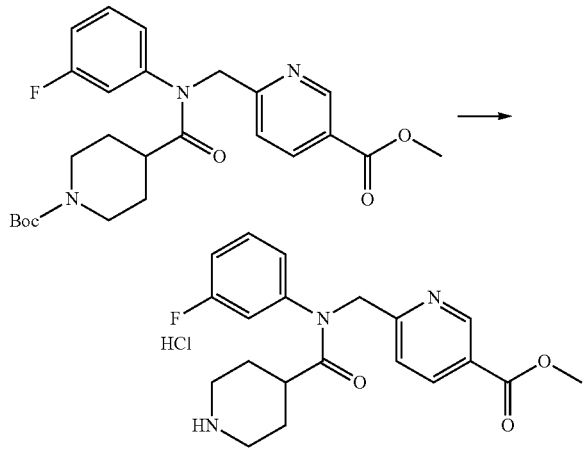

Methyl 6-((1-(tert-butoxycarbonyl)-N-(3-fluorophenyl)piperidine-4-carboxamido)methyl)nicotinate (0.400 g, 0.848 mmol) synthesized in step 1 was dissolved in dichloromethane (30 mL), and hydrochloric acid (4.00 M solution in dioxane, 2.121 mL, 8.483 mmol) was added to the solution at 0° C. The mixture was stirred at room temperature for 12 hours. The reaction mixture was concentrated under reduced pressure to remove the solvent. The title compound was used without further purification (0.340 g, 98.3%) as white solid.

[Step 3] Synthesis of methyl 6-((N-(3-fluorophenyl)-1-methylpiperidine-4-carboxamido)methyl)nicotinate

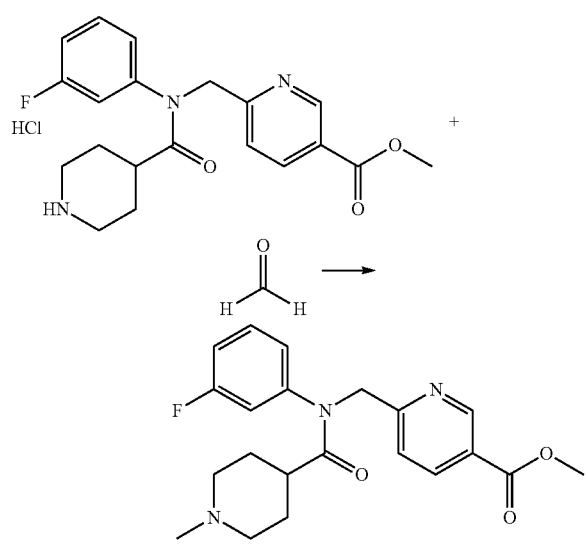

Methyl 6-((N-(3-fluorophenyl)piperidine-4-carboxamido)methyl)nicotinate hydrochloride (0.150 g, 0.368 mmol) synthesized in step 2, formaldehyde (37.00% solution in water, 0.137 mL, 1.839 mmol) and sodium triacetoxyborohydride (0.156 g, 0.736 mmol) were dissolved in dichloromethane (20 mL) at room temperature, and the solution was stirred at the same temperature for 18 hours. Water was added to the reaction mixture, followed by extraction with dichloromethane. The extract was filtered through a plastic filter to remove the solid residue and the aqueous layer, and then concentrated under reduced pressure. The concentrate was purified by column chromatography (SiO$_2$, 12 g cartridge; methanol/dichloromethane=from 0% to 10%) and concentrated to give the title compound (0.130 g, 91.7%) as a foam solid.

[Step 4] Synthesis of N-(3-fluorophenyl)-N-((5-(hydrazinecarbonyl)pyridin-2-yl)methyl)-1-methylpiperidine-4-carboxamide

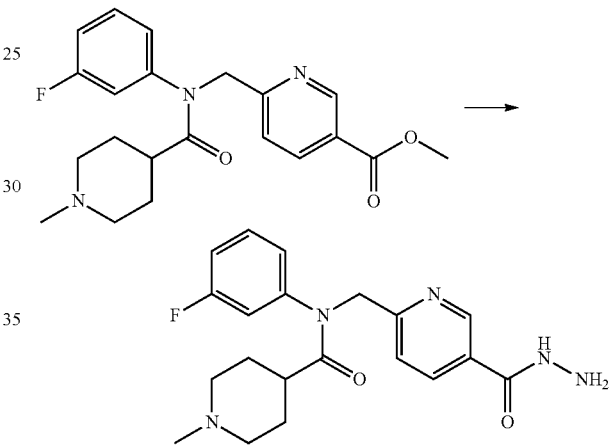

Methyl 6-((N-(3-fluorophenyl)-1-methylpiperidine-4-carboxamido)methyl)nicotinate (0.130 g, 0.337 mmol), synthesized in step 3, and hydrazine monohydrate (0.082 mL, 1.686 mmol) were dissolved in ethanol (10 mL) at room temperature, and the solution was heated under reflux for 12 hours, and then cooled to room temperature to terminate the reaction. The reaction mixture was concentrated under reduced pressure to remove the solvent, and the concentrate was purified by column chromatography (SiO$_2$, 4 g cartridge; methanol/dichloromethane=from 5% to 30%) and concentrated to give the title compound (0.120 g, 92.3%) as a foam solid.

[Step 5] Synthesis of Compound 11418

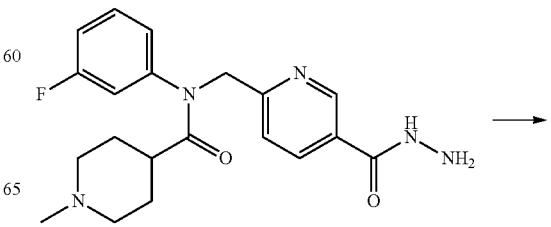

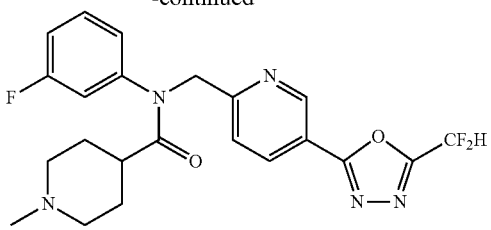

N-(3-fluorophenyl)-N-((5-(hydrazinecarbonyl)pyridin-2-yl)methyl)-1-methylpiperidine-4-carboxamide (0.200 g, 0.519 mmol), synthesized in step 4, and triethylamine (0.145 mL, 1.038 mmol) were dissolved in tetrahydrofuran (13 mL), and 2,2-difluoroacetic anhydride (0.085 mL, 0.778 mmol) was added to the solution at room temperature. The reaction solution was heated under reflux for 12 hours, and then cooled to room temperature to terminate the reaction. Water was added to the reaction mixture, followed by extraction with dichloromethane. The extract was filtered through a plastic filter to remove the solid residue and the aqueous layer, and then concentrated under reduced pressure. The concentrate was purified by column chromatography (SiO$_2$, 12 g cartridge; methanol/dichloromethane=from 0% to 15%) and concentrated, and then the obtained material was further purified by chromatography (SiO$_2$ plate, 20×20×1 mm; methanol/dichloromethane=10%) and concentrated to give the title compound (0.015 g, 6.5%) as a white solid.

$^1$H NMR (400 MHz, CDCl$_3$) δ 9.25 (m, 1H), 8.38 (m, 1H), 7.54 (m, 1H), 7.35 (m, 1H), 7.10-6.82 (m, 4H), 5.05 (s, 2H), 2.95 (m, 2H), 2.42-2.32 (m, 5H), 1.99-1.78 (m, 5H); LRMS (ES) m/z 446.4 (M$^+$+1).

EXAMPLE 84: Synthesis of Compound 11419, N-((5-(5-(difluoromethyl)-1,3,4-oxadiazol-2-yl)pyridin-2-yl)methyl)-1-ethyl-N-(3-fluorophenyl)piperidine-4-carboxamide

[Step 1] Synthesis of methyl 6-((1-ethyl-N-(3-fluorophenyl)piperidine-4-carboxamido)methyl)nicotinate

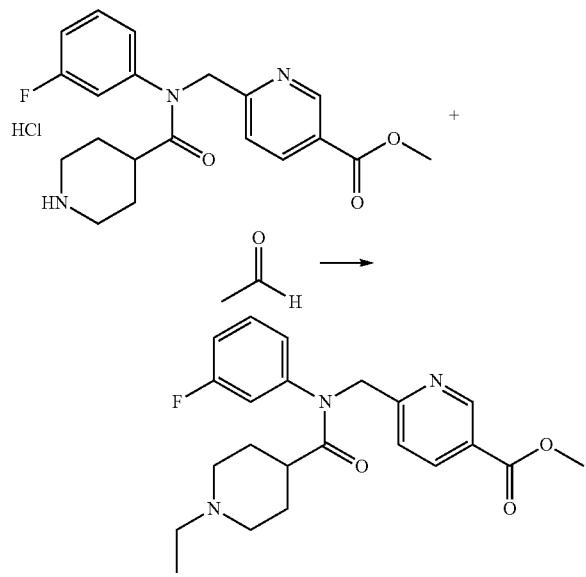

Methyl 6-((N-(3-fluorophenyl)piperidine-4-carboxamido)methyl)nicotinate hydrochloride (0.150 g, 0.368 mmol) synthesized in step 2 of Example 83, acetaldehyde (0.104 mL, 1.839 mmol) and sodium triacetoxyborohydride (0.156 g, 0.736 mmol) were dissolved in dichloromethane (20 mL) at room temperature, and the solution was stirred at the same temperature for 18 hours. Water was added to the reaction mixture, followed by extraction with dichloromethane. The extract was filtered through a plastic filter to remove the solid residue and the aqueous layer, and then concentrated under reduced pressure. The concentrate was purified by column chromatography (SiO$_2$, 12 g cartridge; methanol/dichloromethane=from 0% to 10%) and concentrated to give the title compound (0.130 g, 88.5%) as a foam solid.

[Step 2] Synthesis of 1-ethyl-N-(3-fluorophenyl)-N-((5-(hydrazinecarbonyl)pyridin-2-yl)methyl)piperidine-4-carboxamide

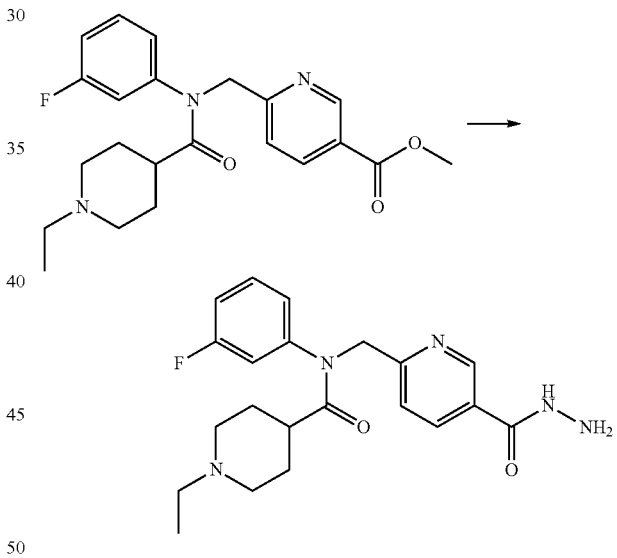

Methyl 6-((1-ethyl-N-(3-fluorophenyl)piperidine-4-carboxamido)methyl)nicotinate (0.130 g, 0.325 mmol), synthesized in step 1, and hydrazine monohydrate (0.079 mL, 1.627 mmol) were dissolved in ethanol (10 mL) at room temperature, and the solution was heated under reflux for 12 hours, and then cooled to room temperature to terminate the reaction. The reaction mixture was concentrated under reduced pressure to remove the solvent, and the concentrate was purified by column chromatography (SiO$_2$, 4 g cartridge; methanol/dichloromethane=from 5% to 30%) and concentrated to give the title compound (0.120 g, 92.3%) as a foam solid.

171

[Step 3] Synthesis of Compound 11419

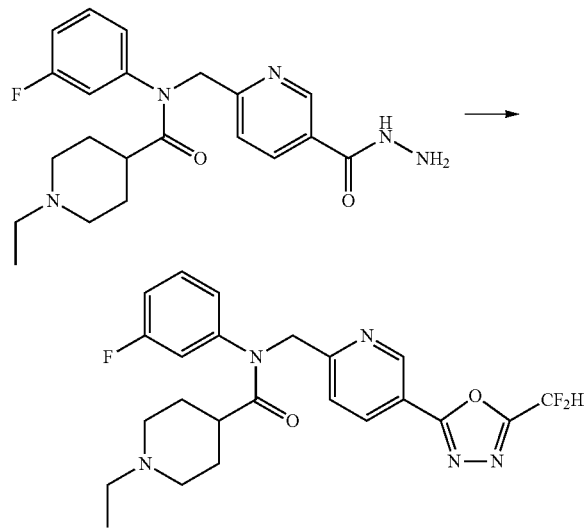

1-ethyl-N-(3-fluorophenyl)-N-((5-(hydrazinecarbonyl) pyridin-2-yl)methyl)piperidine-4-carboxamide (0.200 g, 0.501 mmol), synthesized in step 2, and triethylamine (0.140 mL, 1.001 mmol) were dissolved in tetrahydrofuran (13 mL), and 2,2-difluoroacetic anhydride (0.082 mL, 0.751 mmol) was added to the solution at room temperature. The reaction solution was heated under reflux for 12 hours, and then cooled to room temperature to terminate the reaction. Water was added to the reaction mixture, followed by extraction with dichloromethane. The extract was filtered through a plastic filter to remove the solid residue and the aqueous layer, and then concentrated under reduced pressure. The concentrate was purified by column chromatography (SiO$_2$, 12 g cartridge; methanol/dichloromethane=from 0% to 15%) and concentrated, and then the obtained material was further purified by chromatography (SiO$_2$ plate, 20×20×1 mm; methanol/dichloromethane=10%) and concentrated to give the title compound (0.015 g, 6.5%) as a white solid.

$^1$H NMR (400 MHz, CDCl$_3$) δ 9.25 (m, 1H), 8.37 (m, 1H), 7.52 (m, 1H), 7.36 (m, 1H), 7.12-6.82 (m, 4H), 5.04 (s, 2H), 3.11 (m, 2H), 2.63-2.16 (m, 4H), 2.01-1.90 (m, 5H), 1.18 (m, 3H); LRMS (ES) m/z 460.5 (M$^+$+1).

EXAMPLE 85: Synthesis of Compound 11534, N-(3-chloro-4-fluorophenyl)-N-(4-(5-(difluoromethyl)-1,3,4-oxadiazol-2-yl)-2-fluorobenzyl)-2-(pyrolidin-1-yl)acetamide

[Step 1] Synthesis of 2-(benzyloxy)-N-(4-chloro-3-fluorophenyl)acetamide

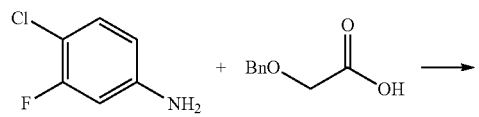

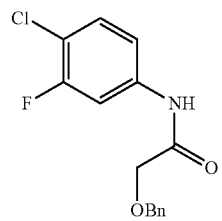

4-chloro-3-fluoroaniline (1.000 g, 6.870 mmol), 2-(benzyloxy)acetic acid (1.179 mL, 8.244 mmol), 1-ethyl-3-(3-dimethylaminopropyl)carbodiimide (EDC, 2.133 g, 13.740 mmol), 1H-benzo[d][1,2,3]triazol-1-ol (HOBt, 1.857 g, 13.740 mmol) and N,N-diisopropylethylamine (2.393 mL, 13.740 mmol) were dissolved in dichloromethane (50 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 0% to 50%) and concentrated to give the title compound (1.880 g, 93.2%) as a yellow solid.

[Step 2] Synthesis of methyl 4-((2-(benzyloxy)-N-(3-chloro-4-fluorophenyl)acetamido)methyl)-3-fluorobenzoate

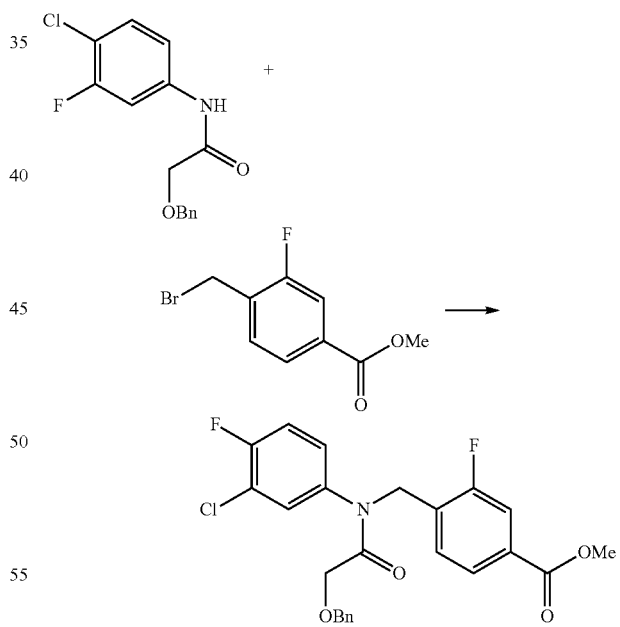

2-(Benzyloxy)-N-(4-chloro-3-fluorophenyl)acetamide (1.880 g, 6.401 mmol), synthesized in step 1, and calcium carbonate (1.327 g, 9.601 mmol) were dissolved in tetrahydrofuran (50 mL) at 0° C., and methyl 4-(bromomethyl)-3-fluorobenzoate (1.898 g, 7.681 mmol) was added to the solution. The mixture was stirred at room temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 0% to 50%) and concentrated to give the title compound (1.780 g, 60.5%) as yellow oil.

[Step 3] Synthesis of 2-(benzyloxy)-N-(3-chloro-4-fluorophenyl)-N-(2-fluoro-4-(hydrazinecarbonyl)benzyl)acetamide

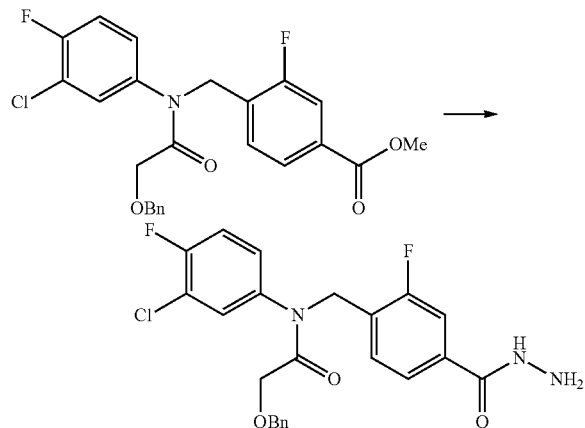

Methyl 4-((2-(benzyloxy)-N-(3-chloro-4-fluorophenyl)acetamido)methyl)-3-fluorobenzoate (1.780 g, 3.871 mmol), synthesized in step 2, and hydrazine monohydrate (5.644 mL, 116.120 mmol) were dissolved in ethanol (8 mL)/water (2 mL) at room temperature, and the solution was stirred at 80° C. for 12 hours, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The title compound was used without further purification (1.580 g, 88.8%, yellow solid).

[Step 4] Synthesis of 2-(benzyloxy)-N-(3-chloro-4-fluorophenyl)-N-(4-(2-(2,2-difluoroacetyl)hydrazine-1-carbonyl)-2-fluorobenzyl)acetamide

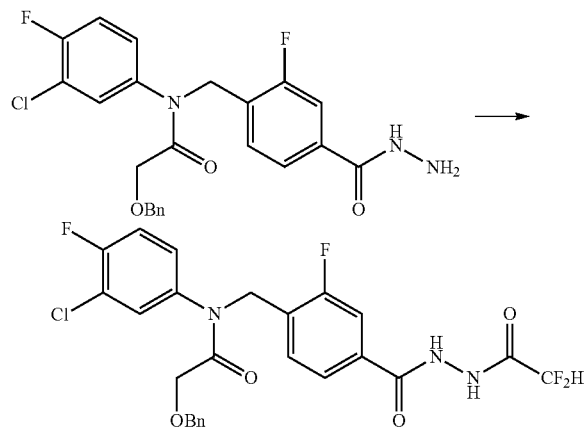

2-(Benzyloxy)-N-(3-chloro-4-fluorophenyl)-N-(2-fluoro-4-(hydrazinecarbonyl)benzyl)acetamide (1.580 g, 3.436 mmol), synthesized in step 3, and triethylamine (0.958 mL, 6.871 mmol) were dissolved in dichloromethane (50 mL) at room temperature, and 2,2-difluoroacetic anhydride (0.513 mL, 4.123 mmol) was added to the solution. The mixture was stirred at the same temperature for 2 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 0% to 80%) and concentrated to give the title compound (1.120 g, 60.6%) as colorless oil.

[Step 5] Synthesis of N-(3-chloro-4-fluorophenyl)-N-(4-(2-(2,2-difluoroacetyl)hydrazine-1-carbonyl)-2-fluorobenzyl)-2-hydroxyacetamide

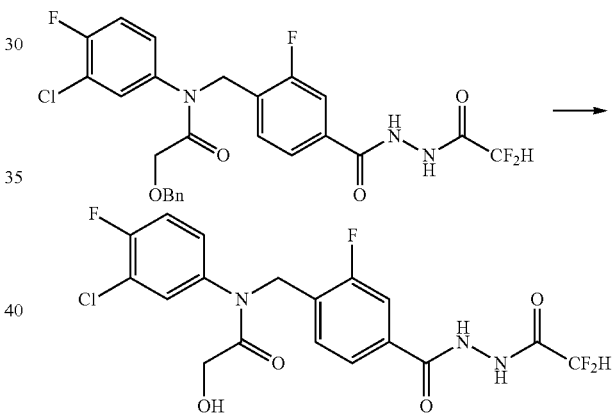

2-(Benzyloxy)-N-(3-chloro-4-fluorophenyl)-N-(4-(2-(2,2-difluoroacetyl)hydrazine-1-carbonyl)-2-fluorobenzyl)acetamide (0.880 g, 1.636 mmol) synthesized in step 4 was dissolved in methanol (50 mL) at room temperature, and 10%-Pd/C (600 mg) was added slowly to the solution. The mixture was stirred at the same temperature for 5 hours under a hydrogen balloon. The reaction mixture was filtered through a celite pad to remove solids, and water was added to the filtrate, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 0% to 80%) and concentrated to give the title compound (0.658 g, 89.8%) as yellow oil.

[Step 6] Synthesis of 2-((3-chloro-4-fluorophenyl)(4-(5-(difluoromethyl)-1,3,4-oxadiazol-2-yl)-2-fluorobenzyl)amino)-2-oxoethyl methanesulfonate

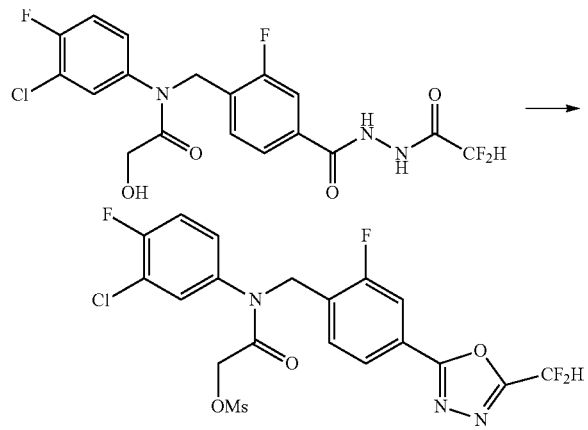

N-(3-chloro-4-fluorophenyl)-N-(4-(2-(2,2-difluoroacetyl)hydrazine-1-carbonyl)-2-fluorobenzyl)-2-hydroxyacetamide (0.658 g, 1.470 mmol), synthesized in step 5, and N,N-diisopropylethylamine (0.768 mL, 4.409 mmol) were dissolved in dichloromethane (50 mL) at room temperature, and methanesulfonyl chloride (0.284 mL, 3.674 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 50%) and concentrated to give the title compound (0.254 g, 34.0%) as yellow oil.

[Step 7] Synthesis of Compound 11534

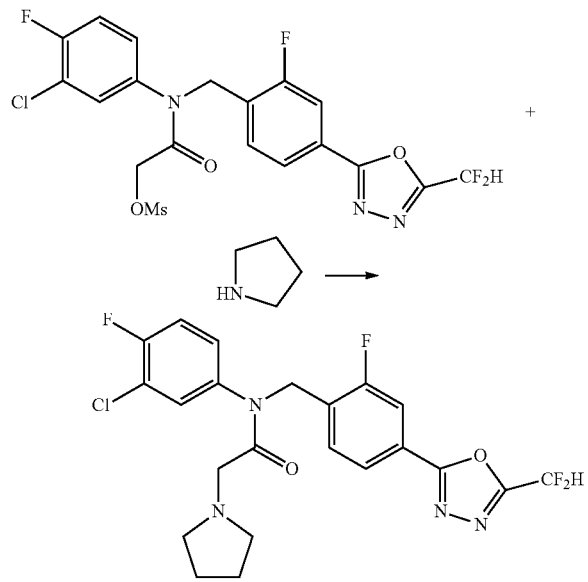

2-((3-chloro-4-fluorophenyl) (4-(5-(difluoromethyl)-1,3,4-oxadiazol-2-yl)-2-fluorobenzyl)amino)-2-oxoethyl methanesulfonate (0.050 g, 0.098 mmol) synthesized in step 6, pyrrolidine (0.011 g, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 15%) and concentrated to give the title compound (0.013 g, 27.3%) as colorless oil.

$^1$H NMR (400 MHz, CDCl$_3$) δ 7.91 (dd, 1H, J=8.0, 1.7 Hz), 7.76 (dd, 1H, J=9.9, 1.7 Hz), 7.65 (t, 1H, J=7.6 Hz), 7.29 (dd, 1H, J=6.2, 2.6 Hz), 7.22-7.07 (m, 2H), 7.06-6.75 (m, 1H), 5.01 (s, 2H), 3.88-3.73 (m, 4H), 3.20 (t, 2H, J=8.7 Hz), 2.17 (d, 4H, J=6.2 Hz); LRMS (ES) m/z 483.4 (M$^+$+1).

EXAMPLE 86: Synthesis of Compound 11535, N-(3-chloro-4-fluorophenyl)-N-(4-(5-(difluoromethyl)-1,3,4-oxadiazol-2-yl)-2-fluorobenzyl)-2-morpholinoacetamide

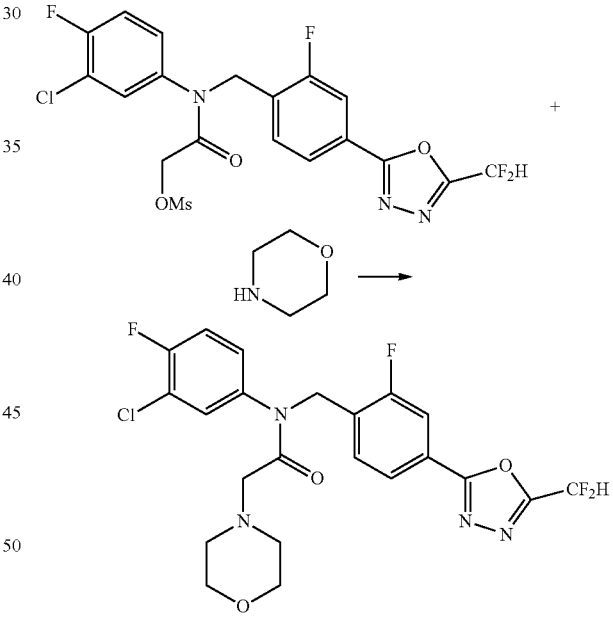

2-((3-chloro-4-fluorophenyl)(4-(5-(difluoromethyl)-1,3,4-oxadiazol-2-yl)-2-fluorobenzyl)amino)-2-oxoethyl methanesulfonate (0.050 g, 0.098 mmol) synthesized in step 6 of Example 85, morpholine (0.013 mL, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/ dichloromethane=from 0% to 15%) and concentrated to give the title compound (0.042 g, 85.5%) as yellow oil.

$^1$H NMR (400 MHz, CDCl$_3$) δ 7.88 (ddd, 1H, J=8.0, 4.9, 1.7 Hz), 7.73 (ddd, 1H, J=9.8, 8.0, 1.7 Hz), 7.62 (td, 1H, J=7.6, 2.3 Hz), 7.27-7.23 (m, 1H), 7.18-7.05 (m, 2H), 7.05-6.76 (m, 1H), 5.03-4.90 (m, 2H), 3.82 (dt, 4H, J=23.4, 4.8 Hz), 3.27-3.04 (m, 2H), 2.77 (d, 4H, J=55.3 Hz); LRMS (ES) m/z 499.5 (M$^+$+1).

EXAMPLE 87: Synthesis of Compound 11536, (S)-N-(3-chloro-4-fluorophenyl)-N-(4-(5-(difluoromethyl)-1,3,4-oxadiazol-2-yl)-2-fluorobenzyl)-2-(3-hydroxypyrrolidin-1-yl)acetamide

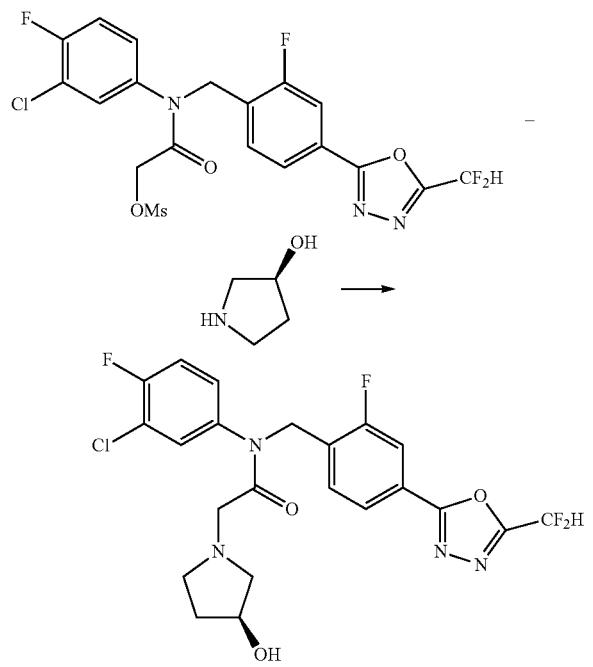

2-((3-chloro-4-fluorophenyl) (4-(5-(difluoromethyl)-1,3,4-oxadiazol-2-yl)-2-fluorobenzyl)amino)-2-oxoethyl methanesulfonate (0.050 g, 0.098 mmol) synthesized in step 6 of Example 85, (S)-pyrrolidin-3-ol (0.013 g, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 30%) and concentrated to give the title compound (0.044 g, 89.6%) as yellow oil.

$^1$H NMR (400 MHz, CDCl$_3$) δ 7.88 (t, 1H, J=7.0 Hz), 7.79-7.51 (m, 2H), 7.24-7.05 (m, 3H), 6.92 (t, 1H, J=51.8 Hz), 5.02 (s, 2H), 4.21-3.43 (m, 4H), 3.27 (d, 1H, J=47.5 Hz), 2.49 (s, 5H); LRMS (ES) m/z 499.5 (M$^+$+1).

EXAMPLE 88: Synthesis of Compound 11537, (R)-N-(3-chloro-4-fluorophenyl)-N-(4-(5-(difluoromethyl)-1,3,4-oxadiazol-2-yl)-2-fluorobenzyl)-2-(2-(hydroxymethyl)pyrrolidin-1-yl)acetamide

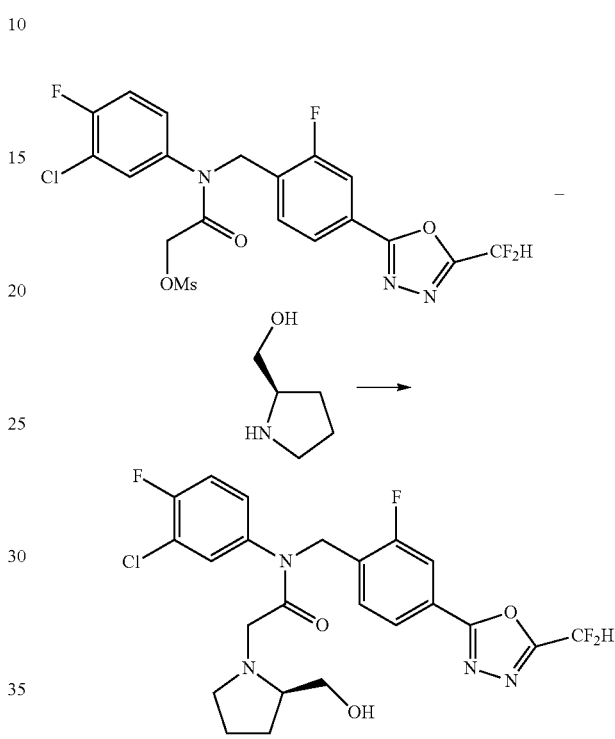

2-((3-chloro-4-fluorophenyl) (4-(5-(difluoromethyl)-1,3,4-oxadiazol-2-yl)-2-fluorobenzyl)amino)-2-oxoethyl methanesulfonate (0.050 g, 0.098 mmol) synthesized in step 6 of Example 85, (R)-pyrrolidin-2-ylmethanol (0.015 g, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/hexane=from 0% to 15%) and concentrated to give the title compound (0.019 g, 37.6%) as colorless oil.

$^1$H NMR (400 MHz, CDCl$_3$) δ 7.89 (ddd, 1H, J=8.2, 6.9, 1.7 Hz), 7.75 (ddd, 1H, J=9.9, 6.1, 1.7 Hz), 7.60 (dt, 1H, J=14.8, 7.6 Hz), 7.25-7.05 (m, 3H), 7.03-6.77 (m, 1H), 5.08-4.92 (m, 2H), 3.92-2.66 (m, 7H), 2.29-1.47 (m, 4H); LRMS (ES) m/z 513.5 (M$^+$+1).

EXAMPLE 89: Synthesis of Compound 11538, (S)-1-(2-((3-chloro-4-fluorophenyl) (4-(5-(difluoromethyl)-1,3,4-oxadiazol-2-yl)-2-fluorobenzyl) amino)-2-oxoethyl)pyrrolidine-2-carboxamide

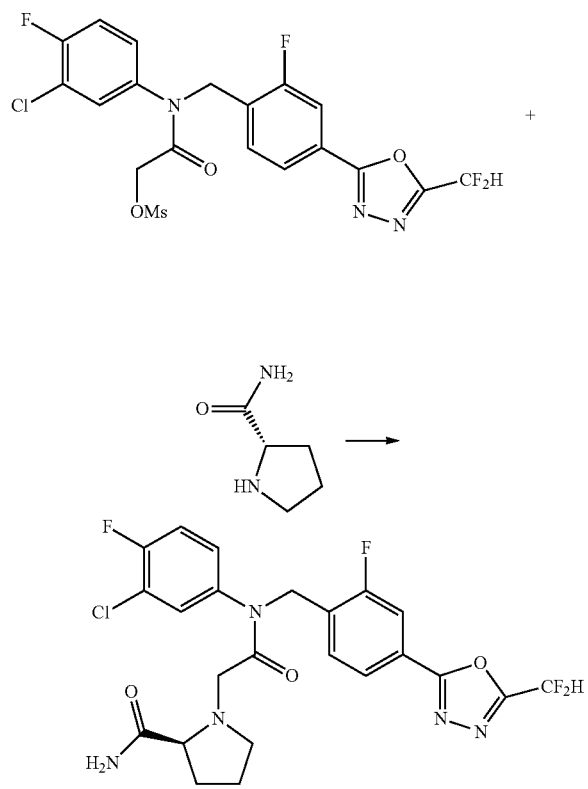

2-((3-chloro-4-fluorophenyl) (4-(5-(difluoromethyl)-1,3,4-oxadiazol-2-yl)-2-fluorobenzyl)amino)-2-oxoethyl methanesulfonate (0.050 g, 0.098 mmol) synthesized in step 6 of Example 85, (S)-pyrrolidin-2-carboxamide (0.017 g, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 4 g cartridge; methanol/dichloromethane=from 0% to 15%) and concentrated to give the title compound (0.041 g, 79.2%) as colorless oil.

$^1$H NMR (400 MHz, CDCl$_3$) δ 7.89 (td, 1H, J=7.4, 1.6 Hz), 7.75 (ddd, 1H, J=9.8, 6.0, 1.6 Hz), 7.60 (dt, 1H, J=14.8, 7.5 Hz), 7.25-7.05 (m, 2H), 7.06-6.76 (m, 2H), 5.09-4.91 (m, 2H), 3.85-2.98 (m, 6H), 3.18-3.02 (m, 1H), 2.22-1.68 (m, 4H); LRMS (ES) m/z 526.5 (M$^+$+1).

EXAMPLE 90: Synthesis of Compound 11584, N-phenyl-N-((5-(5-(trifluoromethyl)-1,3,4-oxadiazol-2-yl)pyridin-2-yl)methyl)isonicotinamide

[Step 1] Synthesis of N-phenyl-N-((5-(2-(2,2,2-trifluoroacetyl)hydrazine-1-carbonyl)pyridin-2-yl) methyl)isonicotinamide

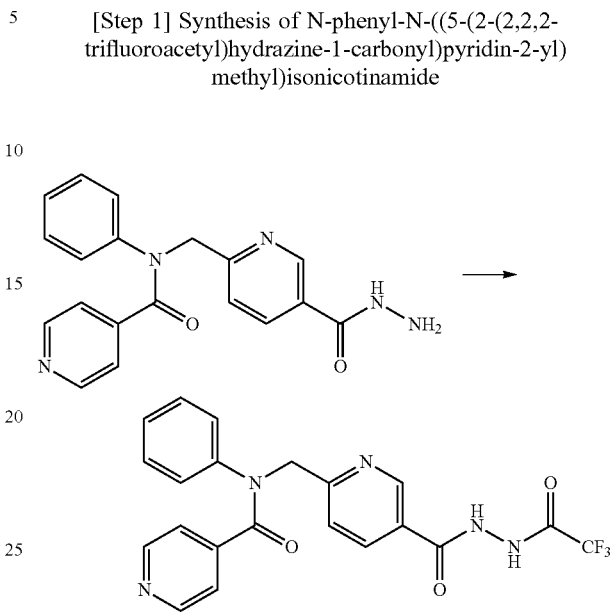

N-((5-(hydrazinecarbonyl)pyridin-2-yl)methyl)-N-phenylisonicotinamide (1.000 g, 2.879 mmol), synthesized in step 2 of Example 75, and triethylamine (0.802 mL, 5.757 mmol) were dissolved in tetrahydrofuran (30 mL), and trifluoroacetic anhydride (0.813 mL, 5.757 mmol) was added to the solution at room temperature. The mixture was heated under reflux for 12 hours, and then cooled to room temperature to terminate the reaction. Saturated aqueous ammonium chloride solution was added to the reaction mixture, followed by extraction with dichloromethane. The organic layer was washed with saturated aqueous sodium chloride solution, dried with magnesium sulfate anhydrous, filtered, and then concentrated under reduced pressure. The title compound was used without further purification (0.750 g, 61.2%) as colorless oil.

[Step 2] Synthesis of Compound 11584

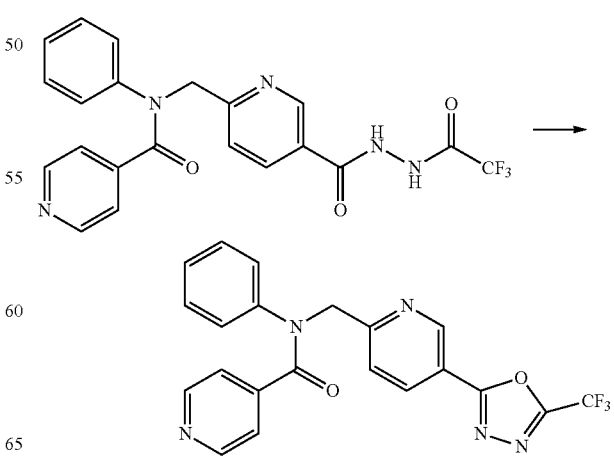

N-phenyl-N-((5-(2-(2,2,2-trifluoroacetyl)hydrazine-1-carbonyl)pyridin-2-yl)methyl)isonicotinamide (0.900 g, 2.030 mmol), synthesized in step 1, 1-methoxy-N-triethylammoniosulfonyl-methanimidate (Burgess reagent, 0.484 g, 2.030 mmol) were mixed in tetrahydrofuran (15 mL) at room temperature, and the mixture was heated by microwave irradiation at 150° C. for 30 minutes, and then cooled to room temperature to terminate the reaction. Water was added to the reaction mixture, followed by extraction with dichloromethane. The extract was filtered through a plastic filter to remove the solid residue and the aqueous layer, and then concentrated under reduced pressure. The concentrate was purified by column chromatography (SiO$_2$, 80 g cartridge; ethyl acetate/hexane=from 10% to 60%) and concentrated, and then the obtained product was further purified by chromatography (SiO$_2$, 40 g cartridge; ethyl acetate/hexane=from 10% to 60%) and concentrated to give the title compound (0.470 g, 54.4%) as a white solid.

$^1$H NMR (400 MHz, CDCl$_3$) δ 9.32 (m, 1H), 8.54 (m, 2H), 8.40 (m, 1H), 7.65 (m, 1H), 7.40 (m, 2H), 7.25 (m, 3H), 7.17 (m, 2H), 5.32 (s, 2H); LRMS (ES) m/z 426.4 (M$^+$+1).

EXAMPLE 91: Synthesis of Compound 11602, N-(3-chloro-4-fluorophenyl)-N-(2-fluoro-4-(5-(trifluoromethyl)-1,3,4-oxadiazol-2-yl)benzyl)tetrahydro-2H-thiopyran-4-carboxamide 1,1-dioxide

[Step 1] Synthesis of N-(3-chloro-4-fluorophenyl)tetrahydro-2H-thiopyran-4-carboxamide 1,1-dioxide

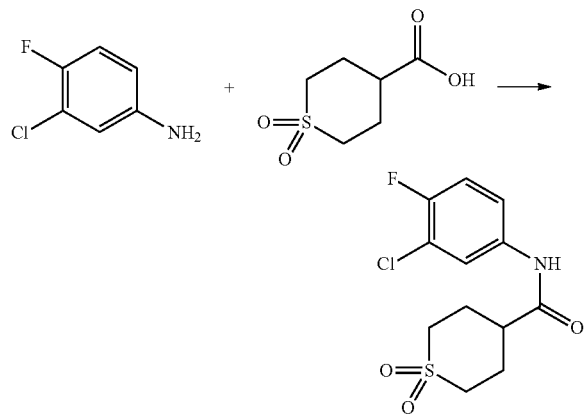

3-Chloro-4-fluoroaniline (0.700 g, 4.809 mmol), tetrahydro-2H-thiopyran-4-carboxylic acid 1,1-dioxide (0.943 g, 5.290 mmol), 1-ethyl-3-(3-dimethylaminopropyl)carbodiimide hydrochloride (EDC-HCl, 1.844 g, 9.618 mmol), 1H-benzo[d][1,2,3]triazol-1-ol (HOBt, 1.300 g, 9.618 mmol) and N,N-diisopropylethylamine (1.675 mL, 9.618 mmol) were dissolved in dichloromethane (100 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 40 g cartridge; ethyl acetate/hexane=from 0% to 80%) and concentrated to give the title compound (0.988 g, 67.2%) as a white solid.

[Step 2] Synthesis of methyl 4-((N-(3-chloro-4-fluorophenyl)-1,1-dioxidotetrahydro-2H-thiopyran-4-carboxamido)methyl)-3-fluorobenzoate

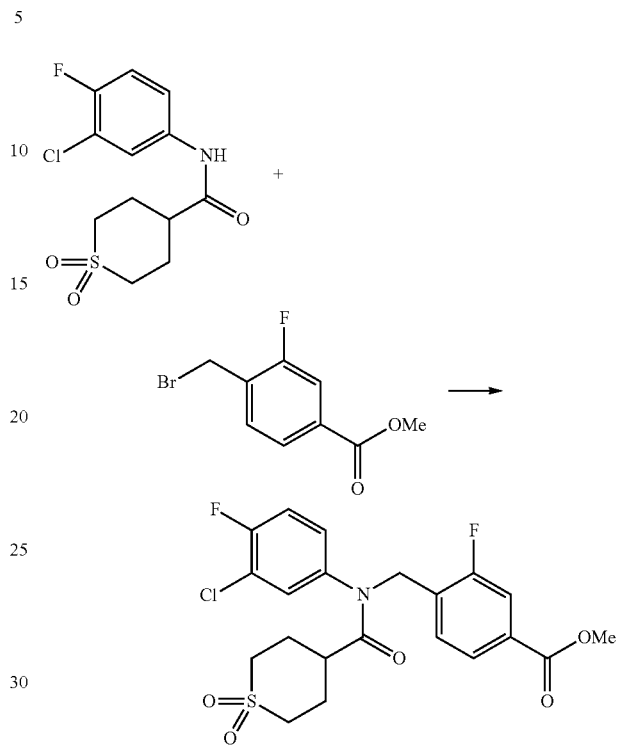

N-(3-chloro-4-fluorophenyl)tetrahydro-2H-thiopyran-4-carboxamide 1,1-dioxide (1.000 g, 3.271 mmol), synthesized in step 1, and sodium hydride (60.00%, 0.262 g, 6.541 mmol) were dissolved in N,N-dimethylformamide (50 mL) at room temperature, and methyl 4-(bromomethyl)-3-fluorobenzoate (1.212 g, 4.906 mmol) was added to the solution. The mixture was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 100%) and concentrated to give the title compound (1.240 g, 80.3%) as a white solid.

[Step 3] Synthesis of N-(3-chloro-4-fluorophenyl)-N-(2-fluoro-4-(hydrazinecarbonyl)benzyl)tetrahydro-2H-thiopyran-4-carboxamide 1,1-dioxide

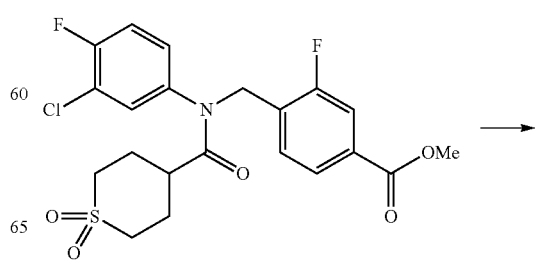

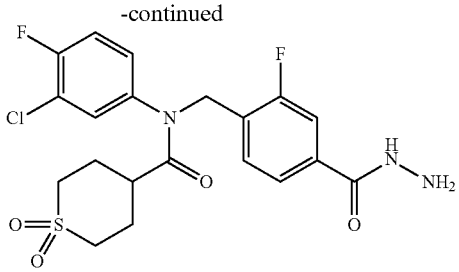

Methyl 4-((N-(3-chloro-4-fluorophenyl)-1,1-dioxidotetrahydro-2H-thiopyran-4-carboxamido)methyl)-3-fluorobenzoate (1.240 g, 2.628 mmol), synthesized in step 2, and hydrazine monohydrate (2.554 mL, 52.554 mmol) were dissolved in ethanol (20 mL)/water (5 mL) at room temperature, and the solution was stirred at 80° C. for 5 hours, and then cooled to room temperature to terminate the reaction. The reaction mixture was concentrated under reduced pressure to remove the solvent. The title compound was used without further purification (1.180 g, 95.2%) as yellow solid.

[Step 4] Synthesis of N-(3-chloro-4-fluorophenyl)-N-(2-fluoro-4-(2-(2,2,2-trifluoroacetyl)hydrazine-1-carbonyl)benzyl)tetrahydro-2H-thiopyran-4-carboxamide 1,1-dioxide

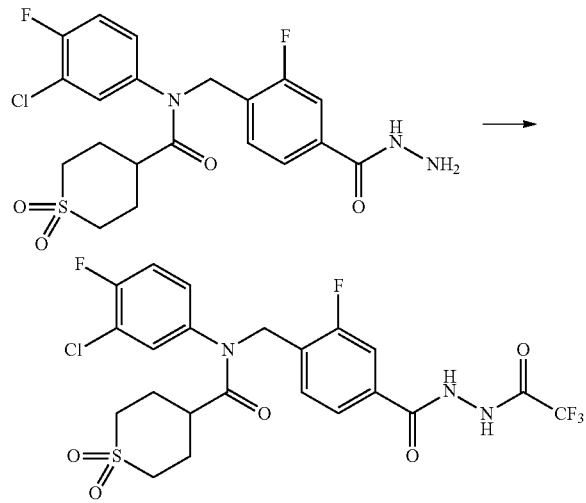

N-(3-chloro-4-fluorophenyl)-N-(2-fluoro-4-(hydrazinecarbonyl)benzyl)tetrahydro-2H-thiopyran-4-carboxamide 1,1-dioxide (0.200 g, 0.424 mmol), synthesized in step 3, 1,1-dioxide (0.200 g, 0.424 mmol) and triethylamine (0.118 mL, 0.848 mmol) were dissolved in tetrahydrofuran (10 mL) at room temperature, and trifluoroacetic anhydride (0.180 mL, 1.271 mmol) was added to the solution. The mixture was stirred at 80° C. for 1 hour, and then cooled to room temperature to terminate the reaction. The reaction mixture was filtered to remove solids, and the filtrate was concentrated under reduced pressure to remove the solvent. The concentrate was purified by column chromatography (SiO$_2$, 12 g cartridge; ethyl acetate/hexane=from 0% to 80%) and concentrated to give the title compound (0.160 g, 66.5%) as colorless oil.

[Step 5] Synthesis of Compound 11602

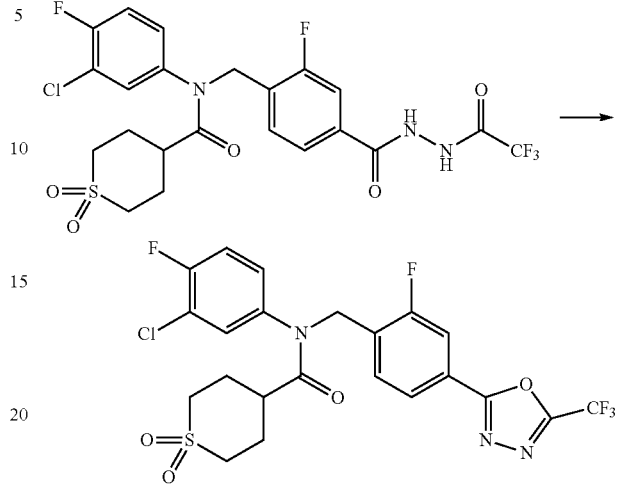

N-(3-chloro-4-fluorophenyl)-N-(2-fluoro-4-(2-(2,2,2-trifluoroacetyl)hydrazine-1-carbonyl)benzyl)tetrahydro-2H-thiopyran-4-carboxamide 1,1-dioxide (0.160 g, 0.282 mmol), synthesized in step 4, and triethylamine (0.079 mL, 0.563 mmol) were dissolved in dichloromethane (15 mL) at room temperature, and methanesulfonyl chloride (0.033 mL, 0.423 mmol) was added to the solution. The mixture was stirred at the same temperature for 2 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.030 g, 19.4%) as a white solid.

$^1$H NMR (400 MHz, CDCl$_3$) δ 7.89 (dd, 1H, J=8.0, 1.7 Hz), 7.76 (dd, 1H, J=9.8, 1.7 Hz), 7.54 (t, 1H, J=7.6 Hz), 7.21-7.12 (m, 2H), 6.91 (ddd, 1H, J=8.7, 4.1, 2.7 Hz), 4.98 (s, 2H), 3.38-3.25 (m, 1H), 2.79 (ddd, 2H, J=13.9, 9.9, 3.7 Hz), 2.50 (tt, 1H, J=7.8, 3.6 Hz), 2.43-2.29 (m, 2H), 2.18-2.06 (m, 3H); LRMS (ES) 550.4 m/z (M$^+$+1).

EXAMPLE 92: Synthesis of Compound 11603, N-(3-chloro-4-fluorophenyl)-N-(4-(5-(difluoromethyl)-1,3,4-oxadiazol-2-yl)-2-fluorobenzyl)tetrahydro-2H-thiopyran-4-carboxamide 1,1-dioxide

[Step 1] Synthesis of N-(3-chloro-4-fluorophenyl)-N-(4-(2-(2,2-difluoroacetyl)hydrazine-1-carbonyl)-2-fluorobenzyl)tetrahydro-2H-thiopyran-4-carboxamide 1,1-dioxide

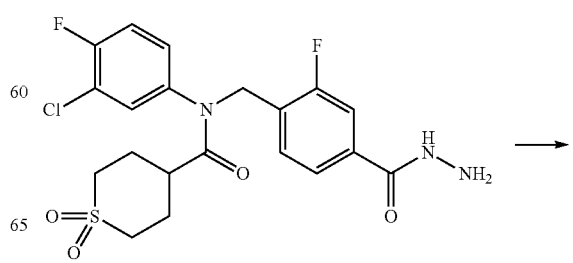

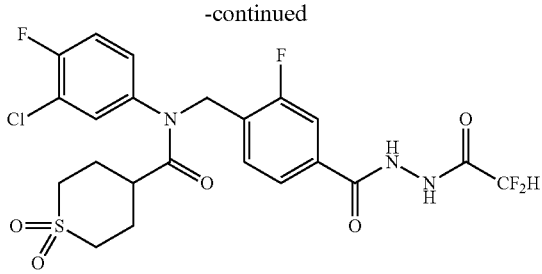

N-(3-chloro-4-fluorophenyl)-N-(2-fluoro-4-(hydrazinecarbonyl)benzyl)tetrahydro-2H-thiopyran-4-carboxamide 1,1-dioxide (0.200 g, 0.424 mmol), synthesized in step 3 of Example 91, and triethylamine (0.118 mL, 0.848 mmol) were dissolved in tetrahydrofuran (10 mL) at room temperature, and 2,2-difluoroacetic anhydride (0.158 mL, 1.271 mmol) was added to the solution. The mixture was stirred at 80° C. for 2 hours, and then cooled to room temperature to terminate the reaction. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.170 g, 72.9%) as colorless oil.

[Step 2] Synthesis of Compound 11603

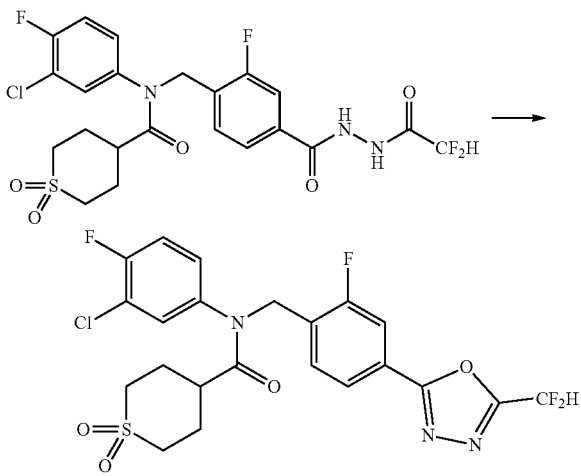

N-(3-chloro-4-fluorophenyl)-N-(4-(2-(2,2-difluoroacetyl)hydrazine-1-carbonyl)-2-fluorobenzyl)tetrahydro-2H-thiopyran-4-carboxamide 1,1-dioxide (0.170 g, 0.309 mmol), synthesized in step 1, and triethylamine (0.086 mL, 0.618 mmol) were dissolved in dichloromethane (15 mL) at room temperature, and methanesulfonyl chloride (0.036 mL, 0.464 mmol) was added to the solution. The mixture was stirred at the same temperature for 2 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 80%) and concentrated to give the title compound (0.015 g, 9.1%) as a white solid.

$^1$H NMR (400 MHz, CDCl$_3$) δ 7.88 (dd, 1H, J=8.0, 1.7 Hz), 7.75 (dd, 1H, J=9.9, 1.7 Hz), 7.52 (t, 1H, J=7.6 Hz), 7.21-7.10 (m, 2H), 7.06-6.76 (m, 2H), 4.97 (s, 2H), 3.37-3.26 (m, 2H), 2.79 (ddd, 2H, J=13.9, 9.8, 3.6 Hz), 2.50 (tt, 1H, J=7.9, 3.6 Hz), 2.42-2.28 (m, 2H), 2.19-2.05 (m, 2H); LRMS (ES) m/z 532.3 (M$^+$+1).

EXAMPLE 93: Synthesis of Compound 11610, N-(3-chloro-4-fluorophenyl)-N-(4-(5-(difluoromethyl)-1,3,4-oxadiazol-2-yl)-2-fluorobenzyl)-2-(1,1-dioxidothiomorpholino)acetamide

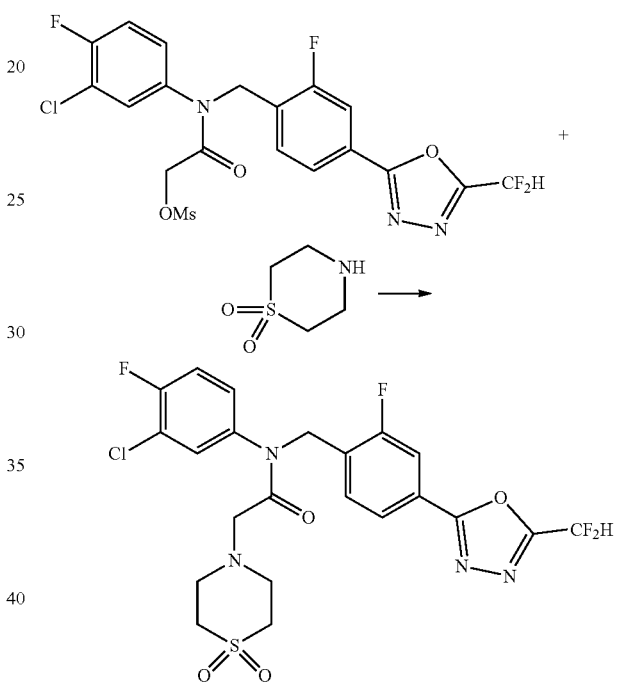

2-((3-chloro-4-fluorophenyl)(4-(5-(difluoromethyl)-1,3,4-oxadiazol-2-yl)-2-fluorobenzyl)amino)-2-oxoethyl methanesulfonate (0.050 g, 0.098 mmol) synthesized in step 6 of Example 85, thiomorpholine 1,1-dioxide (0.020 g, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/dichloromethane=from 0% to 5%) and concentrated to give the title compound (0.030 g, 55.7%) as a white solid.

$^1$H NMR (400 MHz, CDCl$_3$) δ 7.87 (td, 1H, J=7.7, 1.7 Hz), 7.74 (td, 1H, J=9.8, 1.7 Hz), 7.56 (t, 1H, J=7.5 Hz), 7.19 (dd, 1H, J=6.4, 2.6 Hz), 7.15 (t, 1H, J=8.5 Hz), 7.09-6.99 (m, 1H), 6.97-6.77 (m, 1H), 4.99 (d, 2H, J=5.7 Hz), 3.15-3.06 (m, 10H); LRMS (ES) m/z 547.4 (M$^+$+1).

EXAMPLE 94: Synthesis of Compound 11611, 2-(4-acetylpiperazin-1-yl)-N-(3-chloro-4-fluorophenyl)-N-(4-(5-(difluoromethyl)-1,3,4-oxadiazol-2-yl)-2-fluorobenzyl)acetamide

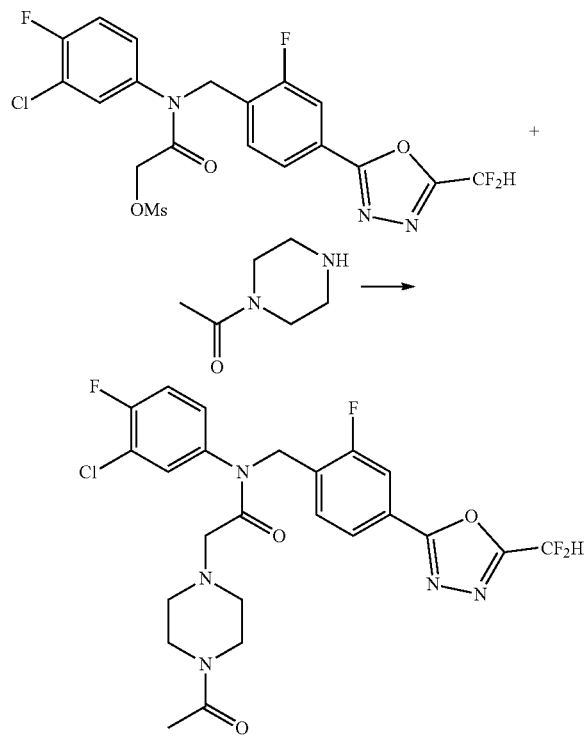

2-((3-chloro-4-fluorophenyl) (4-(5-(difluoromethyl)-1,3,4-oxadiazol-2-yl)-2-fluorobenzyl)amino)-2-oxoethyl methanesulfonate (0.050 g, 0.098 mmol) synthesized in step 6 of Example 85, 1-(piperazin-1-yl)ethane (0.019 g, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/dichloromethane=from 0% to 15%) and concentrated to give the title compound (0.046 g, 86.5%) as brown oil.

$^1$H NMR (400 MHz, CDCl$_3$) δ 7.85 (ddd, 1H, J=8.0, 6.3, 1.7 Hz), 7.72 (td, 1H, J=9.7, 1.7 Hz), 7.63-7.54 (m, 1H), 7.22 (dd, 1H, J=6.4, 2.6 Hz), 7.12 (t, 1H, J=8.5 Hz), 7.07-7.00 (m, 1H), 6.99-6.75 (m, 1H), 4.98 (d, 2H, J=4.5 Hz), 3.62 (dt, 2H, J=10.1, 4.9 Hz), 3.48 (dt, 2H, J=9.9, 4.9 Hz), 3.00 (d, 2H, J=8.3 Hz), 2.64-2.38 (m, 4H), 2.04 (d, 3H, J=1.1 Hz); LRMS (ES) m/z 540.4 (M$^+$+1).

EXAMPLE 95: Synthesis of Compound 11612, N-(3-chloro-4-fluorophenyl)-2-(4-(cyclopropanecarbonyl)piperazin-1-yl)-N-(4-(5-(difluoromethyl)-1,3,4-oxadiazol-2-yl)-2-fluorobenzyl)acetamide

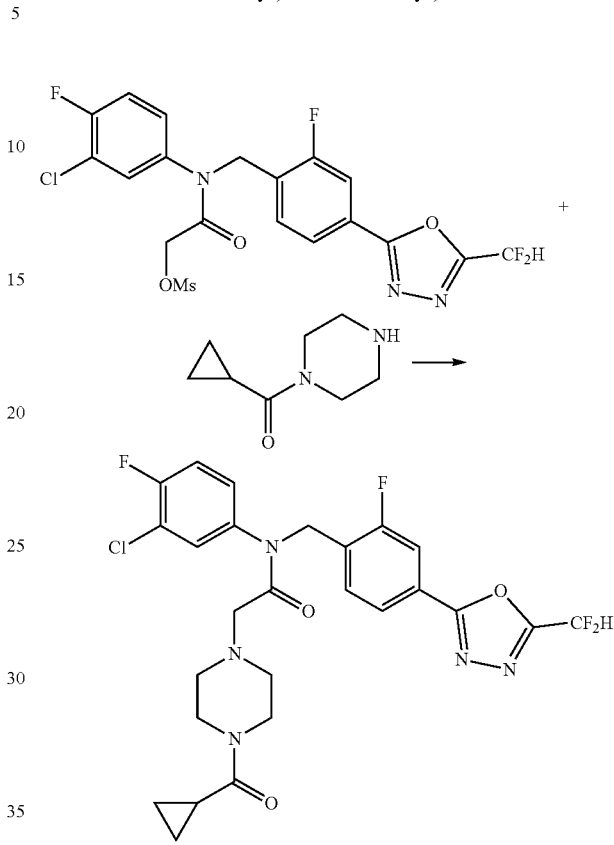

2-((3-chloro-4-fluorophenyl) (4-(5-(difluoromethyl)-1,3,4-oxadiazol-2-yl)-2-fluorobenzyl)amino)-2-oxoethyl methanesulfonate (0.050 g, 0.098 mmol) synthesized in step 6 of Example 85, cyclopropyl(piperazin-1-yl)methanone (0.021 mL, 0.148 mmol) and N,N-diisopropylethylamine (0.034 mL, 0.197 mmol) were dissolved in acetonitrile (5 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/dichloromethane=from 0% to 15%) and concentrated to give the title compound (0.045 g, 80.8%) as yellow oil.

$^1$H NMR (400 MHz, CDCl$_3$) δ 7.86 (td, 1H, J=7.1, 6.2, 1.7 Hz), 7.73 (t, 1H, J=9.6 Hz), 7.60 (t, 1H, J=7.6 Hz), 7.25-7.20 (m, 1H), 7.12 (t, 1H, J=8.5 Hz), 7.04 (d, 1H, J=6.4 Hz), 7.01-6.74 (m, 1H), 4.99 (d, 2H, J=4.6 Hz), 3.68 (s, 4H), 3.03 (d, 2H, J=12.1 Hz), 2.54 (d, 4H, J=35.4 Hz), 1.68 (tt, 1H, J=8.1, 4.6 Hz), 0.95 (dt, 2H, J=6.5, 3.4 Hz), 0.74 (dq, 2H, J=7.2, 3.8 Hz); LRMS (ES) m/z 566.4 (M$^+$+1).

EXAMPLE 96: Synthesis of Compound 11613, N-(3-chloro-4-fluorophenyl)-N-(4-(5-(difluoromethyl)-1,3,4-oxadiazol-2-yl)-2-fluorobenzyl)-2-(4-(methylsulfonyl)piperazin-1-yl)acetamide

[Step 1] Synthesis of N-(3-chloro-4-fluorophenyl)-N-(4-(5-(difluoromethyl)-1,3,4-oxadiazol-2-yl)-2-fluorobenzyl)-2-(piperazin-1-yl)acetamide

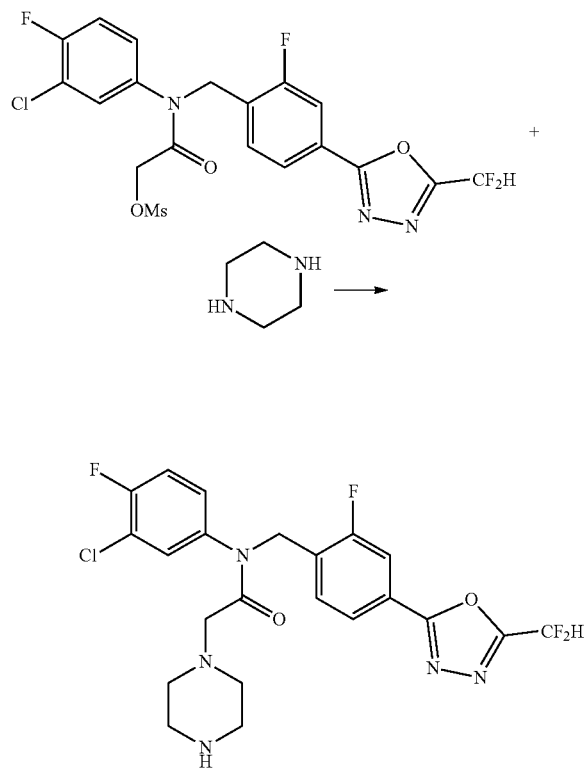

2-((3-chloro-4-fluorophenyl) (4-(5-(difluoromethyl)-1,3,4-oxadiazol-2-yl)-2-fluorobenzyl)amino)-2-oxoethyl methanesulfonate (0.200 g, 0.394 mmol) synthesized in step 6 of Example 85, piperazine (0.051 g, 0.591 mmol) and N,N-diisopropylethylamine (0.137 mL, 0.788 mmol) were dissolved in acetonitrile (10 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; ethyl acetate/hexane=from 0% to 15%) and concentrated to give the title compound (0.158 g, 80.6%) as a white solid.

[Step 2] Synthesis of Compound 11613

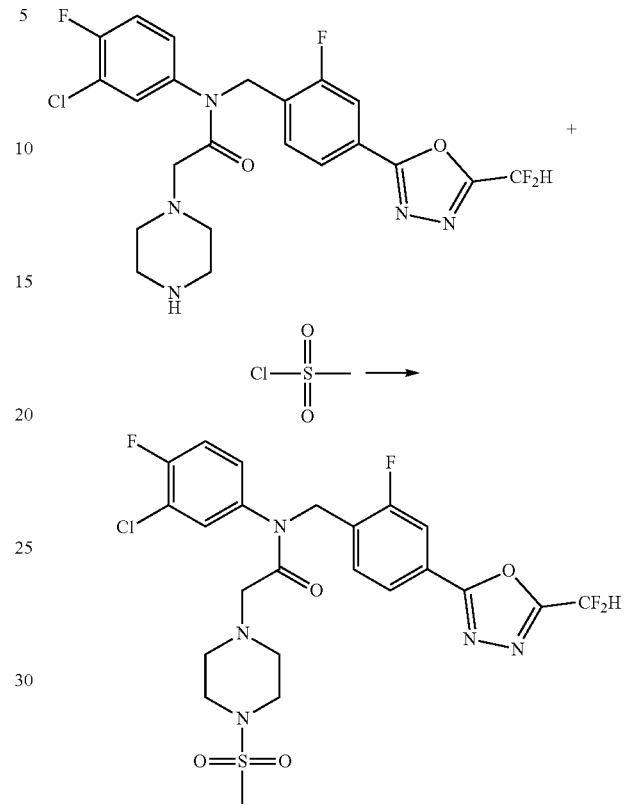

N-(3-chloro-4-fluorophenyl)-N-(4-(5-(difluoromethyl)-1,3,4-oxadiazol-2-yl)-2-fluorobenzyl)-2-(piperazin-1-yl)acetamide (0.050 g, 0.100 mmol) synthesized in step 1, methanesulfonyl chloride (0.012 mL, 0.151 mmol) and N,N-diisopropylethylamine (0.035 mL, 0.201 mmol) were dissolved in dichloromethane (5 mL) at room temperature, and the solution was stirred at the same temperature for 18 hours. 1.0N-hydrochloric acid aqueous solution was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/dichloromethane=from 0% to 5%) and concentrated to give the title compound (0.054 g, 93.4%) as a white solid.

$^1$H NMR (400 MHz, CDCl$_3$) δ 7.85 (ddd, 1H, J=8.2, 6.4, 1.7 Hz), 7.71 (td, 1H, J=9.8, 1.7 Hz), 7.57 (td, 1H, J=7.7, 7.2, 1.7 Hz), 7.20 (dd, 1H, J=6.4, 2.6 Hz), 7.12 (t, 1H, J=8.5 Hz), 7.03 (td, 1H, J=5.3, 4.7, 1.7 Hz), 6.84 (dd, 1H, J=51.7, 1.4 Hz), 4.98 (d, 2H, J=4.6 Hz), 3.28-3.19 (m, 4H), 2.98 (s, 2H), 2.75 (d, 3H, J=1.4 Hz), 2.59 (q, 4H, J=5.7, 4.9 Hz); LRMS (ES) m/z 576.4 (M$^+$+1).

EXAMPLE 97: Synthesis of Compound 11614, N-(3-chloro-4-fluorophenyl)-N-(4-(5-(difluoromethyl)-1,3,4-oxadiazol-2-yl)-2-fluorobenzyl)-2-(4-(oxetan-3-yl)piperazin-1-yl)acetamide

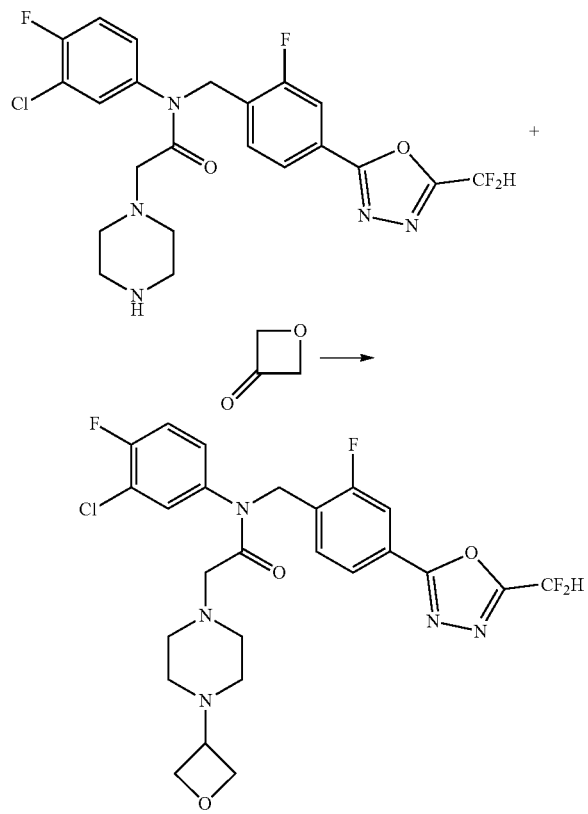

N-(3-chloro-4-fluorophenyl)-N-(4-(5-(difluoromethyl)-1,3,4-oxadiazol-2-yl)-2-fluorobenzyl)-2-(piperazin-1-yl)acetamide (0.050 g, 0.100 mmol) synthesized in step 1 of Example 96, sodium triacetoxyborohydride (0.043 g, 0.201 mmol) and oxetan-3-one (0.011 g, 0.151 mmol) were dissolved in dichloromethane (5 mL) at room temperature, and the solution was stirred at the same temperature for 18 hours. 1.0N-hydrochloric acid aqueous solution was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/dichloromethane=from 0% to 5%) and concentrated to give the title compound (0.046 g, 82.7%) as yellow oil.

$^1$H NMR (400 MHz, CDCl$_3$) δ 7.85 (ddd, 1H, J=7.9, 6.2, 1.7 Hz), 7.71 (td, 1H, J=9.9, 1.7 Hz), 7.59 (td, 1H, J=7.6, 5.4 Hz), 7.22 (dd, 1H, J=6.5, 2.6 Hz), 7.10 (t, 1H, J=8.5 Hz), 7.03 (s, 1H), 7.03-6.75 (m, 1H), 4.98 (d, 2H, J=4.3 Hz), 4.67-4.52 (m, 4H), 3.57-3.44 (m, 1H), 2.94 (s, 2H), 2.44 (d, 8H, J=60.9 Hz); LRMS (ES) m/z 554.5 (M$^+$+1).

EXAMPLE 98: Synthesis of Compound 11621, N-(2-fluoro-4-(5-(trifluoromethyl)-1,3,4-oxadiazol-2-yl)benzyl)-1-(oxetan-3-yl)-N-phenylpiperidine-4-carboxamide

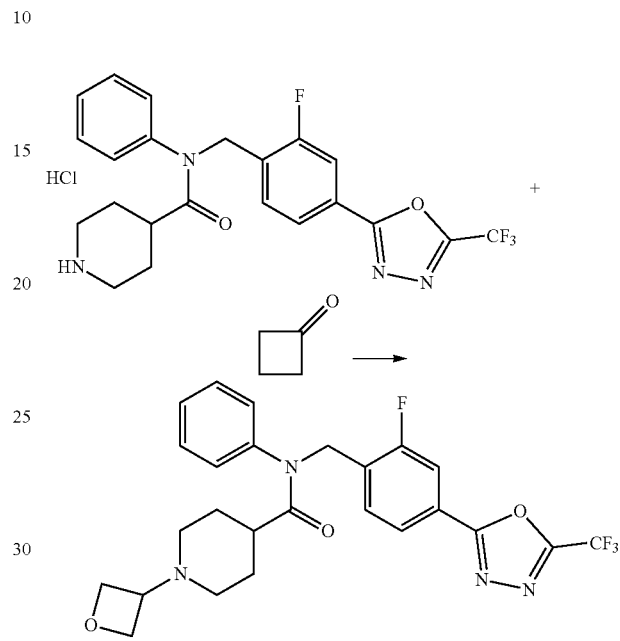

N-(2-fluoro-4-(5-(trifluoromethyl)-1,3,4-oxadiazol-2-yl)benzyl)-N-phenylpiperidine-4-carboxamide hydrochloride (0.150 g, 0.309 mmol) synthesized in step 5 of Example 31, sodium triacetoxyborohydride (0.131 g, 0.619 mmol) and cyclobutanone (0.026 g, 0.371 mmol) were dissolved in dichloromethane (10 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography (SiO$_2$, 12 g cartridge; methanol/dichloromethane=from 0% to 15%) and concentrated to afford N-(4-(5-(difluoromethyl)-1,3,4-oxadiazol-2-yl)-2-fluorobenzyl)-1-(oxetan-3-yl)-N-phenylpiperidine-4-carboxamide (0.130 g, 83.3%) as a white solid.

$^1$H NMR (400 MHz, CDCl$_3$) δ=7.85 (dd, 1H, J=8.0, 1.7 Hz), 7.71 (dd, 1H, J=9.7, 1.7 Hz), 7.56 (t, 1H, J=7.6 Hz), 7.41-7.31 (m, 3H), 7.06-6.99 (m, 2H), 5.02 (s, 2H), 4.66 (s, 2H), 4.59 (t, 2H, J=6.6 Hz), 3.46 (s, 1H), 2.79 (s, 2H), 2.28 (s, 1H), 1.91 (s, 1H), 1.73 (s, 5H); LRMS (ES) m/z 505.2 (M$^+$+1).

EXAMPLE 99: Synthesis of Compound 11622, N-(4-(5-(difluoromethyl)-1,3,4-oxadiazol-2-yl)-2-fluorobenzyl)-1-(oxetan-3-yl)-N-phenylpiperidine-4-carboxamide

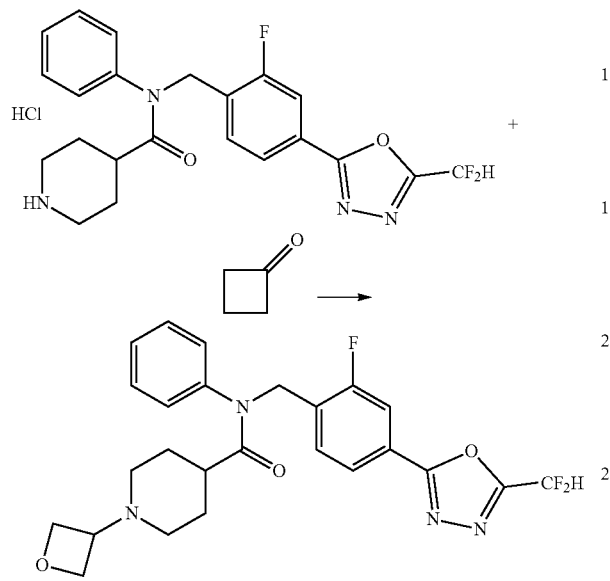

N-(4-(5-(difluoromethyl)-1,3,4-oxadiazol-2-yl)-2-fluorobenzyl)-N-phenylpiperidine-4-carboxamide hydrochloride (0.150 g, 0.321 mmol) synthesized in step 3 of Example 39, sodium triacetoxyborohydride (0.136 g, 0.643 mmol) and cyclobutanone (0.027 g, 0.386 mmol) were dissolved in dichloromethane (10 mL) at room temperature, and the solution was stirred at the same temperature for 18 hours. Water was added to the reaction mixture, followed by extraction with ethyl acetate. The organic layer was washed with saturated aqueous sodium chloride solution, dried with magnesium sulfate anhydrous, filtered, and then concentrated under reduced pressure. The concentrate was purified by column chromatography ($SiO_2$, 12 g cartridge; methanol/dichloromethane=from 0% to 15%) and concentrated to afford N-(4-(5-(difluoromethyl)-1,3,4-oxadiazol-2-yl)-2-fluorobenzyl)-1-(oxetan-3-yl)-N-phenylpiperidine-4-carboxamide (0.130 g, 83.2%) as a white solid.

$^1$H NMR (400 MHz, $CDCl_3$) δ 7.85 (dd, 1H, J=8.0, 1.7 Hz), 7.70 (dd, 1H, J=9.8, 1.7 Hz), 7.54 (t, 1H, J=7.6 Hz), 7.35 (dd, 3H, J=4.9, 2.0 Hz), 7.06-6.99 (m, 2H), 6.84 (d, 1H, J=51.7 Hz), 5.02 (s, 2H), 4.65 (s, 2H), 4.59 (t, 2H, J=6.5 Hz), 3.45 (s, 1H), 2.78 (s, 2H), 2.28 (s, 1H), 2.03-1.85 (m, 2H), 1.73 (s, 4H); LRMS (ES) m/z 487.2 ($M^+$+1).

Measurement of Activity of the Compounds of the Present Invention and Analysis Protocol

Experimental Example 1: HDAC Enzyme Activity Inhibition Assays (In Vitro)

In order to examine the HDAC6 selectivity of the compounds of formula I of the present invention by HDAC1 and HDAC6 enzymatic activity inhibition assays, an experiment was performed using a conventional substance as a control.

HDAC enzyme activity was measured using a HDAC Fluorimetric Drug Discovery Kit (BML-AK511, 516) from Enzo Life Science. For the HDAC1 enzyme activity test, human recombinant HDAC1 (BML-SE456) was used as an enzyme source, and Fluor de Lys®-"SIRT1 (BNL-KI177) was used as a substrate. A 5-fold dilution of the compound was seeded into a 96-well plate, and then 0.3 μg of the enzyme and 10 μM of the substrate were added to each well of the plate and allowed to react at 30° C. for 60 minutes. Then, Fluor de Lys®-Developer II (BML-KI176) was added thereto and allowed to react for 30 minutes, after which the fluorescence value (Ex 360, Em 460) was measured using a multi-plate reader (Flexstation 3, Molecular Device). The HDAC6 enzyme was tested using human recombinant HDAC6 (382180) from Calbiochem, according to the same protocol as the HDAC1 enzyme activity test method. Based on the resulting values, each $IC_{50}$ value was calculated using GraphPad Prism4.0 program.

TABLE 2

Results of HDAC enzyme activity inhibition assays

| Ex. | Comp. | HDAC1 (nM) | HDAC6 (nM) | HDAC6 selectivity (fold) |
|---|---|---|---|---|
| 1 | 11022 | ND | 234 | 427 |
| 2 | 11105 | ND | 191 | 524 |
| 3 | 11106 | ND | 1296 | 77 |
| 4 | 11107 | ND | 509 | 196 |
| 5 | 11108 | ND | 59 | 1695 |
| 6 | 11109 | ND | 55 | 1818 |
| 7 | 11110 | ND | 50 | 2000 |
| 8 | 11134 | ND | 914 | 109 |
| 9 | 11135 | ND | 2754 | 36 |
| 10 | 11136 | ND | 203 | 493 |
| 11 | 11137 | ND | 364 | 275 |
| 12 | 11138 | ND | 285 | 351 |
| 13 | 11139 | ND | 129 | 775 |
| 14 | 11140 | ND | 209 | 478 |
| 15 | 11141 | ND | 327 | 306 |
| 16 | 11142 | ND | 330 | 303 |
| 17 | 11143 | ND | 221 | 452 |
| 18 | 11157 | ND | 90 | 1111 |
| 19 | 11158 | ND | 90 | 1111 |
| 20 | 11159 | ND | 127 | 787 |
| 21 | 11160 | ND | 165 | 606 |
| 22 | 11161 | ND | 489 | 204 |
| 23 | 11162 | ND | 207 | 483 |
| 24 | 11163 | ND | 221 | 452 |
| 25 | 11164 | ND | 336 | 298 |
| 26 | 11165 | ND | 125 | 800 |
| 27 | 11166 | 27248 | 516 | 194 |
| 28 | 11187 | ND | 189 | 144 |
| 29 | 11188 | ND | 107 | 935 |
| 30 | 11189 | ND | 39 | 2564 |
| 31 | 11200 | ND | 131 | 763 |
| 32 | 11201 | ND | 114 | 877 |
| 33 | 11202 | ND | 136 | 735 |
| 34 | 11203 | ND | 144 | 694 |
| 35 | 11204 | ND | 109 | 917 |
| 36 | 11205 | ND | 301 | 332 |
| 37 | 11206 | ND | 372 | 269 |
| 38 | 11207 | ND | 123 | 813 |
| 39 | 11208 | ND | 88 | 1136 |
| 40 | 11209 | ND | 97 | 1031 |
| 41 | 11210 | ND | 239 | 418 |
| 42 | 11211 | ND | 74 | 1351 |
| 43 | 11212 | ND | 89 | 1124 |
| 44 | 11213 | ND | 128 | 781 |
| 45 | 11214 | ND | 140 | 714 |
| 46 | 11215 | ND | 60 | 1667 |
| 47 | 11232 | ND | 52 | 1923 |
| 48 | 11233 | ND | 37 | 2703 |
| 49 | 11234 | ND | 57 | 1754 |
| 50 | 11235 | ND | 65 | 1538 |
| 51 | 11236 | ND | 73 | 1370 |
| 52 | 11237 | ND | 42 | 2381 |
| 53 | 11238 | ND | 45 | 2222 |
| 54 | 11239 | ND | 26 | 3846 |

TABLE 2-continued

Results of HDAC enzyme activity inhibition assays

| Ex. | Comp. | HDAC1 (nM) | HDAC6 (nM) | HDAC6 selectivity (fold) |
|---|---|---|---|---|
| 55 | 11240 | ND | 41 | 2439 |
| 56 | 11241 | ND | 35 | 2857 |
| 57 | 11242 | ND | 39 | 2564 |
| 58 | 11243 | ND | 32 | 3125 |
| 59 | 11244 | ND | 63 | 1587 |
| 60 | 11245 | ND | 47 | 2128 |
| 61 | 11246 | ND | 132 | 758 |
| 62 | 11247 | ND | 53 | 1887 |
| 63 | 11325 | ND | 90 | 1111 |
| 64 | 11326 | ND | 57 | 1754 |
| 65 | 11327 | ND | 49 | 2041 |
| 66 | 11328 | ND | 81 | 1235 |
| 67 | 11329 | ND | 56 | 1786 |
| 68 | 11330 | ND | 51 | 1961 |
| 69 | 11331 | ND | 56 | 1786 |
| 70 | 11332 | ND | 43 | 2326 |
| 71 | 11333 | ND | 29 | 3448 |
| 72 | 11334 | ND | 38 | 2632 |
| 73 | 11339 | ND | 49 | 2041 |
| 74 | 11340 | ND | 92 | 1087 |
| 75 | 11341 | ND | 34 | 2941 |
| 76 | 11356 | ND | 51 | 1961 |
| 77 | 11357 | ND | 87 | 1149 |
| 78 | 11358 | ND | 118 | 847 |
| 79 | 11359 | ND | 34 | 2941 |
| 80 | 11360 | ND | 32 | 3125 |
| 81 | 11376 | ND | 24 | 4167 |
| 82 | 11414 | ND | 40 | 2500 |
| 83 | 11418 | ND | 40 | 2500 |
| 84 | 11419 | ND | 30 | 3333 |
| 85 | 11534 | ND | 73 | 1370 |
| 86 | 11535 | ND | 86 | 1163 |
| 87 | 11536 | ND | 96 | 1042 |
| 88 | 11537 | ND | 70 | 1429 |
| 89 | 11538 | ND | 63 | 1587 |
| 90 | 11584 | ND | 59 | 1695 |
| 91 | 11602 | ND | 380 | 263 |
| 92 | 11603 | ND | 146 | 685 |
| 93 | 11610 | ND | 145 | 690 |
| 94 | 11611 | ND | 160 | 625 |
| 95 | 11612 | ND | 187 | 535 |
| 96 | 11613 | ND | 148 | 676 |
| 97 | 11614 | ND | 84 | 1190 |
| 98 | 11621 | ND | 279 | 358 |
| 99 | 11622 | ND | 140 | 714 |

As can be seen in Table 2 above, the 1,3,4-oxadiazole amide derivative compounds, stereoisomers thereof or pharmaceutically acceptable salts thereof according to the present invention showed about 36 to about 3846 times higher selective HDAC6 inhibitory activities in the HDAC1 and HDAC6 activity inhibition assays.

Experimental Example 2: Analysis of the Effect of HDAC6-Specific Inhibitors on Mitochondrial Axonal Transport (In Vitro)

The effect of HDAC6-specific inhibitors on mitochondrial axonal transport was analyzed. Specifically, in order to examine whether the compounds represented by formula I according to the present invention selectively inhibit HDAC6 activity to increase the acetylation of tubulin, which is a major substrate of HDAC6, thereby improving the mitochondrial axonal transport velocity reduced by amyloid-beta treatment in neuronal axons, a comparison experiment was performed using a compound that have already been developed as a control.

Hippocampal neurons from Sprague-Dawley (SD) rat embryos at embryonic day 17-18 (E17-18) were cultured in an extracellular matrix-coated dish for imaging for 7 days, and then treated with 1 μM of an amyloid-beta peptides. After 24 hours, the neurons were treated with compounds on the 8th days in vitro and 3 hours later, treated with MitoTracker Red CMXRos (Life Technologies, NY, USA) for the last 5 minutes to stain the mitochondria. Axonal transport of the stained mitochondria was imaged using a confocal microscope (Leica SP8; Leica Microsystems, UK) at 1-second intervals for 1 minute, and the transport velocity per second of each mitochondrion was determined using the IMARIS analysis software (BITPLANE, Zurich, Switzerland).

As a result, it was found that the 1,3,4-oxadiazole amide derivative compounds, stereoisomers thereof or pharmaceutically acceptable salts according to the present invention improved the velocity of mitochondrial axonal transport.

The invention claimed is:

1. An 1,3,4-oxadiazole amide derivative compound represented by the following formula I, a stereoisomer thereof or a pharmaceutically acceptable salt thereof:

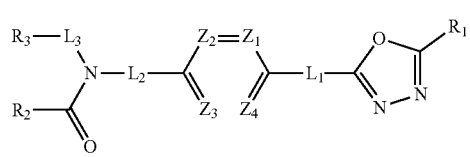

[Formula I]

wherein $L_1$, $L_2$ or $L_3$ are each independently —($C_0$-$C_2$ alkyl)—;

$Z_1$ to $Z_4$ are each independently N or $CR^z$, wherein three or more of $Z_1$ to $Z_4$ may not be simultaneously N, and $R^z$ is —H or —X;

$R_1$ is —$CX_2$H or —$CX_3$;

$R_2$ is —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_3$-$C_6$ cycloalkyl), -aryl, -heteroaryl,

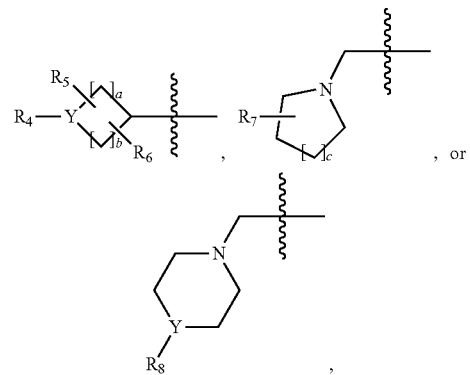

, or

, wherein at least one H of the —($C_3$-$C_6$ cycloalkyl), -aryl or heteroaryl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —$CF_3$, Y is —N—, —O— or —S(=O)$_2$—, when Y is —N—, $R_4$ and $R_8$ are each independently —H, —($C_1$-$C_4$ alkyl), —C(=O)—($C_1$-$C_4$ alkyl), —C(=O)—($C_3$-$C_6$ cycloalkyl), —C(=O)—O($C_1$-$C_4$ alkyl), —C(=O)—$CF_3$, —S(=O)$_2$—($C_1$-$C_4$ alkyl), —($C_2$-$C_6$ heterocycloalkyl), benzyl or amine protecting group, wherein the —($C_2$-$C_6$ heterocycloalkyl) may contain an N, O or S atom in the ring,
and when Y is —O— or —S(=O)$_2$—, $R_4$ and $R_8$ are null,
$R_5$ to $R_8$ are each independently —H, —($C_1$-$C_4$ alkyl), —OH, —CH$_2$OH or —C(=O)—NH$_2$, and a to c are each independently an integer of 1, 2 or 3;
$R_3$ is —H, —($C_1$-$C_4$ alkyl), —($C_1$-$C_4$ alkyl)-O($C_1$-$C_4$ alkyl), —($C_1$-$C_4$ alkyl)-C(=O)—O($C_1$-$C_4$ alkyl), —($C_3$-$C_6$ cycloalkyl), -aryl, -heteroaryl,

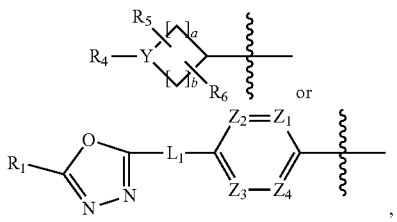

wherein at least one H of the —($C_3$-$C_6$ cycloalkyl), -aryl or -heteroaryl may be each independently substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —CF$_3$, and $R_4$, $R_5$, $R_6$, Y, a, b, $R_1$, $L_1$, $Z_1$, $Z_2$, $Z_3$ and $Z_4$ are as defined above; and
X is F, Cl, Br or I.

2. The 1,3,4-oxadiazole amide derivative compound represented by formula I, stereoisomer thereof or pharmaceutically acceptable salt thereof according to claim 1, wherein
$L_1$ and $L_3$ are —($C_0$ alkyl)—;
$L_2$ is —($C_1$-$C_2$ alkyl)—;
$Z_1$ to $Z_4$ are each independently N or CR$^z$, wherein two or more of $Z_1$ to $Z_4$ may not be simultaneously N, and R$^z$ is —H or —X;
$R_1$ is —CX$_2$H or —CX$_3$;
$R_2$ is —($C_1$-$C_4$ alkyl), —($C_3$-$C_6$ cycloalkyl), -aryl, -heteroaryl,

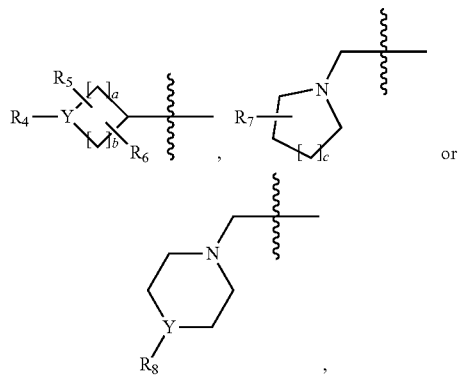

wherein at least one H of the —($C_3$-$C_6$ cycloalkyl), -aryl or heteroaryl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —CF$_3$,
Y is —N—, —O— or —S(=O)$_2$—,
when Y is —N—, $R_4$ and $R_5$ are each independently —H, —($C_1$-$C_4$ alkyl), —C(=O)—($C_1$-$C_4$ alkyl), —C(=O)—CF$_3$, —S(=O)$_2$—($C_1$-$C_4$ alkyl), —($C_2$-$C_6$ heterocycloalkyl), —C(=O)—($C_3$-$C_6$ cycloalkyl), benzyl or amine protecting group, wherein the —($C_2$-$C_6$ heterocycloalkyl) may contain an O atom in the ring,
and when Y is —O— or —S(=O)$_2$—, $R_4$ and $R_8$ are null,
$R_5$ to $R_8$ are each independently —H, —($C_1$-$C_4$ alkyl), —OH, —CH$_2$OH or —C(=O)—NH$_2$, and a to c are each independently an integer of 1, 2 or 3;
$R_3$ is -aryl or -heteroaryl, wherein at least one H of the -aryl or -heteroaryl may be independently substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —CF$_3$; and
X is F, Cl, Br or I.

3. The 1,3,4-oxadiazole amide derivative compound represented by formula I, stereoisomer thereof or pharmaceutically acceptable salt thereof according to claim 2, wherein
$L_1$ and $L_3$ are —($C_0$ alkyl)—;
$L_2$ is —($C_1$ alkyl)—;
$Z_1$ to $Z_4$ are each independently N or CR$^z$, wherein two or more of $Z_1$ to $Z_4$ may not be simultaneously N, and R$^z$ is —H or —X;
$R_1$ is —CF$_2$H or —CF$_3$;
$R_2$ is —($C_1$-$C_4$ alkyl), -pyridinyl or

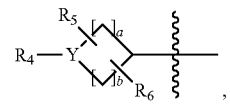

wherein at least one H of the pyridinyl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —CF$_3$,
Y is —N—,
$R_4$ is —($C_1$-$C_4$ alkyl), —C(=O)—($C_1$-$C_4$ alkyl) or —S(=O)$_2$—($C_1$-$C_4$ alkyl),
$R_5$ or $R_6$ are each independently —H or —($C_1$-$C_4$ alkyl), and
a and b are each independently an integer of 1 or 2;
$R_3$ is -aryl, wherein at least one H of the aryl may be substituted with —X; and
X is F, Cl, Br or I.

4. The 1,3,4-oxadiazole amide derivative compound represented by formula I, stereoisomer thereof or pharmaceutically acceptable salt thereof according to claim 3, wherein
$L_1$ and $L_3$ are —($C_0$ alkyl)—;
$L_2$ is —($C_1$ alkyl)—;
$Z_1$ to $Z_4$ are each independently N or CR$^z$, wherein two or more of $Z_1$ to $Z_4$ may not be simultaneously N, and R$^z$ is —H or —X;
$R_1$ is —CF$_2$H or —CF$_3$;
$R_2$ is -pyridinyl or

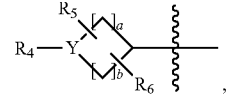

wherein at least one H of the pyridinyl may be substituted with —X, —OH, —($C_1$-$C_4$ alkyl), —O($C_1$-$C_4$ alkyl), —C(=O)—($C_1$-$C_4$ alkyl), —C(=O)—O($C_1$-$C_4$ alkyl) or —CF$_3$,
Y is —N—,
$R_4$ is —($C_1$-$C_4$ alkyl), —C(=O)—($C_1$-$C_4$ alkyl) or —S(=O)$_2$—($C_1$-$C_4$ alkyl),
$R_5$ or $R_6$ are each independently —H, and
a and b are each independently an integer of 1 or 2;

R₃ is -aryl, wherein at least one H of the aryl may be substituted with —X; and

X is F, Cl, Br or I.

5. The 1,3,4-oxadiazole amide derivative compound represented by formula I, stereoisomer thereof or pharmaceutically acceptable salt thereof according to claim 1, wherein the compound represented by formula I is selected from the group consisting of compounds described in the following table:

| Ex. | Comp. | Structure |
|---|---|---|
| 1 | 11022 | 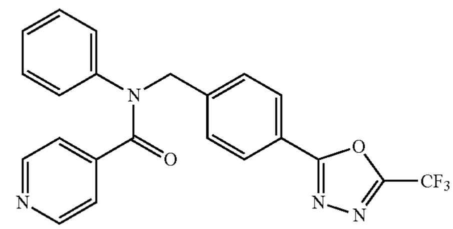 [SMILES: O=C(c1ccncc1)N(Cc1ccc(-c2nnc(C(F)(F)F)o2)cc1)c1ccccc1] |
| 2 | 11105 | 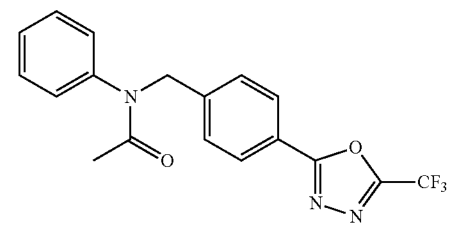 [SMILES: CC(=O)N(Cc1ccc(-c2nnc(C(F)(F)F)o2)cc1)c1ccccc1] |
| 3 | 11106 | 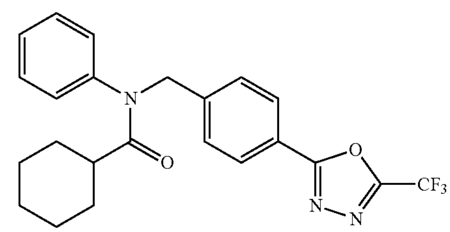 [SMILES: O=C(C1CCCCC1)N(Cc1ccc(-c2nnc(C(F)(F)F)o2)cc1)c1ccccc1] |
| 4 | 11107 | 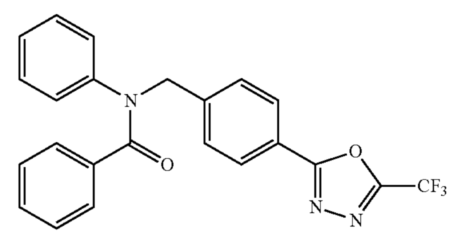 [SMILES: O=C(c1ccccc1)N(Cc1ccc(-c2nnc(C(F)(F)F)o2)cc1)c1ccccc1] |
| 5 | 11108 | 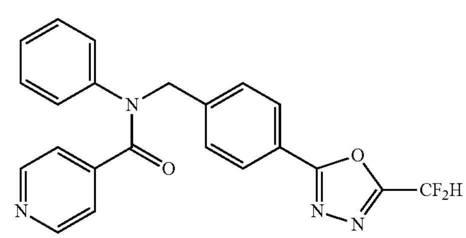 [SMILES: O=C(c1ccncc1)N(Cc1ccc(-c2nnc(C(F)F)o2)cc1)c1ccccc1] |
| 6 | 11109 | 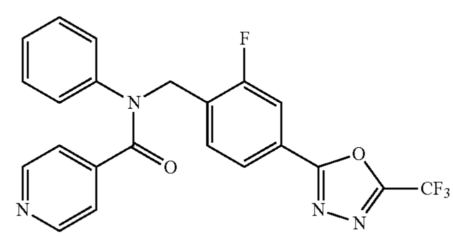 [SMILES: O=C(c1ccncc1)N(Cc1ccc(-c2nnc(C(F)(F)F)o2)cc1F)c1ccccc1] |

-continued
| Ex. | Comp. | Structure |
|---|---|---|
| 7 | 11110 | 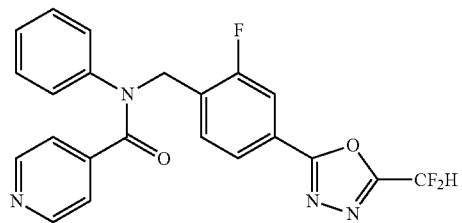 [SMILES: O=C(c1ccncc1)N(Cc1ccc(-c2nnc(C(F)F)o2)cc1F)c1ccccc1] |
| 8 | 11134 | 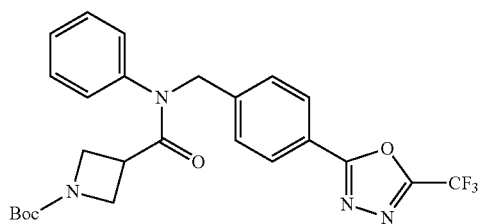 [SMILES: CC(C)(C)OC(=O)N1CC(C(=O)N(Cc2ccc(-c3nnc(C(F)(F)F)o3)cc2)c2ccccc2)C1] |
| 9 | 11135 | 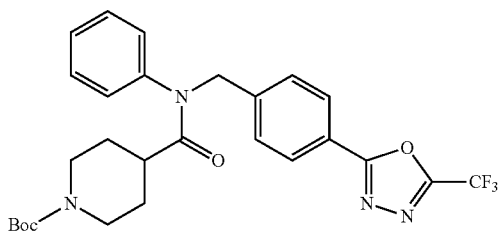 [SMILES: CC(C)(C)OC(=O)N1CCC(C(=O)N(Cc2ccc(-c3nnc(C(F)(F)F)o3)cc2)c2ccccc2)CC1] |
| 10 | 11136 | 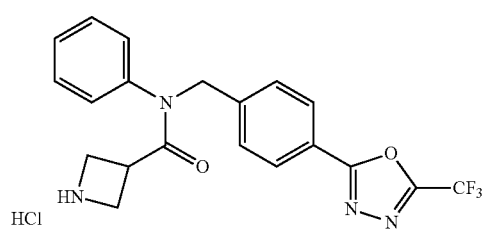 [SMILES: Cl ; O=C(C1CNC1)N(Cc1ccc(-c2nnc(C(F)(F)F)o2)cc1)c1ccccc1] |
| 11 | 11137 | 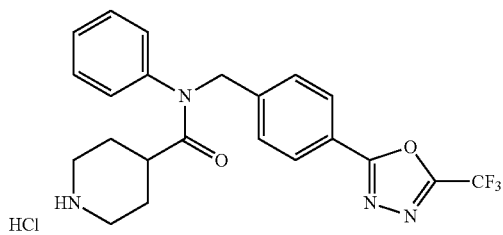 [SMILES: Cl ; O=C(C1CCNCC1)N(Cc1ccc(-c2nnc(C(F)(F)F)o2)cc1)c1ccccc1] |
| 12 | 11138 | 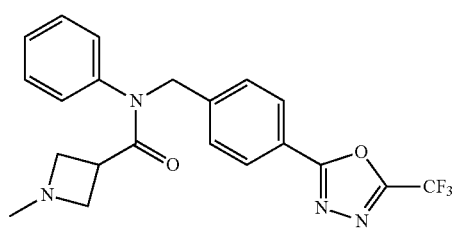 [SMILES: CN1CC(C(=O)N(Cc2ccc(-c3nnc(C(F)(F)F)o3)cc2)c2ccccc2)C1] |

| Ex. | Comp. | Structure |
|---|---|---|
| 13 | 11139 | 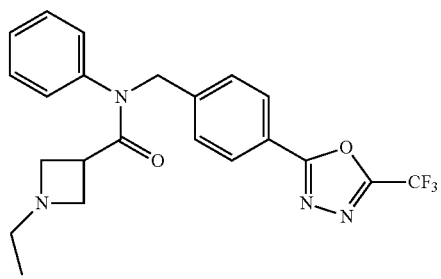 [SMILES: CCN1CC(C(=O)N(Cc2ccc(-c3nnc(C(F)(F)F)o3)cc2)c2ccccc2)C1] |
| 14 | 11140 | 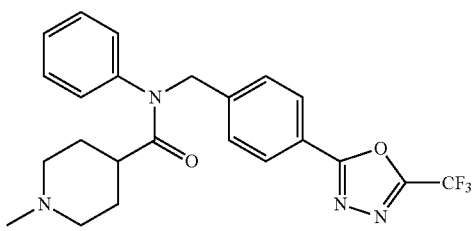 [SMILES: CN1CCC(C(=O)N(Cc2ccc(-c3nnc(C(F)(F)F)o3)cc2)c2ccccc2)CC1] |
| 15 | 11141 | 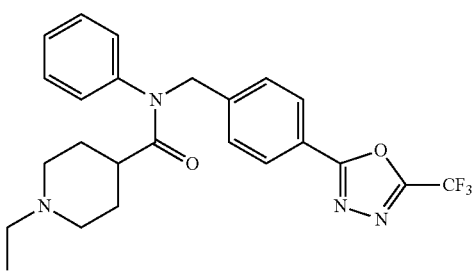 [SMILES: CCN1CCC(C(=O)N(Cc2ccc(-c3nnc(C(F)(F)F)o3)cc2)c2ccccc2)CC1] |
| 16 | 11142 | 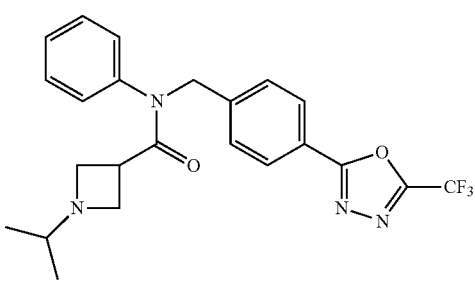 [SMILES: CC(C)N1CC(C(=O)N(Cc2ccc(-c3nnc(C(F)(F)F)o3)cc2)c2ccccc2)C1] |
| 17 | 11143 | 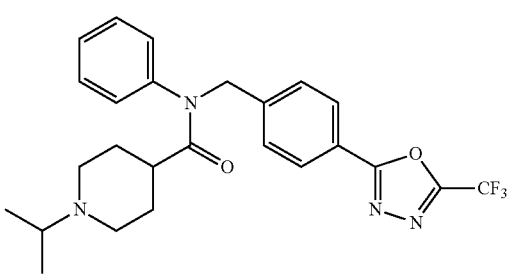 [SMILES: CC(C)N1CCC(C(=O)N(Cc2ccc(-c3nnc(C(F)(F)F)o3)cc2)c2ccccc2)CC1] |

-continued
| Ex. | Comp. | Structure |
|---|---|---|
| 18 | 11157 | 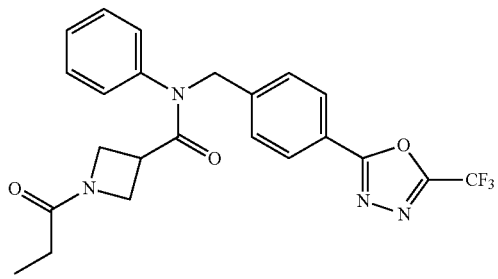 [SMILES: CCC(=O)N1CC(C(=O)N(Cc2ccc(-c3nnc(C(F)(F)F)o3)cc2)c2ccccc2)C1] |
| 19 | 11158 | 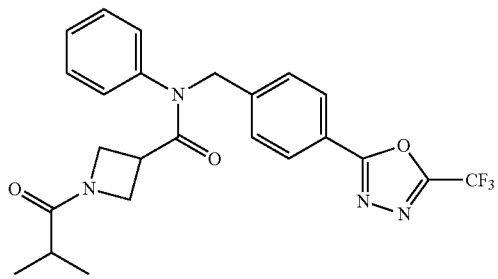 [SMILES: CC(C)C(=O)N1CC(C(=O)N(Cc2ccc(-c3nnc(C(F)(F)F)o3)cc2)c2ccccc2)C1] |
| 20 | 11159 | 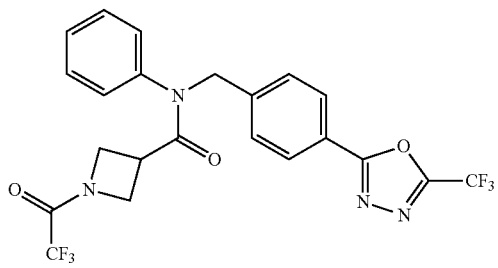 [SMILES: O=C(C1CN(C(=O)C(F)(F)F)C1)N(Cc1ccc(-c2nnc(C(F)(F)F)o2)cc1)c1ccccc1] |
| 21 | 11160 | 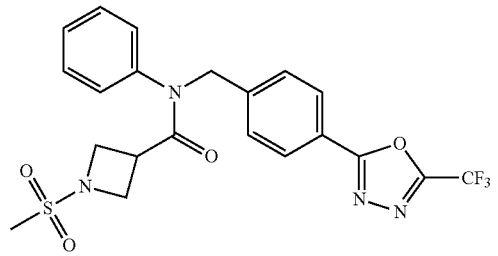 [SMILES: CS(=O)(=O)N1CC(C(=O)N(Cc2ccc(-c3nnc(C(F)(F)F)o3)cc2)c2ccccc2)C1] |
| 22 | 11161 | 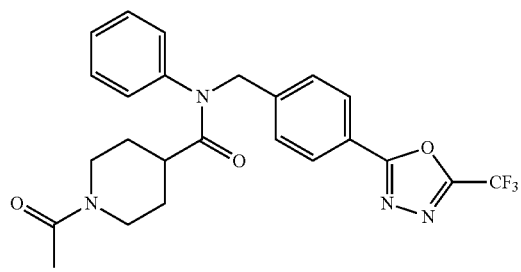 [SMILES: CC(=O)N1CCC(C(=O)N(Cc2ccc(-c3nnc(C(F)(F)F)o3)cc2)c2ccccc2)CC1] |

-continued
| Ex. | Comp. | Structure |
|---|---|---|
| 23 | 11162 | 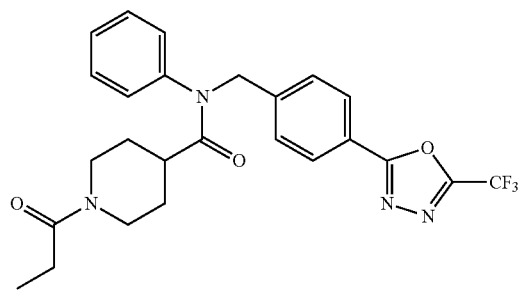 [SMILES: CCC(=O)N1CCC(C(=O)N(Cc2ccc(-c3nnc(C(F)(F)F)o3)cc2)c2ccccc2)CC1] |
| 24 | 11163 | 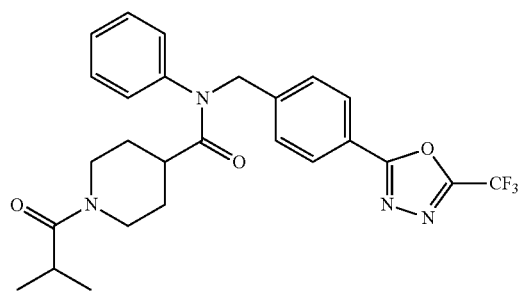 [SMILES: CC(C)C(=O)N1CCC(C(=O)N(Cc2ccc(-c3nnc(C(F)(F)F)o3)cc2)c2ccccc2)CC1] |
| 25 | 11164 | 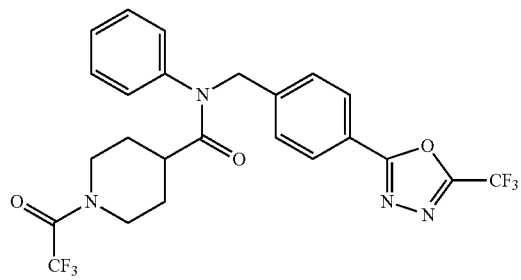 [SMILES: O=C(C1CCN(C(=O)C(F)(F)F)CC1)N(Cc1ccc(-c2nnc(C(F)(F)F)o2)cc1)c1ccccc1] |
| 26 | 11165 | 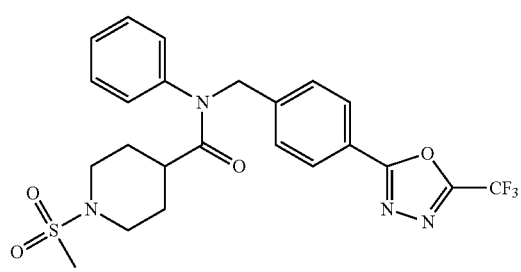 [SMILES: CS(=O)(=O)N1CCC(C(=O)N(Cc2ccc(-c3nnc(C(F)(F)F)o3)cc2)c2ccccc2)CC1] |
| 27 | 11166 | 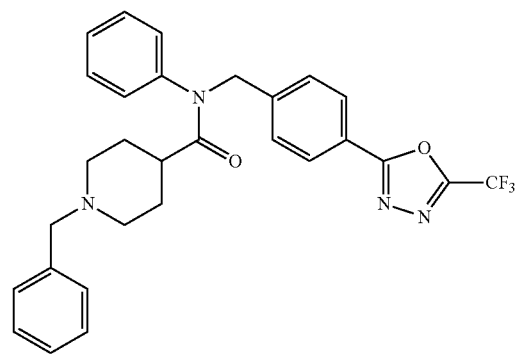 [SMILES: O=C(C1CCN(Cc2ccccc2)CC1)N(Cc1ccc(-c2nnc(C(F)(F)F)o2)cc1)c1ccccc1] |

| Ex. | Comp. | Structure |
|---|---|---|
| 28 | 11187 | 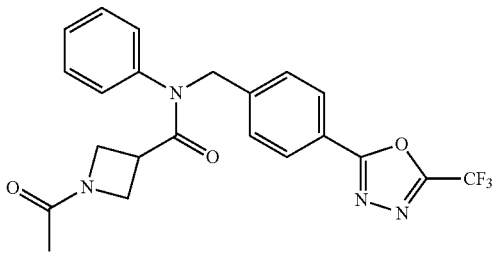 [SMILES: CC(=O)N1CC(C(=O)N(Cc2ccc(-c3nnc(C(F)(F)F)o3)cc2)c2ccccc2)C1] |
| 29 | 11188 | 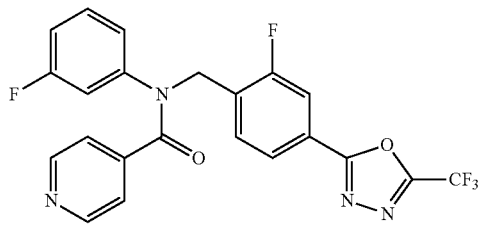 [SMILES: O=C(c1ccncc1)N(Cc1ccc(-c2nnc(C(F)(F)F)o2)cc1F)c1cccc(F)c1] |
| 30 | 11189 | 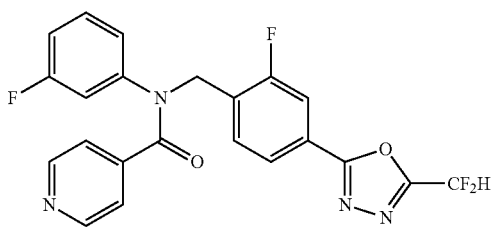 [SMILES: O=C(c1ccncc1)N(Cc1ccc(-c2nnc(C(F)F)o2)cc1F)c1cccc(F)c1] |
| 31 | 11200 | 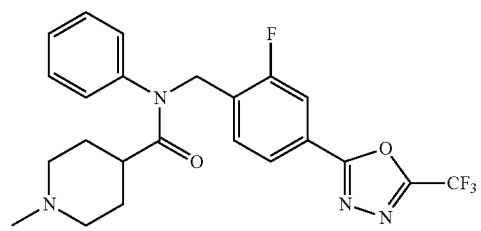 [SMILES: CN1CCC(C(=O)N(Cc2ccc(-c3nnc(C(F)(F)F)o3)cc2F)c2ccccc2)CC1] |
| 32 | 11201 | 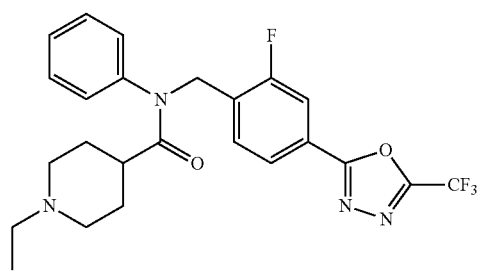 [SMILES: CCN1CCC(C(=O)N(Cc2ccc(-c3nnc(C(F)(F)F)o3)cc2F)c2ccccc2)CC1] |
| 33 | 11202 | 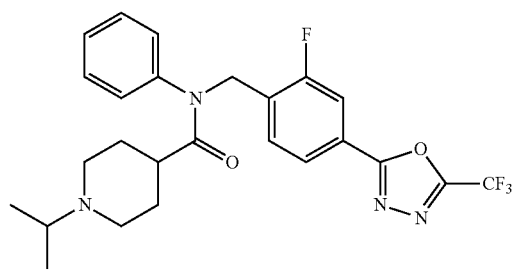 [SMILES: CC(C)N1CCC(C(=O)N(Cc2ccc(-c3nnc(C(F)(F)F)o3)cc2F)c2ccccc2)CC1] |

-continued
| Ex. | Comp. | Structure |
|---|---|---|
| 34 | 11203 | 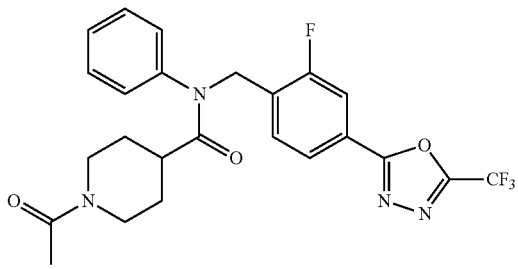 [SMILES: CC(=O)N1CCC(C(=O)N(Cc2ccc(-c3nnc(C(F)(F)F)o3)cc2F)c2ccccc2)CC1] |
| 35 | 11204 | 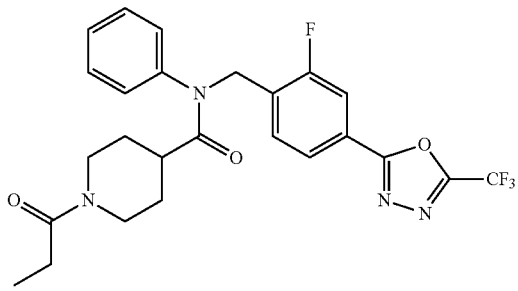 [SMILES: CCC(=O)N1CCC(C(=O)N(Cc2ccc(-c3nnc(C(F)(F)F)o3)cc2F)c2ccccc2)CC1] |
| 36 | 11205 | 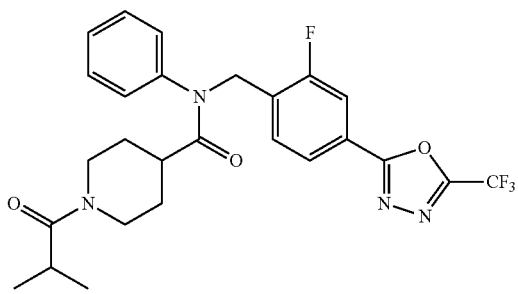 [SMILES: CC(C)C(=O)N1CCC(C(=O)N(Cc2ccc(-c3nnc(C(F)(F)F)o3)cc2F)c2ccccc2)CC1] |
| 37 | 11206 | 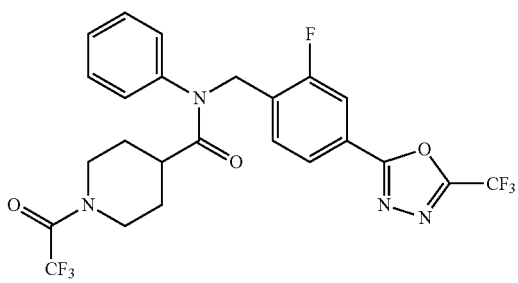 [SMILES: O=C(C1CCN(C(=O)C(F)(F)F)CC1)N(Cc1ccc(-c2nnc(C(F)(F)F)o2)cc1F)c1ccccc1] |
| 38 | 11207 | 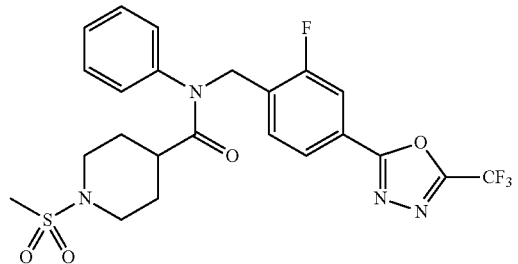 [SMILES: CS(=O)(=O)N1CCC(C(=O)N(Cc2ccc(-c3nnc(C(F)(F)F)o3)cc2F)c2ccccc2)CC1] |

-continued

| Ex. | Comp. | Structure |
|---|---|---|
| 39 | 11208 | *N-methylpiperidine-4-carboxamide, N-phenyl, N-[[2-fluoro-4-[5-(difluoromethyl)-1,3,4-oxadiazol-2-yl]phenyl]methyl]* |
| 40 | 11209 | *1-ethylpiperidine-4-carboxamide, N-phenyl, N-[[2-fluoro-4-[5-(difluoromethyl)-1,3,4-oxadiazol-2-yl]phenyl]methyl]* |
| 41 | 11210 | *1-isopropylpiperidine-4-carboxamide, N-phenyl, N-[[2-fluoro-4-[5-(difluoromethyl)-1,3,4-oxadiazol-2-yl]phenyl]methyl]* |
| 42 | 11211 | *1-acetylpiperidine-4-carboxamide, N-phenyl, N-[[2-fluoro-4-[5-(difluoromethyl)-1,3,4-oxadiazol-2-yl]phenyl]methyl]* |
| 43 | 11212 | *1-propanoylpiperidine-4-carboxamide, N-phenyl, N-[[2-fluoro-4-[5-(difluoromethyl)-1,3,4-oxadiazol-2-yl]phenyl]methyl]* |

| Ex. | Comp. | Structure |
|---|---|---|
| 44 | 11213 | 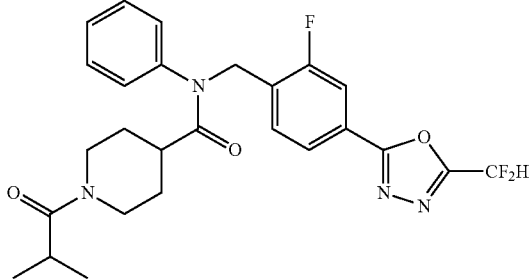 [SMILES: CC(C)C(=O)N1CCC(C(=O)N(Cc2ccc(-c3nnc(C(F)F)o3)cc2F)c2ccccc2)CC1] |
| 45 | 11214 | 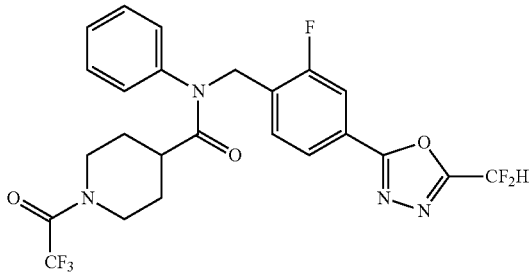 [SMILES: O=C(C1CCN(C(=O)C(F)(F)F)CC1)N(Cc1ccc(-c2nnc(C(F)F)o2)cc1F)c1ccccc1] |
| 46 | 11215 | 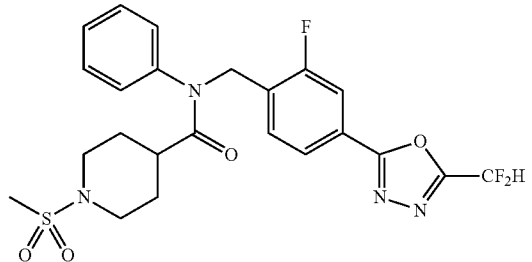 [SMILES: CS(=O)(=O)N1CCC(C(=O)N(Cc2ccc(-c3nnc(C(F)F)o3)cc2F)c2ccccc2)CC1] |
| 47 | 11232 | 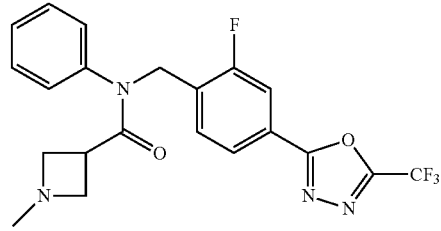 [SMILES: CN1CC(C(=O)N(Cc2ccc(-c3nnc(C(F)(F)F)o3)cc2F)c2ccccc2)C1] |
| 48 | 11233 | 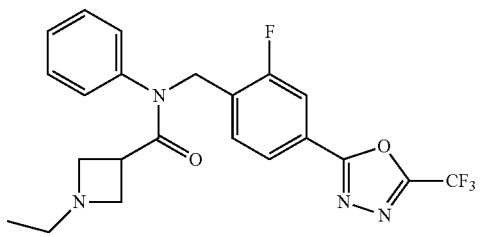 [SMILES: CCN1CC(C(=O)N(Cc2ccc(-c3nnc(C(F)(F)F)o3)cc2F)c2ccccc2)C1] |

-continued

| Ex. | Comp. | Structure |
|---|---|---|
| 49 | 11234 | 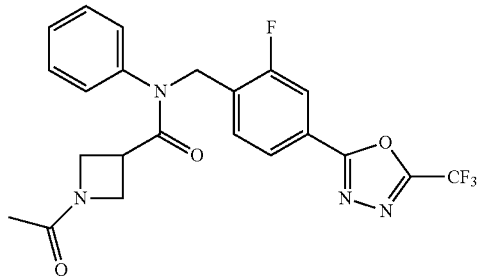 [SMILES: CC(=O)N1CC(C(=O)N(Cc2ccc(-c3nnc(C(F)(F)F)o3)cc2F)c2ccccc2)C1] |
| 50 | 11235 | 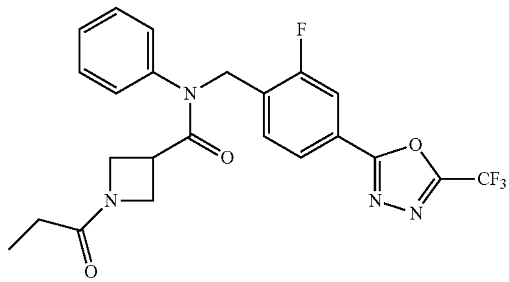 [SMILES: CCC(=O)N1CC(C(=O)N(Cc2ccc(-c3nnc(C(F)(F)F)o3)cc2F)c2ccccc2)C1] |
| 51 | 11236 | 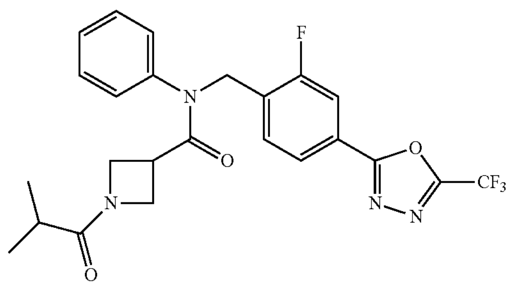 [SMILES: CC(C)C(=O)N1CC(C(=O)N(Cc2ccc(-c3nnc(C(F)(F)F)o3)cc2F)c2ccccc2)C1] |
| 52 | 11237 | 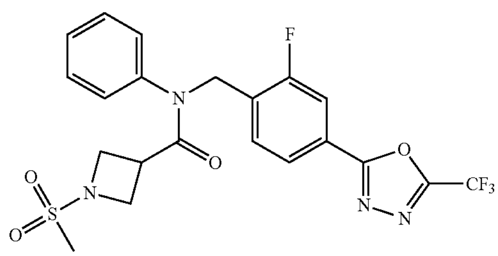 [SMILES: CS(=O)(=O)N1CC(C(=O)N(Cc2ccc(-c3nnc(C(F)(F)F)o3)cc2F)c2ccccc2)C1] |
| 53 | 11238 | 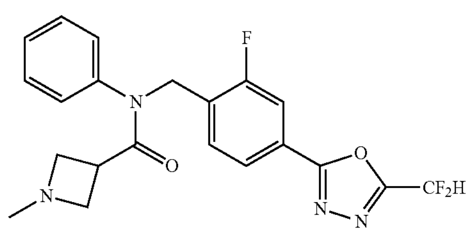 [SMILES: CN1CC(C(=O)N(Cc2ccc(-c3nnc(C(F)F)o3)cc2F)c2ccccc2)C1] |
| 54 | 11239 | 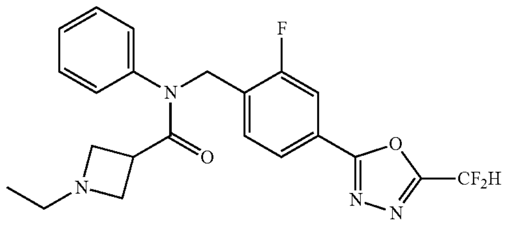 [SMILES: CCN1CC(C(=O)N(Cc2ccc(-c3nnc(C(F)F)o3)cc2F)c2ccccc2)C1] |

-continued

| Ex. | Comp. | Structure |
|---|---|---|
| 55 | 11240 | 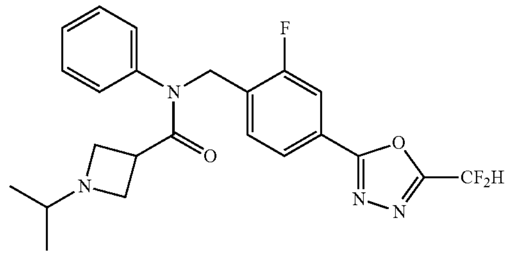 [SMILES: CC(C)N1CC(C(=O)N(Cc2ccc(-c3nnc(C(F)F)o3)cc2F)c2ccccc2)C1] |
| 56 | 11241 | 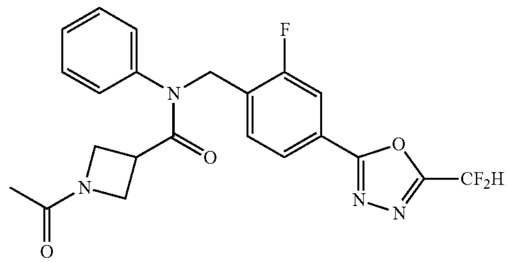 [SMILES: CC(=O)N1CC(C(=O)N(Cc2ccc(-c3nnc(C(F)F)o3)cc2F)c2ccccc2)C1] |
| 57 | 11242 | 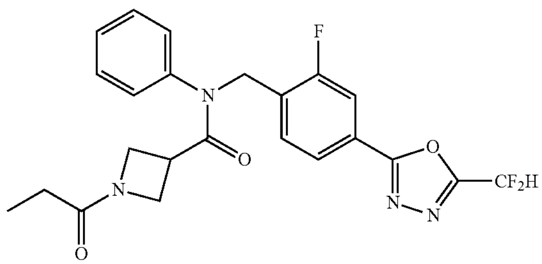 |
| 58 | 11243 | 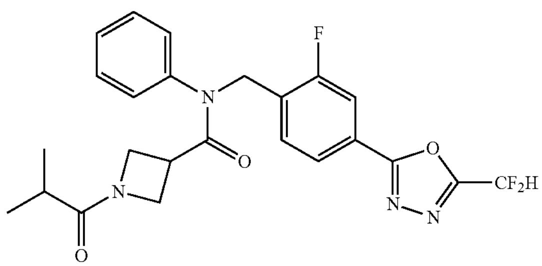 [SMILES: CC(C)C(=O)N1CC(C(=O)N(Cc2ccc(-c3nnc(C(F)F)o3)cc2F)c2ccccc2)C1] |
| 59 | 11244 | 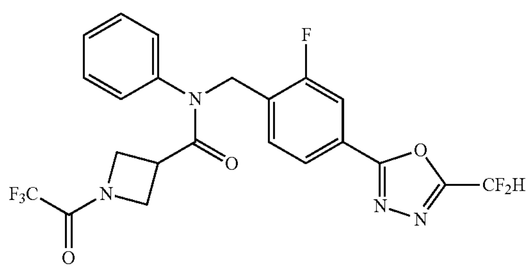 [SMILES: O=C(C1CN(C(=O)C(F)(F)F)C1)N(Cc1ccc(-c2nnc(C(F)F)o2)cc1F)c1ccccc1] |
| 60 | 11245 | 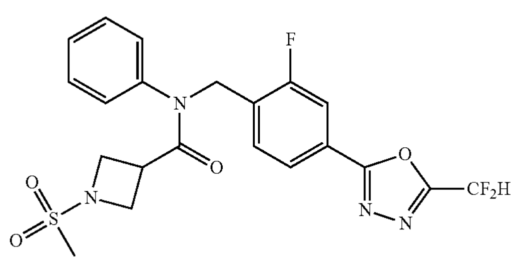 [SMILES: CS(=O)(=O)N1CC(C(=O)N(Cc2ccc(-c3nnc(C(F)F)o3)cc2F)c2ccccc2)C1] |

-continued
| Ex. | Comp. | Structure |
|---|---|---|
| 61 | 11246 | 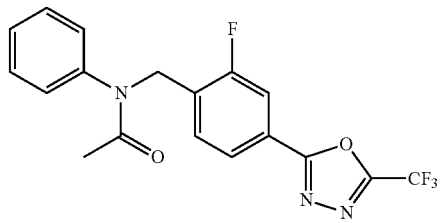 [SMILES: CC(=O)N(Cc1ccc(-c2nnc(C(F)(F)F)o2)cc1F)c1ccccc1] |
| 62 | 11247 | 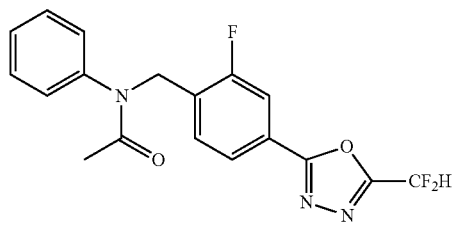 [SMILES: CC(=O)N(Cc1ccc(-c2nnc(C(F)F)o2)cc1F)c1ccccc1] |
| 63 | 11325 | 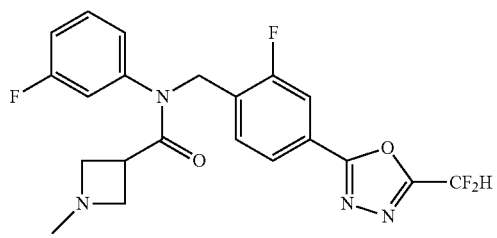 [SMILES: CN1CC(C(=O)N(Cc2ccc(-c3nnc(C(F)F)o3)cc2F)c2cccc(F)c2)C1] |
| 64 | 11326 | 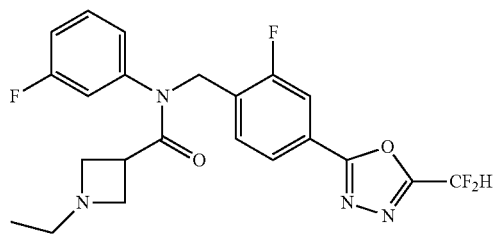 |
| 65 | 11327 | 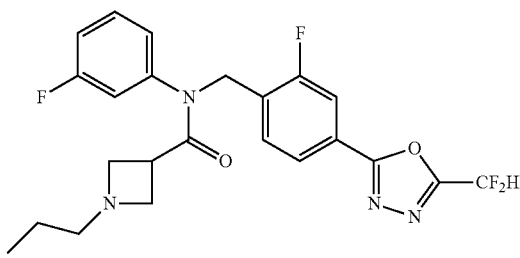 [SMILES: CCCN1CC(C(=O)N(Cc2ccc(-c3nnc(C(F)F)o3)cc2F)c2cccc(F)c2)C1] |
| 66 | 11328 | 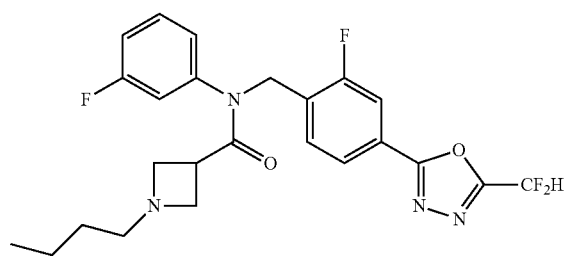 [SMILES: CCCCN1CC(C(=O)N(Cc2ccc(-c3nnc(C(F)F)o3)cc2F)c2cccc(F)c2)C1] |

| Ex. | Comp. | Structure |
|---|---|---|
| 67 | 11329 | 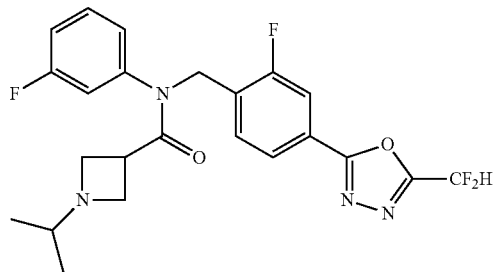 [SMILES: CC(C)N1CC(C(=O)N(Cc2ccc(-c3nnc(C(F)F)o3)cc2F)c2cccc(F)c2)C1] |
| 68 | 11330 | 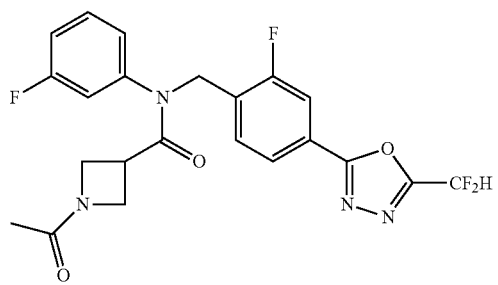 [SMILES: CC(=O)N1CC(C(=O)N(Cc2ccc(-c3nnc(C(F)F)o3)cc2F)c2cccc(F)c2)C1] |
| 69 | 11331 | 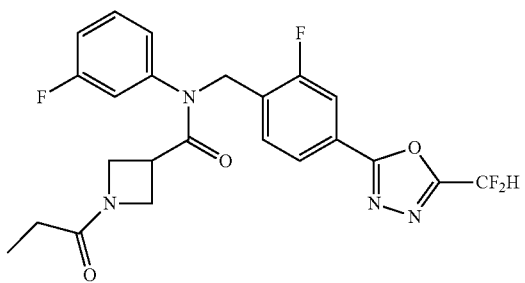 |
| 70 | 11332 | 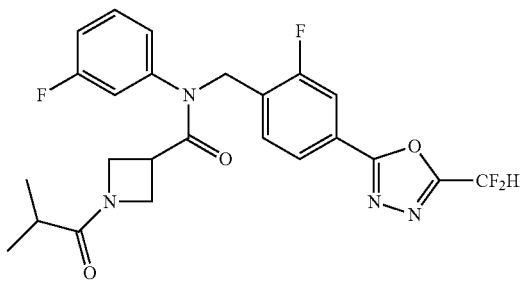 [SMILES: CC(C)C(=O)N1CC(C(=O)N(Cc2ccc(-c3nnc(C(F)F)o3)cc2F)c2cccc(F)c2)C1] |
| 71 | 11333 | 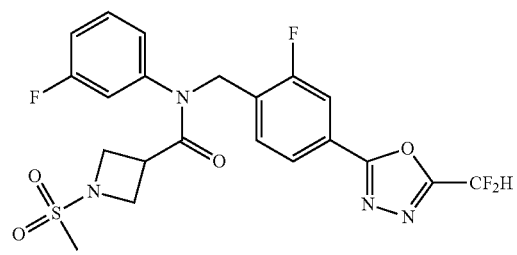 [SMILES: CS(=O)(=O)N1CC(C(=O)N(Cc2ccc(-c3nnc(C(F)F)o3)cc2F)c2cccc(F)c2)C1] |

-continued

| Ex. | Comp. | Structure |
|---|---|---|
| 72 | 11334 | 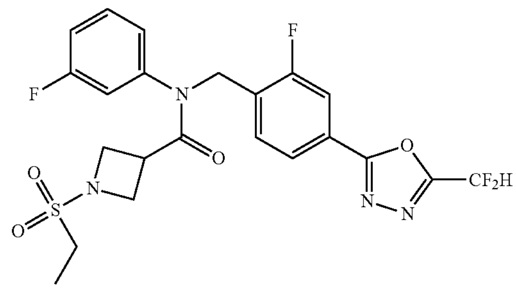 [SMILES: CCS(=O)(=O)N1CC(C(=O)N(Cc2ccc(-c3nnc(C(F)F)o3)cc2F)c2cccc(F)c2)C1] |
| 73 | 11339 | 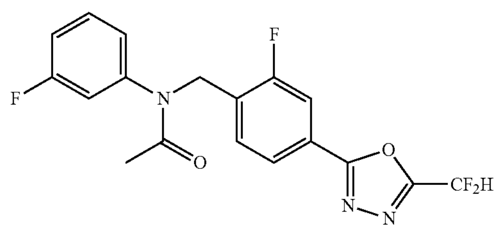 [SMILES: CC(=O)N(Cc1ccc(-c2nnc(C(F)F)o2)cc1F)c1cccc(F)c1] |
| 74 | 11340 | 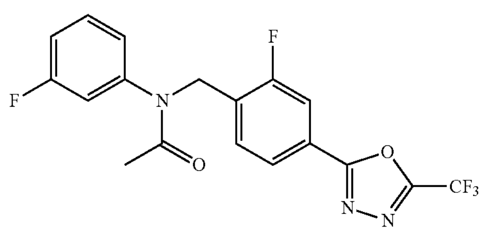 [SMILES: CC(=O)N(Cc1ccc(-c2nnc(C(F)(F)F)o2)cc1F)c1cccc(F)c1] |
| 75 | 11341 | 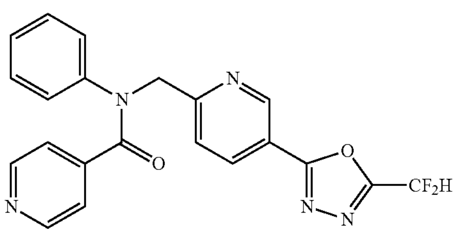 [SMILES: O=C(c1ccncc1)N(Cc1ccc(-c2nnc(C(F)F)o2)cn1)c1ccccc1] |
| 76 | 11356 | 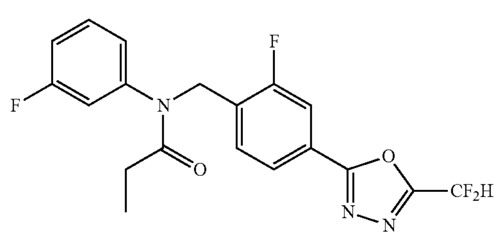 |
| 77 | 11357 | 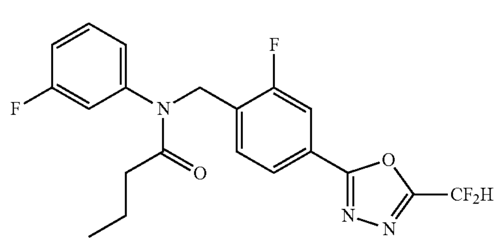 [SMILES: CCCC(=O)N(Cc1ccc(-c2nnc(C(F)F)o2)cc1F)c1cccc(F)c1] |

| Ex. | Comp. | Structure |
|---|---|---|
| 78 | 11358 | 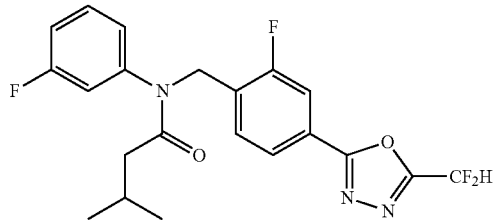 [SMILES: CC(C)CC(=O)N(Cc1ccc(-c2nnc(C(F)F)o2)cc1F)c1cccc(F)c1] |
| 79 | 11359 | 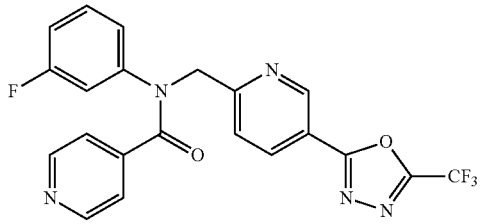 [SMILES: O=C(c1ccncc1)N(Cc1ccc(-c2nnc(C(F)(F)F)o2)cn1)c1cccc(F)c1] |
| 80 | 11360 | 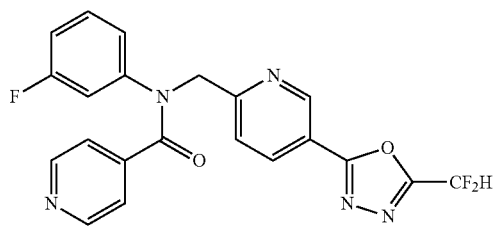 [SMILES: O=C(c1ccncc1)N(Cc1ccc(-c2nnc(C(F)F)o2)cn1)c1cccc(F)c1] |
| 81 | 11376 | 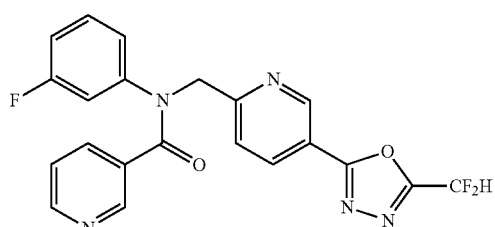 |
| 82 | 11414 | 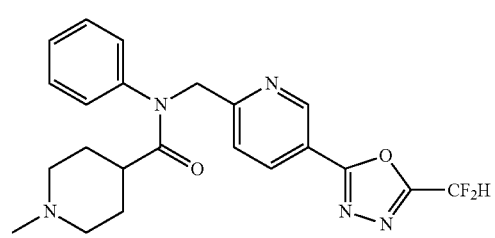 [SMILES: CN1CCC(C(=O)N(Cc2ccc(-c3nnc(C(F)F)o3)cn2)c2ccccc2)CC1] |
| 83 | 11418 | 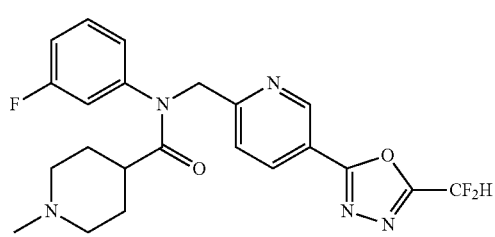 [SMILES: CN1CCC(C(=O)N(Cc2ccc(-c3nnc(C(F)F)o3)cn2)c2cccc(F)c2)CC1] |

-continued
| Ex. | Comp. | Structure |
|---|---|---|
| 84 | 11419 | 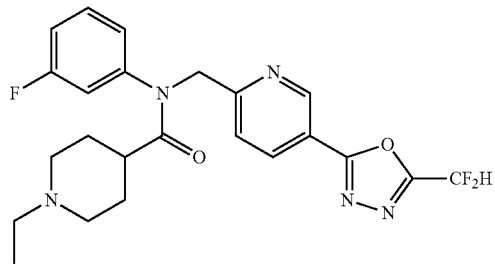 [SMILES: CCN1CCC(C(=O)N(Cc2ccc(-c3nnc(C(F)F)o3)cn2)c2cccc(F)c2)CC1] |
| 85 | 11534 | 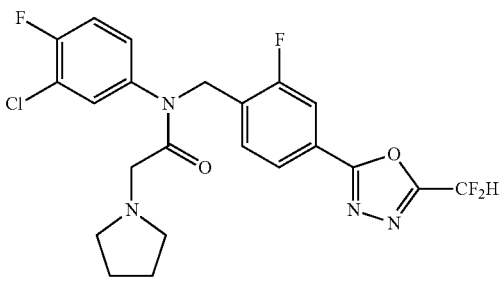 [SMILES: O=C(CN1CCCC1)N(Cc1ccc(-c2nnc(C(F)F)o2)cc1F)c1ccc(F)c(Cl)c1] |
| 86 | 11535 | 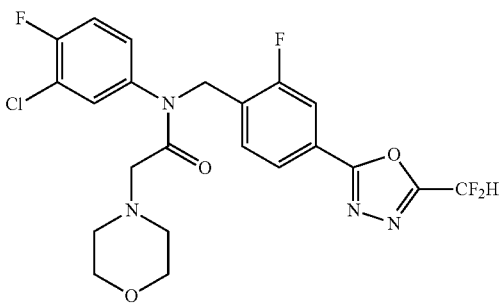 [SMILES: O=C(CN1CCOCC1)N(Cc1ccc(-c2nnc(C(F)F)o2)cc1F)c1ccc(F)c(Cl)c1] |
| 87 | 11536 | 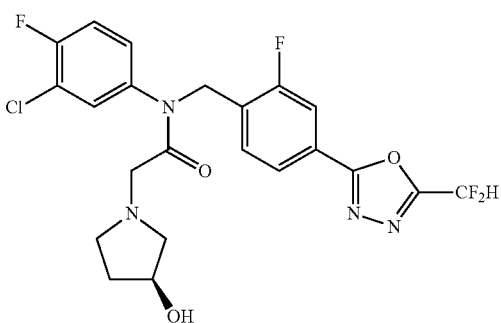 [SMILES: O=C(CN1CC[C@H](O)C1)N(Cc1ccc(-c2nnc(C(F)F)o2)cc1F)c1ccc(F)c(Cl)c1] |
| 88 | 11537 | 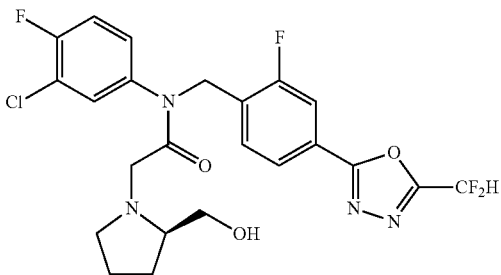 [SMILES: O=C(CN1CCC[C@@H]1CO)N(Cc1ccc(-c2nnc(C(F)F)o2)cc1F)c1ccc(F)c(Cl)c1] |

-continued
| Ex. | Comp. | Structure |
|---|---|---|
| 89 | 11538 | 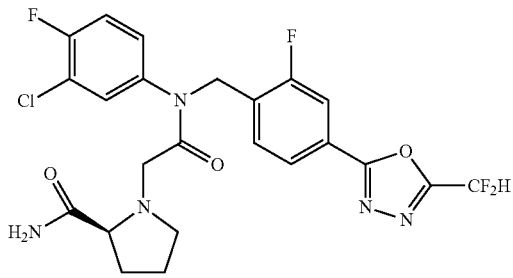 [SMILES: NC(=O)[C@@H]1CCCN1CC(=O)N(Cc1ccc(-c2nnc(C(F)F)o2)cc1F)c1ccc(F)c(Cl)c1] |
| 90 | 11584 | 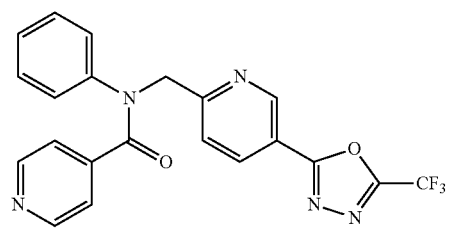 [SMILES: O=C(c1ccncc1)N(Cc1ccc(-c2nnc(C(F)(F)F)o2)cn1)c1ccccc1] |
| 91 | 11602 | 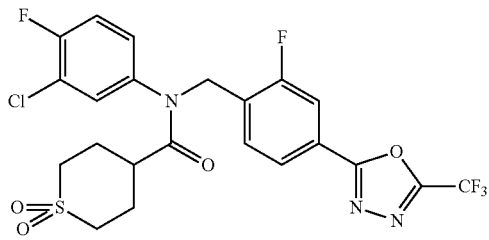 [SMILES: O=C(C1CCS(=O)(=O)CC1)N(Cc1ccc(-c2nnc(C(F)(F)F)o2)cc1F)c1ccc(F)c(Cl)c1] |
| 92 | 11603 | 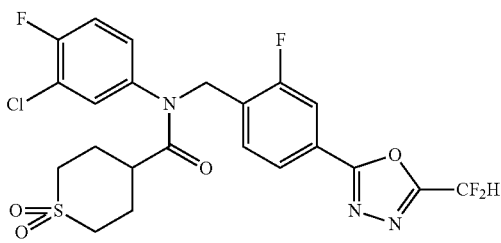 [SMILES: O=C(C1CCS(=O)(=O)CC1)N(Cc1ccc(-c2nnc(C(F)F)o2)cc1F)c1ccc(F)c(Cl)c1] |
| 93 | 11610 | 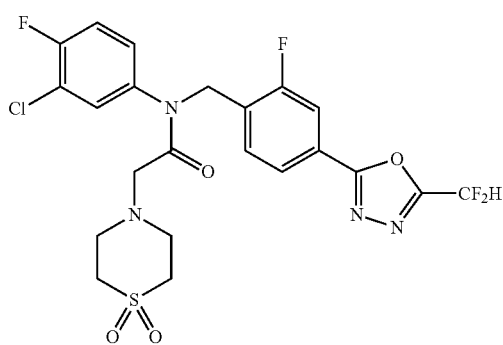 [SMILES: O=C(CN1CCS(=O)(=O)CC1)N(Cc1ccc(-c2nnc(C(F)F)o2)cc1F)c1ccc(F)c(Cl)c1] |

-continued

| Ex. | Comp. | Structure |
|---|---|---|
| 94 | 11611 | 3-chloro-4-fluoro-N-[[2-fluoro-4-[5-(difluoromethyl)-1,3,4-oxadiazol-2-yl]phenyl]methyl]-2-(4-acetylpiperazin-1-yl)acetamide |
| 95 | 11612 | 3-chloro-4-fluoro-N-[[2-fluoro-4-[5-(difluoromethyl)-1,3,4-oxadiazol-2-yl]phenyl]methyl]-2-[4-(cyclopropanecarbonyl)piperazin-1-yl]acetamide |
| 96 | 11613 | 3-chloro-4-fluoro-N-[[2-fluoro-4-[5-(difluoromethyl)-1,3,4-oxadiazol-2-yl]phenyl]methyl]-2-[4-(methanesulfonyl)piperazin-1-yl]acetamide |
| 97 | 11614 | 3-chloro-4-fluoro-N-[[2-fluoro-4-[5-(difluoromethyl)-1,3,4-oxadiazol-2-yl]phenyl]methyl]-2-[4-(oxetan-3-yl)piperazin-1-yl]acetamide |

-continued

| Ex. | Comp. | Structure |
|---|---|---|
| 98 | 11621 | (structure: N-phenyl-N-[(2-fluoro-4-(5-trifluoromethyl-1,3,4-oxadiazol-2-yl)benzyl)]-1-(oxetan-3-yl)piperidine-4-carboxamide) |
| 99 | 11622 | (structure: N-phenyl-N-[(2-fluoro-4-(5-difluoromethyl-1,3,4-oxadiazol-2-yl)benzyl)]-1-(oxetan-3-yl)piperidine-4-carboxamide) |

6. The 1,3,4-oxadiazole amide derivative compound represented by formula I, stereoisomer thereof or pharmaceutically acceptable salt thereof according to claim 5, wherein the compound represented by formula I is selected from the group consisting of compounds described in the following table:

| Ex. | Comp. | Structure |
|---|---|---|
| 7 | 11110 | (structure with pyridine, N-phenyl, 2-fluoro-4-(5-CF₂H-1,3,4-oxadiazol-2-yl)benzyl) |
| 30 | 11189 | (structure with pyridine, N-(3-fluorophenyl), 2-fluoro-4-(5-CF₂H-1,3,4-oxadiazol-2-yl)benzyl) |
| 48 | 11233 | (structure with 1-ethylazetidine-3-carboxamide, N-phenyl, 2-fluoro-4-(5-CF₃-1,3,4-oxadiazol-2-yl)benzyl) |

-continued
| Ex. | Comp. | Structure |
|---|---|---|
| 52 | 11237 | 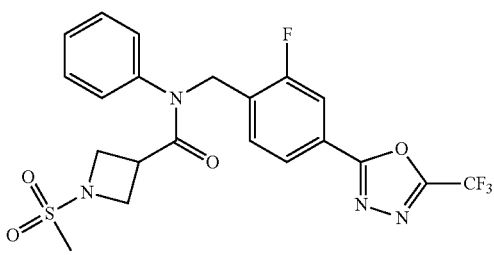 [SMILES: CS(=O)(=O)N1CC(C(=O)N(Cc2ccc(-c3nnc(C(F)(F)F)o3)cc2F)c2ccccc2)C1] |
| 53 | 11238 | 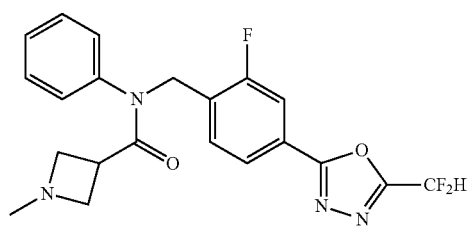 [SMILES: CN1CC(C(=O)N(Cc2ccc(-c3nnc(C(F)F)o3)cc2F)c2ccccc2)C1] |
| 54 | 11239 | 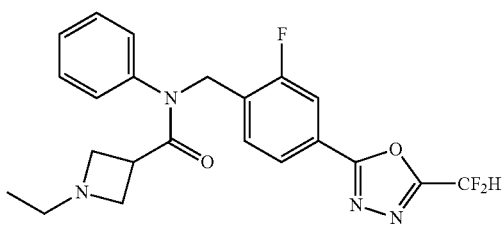 [SMILES: CCN1CC(C(=O)N(Cc2ccc(-c3nnc(C(F)F)o3)cc2F)c2ccccc2)C1] |
| 55 | 11240 | 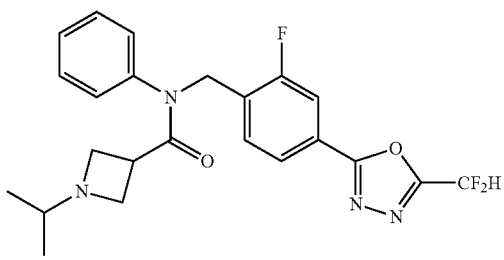 [SMILES: CC(C)N1CC(C(=O)N(Cc2ccc(-c3nnc(C(F)F)o3)cc2F)c2ccccc2)C1] |
| 56 | 11241 | 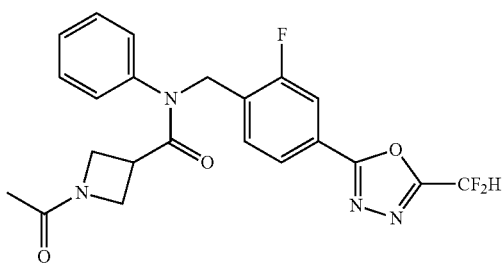 [SMILES: CC(=O)N1CC(C(=O)N(Cc2ccc(-c3nnc(C(F)F)o3)cc2F)c2ccccc2)C1] |
| 57 | 11242 | 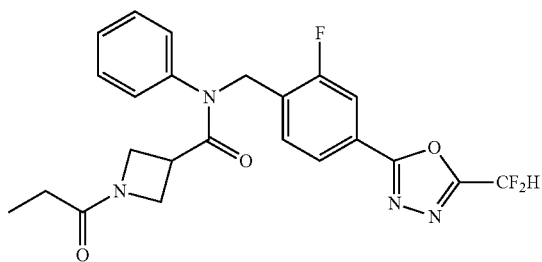 |

| Ex. | Comp. | Structure |
|---|---|---|
| 58 | 11243 | 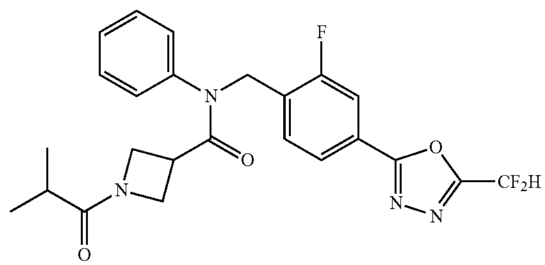 [SMILES: CC(C)C(=O)N1CC(C(=O)N(Cc2ccc(-c3nnc(C(F)F)o3)cc2F)c2ccccc2)C1] |
| 60 | 11245 | 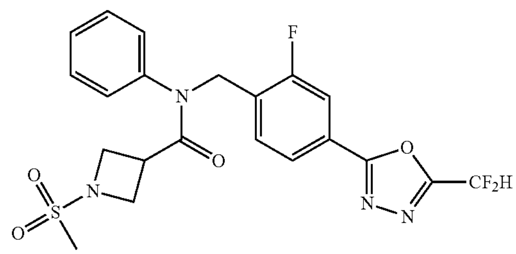 [SMILES: CS(=O)(=O)N1CC(C(=O)N(Cc2ccc(-c3nnc(C(F)F)o3)cc2F)c2ccccc2)C1] |
| 65 | 11327 | 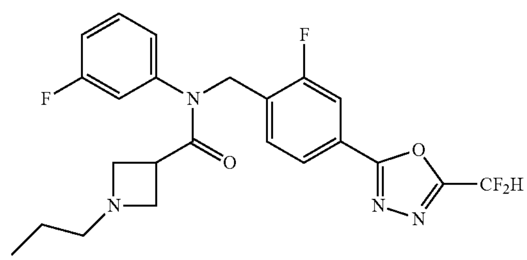 [SMILES: CCCN1CC(C(=O)N(Cc2ccc(-c3nnc(C(F)F)o3)cc2F)c2cccc(F)c2)C1] |
| 70 | 11332 | 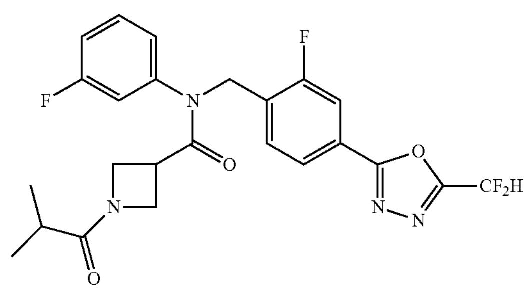 [SMILES: CC(C)C(=O)N1CC(C(=O)N(Cc2ccc(-c3nnc(C(F)F)o3)cc2F)c2cccc(F)c2)C1] |
| 71 | 11333 | 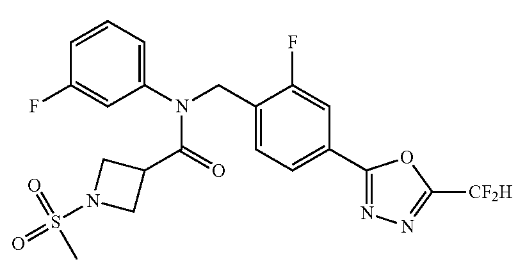 [SMILES: CS(=O)(=O)N1CC(C(=O)N(Cc2ccc(-c3nnc(C(F)F)o3)cc2F)c2cccc(F)c2)C1] |

-continued
| Ex. | Comp. | Structure |
|---|---|---|
| 72 | 11334 | 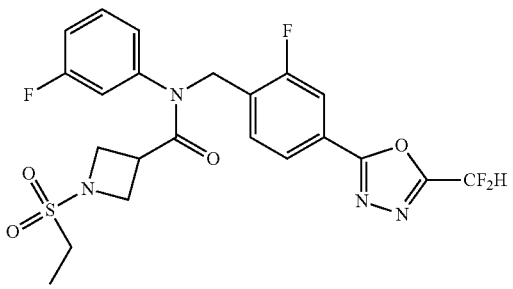 [SMILES: CCS(=O)(=O)N1CC(C(=O)N(Cc2ccc(-c3nnc(C(F)F)o3)cc2F)c2cccc(F)c2)C1] |
| 73 | 11339 | 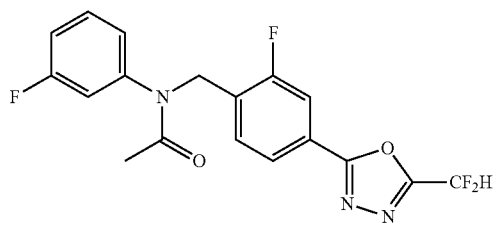 [SMILES: CC(=O)N(Cc1ccc(-c2nnc(C(F)F)o2)cc1F)c1cccc(F)c1] |
| 75 | 11341 | 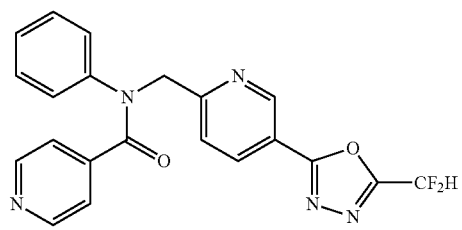 [SMILES: O=C(c1ccncc1)N(Cc1ccc(-c2nnc(C(F)F)o2)cn1)c1ccccc1] |
| 79 | 11359 | 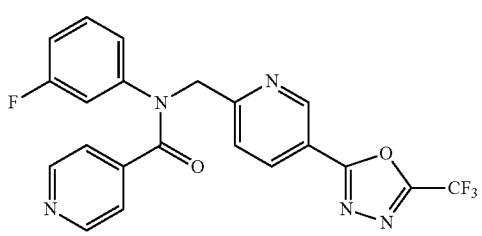 [SMILES: O=C(c1ccncc1)N(Cc1ccc(-c2nnc(C(F)(F)F)o2)cn1)c1cccc(F)c1] |
| 80 | 11360 | 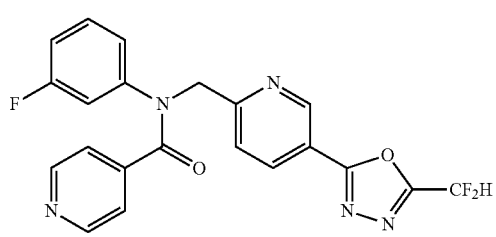 [SMILES: O=C(c1ccncc1)N(Cc1ccc(-c2nnc(C(F)F)o2)cn1)c1cccc(F)c1] |
| 81 | 11376 | 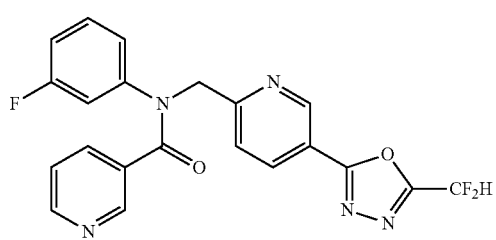 [SMILES: O=C(c1cccnc1)N(Cc1ccc(-c2nnc(C(F)F)o2)cn1)c1cccc(F)c1] |

| Ex. | Comp. | Structure |
|---|---|---|
| 82 | 11414 | 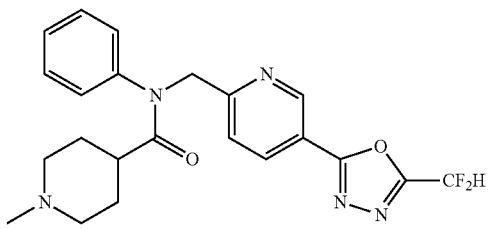 [SMILES: CN1CCC(C(=O)N(Cc2ccc(-c3nnc(C(F)F)o3)cn2)c2ccccc2)CC1] |
| 83 | 11418 | 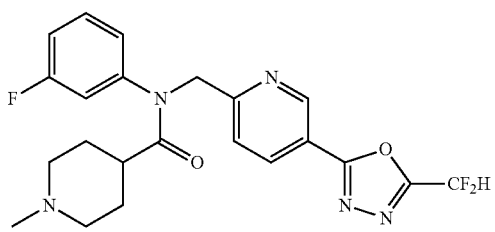 [SMILES: CN1CCC(C(=O)N(Cc2ccc(-c3nnc(C(F)F)o3)cn2)c2cccc(F)c2)CC1] |
| 84 | 11419 | 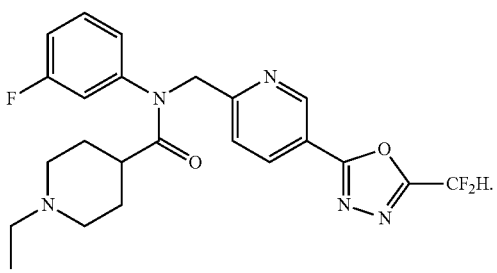 [SMILES: CCN1CCC(C(=O)N(Cc2ccc(-c3nnc(C(F)F)o3)cn2)c2cccc(F)c2)CC1] |
7. The 1,3,4-oxadiazole amide derivative compound represented by formula I, stereoisomer thereof or pharmaceutically acceptable salt thereof according to claim 6, wherein the compound represented by formula I is selected from the group consisting of compounds described in the following table:
| Ex. | Comp. | Structure |
|---|---|---|
| 30 | 11189 | 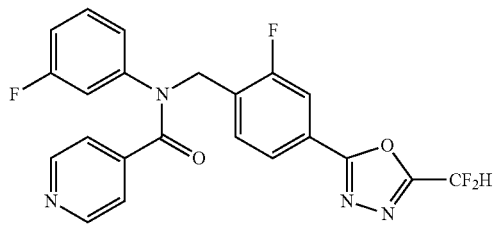 |
| 48 | 11233 | 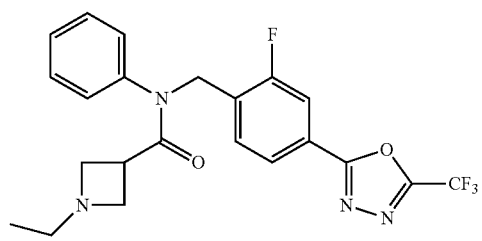 [SMILES: CCN1CC(C(=O)N(Cc2ccc(-c3nnc(C(F)(F)F)o3)cc2F)c2ccccc2)C1] |

| Ex. | Comp. | Structure |
|---|---|---|
| 54 | 11239 | *N-ethyl-azetidine-3-carboxamide, N-phenyl, N-(2-fluoro-4-(5-(difluoromethyl)-1,3,4-oxadiazol-2-yl)benzyl)* |
| 56 | 11241 | *1-acetyl-azetidine-3-carboxamide, N-phenyl, N-(2-fluoro-4-(5-(difluoromethyl)-1,3,4-oxadiazol-2-yl)benzyl)* |
| 57 | 11242 | *1-propanoyl-azetidine-3-carboxamide, N-phenyl, N-(2-fluoro-4-(5-(difluoromethyl)-1,3,4-oxadiazol-2-yl)benzyl)* |
| 58 | 11243 | *1-isobutyryl-azetidine-3-carboxamide, N-phenyl, N-(2-fluoro-4-(5-(difluoromethyl)-1,3,4-oxadiazol-2-yl)benzyl)* |
| 71 | 11333 | *1-(methylsulfonyl)-azetidine-3-carboxamide, N-(3-fluorophenyl), N-(2-fluoro-4-(5-(difluoromethyl)-1,3,4-oxadiazol-2-yl)benzyl)* |
| 72 | 11334 | *1-(ethylsulfonyl)-azetidine-3-carboxamide, N-(3-fluorophenyl), N-(2-fluoro-4-(5-(difluoromethyl)-1,3,4-oxadiazol-2-yl)benzyl)* |

-continued

| Ex. | Comp. | Structure |
|---|---|---|
| 75 | 11341 | N-phenyl-N-((5-(5-(difluoromethyl)-1,3,4-oxadiazol-2-yl)pyridin-2-yl)methyl)isonicotinamide |
| 79 | 11359 | N-(3-fluorophenyl)-N-((5-(5-(trifluoromethyl)-1,3,4-oxadiazol-2-yl)pyridin-2-yl)methyl)isonicotinamide |
| 80 | 11360 | N-(3-fluorophenyl)-N-((5-(5-(difluoromethyl)-1,3,4-oxadiazol-2-yl)pyridin-2-yl)methyl)isonicotinamide |
| 81 | 11376 | N-(3-fluorophenyl)-N-((5-(5-(difluoromethyl)-1,3,4-oxadiazol-2-yl)pyridin-2-yl)methyl)nicotinamide |
| 82 | 11414 | 1-methyl-N-phenyl-N-((5-(5-(difluoromethyl)-1,3,4-oxadiazol-2-yl)pyridin-2-yl)methyl)piperidine-4-carboxamide |
| 83 | 11418 | N-(3-fluorophenyl)-1-methyl-N-((5-(5-(difluoromethyl)-1,3,4-oxadiazol-2-yl)pyridin-2-yl)methyl)piperidine-4-carboxamide |

| Ex. | Comp. | Structure |
|---|---|---|
| 84 | 11419 | 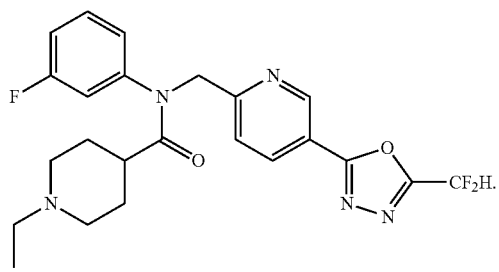 [SMILES: CCN1CCC(C(=O)N(Cc2ccc(-c3nnc(C(F)F)o3)cn2)c2cccc(F)c2)CC1] |
8. A pharmaceutical composition comprising, as an active ingredient, the compound represented by formula I, stereoisomer thereof or pharmaceutically acceptable salt thereof according to claim 1.
* * * * *

UNITED STATES PATENT AND TRADEMARK OFFICE
CERTIFICATE OF CORRECTION

PATENT NO. : 10,584,117 B2  
APPLICATION NO. : 15/748081  
DATED : March 10, 2020  
INVENTOR(S) : Jaekwang Lee et al.

Page 1 of 1

It is certified that error appears in the above-identified patent and that said Letters Patent is hereby corrected as shown below:

In the Claims

Column 196, Line 24:

In Claim 1, should read -- 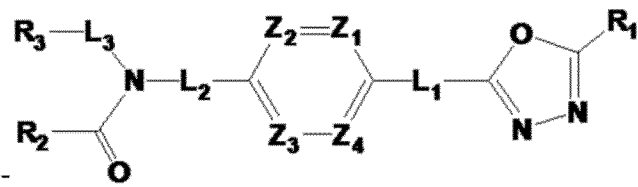 --, therefor.

Column 196, Line 59:
In Claim 1, delete "heteroaryl" and insert -- -heteroaryl --, therefor.

Column 197, Line 60:
In Claim 2, delete "heteroaryl" and insert -- -heteroaryl --, therefor.

Column 197, Line 64:
In Claim 2, delete "$R_5$" and insert -- $R_8$ --, therefor.

Signed and Sealed this  
Second Day of June, 2020

Andrei Iancu  
*Director of the United States Patent and Trademark Office*